(12) United States Patent
Wirth et al.

(10) Patent No.: US 10,738,315 B2
(45) Date of Patent: Aug. 11, 2020

(54) RECOMBINANT PROBIOTIC BACTERIA

(71) Applicant: Aurealis Oy, Kuopio (FI)

(72) Inventors: Thomas Wirth, Kuopio (FI); Juha Yrjänheikki, Kuopio (FI); Haritha Samaranayake, Kuopio (FI); Dirk Weber, Jonen (CH); Igor Mierau, Wapenveld (NL); Peter Allard Bron, Wageningen (NL); Herwig Bachmann, Amsterdam (NL)

(73) Assignee: Aurealis Oy (FI)

( * ) Notice: Subject to any disclaimer, the term of this patent is extended or adjusted under 35 U.S.C. 154(b) by 0 days.

(21) Appl. No.: 15/548,558

(22) PCT Filed: Nov. 2, 2015

(86) PCT No.: PCT/EP2015/075484
§ 371 (c)(1),
(2) Date: Aug. 3, 2017

(87) PCT Pub. No.: WO2016/124266
PCT Pub. Date: Aug. 11, 2016

(65) Prior Publication Data
US 2018/0135062 A1    May 17, 2018

(30) Foreign Application Priority Data
Feb. 4, 2015   (WO) .................. PCT/EP2015/052345

(51) Int. Cl.
| | | |
|---|---|---|
| *A61K 39/02* | (2006.01) | |
| *A01N 63/00* | (2020.01) | |
| *A61K 48/00* | (2006.01) | |
| *C12N 15/74* | (2006.01) | |
| *C07K 14/53* | (2006.01) | |
| *C07K 14/54* | (2006.01) | |
| *A61K 35/74* | (2015.01) | |
| *A61K 38/17* | (2006.01) | |
| *C07K 14/50* | (2006.01) | |
| *A61P 17/00* | (2006.01) | |
| *A61P 17/02* | (2006.01) | |
| *A61K 35/747* | (2015.01) | |
| *A61K 39/00* | (2006.01) | |

(52) U.S. Cl.
CPC ............ *C12N 15/746* (2013.01); *A61K 35/74* (2013.01); *A61K 35/747* (2013.01); *A61K 38/17* (2013.01); *A61P 17/00* (2018.01); *A61P 17/02* (2018.01); *C07K 14/50* (2013.01); *C07K 14/503* (2013.01); *C07K 14/53* (2013.01); *C07K 14/5406* (2013.01); *A61K 2039/522* (2013.01); *C07K 2319/02* (2013.01); *C07K 2319/50* (2013.01)

(58) Field of Classification Search
CPC ... C12N 15/86; A61K 35/74; A61K 2039/522
See application file for complete search history.

(56) References Cited

U.S. PATENT DOCUMENTS

| | | | |
|---|---|---|---|
| 8,759,088 B2 | 6/2014 | Steidler et al. | |
| 9,680,104 B2 | 6/2017 | Udaka et al. | |
| 9,688,742 B2 | 6/2017 | Vergnolle et al. | |
| 9,744,147 B2 | 8/2017 | Stock et al. | |
| 9,750,252 B2 | 9/2017 | Satoh et al. | |
| 2008/0253990 A1 | 10/2008 | Steidler et al. | |
| 2011/0028945 A1* | 2/2011 | Amodei ............... | A61K 9/0024 604/890.1 |
| 2011/0223671 A1 | 9/2011 | Yoder et al. | |
| 2015/0361436 A1* | 12/2015 | Hitchcock ............ | C12N 15/746 424/93.2 |

FOREIGN PATENT DOCUMENTS

| | | |
|---|---|---|
| CN | 101605900 A | 12/2009 |
| CN | 101892189 A | 11/2010 |
| JP | 2007537741 A | 12/2007 |
| JP | 2012019768 A | 2/2012 |
| JP | 2012504390 A | 2/2012 |
| JP | 2012515721 A | 7/2012 |
| JP | 2013517256 A | 5/2013 |
| RU | 2495129 C2 | 2/2011 |
| WO | 2008155120 A2 | 12/2008 |
| WO | 2009114702 A2 | 9/2009 |
| WO | 2011150127 A2 | 12/2011 |
| WO | 2011159880 A1 | 12/2011 |
| WO | WO 2011/15980 * | 12/2011 |
| WO | 2013153358 A1 | 10/2013 |
| WO | 201473446 A1 | 5/2014 |
| WO | 2015195845 A1 | 12/2015 |

OTHER PUBLICATIONS

MedlinePlus, https://medlineplus.gov/ency/patientinstructions/000742.htm, pp. 1-4 accessed on Oct. 29, 2018 (Year: 2018).*
Wound Care Centers disclose, https://www.woundcarecenters.org/article/wound-types/ischemic-wounds, 3 pages, accessed on Oct. 29, 2018 (Year: 2018).*
Mayo Clinic, https://www.mayoclinic.org/diseases-conditions/neurodermatitis/diagnosis-treatment/drc-20375639?p=1, accessed Oct. 29, 2018 (Year: 2018).*
MedlinePlus, https://medlineplus.gov/ency/article/000435.htm; 6 pages accessed on Oct. 29, 2018 (Year: 2018).*
Nishitani et al., Bioscience Microflora, 2010; 29(4): 169-178 (Year: 2010).*
Guo et al., Currently Microbiology, 2013; 66(6): 548-554 (Year: 2013).*
Barrientos et al., Wound Repair Regen, 2014; 22(5):569-578 (Year: 2014).*

(Continued)

*Primary Examiner* — Gary B Nickol
*Assistant Examiner* — Lakia J Jackson-Tongue
(74) *Attorney, Agent, or Firm* — The Webb Law Firm

(57) ABSTRACT

The invention is directed to recombinant probiotic bacteria, especially for use in the treatment of an inflammatory skin dysfunction, as well as a method for treating an inflammatory skin dysfunction.

27 Claims, 65 Drawing Sheets
Specification includes a Sequence Listing.

(56) References Cited

OTHER PUBLICATIONS

Bolotin et al.; "The Complete Genome Sequence of the Lactic Acid Bacterium *Lactococcus lactis* ssp. lactis IL1403"; Genome Res.; 2001; pp. 731-753.
Brown et al.; "PDGF and TGF-α Act Synergistically to Improve Wound Healing in the Genetically Diabetic Mouse"; Journal of Surgical Research; 1994; pp. 562-570; vol. 56.
Bryan et al.; "Improved Vectors for Nisin-Controlled Expression in Gram-Positive Bacteria"; Plasmid; 2000; pp. 183-190; vol. 44; Erratum included showing correction to Fig. 1.
Davis et al.; "Macrophage M1/M2 Polarization Dynamically Adapts to Changes in Cytokine Microenvironments in Cryptococcus neoformans Infection"; mbio; 2013; pp. 1-10; vol. 4:3.
De Ruyter et al.; "Functional Analysis of Promoters in the Nisin Gene Cluster of Lactococcus lactis"; Journal of Bacteriology; 1996; pp. 3434-3439; vol. 178:12.
Duluc et al.; "Tumor-associated leukemia inhibitory factor and IL-6 skew monocyte differentiation into tumor-associated macrophage-like cells"; Blood; 2007; pp. 4319-4330; vol. 110.
EFSA Journal; "Introduction of a Qualified Presumption of Safety (QPS) approach for assessment of selected microorganisms referred to EFSA"; 2007; pp. 1-16; vol. 587, Barlow at al.
Hao et al.; "Macrophages in Tumor Microenvironments and the Progression of Tumors"; Clinical and Developmental Immunology; 2012; pp. 1-11; vol. 2012.
Michaels et al.; "db/db mice exhibit severe wound-healing impairments compared with other murine diabetic strains in a silicone-splinted excisional wound model"; Wound Rep Reg; 2007; pp. 665-670; vol. 15.
Richard et al.; "Effect of Topical Basic Fibroblast Growth Factor on the Healing of Chronic Diabetic Neuropathic Ulcer of the Foot"; Diabetes Care; 1995; pp. 64-69; vol. 18:1.
Steidler et al.; "Therapeutic Drug Delivery by Genetically Modified Lactococcus lactis"; Ann. N.Y. Acad. Sci.; 2006; pp. 176-186; vol. 1072.
Van Asseldonk et al.; "Cloning of usp45, a gene encoding a secreted protein from *Lactococcus lactis* subsp. lactis MG1363"; Gene; 1990; pp. 155-160; vol. 95.
Van Asseldonk et al.; "Functional analysis of the Lactococcus lactis usp45 secretion signal in the secretion of a homologous proteinase and a heterologous α-amylase"; Mol Gen Gene; 1993; pp. 428-434; vol. 240.
Steidler et al.; "Genetically modified Lactococcus lactis: novel tools; for drug delivery"; International Journal of Dairy Technology, May 2006; pp. 140-146; vol. 59, No. 2.
L.C. Lew et al., Bioactives from probiotics for dermal health: functions and benefits; Journal of Applied Microbiology 114, 1241-1253; oi:10.1111/jam.12137.
Rebecca Martin et al., Effects in the use of a genetically engineered strain of Lactococcus lactis delivering in situ IL-10 as a therapy to treat low-grade colon inflammation; Human Vaccines & Immunotherapeutics 10:6, 1611-1621; Jun. 2014; Landes Bioscience; http://dx.doi.org/10.4161/hv.28549.
Lothar Steidler, Genetically engineered probiotics; Best Practice & Research Clinical Gastroenterology vol. 17, No. 5, pp. 861-876, 2003; Doi:10.1016/S1521-6918(03)00072-6.
Lothar Steidler et al., Therapeutic Drug Delivery by Genetically Modified Lactococcus lactis; Annals of The New York Academy of Sciences; Aug. 24, 2006; https://doi.org/10.1196/annals.1326.031.
Supervised by Kazutomo Imahori et al., "Seikagaku Giten" 3rc:1 edition, Tokyo Kagaku Dojin, Oct. 8, 1998, p. 808-809.
Zhang et al., J. Biol. Chem., 2006, vol. 281, No. 23, p. 15694-15700.
Guironnet et al., "Antagonistic Effects of IL-4 and TGF-β1 on Langerhans Cell-Related Antigen Expression by Human Monocytes", Journal of Leukocyte Biology, May 2002, pp. 845-853, vol. 71.
Tang et al., "The Characteristics of Langerhans Cells Derived from the Monocytes in Patients with Psoriasis" Shanghai Med J, Mar. 31, 2000, pp. 138-141, vol. 23, No. 3, English-language Abstract.
Wang et al., "Lactic Acid Bacteria—Application in Animal Husbandry", 2005, pp. 285-289.
Yunqing et al., "Clone and Expression of a Recombinant Vector for GM-CSF/IL-15 Fusion Gene", J Fujian Med Univ, Mar. 2006, pp. 111-113, vol. 40, No. 2, English-language Abstract.

* cited by examiner

FIG. 2B

```
ggatctagtc ttataactat actgacaata gaaacattaa caaatctaaa acagtcttaa    60
ttctatcttg agaaagtatt ggtaataata ttattgtcga taacgcgagc ataataaacg   120
gctctgatta aattctgaag tttgttagat acaatgattt cgttcgaagg aactacaaaa   180
taaattataa ggaggcactc accatgggta ctgcaggcat gcggtaccac tagttctaga   240
gagctcaagc tttctttgaa ccaaaattag aaaaccaagg cttgaaacgt tcaattgaaa   300
tggcaattaa acaaattaca gcacgtgttg ctttgattga tagccaaaaa gcagcagttg   360
ataaagcaat tactgatatt gctgaaaaat tgtaatttat aaataaaaat ccccttttag   420
aggtggtttt tttatttata aattattcgt ttgatttcgc tttcgataga acaatcaaat   480
cgttctgag acgttttagc gtttatttcg tttagttatc ggcataatcg ttaaaacagg   540
cgttatcgta gcgtaaaagc ccttgagcgt agcgtggctt tgcagcgaag atgttgtctg   600
ttagattatg aaagccgatg actgaatgaa ataataagcg cagcgtcctt ctatttcggt   660
tggaggaggc tcaaggagt ttgaggaat gaaattccct catgggtttg attttaaaaa   720
ttgcttgcaa ttttgccgag cggtagcgct ggaaaatttt tgaaaaaaat ttggaatttg   780
gaaaaaaatg gggggaaagg aagcgaattt tgcttccgta ctacgacccc ccattaagtg   840
ccgagtgcca attttttgtgc caaaaacgct ctatcccaac tggctcaagg gtttgagggg   900
ttttttcaatc gccaacgaat cgccaacgtt ttcgccaacg ttttttataa atctatattt   960
aagtagcttt attttttgtt ttatgattac aaagtgatac actaattta taaaattatt  1020
tgattggagt tttttaaatg gtgatttcag aatcgaaaaa aagagttatg atttctctga  1080
caaaagagca agataaaaaa ttaacagata tggcgaaaca aaaagatttt tcaaaatctg  1140
cggttgcggc gttagctata gaagaatatg caagaaagga atcagaacaa aaaaaataag  1200
cgaaagctcg cgtttttaga aggatacgag ttttcgctac ttgttttttga taaggtaatt  1260
atatcatggc tattaaaaat actaaagcta gaattttggg attttttatta tatcctgact  1320
caattcctaa tgattggaaa gaaaaattag agagtttggg cgtatctatg gctgtcagtc  1380
ctttacacga tatggacgaa aaaaaagata aagatacatg gaatagtagt gatgttatac  1440
gaaatggaaa gcactataaa aaaccacact atcacgttat atatattgca cgaaatcctg  1500
taacaataga aagcgttagg aacaagatta agcgaaaatt ggggaatagt tcagttgctc  1560
atgttgagat acttgattat atcaaaggtt catatgaata tttgactcat gaatcaaagg  1620
acgctattgc taagaataaa catatatacg acaaaaaaga tattttgaac attaatgatt  1680
ttgatattga ccgctatata acacttgatg aaagccaaaa aagagaattg aagaatttac  1740
ttttagatat agtggatgac tataatttgg taaatacaaa agatttaatg gcttttattc  1800
gccttagggg agcggagttt ggaattttaa atacgaatga tgtaaaagat attgtttcaa  1860
caaactctag cgcctttaga ttatggtttg agggcaatta tcagtgtgga tatagagcaa  1920
gttatgcaaa ggttcttgat gctgaaacgg gggaaataaa atgacaaaca aagaaaaaga  1980
gttatttgct gaaaatgagg aattaaaaaa agaattaag gacttaaaag agcgtattga  2040
aagatacaga gaaatggaag ttgaattaag tacaacaata gatttattga gaggagggat  2100
tattgaataa ataaaagccc ccctgacgaa agtcgacatg gactgataaa gtatagtaaa  2160
aacataaaac ggaggatatt gttgtgaaca gagaagagat gactctctta gggtttgaaa  2220
ttgttgctta tgctggagat gctcgctcta agcttttaga agcgcttaaa gcggctgaaa  2280
atggtgattt cgctaaggca gatagtcttg tagtagaagc aggaagctgt attgcagagg  2340
ctcacagttc tcagacaggt atgttggctc gagaagcttc tggggaggaa cttccataca  2400
gtgttactat gatgcatggt caggatcact tgatgactac gatcttatta aagatgtgga  2460
ttcatcacct catcgaactt tataaaagag gagcaaagta attaatgcat aaactcattg  2520
aacttattga gaagggaaaa cgacggatca                                    2550
```

FIG. 3

```
  1  tagtcttata actatactga caatagaaac attaacaaat ctaaaacagt cttaattcta tcttgagaaa 71  gtattggtaa taatattatt gtcgataacg cgagcataat aaacggctct gattaaattc tgaagtttgt
                                                            -35   >>...>>

141  tagatacaat gatttcgttc gaaggaacta caaaataaat tataaggagg cactcacc
     -10  >>..>>
                    Start >
                                                        >>SD>>
```

FIG. 5A

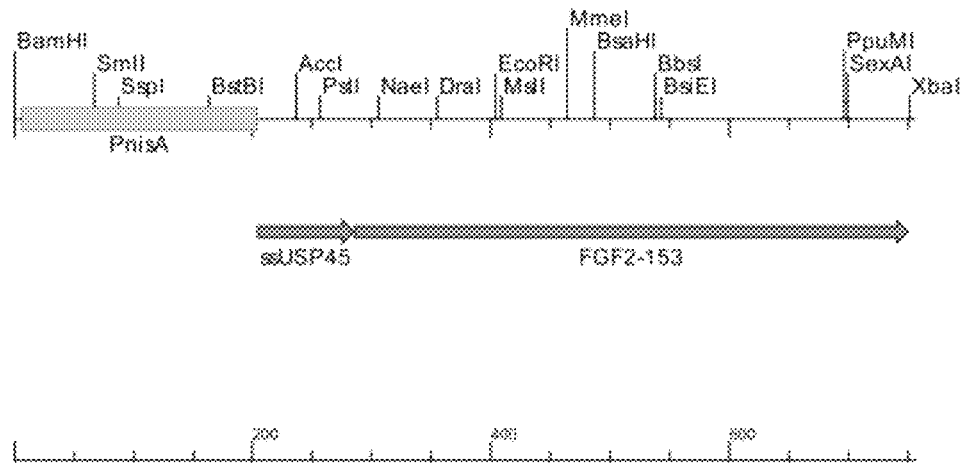

ssUsp45-FGF2-153 (756 bps)

```
  1 GGATCCTAGTCTTATAACTATACTGACAATAGAAACATTAACAAATCTAAAACAGTCTTA   60
 61 ATTCTATCTTGAGAAAGTATTGGTAATAATATTATTGTCGATAACGCGAGCATAATAAAC  120
121 GGCTCTGATTAAATTCTGAAGTTTGTTAGATACAATGATTTCGTTCGAAGGAACTACAAA  180
                      M  K  K  K  I  S  A  I  L  M  S
181 ATAAATTATAAGGAGGCACTCACCATGAAAAAAAAGATTATCTCAGCTATTTTAATGTCT  240
      T  V  I  L  S  A  A  A  P  L  S  G  V  Y  A  A  G  S  I  T
241 ACAGTGATACTTTCTGCTGCAGCCCCGTTGTCAGGTGTTTACGCTGCTGGTTCCATTACG  300
      T  L  P  A  L  P  E  D  G  G  S  G  A  F  P  P  G  H  F  K
301 ACCTTGCCGGCTTTACCAGAGGACGGAGGTTCAGGAGCCTTTCCACCAGGGCACTTTAAA  360
      D  P  K  R  L  Y  C  K  N  G  G  F  F  L  R  I  H  P  D  G
361 GATCCCAAACGTCTATATTGTAAAAATGGAGGCTTCTTTCTGCGAATTCATCCTGATGGA  420
      R  V  D  G  V  R  E  K  S  D  P  H  I  K  L  Q  L  Q  A  E
421 CGTGTAGATGGTGTGCGTGAGAAAAGTGATCCTCATATCAAACTCCAACTTCAGGCAGAA  480
      E  R  G  V  V  S  I  K  G  V  C  A  N  R  Y  L  A  M  K  E
481 GAAAGAGGCGTCGTAAGTATAAAAGGAGTTTGCGCGAATCGTTACTTAGCTATGAAAGAA  540
      D  G  R  L  L  A  S  K  C  V  T  D  E  C  F  F  F  E  R  L
541 GACGGTCGATTATTGGCCTCTAAGTGTGTTACTGATGAATGTTTTTTTTTTGAACGGCTT  600
      E  S  N  N  Y  N  T  Y  R  S  R  K  Y  T  S  W  Y  V  A  L
601 GAATCTAATAATTATAACACTTATAGAAGCAGAAAATATACATCATGGTACGTTGCACTT  660
      K  R  T  G  Q  Y  K  L  G  S  K  T  G  P  G  Q  K  A  I  L
661 AAAAGGACAGGTCAATATAAATTAGGGTCTAAGACAGGACCTGGTCAAAAGCAATTTTG   720
      F  L  P  M  S  A  K  S  *
721 TTCTTACCAATGTCGGCTAAAAGTTAATAATCTAGA                          756
```

FIG. 5B

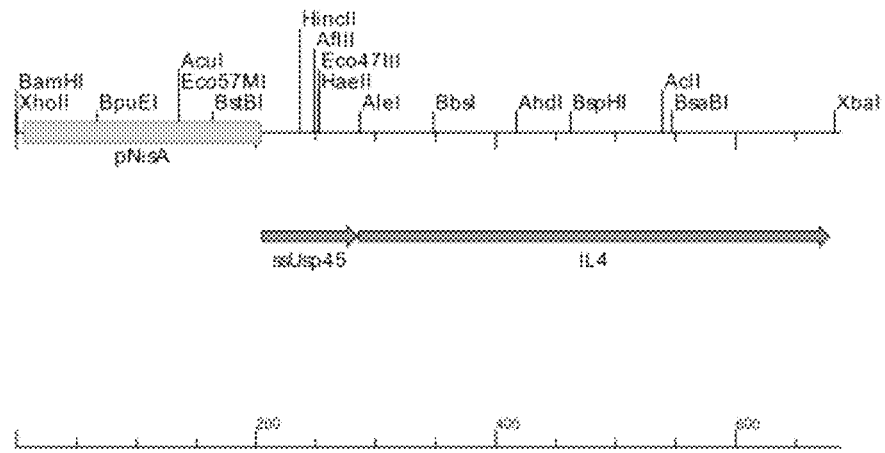

ssUsp45-hIL4 (687 bps)

```
  1 GGATCCTAGTCTTATAACTATACTGACAATAGAAACATTAACAAATCTAAAACAGTCTTA   60
 61 ATTCTATCTTGAGAAAGTATTGGTAATAATATTATTGTCGATAACGCGAGCATAATAAAC  120
121 GGCTCTGATTAAATTCTGAAGTTTGTTAGATACAATGATTTCGTTCGAAGGAACTACAAA  180
                      M  K  K  I  I  S  A  I  L  M  S
181 ATAAATTATAAGGAGGCACTCACCATGAAGAAAAAGATTATTAGTGCAATTTTAATGTCA  240
      T  V  I  L  S  A  A  A  P  L  S  G  V  Y  A  A  H  K  C  D
241 ACGGTCATCTTAAGCGCTGCTGCCCCATTGTCAGGTGTTTATGCAGCACATAAGTGTGAT  300
      I  T  L  Q  E  I  I  K  T  L  N  S  L  T  E  Q  K  T  L  C
301 ATAACATTACAAGAAATTATCAAAACCCTTAATAGTTTAACTGAACAGAAGACTTTGTGT  360
      T  E  L  T  V  T  D  I  F  A  A  S  K  N  T  T  E  K  E  T
361 ACCGAATTAACTGTAACTGATATTTTTGCTGCTTCTAAAAATACAACTGAAAAAGAGACA  420
      F  C  R  A  A  T  V  L  R  Q  F  Y  S  H  H  E  K  D  T  R
421 TTTTGTCGAGCTGCCACAGTGTTAAGACAATTTTACAGTCATCATGAAAAAGACACAAGA  480
      C  L  G  A  T  A  Q  Q  F  H  R  H  K  Q  L  I  R  F  L  K
481 TGTCTTGGTGCTACGGCACAACAATTTCATAGACACAAACAACTTATCCGTTTTCTTAAA  540
      R  L  D  R  N  L  W  G  L  A  G  L  N  S  C  P  V  K  E  A
541 CGTTTGGATCGTAATCTGTGGGGCTTGGCAGGATTGAACAGTTGTCCTGTTAAAGAAGCC  600
      N  Q  S  T  L  E  N  F  L  E  R  L  K  T  I  M  R  E  K  Y
601 AATCAATCTACTCTTGAAAATTTCTTAGAGAGATTGAAAACAATTATGCGAGAAAAATAT  660
      S  K  C  S  S  *
661 TCTAAGTGTTCATCTTAATAATCTAGA                                   687
```

FIG. 5C

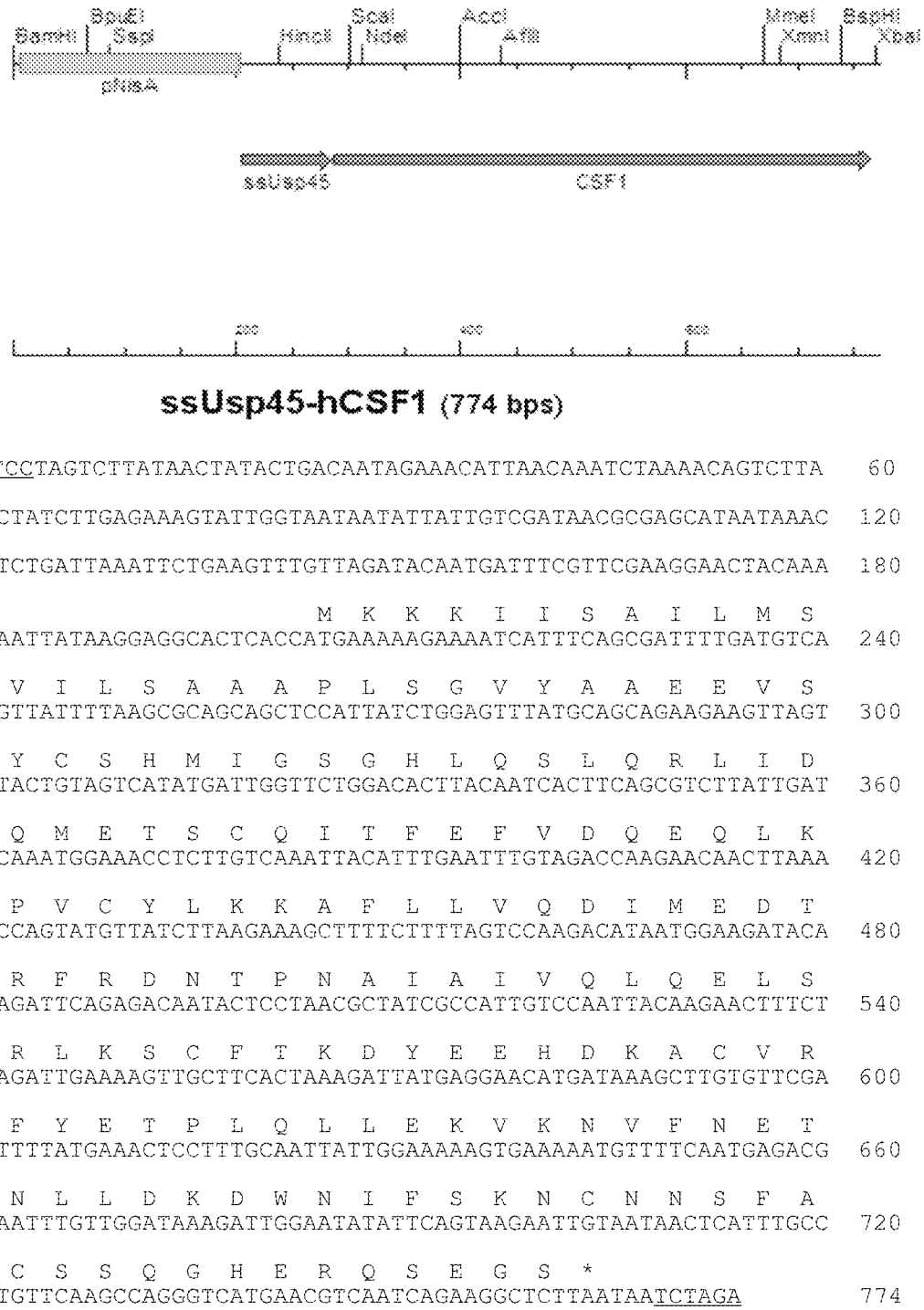

ssUsp45-hCSF1 (774 bps)

```

1  GGATCCTAGTCTTATAACTATACTGACAATAGAAACATTAACAAATCTAAAACAGTCTTA    60
 61  ATTCTATCTTGAGAAAGTATTGGTAATAATATTATTGTCGATAACGCGAGCATAATAAAC   120
121  GGCTCTGATTAAATTCTGAAGTTTGTTAGATACAATGATTTCGTTCGAAGGAACTACAAA   180
                         M  K  K  I  I  S  A  I  L  M  S
181  ATAAATTATAAGGAGGCACTCACCATGAAAAAGAAAATCATTTCAGCGATTTTGATGTCA   240
      T  V  I  L  S  A  A  A  P  L  S  G  V  Y  A  A  E  E  V  S
241  ACGGTTATTTTAAGCGCAGCAGCTCCATTATCTGGAGTTTATGCAGCAGAAGAAGTTAGT   300
      E  Y  C  S  H  M  I  G  S  G  H  L  Q  S  L  Q  R  L  I  D
301  GAGTACTGTAGTCATATGATTGGTTCTGGACACTTACAATCACTTCAGCGTCTTATTGAT   360
      S  Q  M  E  T  S  C  Q  I  T  F  E  F  V  D  Q  E  Q  L  K
361  AGTCAAATGGAAACCTCTTGTCAAATTACATTTGAATTTGTAGACCAAGAACAACTTAAA   420
      D  P  V  C  Y  L  K  K  A  F  L  L  V  Q  D  I  M  E  D  T
421  GATCCAGTATGTTATCTTAAGAAAGCTTTTCTTTTAGTCCAAGACATAATGGAAGATACA   480
      M  R  F  R  D  N  T  P  N  A  I  A  I  V  Q  L  Q  E  L  S
481  ATGAGATTCAGAGACAATACTCCTAACGCTATCGCCATTGTCCAATTACAAGAACTTTCT   540
      L  R  L  K  S  C  F  T  K  D  Y  E  E  H  D  K  A  C  V  R
541  TTAAGATTGAAAAGTTGCTTCACTAAAGATTATGAGGAACATGATAAAGCTTGTGTTCGA   600
      T  F  Y  E  T  P  L  Q  L  L  E  K  V  K  N  V  F  N  E  T
601  ACATTTTATGAAACTCCTTTGCAATTATTGGAAAAAGTGAAAAATGTTTTCAATGAGACG   660
      K  N  L  L  D  K  D  W  N  I  F  S  K  N  C  N  N  S  F  A
661  AAGAATTTGTTGGATAAAGATTGGAATATATTCAGTAAGAATTGTAATAACTCATTTGCC   720
      E  C  S  S  Q  G  H  E  R  Q  S  E  G  S  *
721  GAATGTTCAAGCCAGGGTCATGAACGTCAATCAGAAGGCTCTTAATAATCTAGA         774
```

FIG. 7B

```
ggatcctagt cttataacta tactgacaat agaaacatta acaaatctaa aacagtctta     60
attctatctt gagaaagtat tggtaataat attattgtcg ataacgcgag cataataaac    120
ggctctgatt aaattctgaa gtttgttaga tacaatgatt tcgttcgaag gaactacaaa    180
ataaattata aggaggcact caccatgaaa aaaaagatta tctcagctat tttaatgtct    240
acagtgatac tttctgctgc agccccgttg tcaggtgttt acgctgctgg ttccattacg    300
accttgccgg ctttaccaga ggacggaggt tcaggagcct ttccaccagg gcactttaaa    360
gatcccaaac gtctatattg taaaaatgga ggcttctttc tgcgaattca tcctgatgga    420
cgtgtagatg gtgtgcgtga gaaaagtgat cctcatatca aactccaact tcaggcagaa    480
gaaagaggcg tcgtaagtat aaaaggagtt tgcgcgaatc gttacttagc tatgaaagaa    540
gacggtcgat tattggcctc taagtgtgtt actgatgaat gtttttttt tgaacggctt    600
gaatctaata attataacac ttatagaagc agaaaatata catcatggta cgttgcactt    660
aaaaggacag gtcaatataa attagggtct aagacaggac ctggtcaaaa agcaattttg    720
ttcttaccaa tgtcggctaa aagttaataa tctagagagc tcaagctttc tttgaaccaa    780
aattagaaaa ccaaggcttg aaacgttcaa ttgaaatggc aattaaacaa attacagcac    840
gtgttgcttt gattgatgac caaaaagcag cagttgataa agcaattact gatattgctg    900
aaaaattgta atttataaat aaaaatcacc ttttagaggt ggttttttta tttataaatt    960
attcgtttga tttcgctttc gatagaacaa tcaaatcgtt tctgagacgt tttagcgttt   1020
atttcgttta gttatcggca taatcgttaa aacaggcgtt atcgtagcgt aaaagcccct   1080
gagcgtagcg tggctttgca gcgaagatgt tgtctgttag attatgaaag ccgatgactg   1140
aatgaaataa taagcgcagc gtccttctat ttcggttgga ggaggctcaa gggagtttga   1200
gggaatgaaa ttccctcatg ggtttgattt taaaaattgc ttgcaatttt gccgagcggt   1260
agcgctggaa aatttttgaa aaaaatttgg aatttggaaa aaaatggggg gaaaggaagc   1320
gaattttgct tccgtactac gaccccccat taagtgccga gtgccaattt ttgtgccaaa   1380
aacgctctat cccaactggc tcaagggttt gagggttttt tcaatcgcca acgaatcgcc   1440
aacgttttcg ccaacgtttt ttataaatct atatttaagt agctttattt ttgtttttat   1500
gattacaaag tgatacacta attttataaa attatttgat tggagttttt taaatggtga   1560
tttcagaatc gaaaaaaaga gttatgattt ctctgacaaa agagcaagat aaaaaattaa   1620
cagatatggc gaaacaaaaa gattttttcaa aatctgcggt tgcggcgtta gctatagaag   1680
aatatgcaag aaaggaatca gaacaaaaaa aataagcgaa agctcgcgtt tttagaagga   1740
tacgagtttt cgctacttgt ttttgataag gtaattatat catggctatt aaaaatacta   1800
aagctagaaa ttttggattt ttattatatc ctgactcaat tcctaatgat tggaaagaaa   1860
aattagagag tttgggcgta tctatggctg tcagtccttt acacgatatg gacgaaaaaa   1920
aagataaaga tacatggaat agtagtgatg ttatacgaaa tggaaagcac tataaaaaac   1980
cacactatca cgttatatat attgcacgaa atcctgtaac aatagaaagc gttaggaaca   2040
agattaagcg aaaattgggg aatagttcag ttgctcatgt tgagatactt gattatatca   2100
aaggttcata tgaatatttg actcatgaat caaaggacgc tattgctaag aataaaacat   2160
tatacgacaa aaaagatatt ttgaacatta atgattttga tattgaccgc tatataacac   2220
ttgatgaaag ccaaaaaaga gaattgaaga atttactttt agatatagtg gatgactata   2280
atttggtaaa tacaaaagat ttaatggctt ttattcgcct taggggagcg gagtttggaa   2340
ttttaaatac gaatgatgta aaagatattg tttcaacaaa ctctagcgcc tttagattat   2400
ggttttgaggg caattatcag tgtggatata gagcaagtta tgcaaaggtt cttgatgctg   2460
aaacggggga aataaaatga caaacaaaga aaaagagtta tttgctgaaa atgaggaatt   2520
aaaaaaagaa attaaggact taaaagagcg tattgaaaga tacagagaaa tggaagttga   2580
attaagtaca acaatagatt tattgagagg agggattatt gaataaataa aagcccccct   2640
gacgaaagtc gacatggact gataaagtat agtaaaaaca taaacggag gatattgttg   2700
tgaacagaga agagatgact ctcttagggt tgaaattgt tgcttatgct ggagatgctc   2760
gctctaagct tttagaagcg cttaaagcgg ctgaaaatgg tgatttcgct aaggcagata   2820
gtcttgtagt agaagcagga agctgtattg cagaggctca cagttctcag acaggtatgt   2880
tggctcgaga agcttctggg gaggaacttc catacagtgt tactatgatg catggtcagg   2940
atcacttgat gactacgatc ttattaaaag atgtgattca tcacctcatc gaactttata   3000
aaagaggagc aaagtaatta atgcataaac tcattgaact tattgagaaa gggaaacgac   3060
ggatca                                                              3066
```

FIG. 7D

```
ggatcctagt cttataacta tactgacaat agaaacatta acaaatctaa aacagtctta    60
attctatctt gagaaagtat tggtaataat attattgtcg ataacgcgag cataataaac   120
ggctctgatt aaattctgaa gtttgttaga tacaatgatt tcgttcgaag gaactacaaa   180
ataaattata aggaggcact caccatgaag aaaaagatta ttagtgcaat tttaatgtca   240
acggtcatct taagcgctgc tgccccattg tcaggtgttt atgcagcaca taagtgtgat   300
ataacattac aagaaattat caaaacccct aatagtttaa ctgaacagaa gactttgtgt   360
accgaattaa ctgtaactga tattttgct gcttctaaaa atacaactga aaaagagaca    420
ttttgtcgag ctgccacagt gttaagacaa ttttacagtc atcatgaaaa agacacaaga   480
tgtcttggtg ctacggcaca acaatttcat agacacaaac aacttatccg ttttcttaaa   540
cgtttggatc gtaatctgtg gggcttggca ggattgaaca gttgtcctgt taaagaagcc   600
aatcaatcta ctcttgaaaa tttcttagag agattgaaaa caattatgcg agaaaaatat   660
tctaagtgtt catcttaata atctagagag ctcaagcttt ctttgaacca aaattagaaa   720
accaaggctt gaaacgttca attgaaatgg caattaaaca aattacagca cgtgttgctt   780
tgattgatag ccaaaaagca gcagttgata aagcaattac tgatattgct gaaaaattgt   840
aatttataaa taaaaatcac cttttagagg tggttttttt atttataaat tattcgtttg   900
atttcgcttt cgatagaaca atcaaatcgt ttctgagacg ttttagcgtt tatttcgttt   960
agttatcggc ataatcgtta aaacaggcgt tatcgtagcg taaaagccct tgagcgtagc  1020
gtggctttgc agcgaagatg ttgtctgtta gattatgaaa gccgatgact gaatgaaata  1080
ataagcgcag cgtccttcta tttcggttgg aggaggctca agggagtttg agggaatgaa  1140
attccctcat gggtttgatt ttaaaaattg cttgcaattt tgccgagcgg tagcgctgga  1200
aaattttga aaaaaatttg gaatttggaa aaaaatgggg ggaaggaag cgaattttgc    1260
ttccgtacta cgaccccca ttaagtgccg agtgccaatt tttgtgccaa aaacgctcta   1320
tcccaactgg ctcaagggtt tgaggggttt ttcaatcgcc aacgaatcgc caacgttttc  1380
gccaacgttt tttataaatc tatatttaag tagctttatt tttgtttta tgattacaaa   1440
gtgatacact aatttataa aattatttga ttggagtttt ttaaatggtg atttcagaat    1500
cgaaaaaaag agttatgatt tctctgacaa aagagcaaga taaaaaatta acagatatgg  1560
cgaaacaaaa agatttttca aaatctgcgg ttgcggcgtt agctatagaa gaatatgcaa  1620
gaaaggaatc agaacaaaaa aaataagcga aagctcgcgt tttagaagg atacgagttt    1680
tcgctacttg tttttgataa ggtaattata tcatggctat taaaaatact aaagctagaa  1740
attttggatt tttattatat cctgactcaa ttcctaatga ttggaaagaa aaattagaga  1800
gtttgggcgt atctatggct gtcagtcctt tacacgatat ggacgaaaaa aaagataaag  1860
atacatggaa tagtagtgat gttatacgaa atggaaagca ctataaaaaa ccacactatc  1920
acgttatata tattgcacga aatcctgtaa caatagaaag cgttaggaac aagattaagc  1980
gaaaattggg gaatagttca gttgctcatg ttgagatact tgattatatc aaaggttcat  2040
atgaatattt gactcatgaa tcaaaggacg ctattgctaa gaataaacat atatacgaca  2100
aaaaagatat tttgaacatt aatgatttg atattgaccg ctatataaca cttgatgaaa   2160
gccaaaaaag agaattgaag aatttacttt tagatatagt ggatgactat aatttggtaa  2220
atacaaaaga tttaatggct tttattcgcc ttaggggagc ggagtttgga attttaaata  2280
cgaatgatgt aaaagatatt gtttcaacaa actctagcgc ctttagatta tggtttgagg  2340
gcaattatca gtgtggatat agagcaagtt atgcaaggt tcttgatgct gaaacggggg   2400
aaataaaatg acaaacaaag aaaagagtt atttgctgaa aatgaggaat taaaaaaga    2460
aattaaggac ttaaaagagc gtattgaaag atacagagaa atggaagttg aattaagtac  2520
aacaatagat ttattgagag gaggattat tgaataaata aaagcccccc tgacgaaagt    2580
cgacatggac tgataaagta tagtaaaaac ataaacgga ggatattgtt gtgaacagag    2640
aagagatgac tctcttaggg tttgaaattg ttgcttatgc tggagatgct cgctctaagc  2700
ttttagaagc gcttaaagcg gctgaaaatg gtgatttcgc taaggcagat agtcttgtag  2760
tagaagcagg aagctgtatt gcagaggctc acagttctca gacaggtatg ttggctcgag  2820
aagcttctgg ggaggaactt ccatacagtg ttactatgat gcatggtcag gatcacttga  2880
tgactacgat cttattaaaa gatgtgattc atcacctcat cgaactttat aaaagaggag  2940
caaagtaatt aatgcataaa ctcattgaac ttattgagaa agggaaacga cggatca     2997
```

FIG. 7F

```
ggatcctagt cttataacta tactgacaat agaaacatta acaaatctaa aacagtctta    60
attctatctt gagaaagtat tggtaataat attattgtcg ataacgcgag cataataaac   120
ggctctgatt aaattctgaa gtttgttaga tacaatgatt tcgttcgaag gaactacaaa   180
ataaattata aggaggcact caccatgaaa aagaaaatca tttcagcgat tttgatgtca   240
acggttattt taagcgcagc agctccatta tctggagttt atgcagcaga agaagttagt   300
gagtactgta gtcatatgat tggttctgga cacttacaat cacttcagcg tcttattgat   360
agtcaaatgg aaacctcttg tcaaattaca tttgaatttg tagaccaaga acaacttaaa   420
gatccagtat gttatcttaa gaaagctttt cttttagtcc aagacataat ggaagataca   480
atgagattca gagacaatac tcctaacgct atcgccattg tccaattaca agaactttct   540
ttaagattga aaagttgctt cactaaagat tatgaggaac atgataaagc ttgtgttcga   600
acattttatg aaactccttt gcaattattg gaaaaagtga aaaatgtttt caatgagacg   660
aagaatttgt tggataaaga ttggaatata ttcagtaaga attgtaataa ctcatttgcc   720
gaatgttcaa gccagggtca tgaacgtcaa tcagaaggct cttaataatc tagagagctc   780
aagctttctt tgaaccaaaa ttagaaaacc aaggcttgaa acgttcaatt gaaatggcaa   840
ttaaacaaat tacagcacgt gttgctttga ttgatagcca aaaagcagca gttgataaag   900
caattactga tattgctgaa aaattgtaat ttataaataa aaatcacctt ttagaggtgg   960
tttttttatt tataaattat tcgtttgatt tcgctttcga tagaacaatc aaatcgtttc  1020
tgagacgttt tagcgtttat ttcgtttagt tatcggcata atcgttaaaa caggcgttat  1080
cgtagcgtaa aagcccttga gcgtagcgtg gctttgcagc gaagatgttg tctgttagat  1140
tatgaaagcc gatgactgaa tgaaataata agcgcagcgt ccttctattt cggttggagg  1200
aggctcaagg gagtttgagg gaatgaaatt ccctcatggg tttgattta aaaattgctt  1260
gcaattttgc cgagcggtag cgctggaaaa ttttgaaaa aaatttggaa tttggaaaaa  1320
aatgggggga aaggaagcga attttgcttc cgtactacga cccccccatta agtgccgagt  1380
gccaattttt gtgccaaaaa cgctctatcc caactggctc aagggtttga ggggtttttc  1440
aatcgccaac gaatcgccaa cgtttcgcc aacgtttttt ataatctat atttaagtag  1500
ctttattttt gttttatga ttacaaagtg atacactaat tttataaaat tatttgattg  1560
gagttttta aatggtgatt tcagaatcga aaaaagagt tatgatttct ctgacaaaag  1620
agcaagataa aaaattaaca gatatggcga aacaaaaaga ttttcaaaa tctgcggttg  1680
cggcgttagc tatagaagaa tatgcaagaa aggaatcaga acaaaaaaaa taagcgaaag  1740
ctcgcgtttt tagaaggata cgagttttcg ctacttgttt ttgataaggt aattatatca  1800
tggctattaa aaatactaaa gctagaaatt ttggattttt attatatcct gactcaattc  1860
ctaatgattg gaaagaaaaa ttagagagtt tgggcgtatc tatggctgtc agtcctttac  1920
acgatatgga cgaaaaaaaa gataaagata catggaatag tagtgatgtt atacgaaatg  1980
gaaagcacta taaaaaacca cactatcacg ttatatatat tgcacgaaat cctgtaacaa  2040
tagaaagcgt taggaacaag attaagcgaa aattggggaa tagttcagtt gctcatgttg  2100
agatacttga ttatatcaaa ggttcatatg aatatttgac tcatgaatca aaggacgcta  2160
ttgctaagaa taaacatata tacgacaaaa aagatatttt gaacattaat gattttgata  2220
ttgaccgcta tataacactt gatgaaagcc aaaaaagaga attgaagaat ttacttttag  2280
atatagtgga tgactataat ttggtaaata caaaagattt aatggctttt attcgcctta  2340
ggggagcgga gtttggaatt taaatacga atgatgtaaa agatattgtt tcaacaaact  2400
ctagcgcctt tagattatgg tttgagggca attatcagtg tggatataga gcaagttatg  2460
caaaggttct tgatgctgaa acggggaaa taaaatgaca aacaaagaaa aagagttatt  2520
tgctgaaaat gaggaattaa aaaagaaat taaggactta aaagagcgta ttgaaagata  2580
cagagaaatg gaagttgaat taagtacaac aatagattta ttgagaggag ggattattga  2640
ataaataaaa gccccctga cgaaagtcga catggactga taagtatag taaaaacata  2700
aaacggagga tattgttgtg aacagagaag agatgactct cttagggttt gaaattgttg  2760
cttatgctgg agatgctcgc tctaagcttt tagaagcgct taaagcggct gaaaatgttg  2820
atttcgctaa ggcagatagt cttgtagtag aagcaggaag ctgtattgca gaggctcaca  2880
gttctcagac aggtatgttg gctcgagaag cttctgggga ggaacttcca tacagtgtta  2940
ctatgatgca tggtcaggat cacttgatga ctacgatctt attaaaagat gtgattcatc  3000
acctcatcga actttataaa agaggagcaa agtaattaat gcataaactc attgaactta  3060
ttgagaaagg gaaacgacgg atca                                          3084
```

| Lane | Sample | |
|---|---|---|
| 1 | Marker | 2 μl |
| 2 | FGF2 standard | 0.1 μg |
| 3 | NZ3900 (pFGF2) (n.i.) T=0 | sup |
| 4 | NZ3900 (pFGF2) (n.i.) T=6 | sup |
| 5 | NZ3900 (pFGF2) OD0.5/5 T=0 | sup |
| 6 | NZ3900 (pFGF2) OD0.5/5 T=2 | sup |
| 7 | NZ3900 (pFGF2) OD0.5/5 T=4 | sup |
| 8 | NZ3900 (pFGF2) OD0.5/5 T=6 | sup |
| 9 | NZ3900 (pFGF2) OD3/5 T=4 | sup |
| 10 | NZ3900 (pFGF2) OD3/5 T=6 | sup |

| Lane | Sample | |
|---|---|---|
| 1 | SeeBlue marker | |
| 2 | hIL4 | 1 μg (Coom); 0.1 μg (WB) |
| 3 | Sup | No induction t=0 |
| 4 | Sup | No induction t=6 |
| 5 | Sup | 0.5/5 t=0 |
| 6 | Sup | 0.5/5 t=2 |
| 7 | Sup | 0.5/5 t=4 |
| 8 | Sup | 0.5/5 t=6 |
| 9 | Sup | 3/5 t=4 |
| 10 | Sup | 3/5 t=6 |

| Lane | Sample | |
|---|---|---|
| 1 | SeeBlue marker | |
| 2 | FGF2 | 0.5 µg (Silver), 0.1 µg (WB) |
| 3 | Sup | not induced |
| 4 | Sup pH 5 | 1 ng/ml nisin |
| 5 | Sup pH 5 | 0.1 ng/ml nisin |
| 6 | Sup OD600 = 3 | 1 ng/ml nisin |
| 7 | Sup OD600 = 3 | 0.1 ng/ml nisin |

FIG. 16A

Amino acid sequence of macrophage colony-stimulating factor 1 isoform a precursor from Homo sapiens

```
Met Thr Ala Pro Gly Ala Ala Gly Arg Cys Pro Pro Thr Thr Trp Leu Gly Ser Leu
Leu Leu Leu Val Cys Leu Leu Ala Ser Arg Ser Ile Thr Glu Glu Val Ser Glu Tyr
Cys Ser His Met Ile Gly Ser Gly His Leu Gln Ser Leu Gln Arg Leu Ile Asp Ser
Gln Met Glu Thr Ser Cys Gln Ile Thr Phe Glu Phe Val Asp Gln Glu Gln Leu Lys
Asp Pro Val Cys Tyr Leu Lys Lys Ala Phe Leu Leu Val Gln Asp Ile Met Glu Asp
Thr Met Arg Phe Arg Asp Asn Thr Pro Asn Ala Ile Ala Ile Val Gln Leu Gln Glu
Leu Ser Leu Arg Leu Lys Ser Cys Phe Thr Lys Asp Tyr Glu Glu His Asp Lys Ala
Cys Val Arg Thr Phe Tyr Glu Thr Pro Leu Gln Leu Leu Glu Lys Val Lys Asn Val
Phe Asn Glu Thr Lys Asn Leu Leu Asp Lys Asp Trp Asn Ile Phe Ser Lys Asn Cys
Asn Asn Ser Phe Ala Glu Cys Ser Ser Gln Asp Val Val Thr Lys Pro Asp Cys Asn
Cys Leu Tyr Pro Lys Ala Ile Pro Ser Ser Asp Pro Ala Ser Val Ser Pro His Gln
Pro Leu Ala Pro Ser Met Ala Pro Val Ala Gly Leu Thr Trp Glu Asp Ser Glu Gly
Thr Glu Gly Ser Ser Leu Leu Pro Gly Glu Gln Pro Leu His Thr Val Asp Pro Gly
Ser Ala Lys Gln Arg Pro Pro Arg Ser Thr Cys Gln Ser Phe Glu Pro Pro Glu Thr
Pro Val Val Lys Asp Ser Thr Ile Gly Gly Ser Pro Gln Pro Arg Pro Ser Val Gly
Ala Phe Asn Pro Gly Met Glu Asp Ile Leu Asp Ser Ala Met Gly Thr Asn Trp Val
Pro Glu Glu Ala Ser Gly Glu Ala Ser Glu Ile Pro Val Pro Gln Gly Thr Glu Leu
Ser Pro Ser Arg Pro Gly Gly Gly Ser Met Gln Thr Glu Pro Ala Arg Pro Ser Asn
Phe Leu Ser Ala Ser Ser Pro Leu Pro Ala Ser Ala Lys Gly Gln Gln Pro Ala Asp
Val Thr Gly Thr Ala Leu Pro Arg Val Gly Pro Val Arg Pro Thr Gly Gln Asp Trp
Asn His Thr Pro Gln Lys Thr Asp His Pro Ser Ala Leu Leu Arg Asp Pro Pro Glu
Pro Gly Ser Pro Arg Ile Ser Ser Leu Arg Pro Gln Gly Leu Ser Asn Pro Ser Thr
Leu Ser Ala Gln Pro Gln Leu Ser Arg Ser His Ser Ser Gly Ser Val Leu Pro Leu
Gly Glu Leu Glu Gly Arg Arg Ser Thr Arg Asp Arg Arg Ser Pro Ala Glu Pro Glu
Gly Gly Pro Ala Ser Glu Gly Ala Ala Arg Pro Leu Pro Arg Phe Asn Ser Val Pro
Leu Thr Asp Thr Gly His Glu Arg Gln Ser Glu Gly Ser Ser Ser Pro Gln Leu Gln
Glu Ser Val Phe His Leu Leu Val Pro Ser Val Ile Leu Val Leu Leu Ala Val Gly
Gly Leu Leu Phe Tyr Arg Trp Arg Arg Arg Ser His Gln Glu Pro Gln Arg Ala Asp
Ser Pro Leu Glu Gln Pro Glu Gly Ser Pro Leu Thr Gln Asp Asp Arg Gln Val Glu
Leu Pro Val
```

FIG. 16B

Amino acid sequence of macrophage colony-stimulating factor 1 isoform b precursor from Homo sapiens

```
Met Thr Ala Pro Gly Ala Ala Gly Arg Cys Pro Pro Thr Thr Trp Leu Gly Ser Leu
Leu Leu Leu Val Cys Leu Leu Ala Ser Arg Ser Ile Thr Glu Glu Val Ser Glu Tyr
Cys Ser His Met Ile Gly Ser Gly His Leu Gln Ser Leu Gln Arg Leu Ile Asp Ser
Gln Met Glu Thr Ser Cys Gln Ile Thr Phe Glu Phe Val Asp Gln Glu Gln Leu Lys
Asp Pro Val Cys Tyr Leu Lys Lys Ala Phe Leu Leu Val Gln Asp Ile Met Glu Asp
Thr Met Arg Phe Arg Asp Asn Thr Pro Asn Ala Ile Ala Ile Val Gln Leu Gln Glu
Leu Ser Leu Arg Leu Lys Ser Cys Phe Thr Lys Asp Tyr Glu Glu His Asp Lys Ala
Cys Val Arg Thr Phe Tyr Glu Thr Pro Leu Gln Leu Leu Glu Lys Val Lys Asn Val
Phe Asn Glu Thr Lys Asn Leu Leu Asp Lys Asp Trp Asn Ile Phe Ser Lys Asn Cys
Asn Asn Ser Phe Ala Glu Cys Ser Ser Gln Asp Val Val Thr Lys Pro Asp Cys Asn
Cys Leu Tyr Pro Lys Ala Ile Pro Ser Ser Asp Pro Ala Ser Val Ser Pro His Gln
Pro Leu Ala Pro Ser Met Ala Pro Val Ala Gly Leu Thr Trp Glu Asp Ser Glu Gly
Thr Glu Gly Ser Ser Leu Leu Pro Gly Glu Gln Pro Leu His Thr Val Asp Pro Gly
Ser Ala Lys Gln Arg Pro Pro Arg Ser Thr Cys Gln Ser Phe Glu Pro Pro Glu Thr
Pro Val Val Lys Asp Ser Thr Ile Gly Gly Ser Pro Gln Pro Arg Pro Ser Val Gly
Ala Phe Asn Pro Gly Met Glu Asp Ile Leu Asp Ser Ala Met Gly Thr Asn Trp Val
Pro Glu Glu Ala Ser Gly Glu Ala Ser Glu Ile Pro Val Pro Gln Gly Thr Glu Leu
Ser Pro Ser Arg Pro Gly Gly Gly Ser Met Gln Thr Glu Pro Ala Arg Pro Ser Asn
Phe Leu Ser Ala Ser Ser Pro Leu Pro Ala Ser Ala Lys Gly Gln Gln Pro Ala Asp
Val Thr Gly His Glu Arg Gln Ser Glu Gly Ser Ser Ser Pro Gln Leu Gln Glu Ser
Val Phe His Leu Leu Val Pro Ser Val Ile Leu Val Leu Leu Ala Val Gly Gly Leu
Leu Phe Tyr Arg Trp Arg Arg Arg Ser His Gln Glu Pro Gln Arg Ala Asp Ser Pro
Leu Glu Gln Pro Glu Gly Ser Pro Leu Thr Gln Asp Asp Arg Gln Val Glu Leu Pro
Val
```

FIG. 16C

Amino acid sequence of macrophage colony-stimulating factor 1 isoform c precursor from Homo sapiens

```
Met Thr Ala Pro Gly Ala Ala Gly Arg Cys Pro Pro Thr Thr Trp Leu Gly Ser Leu
Leu Leu Leu Val Cys Leu Leu Ala Ser Arg Ser Ile Thr Glu Glu Val Ser Glu Tyr
Cys Ser His Met Ile Gly Ser Gly His Leu Gln Ser Leu Gln Arg Leu Ile Asp Ser
Gln Met Glu Thr Ser Cys Gln Ile Thr Phe Glu Phe Val Asp Gln Glu Gln Leu Lys
Asp Pro Val Cys Tyr Leu Lys Lys Ala Phe Leu Leu Val Gln Asp Ile Met Glu Asp
Thr Met Arg Phe Arg Asp Asn Thr Pro Asn Ala Ile Ala Ile Val Gln Leu Gln Glu
Leu Ser Leu Arg Leu Lys Ser Cys Phe Thr Lys Asp Tyr Glu Glu His Asp Lys Ala
Cys Val Arg Thr Phe Tyr Glu Thr Pro Leu Gln Leu Leu Glu Lys Val Lys Asn Val
Phe Asn Glu Thr Lys Asn Leu Leu Asp Lys Asp Trp Asn Ile Phe Ser Lys Asn Cys
Asn Asn Ser Phe Ala Glu Cys Ser Ser Gln Gly His Glu Arg Gln Ser Glu Gly Ser
Ser Ser Pro Gln Leu Gln Glu Ser Val Phe His Leu Leu Val Pro Ser Val Ile Leu
Val Leu Leu Ala Val Gly Gly Leu Leu Phe Tyr Arg Trp Arg Arg Arg Ser His Gln
Glu Pro Gln Arg Ala Asp Ser Pro Leu Glu Gln Pro Glu Gly Ser Pro Leu Thr Gln
Asp Asp Arg Gln Val Glu Leu Pro Val
```

FIG. 16D

Amino acid sequence of a partial sequence of macrophage colony-stimulating factor 1 of Homo sapiens

```
Glu Glu Val Ser Glu Tyr Cys Ser His Met Ile Gly Ser Gly His Leu Gln Ser Leu
Gln Arg Leu Ile Asp Ser Gln Met Glu Thr Ser Cys Gln Ile Thr Phe Glu Phe Val
Asp Gln Glu Gln Leu Lys Asp Pro Val Cys Tyr Leu Lys Lys Ala Phe Leu Leu Val
Gln Asp Ile Met Glu Asp Thr Met Arg Phe Arg Asp Asn Thr Pro Asn Ala Ile Ala
Ile Val Gln Leu Gln Glu Leu Ser Leu Arg Leu Lys Ser Cys Phe Thr Lys Asp Tyr
Glu Glu His Asp Lys Ala Cys Val Arg Thr Phe Tyr Glu Thr Pro Leu Gln Leu Leu
Glu Lys Val Lys Asn Val Phe Asn Glu Thr Lys Asn Leu Leu Asp Lys Asp Trp Asn
Ile Phe Ser Lys Asn Cys Asn Asn Ser Phe Ala Glu Cys Ser Ser Gln
```

FIG. 17A

Amino acid sequence of interleukin-34 isoform 1 precursor from Homo sapiens

```
Met Pro Arg Gly Phe Thr Trp Leu Arg Tyr Leu Gly Ile Phe Leu Gly Val Ala Leu
Gly Asn Glu Pro Leu Glu Met Trp Pro Leu Thr Gln Asn Glu Glu Cys Thr Val Thr
Gly Phe Leu Arg Asp Lys Leu Gln Tyr Arg Ser Arg Leu Gln Tyr Met Lys His Tyr
Phe Pro Ile Asn Tyr Lys Ile Ser Val Pro Tyr Glu Gly Val Phe Arg Ile Ala Asn
Val Thr Arg Leu Gln Arg Ala Gln Val Ser Glu Arg Glu Leu Arg Tyr Leu Trp Val
Leu Val Ser Leu Ser Ala Thr Glu Ser Val Gln Asp Val Leu Leu Glu Gly His Pro
Ser Trp Lys Tyr Leu Gln Glu Val Glu Thr Leu Leu Leu Asn Val Gln Gln Gly Leu
Thr Asp Val Glu Val Ser Pro Lys Val Glu Ser Val Leu Ser Leu Leu Asn Ala Pro
Gly Pro Asn Leu Lys Leu Val Arg Pro Lys Ala Leu Leu Asp Asn Cys Phe Arg Val
Met Glu Leu Leu Tyr Cys Ser Cys Cys Lys Gln Ser Ser Val Leu Asn Trp Gln Asp
Cys Glu Val Pro Ser Pro Gln Ser Cys Ser Pro Glu Pro Ser Leu Gln Tyr Ala Ala
Thr Gln Leu Tyr Pro Pro Pro Pro Trp Ser Pro Ser Ser Pro Pro His Ser Thr Gly
Ser Val Arg Pro Val Arg Ala Gln Gly Glu Gly Leu Leu Pro
```

FIG. 17B

Amino acid sequence of interleukin-34 isoform 2 precursor from Homo sapiens

```
Met Pro Arg Gly Phe Thr Trp Leu Arg Tyr Leu Gly Ile Phe Leu Gly Val Ala Leu
Gly Asn Glu Pro Leu Glu Met Trp Pro Leu Thr Gln Asn Glu Glu Cys Thr Val Thr
Gly Phe Leu Arg Asp Lys Leu Gln Tyr Arg Ser Arg Leu Gln Tyr Met Lys His Tyr
Phe Pro Ile Asn Tyr Lys Ile Ser Val Pro Tyr Glu Gly Val Phe Arg Ile Ala Asn
Val Thr Arg Leu Arg Ala Gln Val Ser Glu Arg Glu Leu Arg Tyr Leu Trp Val Leu
Val Ser Leu Ser Ala Thr Glu Ser Val Gln Asp Val Leu Leu Glu Gly His Pro Ser
Trp Lys Tyr Leu Gln Glu Val Glu Thr Leu Leu Leu Asn Val Gln Gln Gly Leu Thr
Asp Val Glu Val Ser Pro Lys Val Glu Ser Val Leu Ser Leu Leu Asn Ala Pro Gly
Pro Asn Leu Lys Leu Val Arg Pro Lys Ala Leu Leu Asp Asn Cys Phe Arg Val Met
Glu Leu Leu Tyr Cys Ser Cys Cys Lys Gln Ser Ser Val Leu Asn Trp Gln Asp Cys
Glu Val Pro Ser Pro Gln Ser Cys Ser Pro Glu Pro Ser Leu Gln Tyr Ala Ala Thr
Gln Leu Tyr Pro Pro Pro Pro Trp Ser Pro Ser Ser Pro Pro His Ser Thr Gly Ser
Val Arg Pro Val Arg Ala Gln Gly Glu Gly Leu Leu Pro
```

FIG. 17C

Amino acid sequence of interleukin-34 from Homo sapiens

```
Asn Glu Pro Leu Glu Met Trp Pro Leu Thr Gln Asn Glu Glu Cys Thr Val Thr Gly
Phe Leu Arg Asp Lys Leu Gln Tyr Arg Ser Arg Leu Gln Tyr Met Lys His Tyr Phe
Pro Ile Asn Tyr Lys Ile Ser Val Pro Tyr Glu Gly Val Phe Arg Ile Ala Asn Val
Thr Arg Leu Gln Arg Ala Gln Val Ser Glu Arg Glu Leu Arg Tyr Leu Trp Val Leu
Val Ser Leu Ser Ala Thr Glu Ser Val Gln Asp Val Leu Leu Glu Gly His Pro Ser
Trp Lys Tyr Leu Gln Glu Val Glu Thr Leu Leu Leu Asn Val Gln Gln Gly Leu Thr
Asp Val Glu Val Ser Pro Lys Val Glu Ser Val Leu Ser Leu Leu Asn Ala Pro Gly
Pro Asn Leu Lys Leu Val Arg Pro Lys Ala Leu Leu Asp Asn Cys Phe Arg Val Met
Glu Leu Leu Tyr Cys Ser Cys Cys Lys Gln Ser Ser Val Leu Asn Trp Gln Asp Cys
Glu Val Pro Ser Pro Gln Ser Cys Ser Pro Glu Pro Ser Leu Gln Tyr Ala Ala Thr
Gln Leu Tyr Pro Pro Pro Pro Trp Ser Pro Ser Ser Pro Pro His Ser Thr Gly Ser
Val Arg Pro Val Arg Ala Gln Gly Glu Gly Leu Leu Pro
```

FIG. 18A

Amino acid sequence of interleukin-4 isoform 1 precursor from Homo sapiens

Met Gly Leu Thr Ser Gln Leu Leu Pro Pro Leu Phe Phe Leu Leu Ala Cys Ala Gly
Asn Phe Val His Gly His Lys Cys Asp Ile Thr Leu Gln Glu Ile Ile Lys Thr Leu
Asn Ser Leu Thr Glu Gln Lys Thr Leu Cys Thr Glu Leu Thr Val Thr Asp Ile Phe
Ala Ala Ser Lys Asn Thr Thr Glu Lys Glu Thr Phe Cys Arg Ala Ala Thr Val Leu
Arg Gln Phe Tyr Ser His His Glu Lys Asp Thr Arg Cys Leu Gly Ala Thr Ala Gln
Gln Phe His Arg His Lys Gln Leu Ile Arg Phe Leu Lys Arg Leu Asp Arg Asn Leu
Trp Gly Leu Ala Gly Leu Asn Ser Cys Pro Val Lys Glu Ala Asn Gln Ser Thr Leu
Glu Asn Phe Leu Glu Arg Leu Lys Thr Ile Met Arg Glu Lys Tyr Ser Lys Cys Ser
Ser

FIG. 18B

Amino acid sequence of interleukin-4 isoform 2 precursor from Homo sapiens

Met Gly Leu Thr Ser Gln Leu Leu Pro Pro Leu Phe Phe Leu Leu Ala Cys Ala Gly
Asn Phe Val His Gly His Lys Cys Asp Ile Thr Leu Gln Glu Ile Ile Lys Thr Leu
Asn Ser Leu Thr Glu Gln Lys Asn Thr Thr Glu Lys Glu Thr Phe Cys Arg Ala Ala
Thr Val Leu Arg Gln Phe Tyr Ser His His Glu Lys Asp Thr Arg Cys Leu Gly Ala
Thr Ala Gln Gln Phe His Arg His Lys Gln Leu Ile Arg Phe Leu Lys Arg Leu Asp
Arg Asn Leu Trp Gly Leu Ala Gly Leu Asn Ser Cys Pro Val Lys Glu Ala Asn Gln
Ser Thr Leu Glu Asn Phe Leu Glu Arg Leu Lys Thr Ile Met Arg Glu Lys Tyr Ser
Lys Cys Ser Ser

FIG. 18C

Amino acid sequence of interleukin-4 from Homo sapiens

His Lys Cys Asp Ile Thr Leu Gln Glu Ile Ile Lys Thr Leu Asn Ser Leu Thr Glu
Gln Lys Thr Leu Cys Thr Glu Leu Thr Val Thr Asp Ile Phe Ala Ala Ser Lys Asn
Thr Thr Glu Lys Glu Thr Phe Cys Arg Ala Ala Thr Val Leu Arg Gln Phe Tyr Ser
His His Glu Lys Asp Thr Arg Cys Leu Gly Ala Thr Ala Gln Gln Phe His Arg His
Lys Gln Leu Ile Arg Phe Leu Lys Arg Leu Asp Arg Asn Leu Trp Gly Leu Ala Gly
Leu Asn Ser Cys Pro Val Lys Glu Ala Asn Gln Ser Thr Leu Glu Asn Phe Leu Glu
Arg Leu Lys Thr Ile Met Arg Glu Lys Tyr Ser Lys Cys Ser Ser

FIG. 19A

Amino acid sequence of interleukin-10 precursor from Homo sapiens

```
Met His Ser Ser Ala Leu Leu Cys Cys Leu Val Leu Leu Thr Gly Val Arg Ala Ser
Pro Gly Gln Gly Thr Gln Ser Glu Asn Ser Cys Thr His Phe Pro Gly Asn Leu Pro
Asn Met Leu Arg Asp Leu Arg Asp Ala Phe Ser Arg Val Lys Thr Phe Phe Gln Met
Lys Asp Gln Leu Asp Asn Leu Leu Leu Lys Glu Ser Leu Leu Glu Asp Phe Lys Gly
Tyr Leu Gly Cys Gln Ala Leu Ser Glu Met Ile Gln Phe Tyr Leu Glu Glu Val Met
Pro Gln Ala Glu Asn Gln Asp Pro Asp Ile Lys Ala His Val Asn Ser Leu Gly Glu
Asn Leu Lys Thr Leu Arg Leu Arg Leu Arg Arg Cys His Arg Phe Leu Pro Cys Glu
Asn Lys Ser Lys Ala Val Glu Gln Val Lys Asn Ala Phe Asn Lys Leu Gln Glu Lys
Gly Ile Tyr Lys Ala Met Ser Glu Phe Asp Ile Phe Ile Asn Tyr Ile Glu Ala Tyr
Met Thr Met Lys Ile Arg Asn
```

FIG. 19B

Amino acid sequence of interleukin-10 from Homo sapiens

```
Ser Pro Gly Gln Gly Thr Gln Ser Glu Asn Ser Cys Thr His Phe Pro Gly Asn Leu
Pro Asn Met Leu Arg Asp Leu Arg Asp Ala Phe Ser Arg Val Lys Thr Phe Phe Gln
Met Lys Asp Gln Leu Asp Asn Leu Leu Leu Lys Glu Ser Leu Leu Glu Asp Phe Lys
Gly Tyr Leu Gly Cys Gln Ala Leu Ser Glu Met Ile Gln Phe Tyr Leu Glu Glu Val
Met Pro Gln Ala Glu Asn Gln Asp Pro Asp Ile Lys Ala His Val Asn Ser Leu Gly
Glu Asn Leu Lys Thr Leu Arg Leu Arg Leu Arg Arg Cys His Arg Phe Leu Pro Cys
Glu Asn Lys Ser Lys Ala Val Glu Gln Val Lys Asn Ala Phe Asn Lys Leu Gln Glu
Lys Gly Ile Tyr Lys Ala Met Ser Glu Phe Asp Ile Phe Ile Asn Tyr Ile Glu Ala
Tyr Met Thr Met Lys Ile Arg Asn
```

FIG. 20A

Amino acid sequence of interleukin-13 precursor from Homo sapiens

```
Met His Pro Leu Leu Asn Pro Leu Leu Leu Ala Leu Gly Leu Met Ala Leu Leu Leu
Thr Thr Val Ile Ala Leu Thr Cys Leu Gly Gly Phe Ala Ser Pro Gly Pro Val Pro
Pro Ser Thr Ala Leu Arg Glu Leu Ile Glu Glu Leu Val Asn Ile Thr Gln Asn Gln
Lys Ala Pro Leu Cys Asn Gly Ser Met Val Trp Ser Ile Asn Leu Thr Ala Gly Met
Tyr Cys Ala Ala Leu Glu Ser Leu Ile Asn Val Ser Gly Cys Ser Ala Ile Glu Lys
Thr Gln Arg Met Leu Ser Gly Phe Cys Pro His Lys Val Ser Ala Gly Gln Phe Ser
Ser Leu His Val Arg Asp Thr Lys Ile Glu Val Ala Gln Phe Val Lys Asp Leu Leu
Leu His Leu Lys Lys Leu Phe Arg Glu Gly Arg Phe Asn
```

FIG. 20B

Amino acid sequence of interleukin-13 from Homo sapiens

```
Gly Pro Val Pro Pro Ser Thr Ala Leu Arg Glu Leu Ile Glu Glu Leu Val Asn Ile
Thr Gln Asn Gln Lys Ala Pro Leu Cys Asn Gly Ser Met Val Trp Ser Ile Asn Leu
Thr Ala Gly Met Tyr Cys Ala Ala Leu Glu Ser Leu Ile Asn Val Ser Gly Cys Ser
Ala Ile Glu Lys Thr Gln Arg Met Leu Ser Gly Phe Cys Pro His Lys Val Ser Ala
Gly Gln Phe Ser Ser Leu His Val Arg Asp Thr Lys Ile Glu Val Ala Gln Phe Val
Lys Asp Leu Leu Leu His Leu Lys Lys Leu Phe Arg Glu Gly Arg Phe Asn
```

FIG. 21A

Amino acid sequence of transforming growth factor beta-1 precursor from Homo sapiens

```
Met Pro Pro Ser Gly Leu Arg Leu Leu Pro Leu Leu Leu Pro Leu Leu Trp Leu Leu
Val Leu Thr Pro Gly Arg Pro Ala Ala Gly Leu Ser Thr Cys Lys Thr Ile Asp Met
Glu Leu Val Lys Arg Lys Arg Ile Glu Ala Ile Arg Gly Gln Ile Leu Ser Lys Leu
Arg Leu Ala Ser Pro Pro Ser Gln Gly Glu Val Pro Pro Gly Pro Leu Pro Glu Ala
Val Leu Ala Leu Tyr Asn Ser Thr Arg Asp Arg Val Ala Gly Glu Ser Ala Glu Pro
Glu Pro Glu Pro Glu Ala Asp Tyr Tyr Ala Lys Glu Val Thr Arg Val Leu Met Val
Glu Thr His Asn Glu Ile Tyr Asp Lys Phe Lys Gln Ser Thr His Ser Ile Tyr Met
Phe Phe Asn Thr Ser Glu Leu Arg Glu Ala Val Pro Glu Pro Val Leu Leu Ser Arg
Ala Glu Leu Arg Leu Leu Arg Leu Lys Leu Lys Val Glu Gln His Val Glu Leu Tyr
Gln Lys Tyr Ser Asn Asn Ser Trp Arg Tyr Leu Ser Asn Arg Leu Leu Ala Pro Ser
Asp Ser Pro Glu Trp Leu Ser Phe Asp Val Thr Gly Val Val Arg Gln Trp Leu Ser
Arg Gly Gly Glu Ile Glu Gly Phe Arg Leu Ser Ala His Cys Ser Cys Asp Ser Arg
Asp Asn Thr Leu Gln Val Asp Ile Asn Gly Phe Thr Thr Gly Arg Arg Gly Asp Leu
Ala Thr Ile His Gly Met Asn Arg Pro Phe Leu Leu Leu Met Ala Thr Pro Leu Glu
Arg Ala Gln His Leu Gln Ser Ser Arg His Arg Arg Ala Leu Asp Thr Asn Tyr Cys
Phe Ser Ser Thr Glu Lys Asn Cys Cys Val Arg Gln Leu Tyr Ile Asp Phe Arg Lys
Asp Leu Gly Trp Lys Trp Ile His Glu Pro Lys Gly Tyr His Ala Asn Phe Cys Leu
Gly Pro Cys Pro Tyr Ile Trp Ser Leu Asp Thr Gln Tyr Ser Lys Val Leu Ala Leu
Tyr Asn Gln His Asn Pro Gly Ala Ser Ala Ala Pro Cys Cys Val Pro Gln Ala Leu
Glu Pro Leu Pro Ile Val Tyr Tyr Val Gly Arg Lys Pro Lys Val Glu Gln Leu Ser
Asn Met Ile Val Arg Ser Cys Lys Cys Ser
```

FIG. 21B

Amino acid sequence of transforming growth factor beta-1 from Homo sapiens

```
Ala Leu Asp Thr Asn Tyr Cys Phe Ser Ser Thr Glu Lys Asn Cys Cys Val Arg Gln
Leu Tyr Ile Asp Phe Arg Lys Asp Leu Gly Trp Lys Trp Ile His Glu Pro Lys Gly
Tyr His Ala Asn Phe Cys Leu Gly Pro Cys Pro Tyr Ile Trp Ser Leu Asp Thr Gln
Tyr Ser Lys Val Leu Ala Leu Tyr Asn Gln His Asn Pro Gly Ala Ser Ala Ala Pro
Cys Cys Val Pro Gln Ala Leu Glu Pro Leu Pro Ile Val Tyr Tyr Val Gly Arg Lys
Pro Lys Val Glu Gln Leu Ser Asn Met Ile Val Arg Ser Cys Lys Cys Ser
```

FIG. 21C

Amino acid sequence of transforming growth factor beta-2 isoform 1 precursor from Homo sapiens

```
Met His Tyr Cys Val Leu Ser Ala Phe Leu Ile Leu His Leu Val Thr Val Ala Leu
Ser Leu Ser Thr Cys Ser Thr Leu Asp Met Asp Gln Phe Met Arg Lys Arg Ile Glu
Ala Ile Arg Gly Gln Ile Leu Ser Lys Leu Lys Leu Thr Ser Pro Pro Glu Asp Tyr
Pro Glu Pro Glu Glu Val Pro Pro Glu Val Ile Ser Ile Tyr Asn Ser Thr Arg Asp
Leu Leu Gln Glu Lys Ala Ser Arg Arg Ala Ala Ala Cys Glu Arg Glu Arg Ser Asp
Glu Glu Tyr Tyr Ala Lys Glu Val Tyr Lys Ile Asp Met Pro Pro Phe Phe Pro Ser
Glu Thr Val Cys Pro Val Val Thr Thr Pro Ser Gly Ser Val Gly Ser Leu Cys Ser
Arg Gln Ser Gln Val Leu Cys Gly Tyr Leu Asp Ala Ile Pro Pro Thr Phe Tyr Arg
Pro Tyr Phe Arg Ile Val Arg Phe Asp Val Ser Ala Met Glu Lys Asn Ala Ser Asn
Leu Val Lys Ala Glu Phe Arg Val Phe Arg Leu Gln Asn Pro Lys Ala Arg Val Pro
Glu Gln Arg Ile Glu Leu Tyr Gln Ile Leu Lys Ser Lys Asp Leu Thr Ser Pro Thr
Gln Arg Tyr Ile Asp Ser Lys Val Val Lys Thr Arg Ala Glu Gly Glu Trp Leu Ser
Phe Asp Val Thr Asp Ala Val His Glu Trp Leu His His Lys Asp Arg Asn Leu Gly
Phe Lys Ile Ser Leu His Cys Pro Cys Cys Thr Phe Val Pro Ser Asn Asn Tyr Ile
Ile Pro Asn Lys Ser Glu Glu Leu Glu Ala Arg Phe Ala Gly Ile Asp Gly Thr Ser
Thr Tyr Thr Ser Gly Asp Gln Lys Thr Ile Lys Ser Thr Arg Lys Lys Asn Ser Gly
Lys Thr Pro His Leu Leu Leu Met Leu Leu Pro Ser Tyr Arg Leu Glu Ser Gln Gln
Thr Asn Arg Arg Lys Lys Arg Ala Leu Asp Ala Ala Tyr Cys Phe Arg Asn Val Gln
Asp Asn Cys Cys Leu Arg Pro Leu Tyr Ile Asp Phe Lys Arg Asp Leu Gly Trp Lys
Trp Ile His Glu Pro Lys Gly Tyr Asn Ala Asn Phe Cys Ala Gly Ala Cys Pro Tyr
Leu Trp Ser Ser Asp Thr Gln His Ser Arg Val Leu Ser Leu Tyr Asn Thr Ile Asn
Pro Glu Ala Ser Ala Ser Pro Cys Cys Val Ser Gln Asp Leu Glu Pro Leu Thr Ile
Leu Tyr Tyr Ile Gly Lys Thr Pro Lys Ile Glu Gln Leu Ser Asn Met Ile Val Lys
Ser Cys Lys Cys Ser
```

FIG. 21D

Amino acid sequence of transforming growth factor beta-2 isoform 2 precursor from Homo sapiens

```
Met His Tyr Cys Val Leu Ser Ala Phe Leu Ile Leu His Leu Val Thr Val Ala Leu
Ser Leu Ser Thr Cys Ser Thr Leu Asp Met Asp Gln Phe Met Arg Lys Arg Ile Glu
Ala Ile Arg Gly Gln Ile Leu Ser Lys Leu Lys Leu Thr Ser Pro Pro Glu Asp Tyr
Pro Glu Pro Glu Glu Val Pro Pro Glu Val Ile Ser Ile Tyr Asn Ser Thr Arg Asp
Leu Leu Gln Glu Lys Ala Ser Arg Arg Ala Ala Ala Cys Glu Arg Glu Arg Ser Asp
Glu Glu Tyr Tyr Ala Lys Glu Val Tyr Lys Ile Asp Met Pro Pro Phe Phe Pro Ser
Glu Asn Ala Ile Pro Pro Thr Phe Tyr Arg Pro Tyr Phe Arg Ile Val Arg Phe Asp
Val Ser Ala Met Glu Lys Asn Ala Ser Asn Leu Val Lys Ala Glu Phe Arg Val Phe
Arg Leu Gln Asn Pro Lys Ala Arg Val Pro Glu Gln Arg Ile Glu Leu Tyr Gln Ile
Leu Lys Ser Lys Asp Leu Thr Ser Pro Thr Gln Arg Tyr Ile Asp Ser Lys Val Val
Lys Thr Arg Ala Glu Gly Glu Trp Leu Ser Phe Asp Val Thr Asp Ala Val His Glu
Trp Leu His His Lys Asp Arg Asn Leu Gly Phe Lys Ile Ser Leu His Cys Pro Cys
Cys Thr Phe Val Pro Ser Asn Asn Tyr Ile Ile Pro Asn Lys Ser Glu Glu Leu Glu
Ala Arg Phe Ala Gly Ile Asp Gly Thr Ser Thr Tyr Thr Ser Gly Asp Gln Lys Thr
Ile Lys Ser Thr Arg Lys Lys Asn Ser Gly Lys Thr Pro His Leu Leu Leu Met Leu
Leu Pro Ser Tyr Arg Leu Glu Ser Gln Gln Thr Asn Arg Arg Lys Lys Arg Ala Leu
Asp Ala Ala Tyr Cys Phe Arg Asn Val Gln Asp Asn Cys Cys Leu Arg Pro Leu Tyr
Ile Asp Phe Lys Arg Asp Leu Gly Trp Lys Trp Ile His Glu Pro Lys Gly Tyr Asn
Ala Asn Phe Cys Ala Gly Ala Cys Pro Tyr Leu Trp Ser Ser Asp Thr Gln His Ser
Arg Val Leu Ser Leu Tyr Asn Thr Ile Asn Pro Glu Ala Ser Ala Ser Pro Cys Cys
Val Ser Gln Asp Leu Glu Pro Leu Thr Ile Leu Tyr Tyr Ile Gly Lys Thr Pro Lys
Ile Glu Gln Leu Ser Asn Met Ile Val Lys Ser Cys Lys Cys Ser
```

Figure 21E

Amino acid sequence of transforming growth factor beta-2 from Homo sapiens

```
Ala Leu Asp Ala Ala Tyr Cys Phe Arg Asn Val Gln Asp Asn Cys Cys Leu Arg Pro
Leu Tyr Ile Asp Phe Lys Arg Asp Leu Gly Trp Lys Trp Ile His Glu Pro Lys Gly
Tyr Asn Ala Asn Phe Cys Ala Gly Ala Cys Pro Tyr Leu Trp Ser Ser Asp Thr Gln
His Ser Arg Val Leu Ser Leu Tyr Asn Thr Ile Asn Pro Glu Ala Ser Ala Ser Pro
Cys Cys Val Ser Gln Asp Leu Glu Pro Leu Thr Ile Leu Tyr Tyr Ile Gly Lys Thr
Pro Lys Ile Glu Gln Leu Ser Asn Met Ile Val Lys Ser Cys Lys Cys Ser
```

FIG. 21F

Amino acid sequence of transforming growth factor beta-3 preproprotein from Homo sapiens

```
Met Lys Met His Leu Gln Arg Ala Leu Val Val Leu Ala Leu Leu Asn Phe Ala Thr
Val Ser Leu Ser Leu Ser Thr Cys Thr Thr Leu Asp Phe Gly His Ile Lys Lys Lys
Arg Val Glu Ala Ile Arg Gly Gln Ile Leu Ser Lys Leu Arg Leu Thr Ser Pro Pro
Glu Pro Thr Val Met Thr His Val Pro Tyr Gln Val Leu Ala Leu Tyr Asn Ser Thr
Arg Glu Leu Leu Glu Glu Met His Gly Glu Arg Glu Glu Gly Cys Thr Gln Glu Asn
Thr Glu Ser Glu Tyr Tyr Ala Lys Glu Ile His Lys Phe Asp Met Ile Gln Gly Leu
Ala Glu His Asn Glu Leu Ala Val Cys Pro Lys Gly Ile Thr Ser Lys Val Phe Arg
Phe Asn Val Ser Ser Val Glu Lys Asn Arg Thr Asn Leu Phe Arg Ala Glu Phe Arg
Val Leu Arg Val Pro Asn Pro Ser Ser Lys Arg Asn Glu Gln Arg Ile Glu Leu Phe
Gln Ile Leu Arg Pro Asp Glu His Ile Ala Lys Gln Arg Tyr Ile Gly Gly Lys Asn
Leu Pro Thr Arg Gly Thr Ala Glu Trp Leu Ser Phe Asp Val Thr Asp Thr Val Arg
Glu Trp Leu Leu Arg Arg Glu Ser Asn Leu Gly Leu Glu Ile Ser Ile His Cys Pro
Cys His Thr Phe Gln Pro Asn Gly Asp Ile Leu Glu Asn Ile His Glu Val Met Glu
Ile Lys Phe Lys Gly Val Asp Asn Glu Asp Asp His Gly Arg Gly Asp Leu Gly Arg
Leu Lys Lys Gln Lys Asp His His Asn Pro His Leu Ile Leu Met Met Ile Pro Pro
His Arg Leu Asp Asn Pro Gly Gln Gly Gly Gln Arg Lys Lys Arg Ala Leu Asp Thr
Asn Tyr Cys Phe Arg Asn Leu Glu Glu Asn Cys Cys Val Arg Pro Leu Tyr Ile Asp
Phe Arg Gln Asp Leu Gly Trp Lys Trp Val His Glu Pro Lys Gly Tyr Tyr Ala Asn
Phe Cys Ser Gly Pro Cys Pro Tyr Leu Arg Ser Ala Asp Thr Thr His Ser Thr Val
Leu Gly Leu Tyr Asn Thr Leu Asn Pro Glu Ala Ser Ala Ser Pro Cys Cys Val Pro
Gln Asp Leu Glu Pro Leu Thr Ile Leu Tyr Tyr Val Gly Arg Thr Pro Lys Val Glu
Gln Leu Ser Asn Met Val Val Lys Ser Cys Lys Cys Ser
```

FIG. 21G

Amino acid sequence of transforming growth factor beta-3 from Homo sapiens

```
Ala Leu Asp Thr Asn Tyr Cys Phe Arg Asn Leu Glu Glu Asn Cys Cys Val Arg Pro
Leu Tyr Ile Asp Phe Arg Gln Asp Leu Gly Trp Lys Trp Val His Glu Pro Lys Gly
Tyr Tyr Ala Asn Phe Cys Ser Gly Pro Cys Pro Tyr Leu Arg Ser Ala Asp Thr Thr
His Ser Thr Val Leu Gly Leu Tyr Asn Thr Leu Asn Pro Glu Ala Ser Ala Ser Pro
Cys Cys Val Pro Gln Asp Leu Glu Pro Leu Thr Ile Leu Tyr Tyr Val Gly Arg Thr
Pro Lys Val Glu Gln Leu Ser Asn Met Val Val Lys Ser Cys Lys Cys Ser
```

FIG. 22A

Amino acid sequence of fibroblast growth factor 2 precursor from Homo sapiens

```
Met Val Gly Val Gly Gly Gly Asp Val Glu Asp Val Thr Pro Arg Pro Gly Gly Cys
Gln Ile Ser Gly Arg Gly Ala Arg Gly Cys Asn Gly Ile Pro Gly Ala Ala Ala Trp
Glu Ala Ala Leu Pro Arg Arg Arg Pro Arg Arg His Pro Ser Val Asn Pro Arg Ser
Arg Ala Ala Gly Ser Pro Arg Thr Arg Gly Arg Arg Thr Glu Glu Arg Pro Ser Gly
Ser Arg Leu Gly Asp Arg Gly Arg Gly Arg Ala Leu Pro Gly Gly Arg Leu Gly Gly
Arg Gly Arg Gly Arg Ala Pro Glu Arg Val Gly Gly Arg Gly Arg Gly Arg Gly Thr
Ala Ala Pro Arg Ala Ala Pro Ala Ala Arg Gly Ser Arg Pro Gly Pro Ala Gly Thr
Met Ala Ala Gly Ser Ile Thr Thr Leu Pro Ala Leu Pro Glu Asp Gly Gly Ser Gly
Ala Phe Pro Pro Gly His Phe Lys Asp Pro Lys Arg Leu Tyr Cys Lys Asn Gly Gly
Phe Phe Leu Arg Ile His Pro Asp Gly Arg Val Asp Gly Val Arg Glu Lys Ser Asp
Pro His Ile Lys Leu Gln Leu Gln Ala Glu Glu Arg Gly Val Val Ser Ile Lys Gly
Val Cys Ala Asn Arg Tyr Leu Ala Met Lys Glu Asp Gly Arg Leu Leu Ala Ser Lys
Cys Val Thr Asp Glu Cys Phe Phe Phe Glu Arg Leu Glu Ser Asn Asn Tyr Asn Thr
Tyr Arg Ser Arg Lys Tyr Thr Ser Trp Tyr Val Ala Leu Lys Arg Thr Gly Gln Tyr
Lys Leu Gly Ser Lys Thr Gly Pro Gly Gln Lys Ala Ile Leu Phe Leu Pro Met Ser
Ala Lys Ser
```

FIG. 22B

Amino acid sequence of fragment of fibroblast growth factor 2 from Homo sapiens

```
Pro Ala Leu Pro Glu Asp Gly Gly Ser Gly Ala Phe Pro Pro Gly His Phe Lys Asp
Pro Lys Arg Leu Tyr Cys Lys Asn Gly Gly Phe Phe Leu Arg Ile His Pro Asp Gly
Arg Val Asp Gly Val Arg Glu Lys Ser Asp Pro His Ile Lys Leu Gln Leu Gln Ala
Glu Glu Arg Gly Val Val Ser Ile Lys Gly Val Cys Ala Asn Arg Tyr Leu Ala Met
Lys Glu Asp Gly Arg Leu Leu Ala Ser Lys Cys Val Thr Asp Glu Cys Phe Phe Phe
Glu Arg Leu Glu Ser Asn Asn Tyr Asn Thr Tyr Arg Ser Arg Lys Tyr Thr Ser Trp
Tyr Val Ala Leu Lys Arg Thr Gly Gln Tyr Lys Leu Gly Ser Lys Thr Gly Pro Gly
Gln Lys Ala Ile Leu Phe Leu Pro Met Ser Ala Lys Ser
```

FIG. 23A

Amino acid sequence of hepatocyte growth factor from Homo sapiens

```
Met Trp Val Thr Lys Leu Leu Pro Ala Leu Leu Leu Gln His Val Leu Leu His Leu
Leu Leu Leu Pro Ile Ala Ile Pro Tyr Ala Glu Gly Gln Arg Lys Arg Arg Asn Thr
Ile His Glu Phe Lys Lys Ser Ala Lys Thr Thr Leu Ile Lys Ile Asp Pro Ala Leu
Lys Ile Lys Thr Lys Lys Val Asn Thr Ala Asp Gln Cys Ala Asn Arg Cys Thr Arg
Asn Lys Gly Leu Pro Phe Thr Cys Lys Ala Phe Val Phe Asp Lys Ala Arg Lys Gln
Cys Leu Trp Phe Pro Phe Asn Ser Met Ser Ser Gly Val Lys Lys Glu Phe Gly His
Glu Phe Asp Leu Tyr Glu Asn Lys Asp Tyr Ile Arg Asn Cys Ile Ile Gly Lys Gly
Arg Ser Tyr Lys Gly Thr Val Ser Ile Thr Lys Ser Gly Ile Lys Cys Gln Pro Trp
Ser Ser Met Ile Pro His Glu His Ser Phe Leu Pro Ser Ser Tyr Arg Gly Lys Asp
Leu Gln Glu Asn Tyr Cys Arg Asn Pro Arg Gly Glu Glu Gly Gly Pro Trp Cys Phe
Thr Ser Asn Pro Glu Val Arg Tyr Glu Val Cys Asp Ile Pro Gln Cys Ser Glu Val
Glu Cys Met Thr Cys Asn Gly Glu Ser Tyr Arg Gly Leu Met Asp His Thr Glu Ser
Gly Lys Ile Cys Gln Arg Trp Asp His Gln Thr Pro His Arg His Lys Phe Leu Pro
Glu Arg Tyr Pro Asp Lys Gly Phe Asp Asp Asn Tyr Cys Arg Asn Pro Asp Gly Gln
Pro Arg Pro Trp Cys Tyr Thr Leu Asp Pro His Thr Arg Trp Glu Tyr Cys Ala Ile
Lys Thr Cys Ala Asp Asn Thr Met Asn Asp Thr Asp Val Pro Leu Glu Thr Thr Glu
Cys Ile Gln Gly Gln Gly Glu Gly Tyr Arg Gly Thr Val Asn Thr Ile Trp Asn Gly
Ile Pro Cys Gln Arg Trp Asp Ser Gln Tyr Pro His Glu His Asp Met Thr Pro Glu
Asn Phe Lys Cys Lys Asp Leu Arg Glu Asn Tyr Cys Arg Asn Pro Asp Gly Ser Glu
Ser Pro Trp Cys Phe Thr Thr Asp Pro Asn Ile Arg Val Gly Tyr Cys Ser Gln Ile
Pro Asn Cys Asp Met Ser His Gly Gln Asp Cys Tyr Arg Gly Asn Gly Lys Asn Tyr
Met Gly Asn Leu Ser Gln Thr Arg Ser Gly Leu Thr Cys Ser Met Trp Asp Lys Asn
Met Glu Asp Leu His Arg His Ile Phe Trp Glu Pro Asp Ala Ser Lys Leu Asn Glu
Asn Tyr Cys Arg Asn Pro Asp Asp Asp Ala His Gly Pro Trp Cys Tyr Thr Gly Asn
Pro Leu Ile Pro Trp Asp Tyr Cys Pro Ile Ser Arg Cys Glu Gly Asp Thr Thr Pro
Thr Ile Val Asn Leu Asp His Pro Val Ile Ser Cys Ala Lys Thr Lys Gln Leu Arg
Val Val Asn Gly Ile Pro Thr Arg Thr Asn Ile Gly Trp Met Val Ser Leu Arg Tyr
Arg Asn Lys His Ile Cys Gly Gly Ser Leu Ile Lys Glu Ser Trp Val Leu Thr Ala
Arg Gln Cys Phe Pro Ser Arg Asp Leu Lys Asp Tyr Glu Ala Trp Leu Gly Ile His
Asp Val His Gly Arg Gly Asp Glu Lys Cys Lys Gln Val Leu Asn Val Ser Gln Leu
Val Tyr Gly Pro Glu Gly Ser Asp Leu Val Leu Met Lys Leu Ala Arg Pro Ala Val
Leu Asp Asp Phe Val Ser Thr Ile Asp Leu Pro Asn Tyr Gly Cys Thr Ile Pro Glu
Lys Thr Ser Cys Ser Val Tyr Gly Trp Gly Tyr Thr Gly Leu Ile Asn Tyr Asp Gly
Leu Leu Arg Val Ala His Leu Tyr Ile Met Gly Asn Glu Lys Cys Ser Gln His His
Arg Gly Lys Val Thr Leu Asn Glu Ser Glu Ile Cys Ala Gly Ala Glu Lys Ile Gly
Ser Gly Pro Cys Glu Gly Asp Tyr Gly Gly Pro Leu Val Cys Glu Gln His Lys Met
Arg Met Val Leu Gly Val Ile Val Pro Gly Arg Gly Cys Ala Ile Pro Asn Arg Pro
Gly Ile Phe Val Arg Val Ala Tyr Tyr Ala Lys Trp Ile His Lys Ile Ile Leu Thr
Tyr Lys Val Pro Gln Ser
```

FIG. 23B

Amino acid sequence of hepatocyte growth factor alpha chain from Homo sapiens

```
Gln Arg Lys Arg Arg Asn Thr Ile His Glu Phe Lys Lys Ser Ala Lys Thr Thr Leu
Ile Lys Ile Asp Pro Ala Leu Lys Ile Lys Thr Lys Lys Val Asn Thr Ala Asp Gln
Cys Ala Asn Arg Cys Thr Arg Asn Lys Gly Leu Pro Phe Thr Cys Lys Ala Phe Val
Phe Asp Lys Ala Arg Lys Gln Cys Leu Trp Phe Pro Phe Asn Ser Met Ser Ser Gly
Val Lys Lys Glu Phe Gly His Glu Phe Asp Leu Tyr Glu Asn Lys Asp Tyr Ile Arg
Asn Cys Ile Ile Gly Lys Gly Arg Ser Tyr Lys Gly Thr Val Ser Ile Thr Lys Ser
Gly Ile Lys Cys Gln Pro Trp Ser Ser Met Ile Pro His Glu His Ser Phe Leu Pro
Ser Ser Tyr Arg Gly Lys Asp Leu Gln Glu Asn Tyr Cys Arg Asn Pro Arg Gly Glu
Glu Gly Gly Pro Trp Cys Phe Thr Ser Asn Pro Glu Val Arg Tyr Glu Val Cys Asp
Ile Pro Gln Cys Ser Glu Val Glu Cys Met Thr Cys Asn Gly Glu Ser Tyr Arg Gly
Leu Met Asp His Thr Glu Ser Gly Lys Ile Cys Gln Arg Trp Asp His Gln Thr Pro
His Arg His Lys Phe Leu Pro Glu Arg Tyr Pro Asp Lys Gly Phe Asp Asp Asn Tyr
Cys Arg Asn Pro Asp Gly Gln Pro Arg Pro Trp Cys Tyr Thr Leu Asp Pro His Thr
Arg Trp Glu Tyr Cys Ala Ile Lys Thr Cys Ala Asp Asn Thr Met Asn Asp Thr Asp
Val Pro Leu Glu Thr Thr Glu Cys Ile Gln Gly Gln Gly Glu Gly Tyr Arg Gly Thr
Val Asn Thr Ile Trp Asn Gly Ile Pro Cys Gln Arg Trp Asp Ser Gln Tyr Pro His
Glu His Asp Met Thr Pro Glu Asn Phe Lys Cys Lys Asp Leu Arg Glu Asn Tyr Cys
Arg Asn Pro Asp Gly Ser Glu Ser Pro Trp Cys Phe Thr Thr Asp Pro Asn Ile Arg
Val Gly Tyr Cys Ser Gln Ile Pro Asn Cys Asp Met Ser His Gly Gln Asp Cys Tyr
Arg Gly Asn Gly Lys Asn Tyr Met Gly Asn Leu Ser Gln Thr Arg Ser Gly Leu Thr
Cys Ser Met Trp Asp Lys Asn Met Glu Asp Leu His Arg His Ile Phe Trp Glu Pro
Asp Ala Ser Lys Leu Asn Glu Asn Tyr Cys Arg Asn Pro Asp Asp Asp Ala His Gly
Pro Trp Cys Tyr Thr Gly Asn Pro Leu Ile Pro Trp Asp Tyr Cys Pro Ile Ser Arg
Cys Glu Gly Asp Thr Thr Pro Thr Ile Val Asn Leu Asp His Pro Val Ile Ser Cys
Ala Lys Thr Lys Gln Leu Arg
```

FIG. 23C

Amino acid sequence of hepatocyte growth factor beta chain from Homo sapiens

```
Val Val Asn Gly Ile Pro Thr Arg Thr Asn Ile Gly Trp Met Val Ser Leu Arg Tyr
Arg Asn Lys His Ile Cys Gly Gly Ser Leu Ile Lys Glu Ser Trp Val Leu Thr Ala
Arg Gln Cys Phe Pro Ser Arg Asp Leu Lys Asp Tyr Glu Ala Trp Leu Gly Ile His
Asp Val His Gly Arg Gly Asp Glu Lys Cys Lys Gln Val Leu Asn Val Ser Gln Leu
Val Tyr Gly Pro Glu Gly Ser Asp Leu Val Leu Met Lys Leu Ala Arg Pro Ala Val
Leu Asp Asp Phe Val Ser Thr Ile Asp Leu Pro Asn Tyr Gly Cys Thr Ile Pro Glu
Lys Thr Ser Cys Ser Val Tyr Gly Trp Gly Tyr Thr Gly Leu Ile Asn Tyr Asp Gly
Leu Leu Arg Val Ala His Leu Tyr Ile Met Gly Asn Glu Lys Cys Ser Gln His His
Arg Gly Lys Val Thr Leu Asn Glu Ser Glu Ile Cys Ala Gly Ala Glu Lys Ile Gly
Ser Gly Pro Cys Glu Gly Asp Tyr Gly Gly Pro Leu Val Cys Glu Gln His Lys Met
Arg Met Val Leu Gly Val Ile Val Pro Gly Arg Gly Cys Ala Ile Pro Asn Arg Pro
Gly Ile Phe Val Arg Val Ala Tyr Tyr Ala Lys Trp Ile His Lys Ile Ile Leu Thr
Tyr Lys Val Pro Gln Ser
```

FIG. 24A

```
ATAAATTATAAGGAGGCACTCACC ATG...    nisA gene
     3'tctttcctccactagg 5'         3' end 16S rDNA TATTAATAAGGAGGCTAACTA ATG...   atpG gene
     3'tctttcctccactagg 5'         3' end of 16S rDNA AAATTTAGGAGGTAGTCCAA ATG...    lacA gene
     3'tctttcctccactagg 5'         3' end of 16S rDNA
```

CSF-RBS1-FGF-RBS2-IL4 (1850 bps)

GGATCCTAGTCTTATAACTATACTGACAATAGAAACATTAACAAATCTAAAACAGTCTTAATTCTATCTTGAGAAAGT
ATTGGTAATAATATTATTGTCGATAACGCGAGCATAATAAACGGCTCTGATTAAATTCTGAAGTTTGTTAGATACAAT
GATTTCGTTCGAAGGAACTACAAAATAAATTATAAGGAGGCACTCACCATGAAAAAGAAAATCATTTCAGCGATTTTG
ATGTCAACGGTTATTTTAAGCGCAGCAGCTCCATTATCTGGAGTTTATGCAGCAGAAGAAGTTAGTGAGTACTGTAGT
CATATGATTGGTTCTGGACACTTACAATCACTTCAGCGTCTTATTGATAGTCAAATGGAAACCTCTTGTCAAATTACA
TTTGAATTTGTAGACCAAGAACAACTTAAAGATCCAGTATGTTATCTTAAGAAAGCTTTTCTTTTAGTCCAAGACATA
ATGGAAGATACAATGAGATTCAGAGACAATACTCCTAACGCTATCGCCATTGTCCAATTACAAGAACTTTCTTTAAGA
TTGAAAAGTTGCTTCACTAAAGATTATGAGGAACATGATAAAGCTTGTGTTCGAACATTTTATGAAACTCCTTTGCAA
TTATTGGAAAAAGTGAAAAATGTTTTCAATGAGACGAAGAATTTGTTGGATAAAGATTGGAATATATTCAGTAAGAAT
TGTAATAACTCATTTGCCGAATGTTCAAGCCAGGGTCATGAACGTCAATCAGAAGGCTCTTAATAAACGCGTATTAAT
AAGGAGGCTAACTAATGAAAAAAAAGATTATCTCAGCTATTTTAATGTCTACAGTGATACTTTCTGCTGCAGCCCCGT
TGTCAGGTGTTTACGCTGCTGGTTCCATTACGACCTTGCCGGCTTTACCAGAGGACGGAGGTTCAGGAGCCTTTCCAC
CAGGGCACTTTAAAGATCCCAAACGTCTATATTGTAAAAATGGAGGCTTCTTTCTGCGAATTCATCCTGATGGACGTG
TAGATGGTGTGCGTGAGAAAAGTGATCCTCATATCAAACTCCAACTTCAGGCAGAAGAAAGAGGCGTCGTAAGTATAA
AAGGAGTTTGCGCGAATCGTTACTTAGCTATGAAAGAAGACGGTCGATTATTGGCCTCTAAGTGTGTTACTGATGAAT
GTTTTTTTTTTGAACGGCTTGAATCTAATAATTATAACACTTATAGAAGCAGAAAATATACATCATGGTACGTTGCAC
TTAAAAGGACAGGTCAATATAAATTAGGGTCTAAGACAGGACCTGGTCAAAAAGCAATTTTGTTCTTACCAATGTCGG
CTAAAAGTTAATAAACGCGTGAAATTTAGGAGGTAGTCCAAATGAAGAAAAAGATTATTAGTGCAATTTTAATGTCAA
CGGTCATCTTAAGCGCTGCTGCCCCATTGTCAGGTGTTTATGCAGCACATAAGTGTGATATAACATTACAAGAAATTA
TCAAAACCCTTAATAGTTTAACTGAACAGAAGACTTTGTGTACCGAATTAACTGTAACTGATATTTTTGCTGCTTCTA
AAAATACAACTGAAAAAGAGACATTTTGTCGAGCTGCCACAGTGTTAAGACAATTTTACAGTCATCATGAAAAAGACA
CAAGATGTCTTGGTGCTACGGCACAACAATTTCATAGACACAAACAACTTATCCGTTTTCTTAAACGTTTGGATCGTA
ATCTGTGGGGCTTGGCAGGATTGAACAGTTGTCCTGTTAAAGAAGCCAATCAATCTACTCTTGAAAATTTCTTAGAGA
GATTGAAAACAATTATGCGAGAAAAATATTCTAAGTGTTCATCTTAATAACCATGG

FIG. 24C

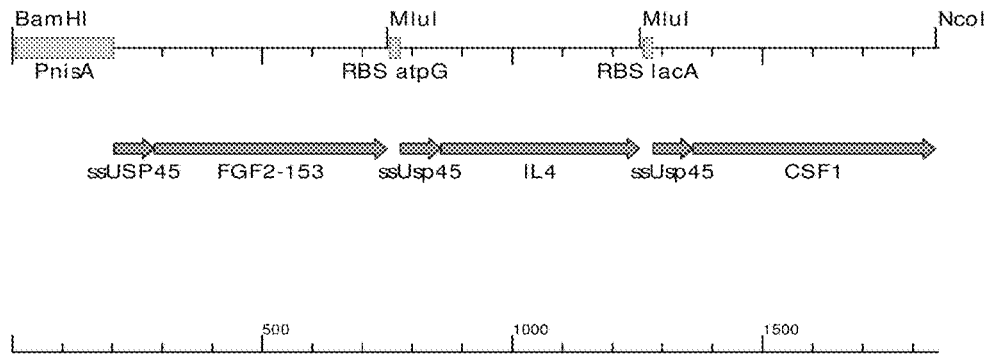

FGF-RBS1-IL4-RBS2-CSF (1850 bps)

```
GGATCCTAGTCTTATAACTATACTGACAATAGAAACATTAACAAATCTAAAACAGTCTTAATTCTATCTTGAGAAAGT
ATTGGTAATAATATTATTGTCGATAACGCGAGCATAATAAACGGCTCTGATTAAATTCTGAAGTTTGTTAGATACAAT
GATTTCGTTCGAAGGAACTACAAAATAAATTATAAGGAGGCACTCACCATGAAAAAAAAGATTATCTCAGCTATTTTA
ATGTCTACAGTGATACTTTCTGCTGCAGCCCCGTTGTCAGGTGTTTACGCTGCTGGTTCCATTACGACCTTGCCGGCT
TTACCAGAGGACGGAGGTTCAGGAGCCTTTCCACCAGGGCACTTTAAAGATCCCAAACGTCTATATTGTAAAAATGGA
GGCTTCTTTCTGCGAATTCATCCTGATGGACGTGTAGATGGTGTGCGTGAGAAAAGTGATCCTCATATCAAACTCCAA
CTTCAGGCAGAAGAAAGAGGCGTCGTAAGTATAAAAGGAGTTTGCGCGAATCGTTACTTAGCTATGAAAGAAGACGGT
CGATTATTGGCCTCTAAGTGTGTTACTGATGAATGTTTTTTTTTTGAACGGCTTGAATCTAATAATTATAACACTTAT
AGAAGCAGAAAATATACATCATGGTACGTTGCACTTAAAAGGACAGGTCAATATAAATTAGGGTCTAAGACAGGACCT
GGTCAAAAAGCAATTTTGTTCTTACCAATGTCGGCTAAAAGTTAATAAACGCGTATTAATAAGGAGGCTAACTAATGA
AGAAAAAGATTATTAGTGCAATTTTAATGTCAACGGTCATCTTAAGCGCTGCTGCCCCATTGTCAGGTGTTTATGCAG
CACATAAGTGTGATATAACATTACAAGAAATTATCAAAACCCTTAATAGTTTAACTGAACAGAAGACTTTGTGTACCG
AATTAACTGTAACTGATATTTTTGCTGCTTCTAAAAATACAACTGAAAAAGAGACATTTTGTCGAGCTGCCACAGTGT
TAAGACAATTTTACAGTCATCATGAAAAAGACACAAGATGTCTTGGTGCTACGGCACAACAATTTCATAGACACAAAC
AACTTATCCGTTTTCTTAAACGTTTGGATCGTAATCTGTGGGGCTTGGCAGGATTGAACAGTTGTCCTGTTAAAGAAG
CCAATCAATCTACTCTTGAAAATTTCTTAGAGAGATTGAAAACAATTATGCGAGAAAAATATTCTAAGTGTTCATCTT
AATAAACGCGTGAAATTTAGGAGGTAGTCCAAATGAAAAAGAAAATCATTTCAGCGATTTTGATGTCAACGGTTATTT
TAAGCGCAGCAGCTCCATTATCTGGAGTTTATGCAGCAGAAGAAGTTAGTGAGTACTGTAGTCATATGATTGGTTCTG
GACACTTACAATCACTTCAGCGTCTTATTGATAGTCAAATGGAAACCTCTTGTCAAATTACATTTGAATTTGTAGACC
AAGAACAACTTAAAGATCCAGTATGTTATCTTAAGAAAGCTTTTCTTTTAGTCCAAGACATAATGGAAGATACAATGA
GATTCAGAGACAATACTCCTAACGCTATCGCCATTGTCCAATTACAAGAACTTTCTTTAAGATTGAAAAGTTGCTTCA
CTAAAGATTATGAGGAACATGATAAAGCTTGTGTTCGAACATTTTATGAAACTCCTTTGCAATTATTGGAAAAAGTGA
AAAATGTTTTCAATGAGACGAAGAATTTGTTGGATAAAGATTGGAATATATTCAGTAAGAATTGTAATAACTCATTTG
CCGAATGTTCAAGCCAGGGTCATGAACGTCAATCAGAAGGCTCTTAATAACCATGG
```

FIG. 24D

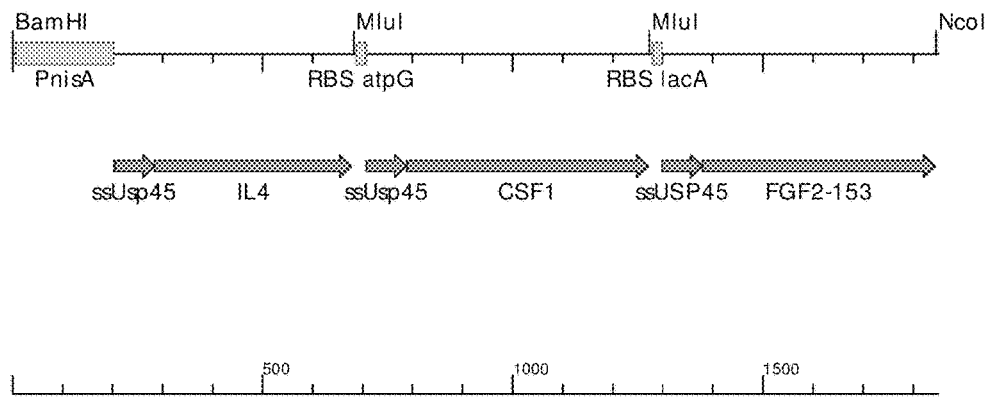

IL4-RBS1-CSF-RBS2-FGF (1850 bps)

```
GGATCCTAGTCTTATAACTATACTGACAATAGAAACATTAACAAATCTAAAACAGTCTTAATTCTATCTTGAGAAAGT
ATTGGTAATAATATTATTGTCGATAACGCGAGCATAATAAACGGCTCTGATTAAATTCTGAAGTTTGTTAGATACAAT
GATTTCGTTCGAAGGAACTACAAAATAAATTATAAGGAGGCACTCACCATGAAGAAAAAGATTATTAGTGCAATTTTA
ATGTCAACGGTCATCTTAAGCGCTGCTGCCCCATTGTCAGGTGTTTATGCAGCACATAAGTGTGATATAACATTACAA
GAAATTATCAAAACCCTTAATAGTTTAACTGAACAGAAGACTTTGTGTACCGAATTAACTGTAACTGATATTTTTGCT
GCTTCTAAAAATACAACTGAAAAAGAGACATTTTGTCGAGCTGCCACAGTGTTAAGACAATTTTACAGTCATCATGAA
AAAGACACAAGATGTCTTGGTGCTACGGCACAACAATTTCATAGACACAAACAACTTATCCGTTTTCTTAAACGTTTG
GATCGTAATCTGTGGGGCTTGGCAGGATTGAACAGTTGTCCTGTTAAAGAAGCCAATCAATCTACTCTTGAAAATTTC
TTAGAGAGATTGAAAACAATTATGCGAGAAAAATATTCTAAGTGTTCATCTTAATAAACGCGTATTAATAAGGAGGCT
AACTAATGAAAAAGAAAATCATTTCAGCGATTTTGATGTCAACGGTTATTTTAAGCGCAGCAGCTCCATTATCTGGAG
TTTATGCAGCAGAAGAAGTTAGTGAGTACTGTAGTCATATGATTGGTTCTGGACACTTACAATCACTTCAGCGTCTTA
TTGATAGTCAAATGGAAACCTCTTGTCAAATTACATTTGAATTTGTAGACCAAGAACAACTTAAAGATCCAGTATGTT
ATCTTAAGAAAGCTTTTCTTTTAGTCCAAGACATAATGGAAGATACAATGAGATTCAGAGACAATACTCCTAACGCTA
TCGCCATTGTCCAATTACAAGAACTTTCTTTAAGATTGAAAAGTTGCTTCACTAAAGATTATGAGGAACATGATAAAG
CTTGTGTTCGAACATTTTATGAAACTCCTTTGCAATTATTGGAAAAAGTGAAAAATGTTTTCAATGAGACGAAGAATT
TGTTGGATAAAGATTGGAATATATTCAGTAAGAATTGTAATAACTCATTTGCCGAATGTTCAAGCCAGGGTCATGAAC
GTCAATCAGAAGGCTCTTAATAAACGCGTGAAATTTAGGAGGTAGTCCAAATGAAAAAAAAGATTATCTCAGCTATTT
TAATGTCTACAGTGATACTTTCTGCTGCAGCCCCGTTGTCAGGTGTTTACGCTGCTGGTTCCATTACGACCTTGCCGG
CTTTACCAGAGGACGGAGGTTCAGGAGCCTTTCCACCAGGGCACTTTAAAGATCCCAAACGTCTATATTGTAAAAATG
GAGGCTTCTTTCTGCGAATTCATCCTGATGGACGTGTAGATGGTGTGCGTGAGAAAGTGATCCTCATATCAAACTCC
AACTTCAGGCAGAAGAAAGAGGCGTCGTAAGTATAAAAGGAGTTTGCGCGAATCGTTACTTAGCTATGAAAGAAGACG
GTCGATTATTGGCCTCTAAGTGTGTTACTGATGAATGTTTTTTTTTGAACGGCTTGAATCTAATAATTATAACACTT
ATAGAAGCAGAAAATATACATCATGGTACGTTGCACTTAAAAGGACAGGTCAATATAAATTAGGGTCTAAGACAGGAC
CTGGTCAAAAAGCAATTTTGTTCTTACCAATGTCGGCTAAAAGTTAATAACCATGG
```

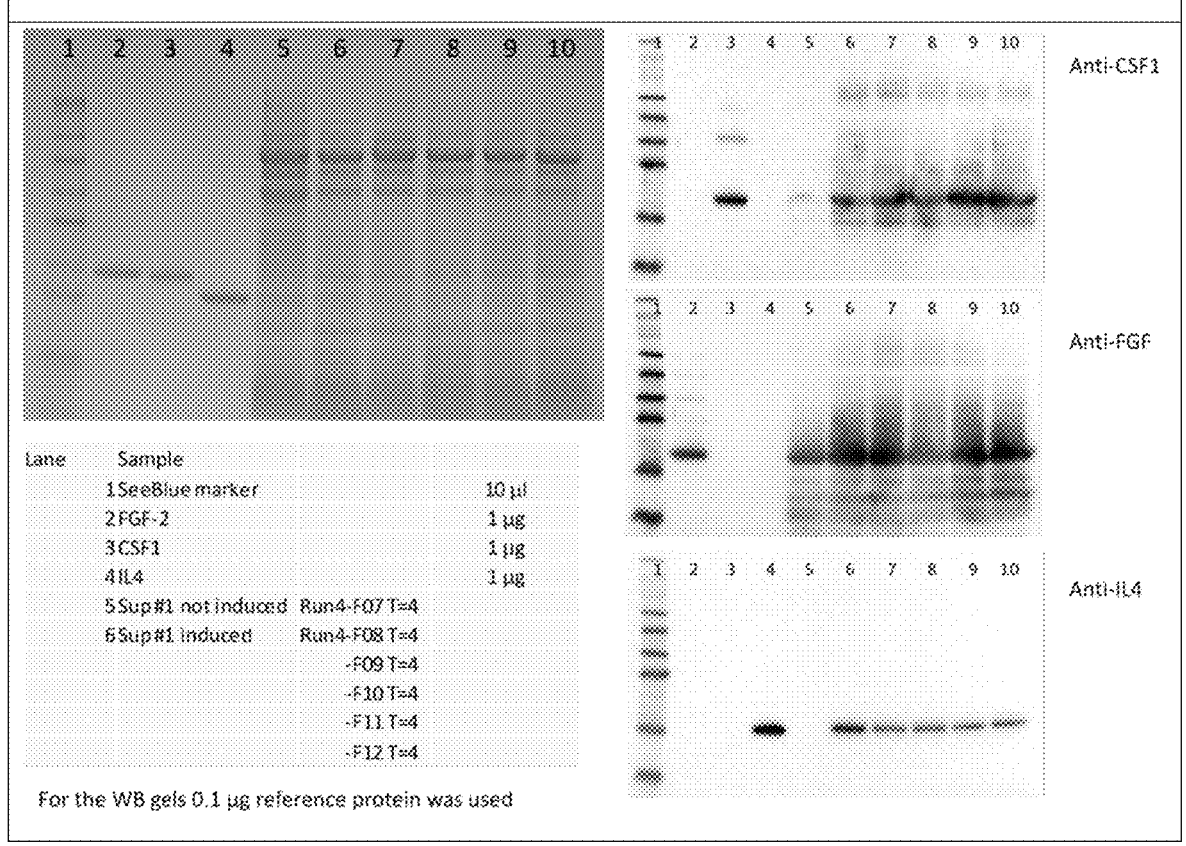

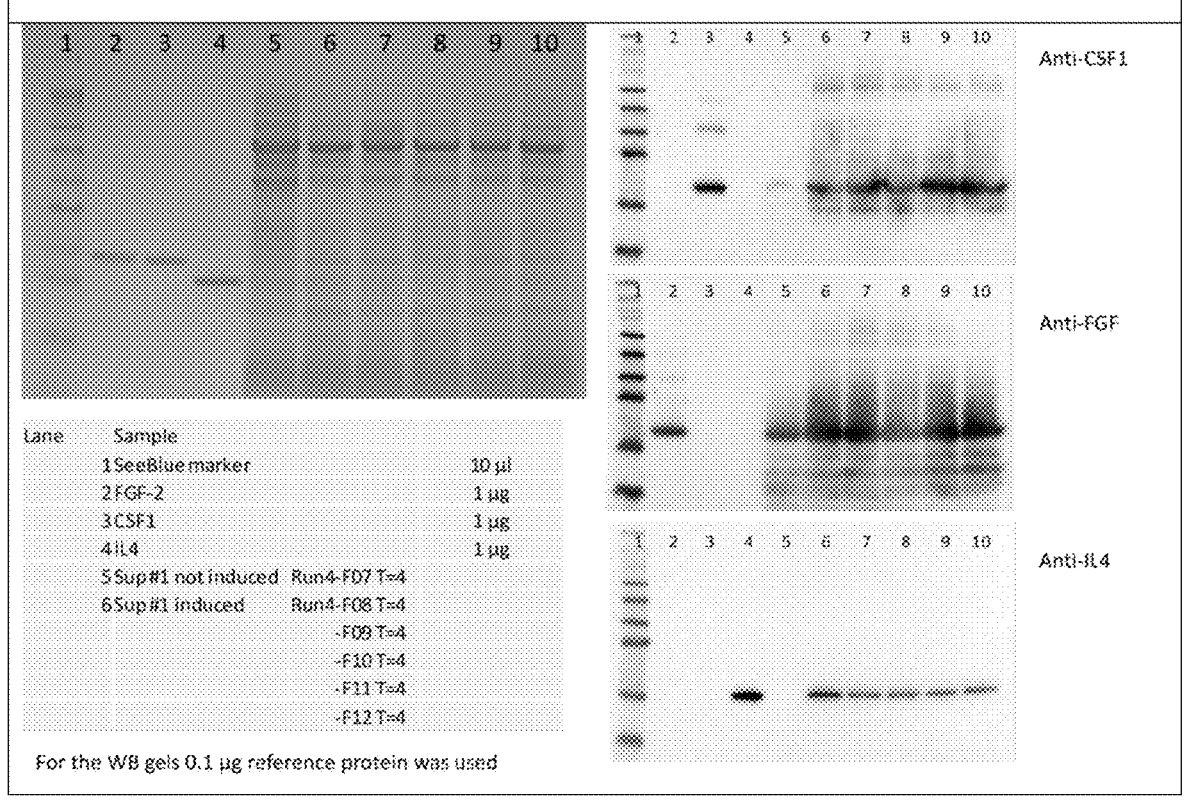

FIG. 25A

Amino acid sequence of epidermal growth factor isoform 1 preproprotein from Homo sapiens

```
MLLTLIILLP VVSKFSFVSL SAPQHWSCPE GTLAGNGNST CVGPAPFLIF
SHGNSIFRID TEGTNYEQLV VDAGVSVIMD FHYNEKRIYW VDLERQLLQR
VFLNGSRQER VCNIEKNVSG MAINWINEEV IWSNQQEGII TVTDMKGNNS
HILLSALKYP ANVAVDPVER FIFWSSEVAG SLYRADLDGV GVKALLETSE
KITAVSLDVL DKRLFWIQYN REGSNSLICS CDYDGGSVHI SKHPTQHNLF
AMSLFGDRIF YSTWKMKTIW IANKHTGKDM VRINLHSSFV PLGELKVVHP
LAQPKAEDDT WEPEQKLCKL RKGNCSSTVC GQDLQSHLCM CAEGYALSRD
RKYCEDVNEC AFWNHGCTLG CKNTPGSYYC TCPVGFVLLP DGKRCHQLVS
CPRNVSECSH DCVLTSEGPL CFCPEGSVLE RDGKTCSGCS SPDNGGCSQL
CVPLSPVSWE CDCFPGYDLQ LDEKSCAASG PQPFLLFANS QDIRHMHFDG
TDYGTLLSQQ MGMVYALDHD PVENKIYFAH TALKWIERAN MDGSQRERLI
EEGVDVPEGL AVDWIGRRFY WTDRGKSLIG RSDLNGKRSK IITKENISQP
RGIAVHPMAK RLFWTDTGIN PRIESSSLQG LGRLVIASSD LIWPSGITID
FLTDKLYWCD AKQSVIEMAN LDGSKRRRLT QNDVGHPFAV AVFEDYVWFS
DWAMPSVMRV NKRTGKDRVR LQGSMLKPSS LVVVHPLAKP GADPCLYQNG
GCEHICKKRL GTAWCSCREG FMKASDGKTC LALDGHQLLA GGEVDLKNQV
TPLDILSKTR VSEDNITESQ HMLVAEIMVS DQDDCAPVGC SMYARCISEG
EDATCQCLKG FAGDGKLCSD IDECEMGVPV CPPASSKCIN TEGGYVCRCS
EGYQGDGIHC LDIDECQLGE HSCGENASCT NTEGGYTCMC AGRLSEPGLI
CPDSTPPPHL REDDHHYSVR NSDSECPLSH DGYCLHDGVC MYIEALDKYA
CNCVVGYIGE RCQYRDLKWW ELRHAGHGQQ QKVIVVAVCV VVLVMLLLS
LWGAHYYRTQ KLLSKNPKNP YEESSRDVRS RRPADTEDGM SSCPQPWFVV
IKEHQDLKNG GQPVAGEDGQ AADGSMQPTS WRQEPQLCGM GTEQGCWIPV
SSDKGSCPQV MERSFHMPSY GTQTLEGGVE KPHSLLSANP LWQQRALDPP
HQMELTQ
```

FIG. 25B
Amino acid sequence of epidermal growth factor isoform 2 preproprotein from Homo sapiens

```
MLLTLIILLP VVSKFSFVSL SAPQHWSCPE GTLAGNGNST CVGPAPFLIF
SHGNSIFRID TEGTNYEQLV VDAGVSVIMD FHYNEKRIYW VDLERQLLQR
VFLNGSRQER VCNIEKNVSG MAINWINEEV IWSNQQEGII TVTDMKGNNS
HILLSALKYP ANVAVDPVER FIFWSSEVAG SLYRADLDGV GVKALLETSE
KITAVSLDVL DKRLFWIQYN REGSNSLICS CDYDGGSVHI SKHPTQHNLF
AMSLFGDRIF YSTWKMKTIW IANKHTGKDM VRINLHSSFV PLGELKVVHP
LAQPKAEDDT WEPDVNECAF WNHGCTLGCK NTPGSYYCTC PVGFVLLPDG
KRCHQLVSCP RNVSECSHDC VLTSEGPLCF CPEGSVLERD GKTCSGCSSP
DNGGCSQLCV PLSPVSWECD CFPGYDLQLD EKSCAASGPQ PFLLFANSQD
IRHMHFDGTD YGTLLSQQMG MVYALDHDPV ENKIYFAHTA LKWIERANMD
GSQRERLIEE GVDVPEGLAV DWIGRRFYWT DRGKSLIGRS DLNGKRSKII
TKENISQPRG IAVHPMAKRL FWTDTGINPR IESSSLQGLG RLVIASSDLI
WPSGITIDFL TDKLYWCDAK QSVIEMANLD GSKRRRLTQN DVGHPFAVAV
FEDYVWFSDW AMPSVMRVNK RTGKDRVRLQ GSMLKPSSLV VVHPLAKPGA
DPCLYQNGGC EHICKKRLGT AWCSCREGFM KASDGKTCLA LDGHQLLAGG
EVDLKNQVTP LDILSKTRVS EDNITESQHM LVAEIMVSDQ DDCAPVGCSM
YARCISEGED ATCQCLKGFA GDGKLCSDID ECEMGVPVCP PASSKCINTE
GGYVCRCSEG YQGDGIHCLD IDECQLGEHS CGENASCTNT EGGYTCMCAG
RLSEPGLICP DSTPPPHLRE DDHHYSVRNS DSECPLSHDG YCLHDGVCMY
IEALDKYACN CVVGYIGERC QYRDLKWWEL RHAGHGQQQK VIVVAVCVVV
LVMLLLLSLW GAHYYRTQKL LSKNPKNPYE ESSRDVRSRR PADTEDGMSS
CPQPWFVVIK EHQDLKNGGQ PVAGEDGQAA DGSMQPTSWR QEPQLCGMGT
EQGCWIPVSS DKGSCPQVME RSFHMPSYGT QTLEGGVEKP HSLLSANPLW
QQRALDPPHQ MELTQ
```

FIG. 25C

Amino acid sequence of epidermal growth factor isoform 3 preproprotein from Homo sapiens

```
MLLTLIILLP VVSKFSFVSL SAPQHWSCPE GTLAGNGNST CVGPAPFLIF
SHGNSIFRID TEGTNYEQLV VDAGVSVIMD FHYNEKRIYW VDLERQLLQR
VFLNGSRQER VCNIEKNVSG MAINWINEEV IWSNQQEGII TVTDMKGNNS
HILLSALKYP ANVAVDPVER FIFWSSEVAG SLYRADLDGV GVKALLETSE
KITAVSLDVL DKRLFWIQYN REGSNSLICS CDYDGGSVHI SKHPTQHNLF
AMSLFGDRIF YSTWKMKTIW IANKHTGKDM VRINLHSSFV PLGELKVVHP
LAQPKAEDDT WEPEQKLCKL RKGNCSSTVC GQDLQSHLCM CAEGYALSRD
RKYCEDVNEC AFWNHGCTLG CKNTPGSYYC TCPVGFVLLP DGKRCHQLVS
CPRNVSECSH DCVLTSEGPL CFCPEGSVLE RDGKTCSGCS SPDNGGCSQL
CVPLSPVSWE CDCFPGYDLQ LDEKSCAASG PQPFLLFANS QDIRHMHFDG
TDYGTLLSQQ MGMVYALDHD PVENKIYFAH TALKWIERAN MDGSQRERLI
EEGVDVPEGL AVDWIGRRFY WTDRGKSLIG RSDLNGKRSK IITKENISQP
RGIAVHPMAK RLFWTDTGIN PRIESSSLQG LGRLVIASSD LIWPSGITID
FLTDKLYWCD AKQSVIEMAN LDGSKRRRLT QNDVGHPFAV AVFEDYVWFS
DWAMPSVMRV NKRTGKDRVR LQGSMLKPSS LVVVHPLAKP GADPCLYQNG
GCEHICKKRL GTAWCSCREG FMKASDGKTC LALDGHQLLA GGEVDLKNQV
TPLDILSKTR VSEDNITESQ HMLVAEIMVS DQDDCAPVGC SMYARCISEG
EDATCQCLKG FAGDGKLCSD IDECEMGVPV CPPASSKCIN TEGGYVCRCS
EGYQGDGIHC LDSTPPPHLR EDDHHYSVRN SDSECPLSHD GYCLHDGVCM
YIEALDKYAC NCVVGYIGER CQYRDLKWWE LRHAGHGQQQ KVIVVAVCVV
VLVMLLLLSL WGAHYYRTQK LLSKNPKNPY EESSRDVRSR RPADTEDGMS
SCPQPWFVVI KEHQDLKNGG QPVAGEDGQA ADGSMQPTSW RQEPQLCGMG
TEQGCWIPVS SDKGSCPQVM ERSFHMPSYG TQTLEGGVEK PHSLLSANPL
WQQRALDPPH QMELTQ
```

FIG. 25D

Amino acid sequence of the mature epidermal growth factor from Homo sapiens

```
NSDSECPLSH DGYCLHDGVC MYIEALDKYA CNCVVGYIGE RCQYRDLKWW
ELR
```

FIG. 26A

Amino acid sequence of the heparin-binding EGF-like growth factor precursor from Homo sapiens

```
MKLLPSVVLK LFLAAVLSAL VTGESLERLR RGLAAGTSNP DPPTVSTDQL
LPLGGGRDRK VRDLQEADLD LLRVTLSSKP QALATPNKEE HGKRKKKGKG
LGKKRDPCLR KYKDFCIHGE CKYVKELRAP SCICHPGYHG ERCHGLSLPV
ENRLYTYDHT TILAVVAVVL SSVCLLVIVG LLMFRYHRRG GYDVENEEKV
KLGMTNSH
```

FIG. 26B

Amino acid sequence of the mature heparin-binding EGF-like growth factor from Homo sapiens

```
DLQEADLDLL RVTLSSKPQA LATPNKEEHG KRKKKGKGLG KKRDPCLRKY
KDFCIHGECK YVKELRAPSC ICHPGYHGER CHGLSL
```

FIG. 27A

Amino acid sequence of transforming growth factor alpha isoform 1 preproprotein from Homo sapiens

```
MVPSAGQLAL FALGIVLAAC QALENSTSPL SADPPVAAAV VSHFNDCPDS
HTQFCFHGTC RFLVQEDKPA CVCHSGYVGA RCEHADLLAV VAASQKKQAI
TALVVVSIVA LAVLIITCVL IHCCQVRKHC EWCRALICRH EKPSALLKGR
TACCHSETVV
```

FIG. 27B

Amino acid sequence of transforming growth factor alpha isoform 2 preproprotein from Homo sapiens

```
MVPSAGQLAL FALGIVLAAC QALENSTSPL SDPPVAAAVV SHFNDCPDSH
TQFCFHGTCR FLVQEDKPAC VCHSGYVGAR CEHADLLAVV AASQKKQAIT
ALVVVSIVAL AVLIITCVLI HCCQVRKHCE WCRALICRHE KPSALLKGRT
ACCHSETVV
```

FIG. 27C

Amino acid sequence of transforming growth factor alpha isoform 3 preproprotein from Homo sapiens

```
MVPSAGQLAL FALGIVLAAC QALENSTSPL SDPPVAAAVV SHFNDCPDSH
TQFCFHGTCR FLVQEDKPAC VCHSGYVGAR CEHADLLAVV AASQKKQAIT
ALVVVSIVAL AVLIITCVLI HCCQVRKHCE WCRALICRHE KPSALLKGRT
ACCHSETATL G
```

FIG. 27D

Amino acid sequence of transforming growth factor alpha isoform 4 preproprotein from Homo sapiens

```
MVPSAGQLAL FALGIVLAAC QALENSTSPL SADPPVAAAV VSHFNDCPDS
HTQFCFHGTC RFLVQEDKPA CVCHSGYVGA RCEHADLLAV VAASQKKQAI
TALVVVSIVA LAVLIITCVL IHCCQVRKHC EWCRALICRH EKPSALLKGR
TACCHSETGC RLY
```

FIG. 27E

Amino acid sequence of transforming growth factor alpha isoform 5 preproprotein from Homo sapiens

```
MVPSAGQLAL  FALGIVLAAC  QALENSTSPL  SDPPVAAAVV  SHFNDCPDSH
TQFCFHGTCR  FLVQEDKPAC  VCHSGYVGAR  CEHADLLAVV  AASQKKQAIT
ALVVVSIVAL  AVLIITCVLI  HCCQVRKHCE  WCRALICRHE  KPSALLKGRT
ACCHSETGCR  LY
```

FIG. 27F

Amino acid sequence of the mature transforming growth factor alpha from Homo sapiens

```
VVSHFNDCPD  SHTQFCFHGT  CRFLVQEDKP  ACVCHSGYVG  ARCEHADLLA
```

FIG. 28A

Amino acid sequence of amphiregulin preproprotein from Homo sapiens

```
MRAPLLPPAP  VVLSLLILGS  GHYAAGLDLN  DTYSGKREPF  SGDHSADGFE
VTSRSEMSSG  SEISPVSEMP  SSSEPSSGAD  YDYSEEYDNE  PQIPGYIVDD
SVRVEQVVKP  PQNKTESENT  SDKPKRKKKG  GKNGKNRRNR  KKKNPCNAEF
QNFCIHGECK  YIEHLEAVTC  KCQQEYFGER  CGEKSMKTHS  MIDSSLSKIA
LAAIAAFMSA  VILTAVAVIT  VQLRRQYVRK  YEGEAEERKK  LRQENGNVHA
IA
```

FIG. 28B

Amino acid sequence of the mature amphiregulin from Homo sapiens

```
SVRVEQVVKP  PQNKTESENT  SDKPKRKKKG  GKNGKNRRNR  KKKNPCNAEF  QNFCIHGECK
YIEHLEAVTC  KCQQEYFGER  CGEKSMK
```

FIG. 29A

Amino acid sequence of epiregulin preproprotein from Homo sapiens

```
MTAGRRMEML CAGRVPALLL CLGFHLLQAV LSTTVIPSCI PGESSDNCTA
LVQTEDNPRV AQVSITKCSS DMNGYCLHGQ CIYLVDMSQN YCRCEVGYTG
VRCEHFFLTV HQPLSKEYVA LTVILIILFL ITVVGSTYYF CRWYRNRKSK
EPKKEYERVT SGDPELPQV
```

FIG. 29B

Amino acid sequence of the mature epiregulin from Homo sapiens

```
VAQVSITKCS SDMNGYCLHG QCIYLVDMSQ NYCRCEVGYT GVRCEHFFL
```

FIG. 30A

Amino acid sequence of the epigen isoform 1 precursor from Homo sapiens

```
MALGVPISVY LLFNAMTALT EEAAVTVTPP ITAQQGNWTV NKTEADNIEG
PIALKFSHLC LEDHNSYCIN GACAFHHELE KAICRCFTGY TGERCEHLTL
TSYAVDSYEK YIAIGIGVGL LLSGFLVIFY CYIRKRCLKL KSPYNVCSGE
RRPL
```

FIG. 30B

Amino acid sequence of the epigen isoform 2 precursor from Homo sapiens

```
MALGVPISVY LLFNAMTALT EEAAVTVTPP ITAQQADNIE GPIALKFSHL
CLEDHNSYCI NGACAFHHEL EKAICRCFTG YTGERCEHLT LTSYAVDSYE
KYIAIGIGVG LLLSGFLVIF YCYIRKRYEK DKI
```

FIG. 30C

Amino acid sequence of the epigen isoform 3 precursor from Homo sapiens

```
MALGVPISVY LLFNAMTALT EEAAVTVTPP ITAQQGNWTV NKTEADNIEG
PIALKFSHLC LEDHNSYCIN GACAFHHELE KAICRCFTGY TGERCLKLKS
PYNVCSGERR PL
```

FIG. 30D

Amino acid sequence of the epigen isoform 4 precursor from Homo sapiens

```
MALGVPISVY LLFNAMTALT EEAAVTVTPP ITAQQGNWTV NKTEADNIEG
PIALKFSHLC LEDHNSYCIN GACAFHHELE KAICRCLKLK SPYNVCSGER
RPL
```

FIG. 30E

Amino acid sequence of the epigen isoform 5 precursor from Homo sapiens

```
MALGVPISVY LLFNAMTALT EEAAVTVTPP ITAQQADNIE GPIALKFSHL
CLEDHNSYCI NGACAFHHEL EKAICRCFTG YTGERCLKLK SPYNVCSGER
RPL
```

FIG. 30F

Amino acid sequence of the epigen isoform 6 precursor from Homo sapiens

```
MALGVPISVY LLFNAMTALT EEAAVTVTPP ITAQQADNIE GPIALKFSHL
CLEDHNSYCI NGACAFHHEL EKAICRCLKL KSPYNVCSGE RRPL
```

FIG. 30G

Amino acid sequence of the epigen isoform 7 precursor from Homo sapiens

```
MALGVPISVY LLFNADNIEG PIALKFSHLC LEDHNSYCIN GACAFHHELE
KAICRCLKLK SPYNVCSGER RPL
```

FIG. 30H

Amino acid sequence of the mature epigen from Homo sapiens

```
AAVTVTPPIT AQQGNWTVNK TEADNIEGPI ALKFSHLCLE DHNSYCINGA CAFHHELEKA
ICRCFTGYTG ERCEHLTLTS YAVDSYEKYI AIGIGVGLLL SGFLVIFYCY IRKRCLKLKS
PYNVCSGERR PL
```

FIG. 31A

Amino acid sequence of the betacellulin precursor from Homo sapiens

```
MDRAARCSGA SSLPLLLALA LGLVILHCVV ADGNSTRSPE TNGLLCGDPE
ENCAATTTQS KRKGHFSRCP KQYKHYCIKG RCRFVVAEQT PSCVCDEGYI
GARCERVDLF YLRGDRGQIL VICLIAVMVV FIILVIGVCT CCHPLRKRRK
RKKKEEEMET LGKDITPINE DIEETNIA
```

FIG. 31B

Amino acid sequence of the mature betacellulin from Homo sapiens

```
DGNSTRSPET NGLLCGDPEE NCAATTTQSK RKGHFSRCPK QYKHYCIKGR CRFVVAEQTP
SCVCDEGYIG ARCERVDLFY
```

FIG. 32A

Amino acid sequence of the mature fibroblast growth factor 2 from Homo sapiens

```
MAAGSITTLP ALPEDGGSGA FPPGHFKDPK RLYCKNGGFF LRIHPDGRVD
GVREKSDPHI KLQLQAEERG VVSIKGVCAN RYLAMKEDGR LLASKCVTDE
CFFFERLESN NYNTYRSRKY TSWYVALKRT GQYKLGSKTG PGQKAILFLP
MSAKS
```

FIG. 32B

Amino acid sequence of the fibroblast growth factor 2 variant hFGF2-153 used in the Examples

```
AGSITTLPAL PEDGGSGAFP PGHFKDPKRL YCKNGGFFLR IHPDGRVDGV
REKSDPHIKL QLQAEERGVV SIKGVCANRY LAMKEDGRLL ASKCVTDECF
FFERLESNNY NTYRSRKYTS WYVALKRTGQ YKLGSKTGPG QKAILFLPMS
AKS
```

FIG. 33

Amino acid sequence of the human interleukin 4 (hIL-4) variant used in the Examples

```
AHKCDITLQE  IIKTLNSLTE  QKTLCTELTV  TDIFAASKNT  TEKETFCRAA
TVLRQFYSHH  EKDTRCLGAT  AQQFHRHKQL  IRFLKRLDRN  LWGLAGLNSC
PVKEANQSTL  ENFLERLKTI  MREKYSKCSS
```

FIG. 34

Amino acid sequence of the human colony stimulating factor 1 (hCSF-1) variant used in the Examples

```
AEEVSEYCSH  MIGSGHLQSL  QRLIDSQMET  SCQITFEFVD  QEQLKDPVCY
LKKAFLLVQD  IMEDTMRFRD  NTPNAIAIVQ  LQELSLRLKS  CFTKDYEEHD
KACVRTFYET  PLQLLEKVKN  VFNETKNLLD  KDWNIFSKNC  NNSFAECSSQ
```
GHERQSEGS

FIG. 35

Amino acid sequence of the secretion signal of the Lactococcus protein Usp45 used in the Examples

```
MKKKIISAIL  MSTVILSAAA  PLSGVYA
```

RECOMBINANT PROBIOTIC BACTERIA

CROSS-REFERENCE TO RELATED APPLICATIONS

This application is the United States national phase of PCT International Application No. PCT/EP2015/075484 filed Nov. 2, 2015, which claims priority to PCT International Application No. PCT/EP2015/052345, filed Feb. 4, 2015, the disclosures of each of which are hereby incorporated by reference in their entireties.

The Sequence Listing associated with this application is filed in electronic format via EFS-Web and is hereby incorporated by reference into the specification in its entirety. The name of the text file containing the Sequence Listing is 1706092_ST25.txt. The size of the text file is 158,802 bytes, and the text file was created on Aug. 2, 2017.

BACKGROUND OF THE INVENTION

Field of the Invention

The invention is directed to recombinant probiotic bacteria, especially for use in the treatment of an inflammatory skin dysfunction, as well as a method for treating an inflammatory skin dysfunction.

Macrophages are a type of white blood cell that can be found in essentially all tissues. Macrophages play a critical role in non-specific defence and also help initiate specific defence mechanisms by recruiting other immune cells such as lymphocytes.

Macrophages exist as resilient tissue-specific macrophages or are derived from circulating blood monocytes which differentiate into macrophages.

Macrophages display various activation states. Two opposite activation states are known as classically activated macrophages, which are also designated as M1-polarized macrophages, and alternatively activated macrophages, which are also designated as M2-polarized macrophages.

The M1-polarized macrophages comprise immune effector cells with an active inflammatory phenotype. M1-polarized macrophages are characterized by the expression of high levels of pro-inflammatory cytokines, high production of reactive nitrogen and oxygen intermediates, promotion of $T_h1$ response, and strong microbicidal and tumoricidal activity.

The M2-polarized macrophages are an anti-inflammatory phenotype. M2-polarized macrophages are considered to be involved in parasite containment and promotion of tissue remodelling and tumor progression and to have immunoregulatory functions. M2-macrophages are also characterized by efficient phagocytic activity, high expression of scavenging molecules.

Plasticity and flexibility are features of mononuclear phagocytes of their activation states. For example, the phenotype of M1-polarized or M2-polarized macrophages can be reversed in vitro and in vivo.

Macrophages can change, depending on the stimulus in the micro-environment, the secretion pattern of cytokine and chemokines several times. For example, human primary M1-polarized macrophages can be repolarized by secreted factors from their own counterparts, to M2-polarized macrophages, and vice versa in vitro and in vivo.

In addition to presenting a first line of defence against pathogens, mononuclear phagocytes contribute to remodelling and repair of tissue under homeostatic and damaged conditions.

Moreover, macrophages are essential contributors towards the control of inflammation with M1-polarized macrophages implicated in initiating and sustaining inflammation and M2-polarized macrophages associated with the control of chronic inflammation.

For example, macrophages undergo dynamic changes during different phases of wound healing. M1-polarized macrophages mediate tissue damage and initiate inflammatory responses. Furthermore, during the early stages of repair response of a wound, the skin infiltrating macrophages show an M2-polarized phenotype and support the formation of a highly vascularized, cellular granulation tissue.

Inflammation can be characterized as acute inflammation, in settings such as sepsis, trauma, and wound healing, or as chronic inflammation, for example in diseases such as rheumatoid arthritis, ulcerative colitis, Crohn's disease, etc. Many other diseases, such as cancer, diabetes, arteriosclerosis, Alzheimer's and obesity are also associated with deregulated inflammation.

The acute inflammatory response involves a cascade of events, mediated by a large array of cells and molecules that locate invading pathogens or damaged tissue, alert and recruit other cells and molecules, eliminate the offending agents and finally restore the body to equilibrium.

In sepsis and trauma, this response is accompanied by macroscopic manifestations such as fever and elevated heart rate. In other tissues, inflammation manifests as redness, swelling and pain.

A feed-forward-loop of inflammation leading to damage/dysfunction leading to inflammation can result in a persistent, deregulated inflammation that promotes organ dysfunction and death. A well-regulated inflammatory response is necessary for proper tissue healing.

Restoration of skin integrity and homeostasis following injuries requires a complex and dynamic interplay of epithelial and mesenchymal cells together with tissue-resident and recruited hematopoietic cells to accomplish the sequential phases of the repair response: inflammation, tissue formation, and maturation. The early stage of the repair response is dominated by the inflammatory phase, which is characterized by local activation of the innate immune system resulting in an immediate influx of neutrophiles followed by subsequent invasion of blood monocytes, which differentiate into macrophages.

The mid-stage of the repair response includes the phase of tissue formation, which is characterized by the development of granulation tissue that refills the dermal wound space. Granulation tissue formation encompasses the invasion of endothelial cells resulting in angiogenesis, the influx of fibroblasts and the accumulation of additional macrophages.

Deposition of provisional extracellular wound matrix facilitates cell adhesion, migration and proliferation. Furthermore, at the wound edge, complex epidermal-mesenchymal interactions stimulate keratinocyte proliferation and migration to restore the epidermal barrier.

Granulation tissue formation continues until the wound space is refilled and the overlaying epidermis is restored. Upon completion of the epidermal barrier, the repair response enters the late stage, which is characterized by tissue maturation. During the phase of tissue maturation, granulation tissue transforms into scar tissue.

During skin repair, the innate immune response of resident cells as well as the recruited inflammatory cells combat invading microbes, contribute to the debridement, but may also support the repair process by releasing a spectrum of growth factors.

However, due to the release of proinflammatory and cytotoxic mediators, uncontrolled activity of macrophages may also be detrimental to tissue repair.

An imbalanced inflammation characterized by increased numbers of macrophages is a hallmark of an attenuated repair response in human diseases leading to the formation of non-healing chronic wounds. Additional factors that contribute to non-healing chronic wounds are, for example, diabetes, venal or arterial diseases, infection, and metabolic deficiencies in old age.

Various methods exist to treat chronic wounds, including the use of antibiotics for treating infections, debridement, vacuum-assisted closure, and oxygenation.

Further methods include, for example, the application of growth factors.

For example, becaplermin is a recombinant human platelet-derived growth factor BB. Becaplermin is sold under the trade name Regranex and is indicated for the treatment of lower extremity diabetic neuropathic ulcers that extend into the subcutaneous tissue or beyond and have an adequate blood supply.

Becaplermin is further indicated as an adjunct to, and not as a substitute for, foot ulcer care practices including initial sharp debridement, pressure release and infection control.

However, an increased rate of mortality secondary to malignancy was observed in patients treated with three or more tubes of Regranex gel in a post-marketing retrospective cohort study.

Another growth factor used is a recombinant human epidermal growth factor which is sold under the trade name REGEN-D gel and which is used for treating chronic diabetic foot ulcers.

Furthermore, trafermine is a recombinant form of human fibroblast growth factor 2, which is sold under the trade name "Fiblast Spray". Trafermine is used for the treatment of pressure ulcers and other skin ulcers including burn ulcers and black ulcers.

After daily application of trafermine or placebo during six weeks period to patients suffering from chronic diabetic neuropathic ulcer of the foot ulcer size was assessed through weekly clinical examination and computerized photographs. The weekly reduction in ulcer perimeter and area was identical in both groups, as was the rate of linear advance from entry to the sixth week of treatment. Moreover, the percentage of the healed area at the end of the study did not differ significantly. According to Richards et al. (1995) topical application of trafermine had no advantage over the placebo for healing chronic neuropathic diabetic ulcer of the foot.

Commercially available are also two dermal substitutes containing human embryonic cells, which secrete various growth factors after application to the diseased wound area.

The dermal substitute Dermagraft is composed of fibroblasts, extracellular matrix and a bioabsorbable scaffold. Dermagraf is manufactured from human fibroblast cells derived from donated newborn foreskin tissue.

During the manufacture process, the human fibroblasts are seeded onto a bioabsorbable polyglactin scaffold.

The commercially available dermal substitute Apligraf contains two cell types derived from neonatal foreskin. Living human keratinocytes and fibroblasts are embedded in a wound type 1 collagen matrix.

The disadvantage of the afore-mentioned dermal substitutes is a comparable high price which results from the manufacturing process. For example, maternal blood is tested for evidence of infection with human viruses, such as immuno deficiency virus type 1 and 2, hepatitis B virus, hepatitis C virus, syphilis, human T-lymphotropic type 1 and 2 as well as Epstein Barr virus.

A further commercially available product is sold under the tradename Procuren. Procuren is a platelet-derived wound healing formula for treating non-healing wounds. Procuren is an autologous platelet-derived product that is prepared from a sample of the patient's blood.

However, there is insufficient evidence regarding the effectiveness of autologous platelet-derived products, including autologous platelet-derived growth factor, for the treatment of chronic non-healing wounds or the treatment of other conditions such as acute surgical wounds.

Furthermore, the amount of growth factors supplied by the above-mentioned dermal substitutes as well as autologous platelet-derived product varies significantly depending on the quality of the starting material.

SUMMARY OF THE INVENTION

In some examples, provided herein is a recombinant probiotic bacteria, comprising: a nucleic acid sequence(s) encoding for a first heterologous factor, a nucleic acid sequence(s) encoding for a second heterologous factor, and optionally a nucleic acid sequence(s) encoding for a third heterologous factor, wherein said first factor, said second factor, and said third factor (if present) are functionally different from each other, wherein said first factor is a growth factor, wherein said second factor is selected from the group consisting of M2-polarizing factors, and wherein said third factor is selected from the group consisting of M2-polarizing factors and growth factors.

Also provided herein is a method of treating an inflammatory skin dysfunction, comprising the step of administering the above-described recombinant probiotic bacteria.

BRIEF DESCRIPTION OF THE DRAWINGS

The foregoing summary, as well as the detailed description, will be better understood when read in conjunction with the appended drawings. The present invention is described herein in greater detail using an embodiment and associated drawings. In the drawings:

FIG. 3 shows the nucleic acid sequence of the nisinA promoter of *L. lactis*, which is also shown in SEQ ID No. 44.

FIGS. 5a, 5b, and 5c show the synthesized inserts used in Example 1 as well as the corresponding amino acid sequence. "FGF2-153" denotes the human FGF-2 coding insert. "h1L4" denotes the human IL4 coding insert. "hCSF1" denotes the human CSF1 coding insert. "PnisA" denotes the nisinA promoter of the *Lactococcus lactis* nisin operon. "ssUsp45" denotes the signal sequence of the usp45 gene of *Lactococcus lactis*. An asterisk denotes a stop codon. The respective nucleic acid sequences are also depicted in SEQ ID No. 45, SEQ ID No. 47, and SEQ ID No. 49.

FIG. 16a shows the amino acid sequence of macrophage colony-stimulating factor 1 isoform a precursor from *Homo sapiens*. FIG. 16b shows the amino acid sequence of macrophage colony-stimulating factor 1 isoform b precursor from *Homo sapiens*. FIG. 16c shows the amino acid sequence of macrophage colony-stimulating factor 1 isoform c precursor from *Homo sapiens*. FIG. 16d shows the amino acid sequence of the mature human macrophage colony-stimulating factor 1.

FIG. 17a shows the amino acid sequence of interleukin-34 isoform 1 precursor from *Homo sapiens*. FIG. 17b shows the amino acid sequence of interleukin-34 isoform 2 precursor from *Homo sapiens*. FIG. 17c shows the amino acid sequence of interleukin-34 from *Homo sapiens*.

FIG. 18a shows the amino acid sequence of interleukin-4 isoform 1 precursor from *Homo sapiens*. FIG. 18b shows the amino acid sequence of interleukin-4 isoform 2 precursor from *Homo sapiens*. FIG. 18c shows the amino acid sequence of interleukin-4 from *Homo sapiens*.

FIG. 19a shows the amino acid sequence of interleukin-10 precursor from *Homo sapiens*. FIG. 19b shows the amino acid sequence of interleukin-10 from *Homo sapiens*.

FIG. 20a shows the amino acid sequence of interleukin-13 precursor from *Homo sapiens*. FIG. 20b shows the amino acid sequence of interleukin-13 from *Homo sapiens*.

FIG. 21a shows the amino acid sequence of transforming growth factor beta-1 precursor from *Homo sapiens*. FIG. 21b shows the amino acid sequence of transforming growth factor beta-1 from *Homo sapiens*. FIG. 21c shows the amino acid sequence of transforming growth factor beta-2 isoform 1 precursor from *Homo sapiens*. FIG. 21d shows the amino acid sequence of transforming growth factor beta-2 isoform 2 precursor from *Homo sapiens*. FIG. 21e shows the amino acid sequence of transforming growth factor beta-2 from *Homo sapiens*. FIG. 21f shows the amino acid sequence of transforming growth factor beta-3 preproprotein from *Homo sapiens*. FIG. 21g shows the amino acid sequence of transforming growth factor beta-3 from *Homo sapiens*.

FIG. 22a shows the amino acid sequence of fibroblast growth factor 2 precursor from *Homo sapiens*. FIG. 22b shows the amino acid sequence of a fragment of fibroblast growth factor 2 from *Homo sapiens*.

FIG. 23a: Amino acid sequence of hepatocyte growth factor from *Homo sapiens*. FIG. 23b: Amino acid sequence of hepatocyte growth factor alpha chain from *Homo sapiens*. FIG. 23c: Amino acid sequence of hepatocyte growth factor beta chain from *Homo sapiens*.

FIG. 25*a* shows the amino acid sequence of epidermal growth factor isoform 1 preproprotein from *Homo sapiens*. FIG. 25*b* shows the amino acid sequence of epidermal growth factor isoform 2 preproprotein from *Homo sapiens*. FIG. 25*c* shows the amino acid sequence of epidermal growth factor isoform 3 preproprotein from *Homo sapiens*. FIG. 25*d* shows the amino acid sequence of the mature epidermal growth factor from *Homo sapiens*.

FIG. 26*a* shows the amino acid sequence of the heparin-binding EGF-like growth factor precursor from *Homo sapiens*. FIG. 26*b* shows the amino acid sequence of the mature heparin-binding EGF-like growth factor from *Homo sapiens*.

FIG. 27*a* shows the amino acid sequence of transforming growth factor alpha isoform 1 preproprotein from *Homo sapiens*. FIG. 27*b* shows the amino acid sequence of transforming growth factor alpha isoform 2 preproprotein from *Homo sapiens*. FIG. 27*c* shows the amino acid sequence of transforming growth factor alpha isoform 3 preproprotein from *Homo sapiens*. FIG. 27*d* shows the amino acid sequence of transforming growth factor alpha isoform 4 preproprotein from *Homo sapiens*. FIG. 27*e* shows the amino acid sequence of transforming growth factor alpha isoform 5 preproprotein from *Homo sapiens*. FIG. 27*f* shows the amino acid sequence of the mature transforming growth factor alpha from *Homo sapiens*.

FIG. 28*a* shows the amino acid sequence of amphiregulin preproprotein from *Homo sapiens*. FIG. 28*b* shows the amino acid sequence of the mature amphiregulin from *Homo sapiens*.

FIG. 29*a* shows the amino acid sequence of epiregulin preproprotein from *Homo sapiens*. FIG. 29*b* shows the amino acid sequence of the mature epiregulin from *Homo sapiens*.

FIG. 30*a* shows the amino acid sequence of the human epigen isoform 1 precursor from *Homo sapiens*. FIG. 30*b* shows the amino acid sequence of the human epigen isoform 2 precursor from *Homo sapiens*. FIG. 30*c* shows the amino acid sequence of the human epigen isoform 3 precursor from *Homo sapiens*. FIG. 30*d* shows the amino acid sequence of the human epigen isoform 4 precursor from *Homo sapiens*. FIG. 30*e* shows the amino acid sequence of the human epigen isoform 5 precursor from *Homo sapiens*. FIG. 30*f* shows the amino acid sequence of the human epigen isoform 6 precursor from *Homo sapiens*. FIG. 30*g* shows the amino acid sequence of the human epigen isoform 7 precursor from *Homo sapiens*. FIG. 30*h* shows the amino acid sequence of the mature epigen from *Homo sapiens*.

FIG. 31 *a* shows the amino acid sequence of the betacellulin precursor from *Homo sapiens*. FIG. 31 *b* shows the amino acid sequence of the mature betacellulin from *Homo sapiens*.

FIG. 32*a* shows the amino acid sequence of the mature fibroblast growth factor 2 from *Homo sapiens*. FIG. 32*b* shows the amino acid sequence of the fibroblast growth factor 2 variant hFGF2-153 used in the Examples.

FIG. 33 shows the amino acid sequence of the human interleukin 4 (hIL-4) variant used in the Examples.

FIG. 34 shows the amino acid sequence of the human colony stimulating factor 1 (hCSF-1) variant used in the Examples.

FIG. 35 shows the amino acid sequence of the secretion signal of the *Lactococcus* protein Usp45 used in the Examples.

DETAILED DESCRIPTION

Figure 1:
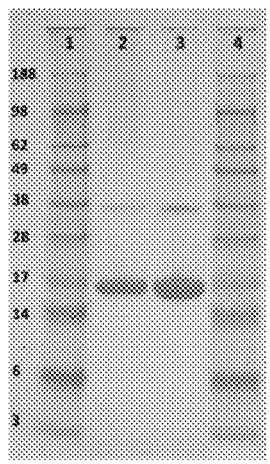
FIG. 1 shows a SDS-PAGE of a human FGF2 reference protein.

It is an object of the present invention to enable an alternative treatment of an inflammatory skin dysfunction, especially a chronic inflammatory skin dysfunction, which allows for an easy application of beneficial factors to the, preferably chronic, inflammatory skin dysfunction.

Furthermore, a controlled amount of beneficial factors supporting healing should be provided for treating an inflammatory skin dysfunction.

The object of the present invention is solved by providing recombinant probiotic bacteria according to claim 1 comprising (a) nucleic acid sequence(s) encoding for a first heterologous factor, (a) nucleic acid sequence(s) encoding for a second heterologous factor, and preferably (a) nucleic acid sequence(s) encoding for a third heterologous factor, with the proviso that said first factor, said second factor, and said third factor are functionally different from each other, wherein said first factor is a growth factor, wherein said second factor is selected from the group consisting of M2-polarizing factors, and wherein preferably said third factor is selected from the group consisting of M2-polarizing factors and growth factors.

Preferably, said recombinant probiotic bacteria according to claim 1 comprise at least one nucleic acid sequence encoding for a first heterologous factor, at least one nucleic acid sequence encoding for a second heterologous factor, and at least one nucleic acid sequence encoding for a third heterologous factor, with the proviso that said first factor, said second factor, and said third factor are functionally different from each other, wherein said first factor is a growth factor, wherein said second factor is selected from the group consisting of M2-polarizing factors and wherein said third factor is selected from the group consisting of M2-polarizing factors and growth factors.

Preferred embodiments of the recombinant probiotic bacteria are disclosed in dependent claims 2 to 22.

The object of the present invention is further solved by providing recombinant probiotic bacteria according to claim 17 for use in the treatment of an inflammatory skin dysfunction, preferably a chronic inflammatory skin dysfunction, said recombinant probiotic bacteria comprising:

at least one nucleic acid sequence encoding for a first heterologous factor, and at least one nucleic acid sequence encoding for a second heterologous factor, wherein said first factor is a growth factor and wherein said second factor is selected from the group consisting of M2-polarizing factors.

Preferably, said recombinant probiotic bacteria according to claim 17 comprise at least one nucleic acid sequence encoding for a first heterologous factor, at least one nucleic acid sequence encoding for a second heterologous factor, and at least one nucleic acid sequence encoding for a third heterologous factor, with the proviso that said first factor, said second factor, and said third factor are functionally different from each other, wherein said first factor is a growth factor, wherein said second factor is selected from the group consisting of M2-polarizing factors and wherein said third factor is selected from the group consisting of M2-polarizing factors and growth factors.

The object of the present invention is further solved by providing a method for treating an inflammatory skin dysfunction, preferably a chronic inflammatory skin dysfunction, according to claim 23, wherein said method comprises the step of administering recombinant probiotic bacteria according to any one of claims 1 to 22 to an individual suffering from said skin dysfunction.

The inventors surprisingly found that recombinant probiotic bacteria comprising the above-mentioned nucleic acid sequences could be used in the treatment of an inflammatory skin dysfunction, preferably a chronic inflammatory skin dysfunction.

Preferred embodiments of the present invention are disclosed in dependent claims.

According to the invention the term "functionally different factor" or "functionally different from each other" means that the respective factors preferably bind to different receptors and/or activate different second messengers in a target cell. Second messengers are intracellular signalling molecules released by the cell to trigger physiological changes.

According to the invention the term "functional analog" of a factor means an agent that binds to identical receptor(s) as the respective factor and preferably activates identical second messengers in a target cell.

For example, a functional analog of nisin binds to NisK, which acts as a receptor for the mature nisin molecule or a functional analog thereof, and, preferably, leads to a subsequent phosphorylation of NisR. Phosphorylated NisR induces transcription from the respective nisin promoter.

Preferably, "a functional analog" of said first, second, and third heterologous factor has a sequence identity of the amino acid sequence of at least 80%, further preferably of at least 90%, further preferably of at least 93%, further preferably of at least 95%, further preferably of at least 97%.

According to the invention the term "heterologous factor" means a factor, preferably a protein, which is not naturally occurring in or expressed by said probiotic bacteria used.

A "functional analog" can also be designated as biosimilar.

When referring to "heterologous factor(s)" in general or when referring to specific "heterologous factor(s)" such as, e.g. FGF-2, IL-4, CSF-1, etc., it is intended that this term includes also functional analog(s) thereof.

The recombinant probiotic bacteria comprising the above-mentioned nucleic acid sequences are able to constantly and/or upon induction produce a unique combination of the respective first, second, and, preferably third, heterologous factor by transcribing and translating the respective nucleic acid sequences.

This unique combination of factors comprises at least one growth factor, and at least one M2-polarizing factor.

Preferably, this unique combination of factors comprises a growth factor, a first M2-polarizing factor, and a second M2-polarizing factor different from said first M2-polarizing factor. Alternatively, this unique combination of factors comprises a first growth factor, a M2-polarizing factor, and a second growth factor different from said first growth factor.

The recombinant probiotic bacteria preferably deliver a variety of at least two, preferably at least three, heterologous factors as recited in claim 1 to diseased tissue, thus modulating local immune system and enabling healing.

Preferably, the recombinant probiotic bacteria release the respective first heterologous factor and second heterologous factor, and preferably third heterologous factor, after application to said inflammatory skin dysfunction, preferably said chronic inflammatory skin dysfunction.

Furthermore, the recombinant probiotic bacteria used according to the present invention preferably provide for a constant release of respective first heterologous factor and second heterologous factor, and preferably third heterologous factor, after application to the site of the inflammatory skin dysfunction, preferably chronic inflammatory skin dysfunction.

Thereby, a much-improved, safer, and more cost-effective treatment option for subjects suffering from said inflammatory skin dysfunction, preferably said chronic inflammatory skin dysfunction, is available.

Preferably, the respective first, second, and third heterologous factor, after release from the bacteria, exert a biological active function supporting healing of said inflammatory skin dysfunction, preferably chronic inflammatory skin dysfunction.

The first heterologous factor is a growth factor.

Preferably, said growth factor is selected from the group consisting of fibroblast growth factors (FGF), vascular endothelial growth factors (VEGF), epidermal growth factors (EGF), insulin-like growth factors (IGF), platelet-derived growth factors (PDGF), transforming growth factor beta (TGF-beta), nerve growth factor (NGF), activins, functional analogues thereof, biosimilars thereof, and mixtures thereof.

Of course, functional analogues of the aforementioned or below mentioned factors or biosimilars thereof can also be used within the scope of the invention as claimed.

Fibroblast growth factors are a family of growth factors, which are involved in angiogenesis, wound healing, and various endocrine signalling pathways.

In humans, 22 members of the FGF family have been identified, FGF-1 to FGF-14 and FGF-16 to FGF-23, which can be used in the present invention.

FGF-1 through FGF-10 bind the fibroblast growth factor receptors (FGFRs).

Fibroblast growth factor 1 is also known as acidic fibroblast growth factor. Fibroblast growth factor 2 is also known as basic fibroblast growth factor. Furthermore, fibroblast growth factor 7 is also known as keratinocyte growth factor (KGF) and fibroblast growth factor 10 is also known a keratinocyte growth factor 2 (KGF-2).

In a preferred embodiment, the fibroblast growth factors are selected from the group consisting of FGF-1, FGF-2, FGF-3, FGF-4, FGF-5, FGF-6, FGF-7, FGF-8, FGF-9, FGF-10, and mixtures thereof, further preferably FGF-1, FGF-2, FGF-7, FGF-10, and mixtures thereof, further preferably, FGF-2, FGF-7, functional analogues thereof, biosimilars thereof, and mixtures thereof, further preferably FGF-2.

For example, FGF-1 and FGF-2 can stimulate angiogenesis and are mitogenic for several cell types present at the site of an inflammatory skin dysfunction, including fibroblasts and keratinocytes. Furthermore, FGF-7 can stimulate wound reepithelization in a paracrine manner.

Fibroblast growth factor 2 (FGF-2), preferably human fibroblast growth factor 2 (hFGF-2), is implicated in diverse biological processes, including wound healing and tumor growth.

The mRNA for this gene contains multiple polyadenylation sites and is alternatively translated from non-AUG and AUG initiation codons, resulting in five different isoforms with distinct properties. The non-AUG isoforms are localized in the nucleus and are responsible for the intracrine effect whereas the AUG-initiated form is mostly cytosolic and is responsible for the paracrine and autocrine effects of FGF-2.

The nucleic acid sequence of the mRNA of the human fibroblast growth factor 2 (hFGF-2) is available under the NCBI accession number NM_002006.4. The respective amino acid sequence of the AUG-isomer is available under the NCBI accession number NP_001997.5 as well as the UniProt accession number P09038-version 182 and is also shown in FIG. 22A.

The preproprotein includes a propeptide, which spans the amino acids 1 to 142 of the preproprotein, and the mature human fibroblast growth factor 2 peptide, which spans the amino acids 143 to 288 of the preproprotein.

In a preferred embodiment, fibroblast growth factor 2 comprises one or at least one of the amino acid sequences of SEQ IDs 26 to 30, further preferably the amino acid sequence of SEQ ID 28. The amino acid sequence of SEQ ID 28 is depicted in FIG. 22B.

The insulin-like growth factors (IGFs) are proteins with a high sequence similarity to insulin. The insulin-like growth factors comprise two proteins IGF-1 and IGF-2, which can be used in the present invention.

The family of epidermal growth factors (EGFs) are proteins with highly similar structural and functional characteristics and comprises the proteins epidermal growth factor (EGF), heparin-binding EGF-like growth factor (HB-EGF), transforming growth factor-α (TGF-α), amphiregulin (AR), epiregulin (EPR), epigen (EPGN), betacellulin (BTC), neuregulin-1 (NRG1), neuregulin-2 (NRG2), neuregulin-3 (NRG3), and neuregulin-4 (NRG4), preferably epidermal growth factor (EGF), heparin-binding EGF-like growth factor (HB-EGF), transforming growth factor-α (TGF-α), amphiregulin (AR), epiregulin (EPR), epigen (EPGN), and betacellulin (BTC), further preferably epidermal growth factor (EGF), heparin-binding EGF-like growth factor (HB-EGF), and transforming growth factor-α (TGF-α), which can be used in the present invention.

Epidermal growth factor (EGF), preferably human epidermal growth factor (hEGF), stimulates the growth of various epidermal and epithelial tissues in vivo and in vitro and of some fibroblasts in cell culture. Furthermore, hEGF has a profound effect on the differentiation of specific cells in vivo and is a potent mitogenic factor for a variety of cultured cells of both ectodermal and mesodermal origin.

Human epidermal growth factor exists in at least three isoforms produced by alternative splicing.

The amino acid sequence of the human epidermal growth factor isoform 1 preproprotein is available under the NCBI accession number NP_001954.1. The respective nucleic acid sequence of the mRNA is available under the NCBI accession number NM_001963.2.

The preproprotein of isoform 1 includes a signal peptide, which spans the amino acids 1 to 22 of the preproprotein, a propeptide which spans the amino acids 23 to 1207 of the preproprotein and the mature human epidermal growth factor peptide, which spans the amino acids 971 to 1023 of the preproprotein.

The amino acid sequence of the human epidermal growth factor isoform 2 preproprotein is available under the NCBI accession number NP_001171601.1. The respective nucleic acid sequence of the mRNA is available under the NCBI accession number NM_001178130.1. The amino acid sequence of the human epidermal growth factor isoform 3 preproprotein is available under the NCBI accession number NP_001171602.1. The respective nucleic acid sequence of the mRNA is available under the NCBI accession number NM_001178131.1. The amino acid sequences of the human epidermal growth factor isoforms 1 to 3 are also available under UniProt accession number P01133—version 180 and are also shown in FIGS. 25A-25C. The amino acid sequence of the mature human epidermal growth factor is shown in FIG. 25D.

Heparin-binding EGF-like growth factor (HB-EGF), preferably human heparin-binding EGF-like growth factor (hHB-EGF), is an important growth factor in the epithelialization required for cutaneous wound healing. hHB-EGF has a mitogenic and migratory effects on keratinocytes and fibroblasts. hHB-EGF further promotes dermal repair and angiogenesis which is necessary for wound healing. hHB-EGF is a major component of wound fluids. hHB-EGF is released by macrophages, monocytes, and keratinoctyes. Furthermore, hHB-EGF cell surface binding to heparan sulfate proteoglycans enhances mitogen promoting capabilities increasing the rate of skin wound healing, decreasing human skin graft healing times, and promotes rapid healing of ulcers, burns, and epidermal split thickness wounds.

The amino acid sequence of the human heparin-binding EGF-like growth factor preproprotein is available under the NCBI accession number NP_001936.1. The respective nucleic acid sequence of the mRNA is available under the NCBI accession number NM_001945.2.

The precursor of human heparin-binding EGF-like growth factor includes a signal peptide, which spans the amino acids 1 to 19 of the precursor, proheparin-binding EGF-like growth factor which spans the amino acids 20 to 208 of the precursor and the mature human epidermal growth factor peptide, which spans the amino acids 63 to 148 of the precursor.

The amino acid sequence of human heparin-binding EGF-like growth factor is also available under UniProt accession number Q99075—version 151 and is also shown in FIG. 26A. The amino acid sequence of the mature human heparin-binding EGF-like growth factor is shown in FIG. 26B.

Transforming growth factor-α (TGF-α), preferably human transforming growth factor-α (hTGF-α), can be produced in macrophages, brain cells, and keratinocytes. hTGF-α induces epithelial development. hTGF-α and hEGF bind to the same receptor, epidermal growth factor receptor (EGFR; ErbB-1; HER1 in humans). When TGF-α binds to EGFR it can initiate multiple cell proliferation events including wound healing.

Human transforming growth factor—a exists in at least five isoforms produced by alternative splicing.

The amino acid sequence of the human transforming growth factor alpha isoform 1 preproprotein is available under the NCBI accession number NP_003227.1. The respective nucleic acid sequence of the mRNA is available under the NCBI accession number NM_003236.2.

The precursor of human transforming growth factor alpha isoform 1 includes a signal peptide, which spans the amino acids 1 to 23 of the precursor, protransforming growth factor alpha isoform 1 which spans the amino acids 24 to 160 of the precursor and the mature transforming growth factor alpha peptide, which spans the amino acids 40 to 89 of the precursor.

The amino acid sequence of the human transforming growth factor alpha isoform 2 preproprotein is available under the NCBI accession number NP_001093161.1. The respective nucleic acid sequence of the mRNA is available under the NCBI accession number NM_001099691.1.

The amino acid sequence of the human transforming growth factor alpha isoform 3 preproprotein is available under the NCBI accession number NP_001295087.1. The respective nucleic acid sequence of the mRNA is available under the NCBI accession number NM_001308158.1.

The amino acid sequence of the human transforming growth factor alpha isoform 4 preproprotein is available under the NCBI accession number NP_001295088.1. The respective nucleic acid sequence of the mRNA is available under the NCBI accession number NM_001308159.1.

The amino acid sequence of the human transforming growth factor alpha isoform 5 preproprotein is available under the NCBI accession number AAF05090.1. The respective nucleic acid sequence of the mRNA is available under the NCBI accession number AF149097.1.

The amino acid sequences of the precursors of human transforming growth factor alpha isoforms 1 to 5 are also available under UniProt accession number P01135—version 168 and are shown in FIGS. 27A-27E. The amino acid sequence of the mature human transforming growth factor alpha is shown in FIG. 27F.

Amphiregulin (AREG), preferably human amphiregulin (hAREG), is another ligand of the EGF receptor. Human amphiregulin is an autocrine growth factor as well as a mitogen for a broad range of target cells including astrocytes, schwann cells and fibroblasts. Human amphiregulin promotes the growth of epithelial cells.

The amino acid sequence of the human amphiregulin preproprotein is available under the NCBI accession number NP_001648.1. The respective nucleic acid sequence of the mRNA is available under the NCBI accession number NM_001657.3.

The precursor of human amphiregulin preproprotein includes a signal peptide, which spans the amino acids 1 to 19 of the preproprotein, a propeptide which spans the amino acids 20 to 100 of the preproprotein and the mature transforming growth factor alpha peptide, which spans the amino acids 101 to 187 of the preproprotein.

The amino acid sequence of the human amphiregulin preproprotein is also available under UniProt accession number P15514—version 147 and is also shown in FIG. 28A. The amino acid sequence of the mature human amphiregulin is shown in FIG. 28B.

Epiregulin (EPR), preferably human epiregulin (hEPR), is a ligand of the EGF receptor which can stimulate cell proliferation and/or angiogenesis.

The amino acid sequence of the human epiregulin preproprotein is available under the NCBI accession number NP_001423.1. The respective nucleic acid sequence of the mRNA is available under the NCBI accession number NM_001432.1.

The preproprotein of human epiregulin includes a signal peptide, which spans the amino acids 1 to 29 of the preproprotein, proepiregulin which spans the amino acids 30 to 169 of the preproprotein and the mature epiregulin, which spans the amino acids 60 to 108 of the preproprotein.

The amino acid sequence of the human epiregulin preproprotein is also available under UniProt accession number O14944—version 146 and is also shown in FIG. 29A. The amino acid sequence of the mature human epiregulin is shown in FIG. 29B.

Epigen (EPGN), preferably human epigen (hEPGN), promotes the growth of epithelial cells. Human epigen exists in at least seven isoforms produced by alternative splicing.

The amino acid sequence of the human epigen isoform 1 precursor is available under the NCBI accession number NP_001257918.1. The respective nucleic acid sequence of the mRNA is available under the NCBI accession number NM_001270989.1.

The human epigen isoform 1 precursor includes a signal peptide, which spans the amino acids 1 to 22 of the precursor and the mature epiregulin, which spans the amino acids 23 to 154 of the precursor.

The amino acid sequence of the human epigen isoforms 1 to 7 precursors is also available under UniProt accession number Q6UW88—version 101 and is also shown in FIGS. 30A-30G. The amino acid sequence of the mature human epigen is shown in FIG. 30H.

Betacellulin (BTC), preferably human betacellulin (hBTC), is a growth factor that also binds to epidermal growth factor receptor and that is synthesized by a wide range of adult tissues and in many cultured cells, including smooth muscle cells and epithelial cells. The amino acid sequence of the human probetacellulin precursor is available under the NCBI accession number NP_001720.1. The respective nucleic acid sequence of the mRNA is available under the NCBI accession number NM_001729.1.

The precursor of human probetacellulin includes a signal peptide, which spans the amino acids 1 to 31 of the precursor, probetacellulin, which spans the amino acids 32 to 178 of the precursor, and the mature betacellulin, which spans the amino acids 32 to 111 of the precursor.

The amino acid sequence of the human probetacellulin precursor is also available under UniProt accession number P35070—version 139 and is also shown in FIG. 31A. The amino acid sequence of the mature human betacellulin is shown in FIG. 31B.

Insulin-like growth factor 1 (IGF-1) is also called somatomedin C. The nucleic acid sequence of the mRNA of the human IGF-1 is available under the NCBI accession number NM_000618.2. The respective amino acid sequence is available under NCBI accession number NP_000609.1 as well as the UniProt accession number P05019—version 178.

The preproprotein includes a signal peptide, which spans the amino acids 1 to 21 of the preproprotein, and the human insulin-like growth factor 1 peptide, which spans the amino acids 49 to 118 of the preproprotein.

The nucleic acid sequence of the mRNA of the human insulin-like growth factor 2 (hIGF-2) is available under the NCBI accession number NM_000612.4. The respective amino acid sequence of the human insulin-like growth factor 2 preproprotein is available under the NCBI accession number NP_000603.1 as well as the UniProt accession number P01344—version 192.

The preproprotein includes a signal peptide, which spans the amino acids 1 to 24 of the preproprotein, and the mature chain of the insulin-like growth factor 2, which spans the amino acids 25 to 91 of the preproprotein.

The family of vascular endothelial growth factors (VEGF) is a group of growth factors which include VEGF-A, VEGF-B, VEGF-C, VEGF-D and placental growth factor (PGF), which can be used in the present invention.

In a preferred embodiment, the vascular endothelial growth factor is the vascular endothelial growth factor A (VEGF-A).

VEGF-A can induce angiogenesis, vasculogenesis and endothelial cell growth.

The nucleic acid sequence of the mRNA of the human vascular endothelial growth factor A (hVEGF-A) is available under the NCBI accession number NM_001025366.1. The respective amino acid sequence of the human vascular endothelial growth factor A is available under the NCBI accession number NP_001020537.2 as well as the UniProt accession number P15692—version 197.

The precursor protein of the human vascular endothelial growth factor A includes a signal peptide, which spans the amino acids 1 to 26 of the precursor protein, as well as the mature human vascular endothelial growth factor A, which spans the amino acids 27 to 232 of the precursor protein.

Platelet-derived growth factor (PDGF) regulates cell growth and division. Human platelet-derived growth factor (hPDGF) has four subunits, PDGF-A, PDGF-B, PDGF-C and PDGF-D, which form either homo- or heterodimers of the respective subunits, which can be used in the present invention.

Preferably, the platelet-derived growth factor is PDGF-AA, PDGF-BB, PDGF-AB, PDGF-CC, PDGF-DD, or a mixture thereof.

Further preferably, the platelet-derived growth factor is a dimeric protein composed of two PDGF-A subunits, a dimeric glycoprotein composed of two PDGF-B subunits, a dimeric glycoprotein composed of a PDGF-A subunit and a PDGF-B subunit, or a mixture thereof.

The nucleic acid sequence of the mRNA of the human platelet-derived growth factor subunit A (hPDGF-A) is available under the NCBI accession number NM_002607.4. The respective amino acid sequence is available under the NCBI accession number NP_002598.4 as well as the UniProt accession number P04085—version 159.

The respective preproprotein of the human PDGF-A subunit encodes a signal peptide, which spans the amino acids 1 to 20 of the preproprotein, and the mature human platelet-derived growth factor subunit A which spans the amino acids 87 to 211 of the preproprotein.

The nucleic acid sequence of the mRNA of the human platelet-derived growth factor subunit B (hPDGF) is available under the NCBI accession number NM_002608.1. The respective amino acid sequence of the human platelet-derived growth factor subunit preproprotein is available under the NCBI accession number NP_002599.1 as well as the UniProt accession number P01127—version 181.

The preproprotein of the human PDGF-B subunit encodes a signal peptide, spanning the amino acids 1 to 20 of the preproprotein, and the mature form of the human platelet-derived growth factor subunit B, which spans the amino acids 82 to 190 of the preproprotein.

Hepatocyte growth factor (HGF) is a growth factor which is secreted by mesenchymal cells and acts primarily upon epithelial cells and endothelial cells but also on hemapoeitic progenitor cells and can be used in the present invention.

HGF is secreted as a single preproprotein and is cleaved by serine proteinase into a 69-kGa alpha chain and a 34-kDa beta chain. The amino acid sequence of the preproprotein as well as the respective alpha and beta chain are depicted in FIGS. 23A-23C.

The nucleic acid sequence of the mRNA of the human hepatocyte growth factor (hHGF) is available under the NCBI accession number NM_000601.3. The respective amino acid sequence of the human hepatocyte growth factor preproprotein is available under the NCBI accession number NP_000592.3 as well as the UniProt accession number P14210—version 186.

The preproprotein includes a signal peptide, which spans the amino acids 1 to 31 of the preproprotein, the human hepatocyte growth factor alpha chain, which spans the amino acids 32 to 494 of the preproprotein, and the human hepatocyte growth factor beta chain, which spans the amino acids 495 to 728 of the preproprotein.

Transforming growth factor β (TGF-β), preferably human transforming growth factor β (hTGF-β), is a cytokine which is secreted by many cell types, including macrophages. TGF-β exists in at least three isoforms, TGF-β1, TFG-β2 and TGF-β3, which can be used in the present invention. The amino acid sequences of the respective precursor proteins and of the mature proteins is depicted in FIGS. 21A-21G.

Human transforming growth factor β is a secreted protein that is cleaved into a latency-associated peptide (LAP) and a mature TGF-β1 peptide. The mature peptide may either form TGF-β1 homodimers or heterodimers with other TGF-β family members.

The nucleic acid sequence of the mRNA of the human transforming growth factor β1 precursor can be obtained by the NCBI accession number NM_000660.4. The respective amino acid sequence is available under the NCBI accession number NP_000651.3 or the UniProt accession number P01137—version 199.

The amino acid sequence of the human TGF-β1 precursor includes a signal peptide, which spans the amino acids 1 to 29 of the precursor protein, the latency-associated peptide, which spans the amino acid 30 to 278 of the precursor protein, and the mature transforming growth factor β1, which spans the amino acids 279 to 390 of the precursor protein.

Transforming growth factor β2 (TGF-β2), preferably human transforming growth factor β2 (hTGF-β2), is a multifunctional cytokine that regulates proliferation, differentiation, adhesion, and migration of many cell types.

Alternatively spliced transcript variants of the human transforming growth factor β2 gene have been identified, which encode two different isoforms.

The nucleic acid sequence of the mRNA of the human human transforming growth factor beta 2 isoform 1 precursor is available under the NCBI accession number NM_001135599.3. The respective amino acid sequence is available under the NCBI accession number NP_001129071.1.

The human transforming growth factor beta 2 isoform 1 precursor includes a signal peptide spanning the amino acids 1 to 20 of the precursor protein, a latency-associated peptide, which spans the amino acids 21 to 302 of the precursor protein, and the mature transforming growth factor beta 2, which spans the amino acids 303 to 414 of the precursor protein.

The nucleic acid sequence of the mRNA of the human transforming growth factor β2 isoform 2 precursor is available under the NCBI accession number NM_003238.3. The respective amino acid sequence is available under the NCBI accession number NP_003229.1. The precursor protein includes a signal peptide, which spans the amino acids 1 to 20 of the precursor protein, a latency associated peptide, which spans the amino acids 21 to 302 of the precursor protein, and the mature TGF-β2 peptide, which spans the amino acids 303 to 414 of the precursor protein.

The amino acid sequence of transforming growth factor β2 is further available under the UniProt accession number P61812—version 128.

Transforming growth factor β3 (TGF-β3), preferably human transforming growth factor β3 (hTGF-β3), is a secreted cytokine that is involved in embryogenesis and cell differentiation.

The nucleic acid sequence of the mRNA of the human transforming growth factor β3 precursor protein is available under the NCBI accession number NM_003239.3. The corresponding amino acid sequence is available under the NCBI accession number NP_003230.1 as well as the UniProt accession number P10600—version 170.

The precursor protein includes a signal peptide, which includes the amino acids 1 to 23 of the precursor protein, a latency associated peptide, which includes the amino acids 24 to 30 of the precursor protein, and the mature transforming growth factor β3 peptide, which spans the amino acids 301 to 412 of the precursor protein.

Preferably, transforming growth factor β comprises one or at least one of the amino acid sequences of SEQ IDs 19 to 25

Activins are disulfide-linked dimeric proteins originally purified from gonadal fluids as proteins that stimulated pituitary follicle stimulating hormone (FSH) release. Activin proteins have a wide range of biological activities, including mesoderm induction, neural cell differentiation, bone remodeling, hematopoiesis and roles in reproductive physiology.

Activins are homodimers or heterodimers of the various beta subunit isoforms, while inhibins are heterodimers of a unique alpha subunit and one of the various beta subunits.

Four beta subunits are known, beta A, beta B, beta C, and beta E.

The second heterologous factor is selected from the group consisting of M2-polarizing factors.

Preferably, M2-polarzing factors act on unpolarized macrophages, M1-polarized macrophages as well as undifferentiated monocytes, and other macrophage progenitor cells.

Further preferably, said M2-polarzing factors induce M2-polarization of unpolarized macrophages, M1-polarized macrophages as well as undifferentiated monocytes, and other macrophage progenitor cells.

It is known to the skilled person that Macrophages can undergo specific differentiation depending on the local tissue environment. Similar to the T-helper type 1 ($T_H1$) and T-helper type 2 ($T_H2$) polarization, two distinct states of polarization of macrophages have been defined: the classically activated (M1-polarized) macrophage phenotype and the alternatively activated (M2-polarized) macrophage phenotype.

The M2-polarized macrophage phenotype can be further divided into subsets: M2a-polarized, M2b-polarized and M2c-polarized phenotype based on gene expression profiles.

M1-polarized and M2-polarized macrophages have distinct chemokines and chemokine receptor profiles.

M1-polarized macrophages secrete preferably the $T_H1$ cell-attracting chemokines chemokine (C-X-C motif) ligand 9 (CXCL9) and C-X-C motif chemokine 10 (CXCL10). M2-polarized macrophages secrete preferably the chemokines chemokine (C-C motif) ligand 17 (CCL17), C-C motif chemokine 22 (CCL22), and chemokine (C-C motif) ligand 24 (CCL24).

An M2-polarising effect of a heterologous factor can, for example, be determined by contacting unpolarized macrophages, M1-polarized macrophages, or macrophage progenitor cells, preferably monocytes, with at least one M2-polarizing factor, and, subsequently, determining the expression and/or secretion of M2-polarization markers.

For example, a murine unpolarized macrophage cell line, a murine M1-polarized macrophage cell line, or a murine macrophage progenitor cell line, preferably a murine monocyte cell line, can be contacted with at least one M2-polarizing factor generating a murine M2-polarized macrophage cell line. M2-polarization of murine macrophage cell lines can, for example, be detected by determining expression of the following factors: arginase 1 (Arg1), interleukin 10 (IL-10), mannose receptor C type 1 (Mrc1) and Ym1, which is also called T-lymphocyte-derived eosinophil chemotactic factor (ECF-L) or Chitinase-like protein 3 (Chil3). M1 polarization of murine macrophage cell lines can, for example, be detected by determining expression and/or release of the following factors: tumor necrosis factor alpha (TNFalpha, TNFα), interleukin 6 (IL-6), chemokine (C-C motif) ligand 2 (CCL2), and chemokine (C-C motif) ligand 4 (CCL4).

Preferably human M2-polarized macrophages are derived from human monocytes, which are incubated with at least one M2-polarzing factor. M2-polarization of macrophages derived from human monocytes can, for example, be detected by determining expression and/or release of the following factors: interleukin 1 receptor antagonist (IL1RA), prostaglandin E2 (PGE2), interleukin 10 (IL-10), and transforming growth factor beta (TGF-β).

It has recently been demonstrated that, in vitro, macrophages are capable of reverse polarization from M2 to M1, and vice versa, in response to changes in the cytokine environment (Davis et al. (2013)). Furthermore, the change in polarization is rapid and occurs at the level of gene expression, protein, metabolite, and microbicidal activity.

Furthermore, macrophages are one of the major populations of infiltrating leukocytes associated with solid tumors. Tumor associated macrophages (TAMs) play an important role in tumor immunity and show similar functions to M2-polarization, also designated M2d TAM polarization.

The respective factors necessary for stimulation and/or activation of the respective polarization (M1, M2a, M2b, M2c, and M2d TAM) are known to the skilled person and, for example, are disclosed in Hao et al. (2012) or Duluc et al. (2007).

Preferably, the respective second heterologous factors and, optionally, third heterologous factor induce M2-polarization after expression in said recombinant probiotic bacteria and release from the bacteria into the site of the inflammatory, preferably chronic inflammatory, skin dysfunction.

Anti-inflammatory M2-polarized macrophages then preferably promote angiogenesis, connective tissue deposition, and wound repair, which leads to an improval, preferably curing, of said inflammatory, preferably chronic inflammatory, skin dysfunction to be treated.

In a preferred embodiment, said M2 polarizing factor is selected from the group consisting of M2-polarizing cytokines, M2-polarizing chemokines, and mixtures thereof. Preferably, said M2 polarizing factor induces M2c polarization.

Further preferably, said M2-polarizing factor is selected from the group consisting of interleukin 4 (IL-4), interleukin 10 (IL-10), interleukin 13 (IL-13), colony stimulating factor-1 (CSF1), interleukin 34 (IL34), functional analogues thereof, biosimilars thereof, and mixtures thereof, preferably interleukin 4 (IL-4), interleukin 10 (IL-10), interleukin 13 (IL-13), colony stimulating factor-1 (CSF1), interleukin 34 (IL34), and mixtures thereof, further preferably colony stimulating factor-1 (CSF1), interleukin 34 (IL34) interleukin 4 (IL-4), interleukin 13 (IL-13), functional analogues thereof, biosimilars thereof, and mixtures thereof, further preferably colony stimulating factor-1 (CSF1), interleukin 34 (IL34) interleukin 4 (IL-4), interleukin 13 (IL-13), and mixtures thereof.

Interleukin 4 (IL-4), preferably human interleukin 4 (hIL-4), is a pleiotropic cytokine. Interleukin 4 is a ligand for the interleukin 4 receptor. The interleukin 4 receptor also binds to interleukin 13 (IL-13), which may contribute to many overlapping functions of interleukin 4 and interleukin 13.

Interleukin 4 (IL-4) has also shown to have proliferation inducing properties. Furthermore, interleukin 4 (IL-4) induces the production of collagen.

The nucleic acid sequence of the mRNA of the human interleukin 4 isoform 1 precursor is available under the NCPI-accession number NM_000589.3. The respective amino acid sequence is available under the NCBI accession number NP_000580.1 and is depicted in FIG. 18A.

The nucleic acid sequence of the mRNA of the human interleukin 4 isoform 2 precursor is available under the NCBI accession number NM_172348.2. The respective amino acid sequence is available under the NCBI accession number NP_758858.1 and is depicted in FIG. 18B.

The amino acid sequence of human interleukin 4 is also available under the UniProt accession number P05112—version 178.

The amino acid sequences comprise a signal peptide which spans the amino acids 1 to 24 of the interleukin 4 isoform 1 and isoform 2 precursors.

Preferably, human interleukin 4 comprises one or at least one of the amino acid sequences of SEQ IDs 10 to 14.

Interleukin 13 (IL-13), preferably human interleukin 13 (hIL-13), is an immuno-regulatory cytokine produced primarily by activated $T_H2$ cells.

The nucleic acid sequence of the mRNA of the human interleukin 13 precursor is available under the NCBI accession number NM_002188.2. The respective amino acid sequence is available under the NCBI accession number NP_002179.2 as well as the UniProt accession number P35225—version 157 and is depicted in FIG. 20A.

The interleukin 13 precursor comprises a signal peptide which spans the amino acids 1 to 24 of the interleukin 13 precursor protein deposited under UniProt accession number P35225—version 157.

Preferably, interleukin 13 comprises one or at least one of the amino acid sequence of SEQ IDs 17 and 18.

Interleukin 10 (IL-10), preferably human interleukin 10 (hIL-10), is a cytokine produced primarily by monocytes and to a lesser extend by lymphocytes. Interleukin 10 has pleiotropic effects in immunoregulation and inflammation. For example interleukin 10 down-regulates the expression of $T_H1$ cytokines.

The nucleic acid sequence of the mRNA of the human interleukin 10 precursor can be found under the NCBI accession number NM_000572.2. The respective amino acid sequence can be found under the NCBI accession number NP_000563.1 as well as the UniProt accession number P22301—version 156 and is depicted in FIG. 19A.

The amino acid sequence of the human interleukin 10 precursor includes a signal peptide spanning the amino acids 1 to 18 of the human interleukin 10 precursor protein.

Preferably, interleukin 10 comprises one or at least one of the amino acid sequences of SEQ IDs 15 to 16.

Colony stimulating factor-1 (CSF-1), which is also known as macrophage colony-stimulating factor (M-CSF), is a cytokine that controls the production, differentiation, and function of macrophages.

Due to alternative splicing, the human CSF-1 exists in different isoforms, which can be used in the present invention.

The nucleic acid sequence of the mRNA of the human CSF-1 isoform 1, which is also designated as macrophage colony-stimulating factor 1 isoform A precursor, is available under the NCBI accession number NM_000757.5. The corresponding amino acid sequence is available under the NCBI accession number NP_000748.3 and is depicted in FIG. 16A.

The nucleic acid sequence of the mRNA of the human CSF-1 isoform 2 precursor, which is also designated human macrophage colony-stimulating factor 1 isoform B precursor, is available under the NCBI accession number NM_172210.2. The corresponding amino acid sequence is available under the NCBI accession number NP_757349.1 and is depicted in FIG. 16B.

The nucleic acid sequence of the mRNA of the human CSF-1 isoform 3 precursor, which is also designated as macrophage colony-stimulating factor 1 isoform C precursor, is available under the NCBI accession number NM_172211.3. The corresponding amino acid sequence is available under the NCBI accession number NP_757350.1 and is depicted in FIG. 16C.

The respective amino acid sequences are also available under the UniProt accession number P09603—version 158. Isoform 1 has been chosen as canonical UniProt sequence.

The respective protein sequences of the human CSF-1 precursor isoforms 1 to 3 include an N-terminal signal peptide, which spans the amino acid number 1 to amino acid number 32 of the respective amino acid sequences.

The active form of human CSF-1 can be found extracellularly as a disulfide-linked homodimer. The active form is produced by proteolytic cleavage of a membrane-bound precursor resulting in the loss of the N-terminal signal peptide.

Preferably, colony stimulating factor 1 comprises one or at least one of the amino acid sequences of SEQ IDs 1 to 6.

Interleukin 34 (IL-34) is a cytokine that also promotes the differentiation and viability of monocytes and macrophages.

Due to alternative splicing, human interleukin 34 exists in two isoforms, which can be used in the present invention.

The nucleic acid sequence of the mRNA of the human interleukin 34 isoform 1 precursor is available under the NCBI accession number NM_001172772.1. The corresponding amino acid sequence is available under the NCBI accession number NP_001166243.1 and is depicted in FIG. 17A.

The nucleic acid sequence of the mRNA of the human interleukin 34 isoform 2 precursor is available under the NCBI accession number NM_001172771.1. The corresponding amino acid sequence is available under the NCBI accession number NP_001166242.1 and is depicted in FIG. 17B.

The respective amino acid sequence is also available under the UniProt accession number Q6ZMJ4—version 80.

The human interleukin 34 precursor includes a signal peptide, which spans the amino acids 1 to 20 of the respective amino acid sequences of the precursor proteins.

Preferably, interleukin 34 comprises one or at least of the amino acid sequences of SEQ IDs 7 to 9.

In a preferred embodiment, said M2-polarizing factor promotes the differentiation and viability of monocytes and macrophages through binding to the colony stimulating factor-1 receptor.

Colony stimulating factor-1 receptor (CSF1R), which is also known as macrophage colony stimulating-factor receptor, is a tyrosine protein-kinase that acts as a cell surface receptor and plays an essential role at the regulation of survival, proliferation and differentiation of macrophages and monocytes.

CSF1R promotes, for example, the release of pro-inflammatory chemokines in response to the binding of CSF1R ligand and thereby plays an important role at innate immunity and in inflammatory processes.

Preferably said M2-polarizing factor is at least one colony stimulating factor-1 receptor (CSF1R) ligand.

CSF1R ligands are known to the skilled person and include interleukin 34 (IL-34) and colony stimulating-factor 1 (CSF-1). Preferably, said colony stimulating factor-1 receptor ligand is selected from the group consisting of colony stimulating factor-1 (CSF-1), interleukin 34 (IL-34), functional analogs thereof, and biosimilars thereof.

Further preferably, said colony stimulating factor-1 receptor ligand is a human colony stimulating factor-1 receptor ligand, further preferably selected from the group consisting of human colony stimulating factor-1 (hCSF-1), human interleukin 34 (hIL-34), functional analogs thereof, and biosimilars thereof.

In a further preferred embodiment, said colony stimulating factor-1 receptor ligand is a protein having one or at least one of the amino acid sequences of SEQ IDs No. 1 to 9.

In a preferred embodiment, said first, second, and/or third heterologous factor is expressed with a secretory signal sequence, preferably N-terminal signal peptide or propeptide. After expression of the respective factor, the secretory signal sequence, preferably N-terminal signal peptide or propeptide, can be removed by posttranslational modification. Alternatively, said first, second, and/or third heterologous factor might be expressed in mature form, preferably without a secretory signal sequence, preferably N-terminal signal peptide or propeptide.

In a preferred embodiment, said recombinant probiotic bacteria according to claim 1 comprise at least one nucleic acid sequence encoding for a first heterologous factor, at least one nucleic acid sequence encoding for a second heterologous factor, and at least one nucleic acid sequence encoding for a third heterologous factor, with the proviso that said first factor, said second factor, and said third factor are functionally different from each other, wherein said first factor is a growth factor, wherein said second factor is selected from the group consisting of M2-polarizing factors and wherein said third factor is selected from the group consisting of M2-polarizing factors and growth factors.

In a preferred embodiment, said second heterologous factor and said third heterologous factor are selected from the group consisting of M2-polarizing factors, wherein said second factor and said third factor are functionally different M2-polarizing factors.

This is to say, said second heterologous factor is a first M2-polarizing factor and said third heterologous factor is a second M2-polarizing factor functionally different from said first M2-polarizing factor.

Preferably, said first M2-polarizing factor is a M2-polarizing factor selected from the group consisting of colony stimulating factor-1 (CSF-1), interleukin 34 (IL-34), interleukin 4 (IL-4), and interleukin 13 (IL-13), and said second M2-polarizing factor is a M2-polarizing factor selected from the group consisting of colony stimulating factor-1 (CSF-1), interleukin 34 (IL-34), interleukin 4 (IL-4), interleukin 10 (IL-10), and interleukin 13 (IL-13), with the proviso that said second M2-polarizing factor is functionally different from said first M2-polarizing factor.

Further preferably, said first M2-polarizing factor is a colony stimulating factor-1 receptor (CSF1R) ligand and said second M2-polarizing factor is a M2-polarizing factor selected from the group consisting of interleukin 4 (IL-4), interleukin 10 (IL-10), interleukin 13 (IL-13), functional analogs thereof, biosimilars thereof, and mixtures thereof.

Further preferred combinations of M2-polarizing factors are:
colony stimulating factor-1 and interleukin 4,
colony stimulating factor-1 and interleukin 13,
colony stimulating factor-1 and interleukin 10,
interleukin 34 and interleukin 4,
interleukin 34 and interleukin 13,
interleukin 34 and interleukin 10,
interleukin 4 and interleukin 10, or
interleukin 13 and interleukin 10.

The above mentioned further preferred combinations of M2-polarizing factors are combined with at least one of the above mentioned growth factors, preferably with a growth factor selected from the group consisting of fibroblast growth factor 1, fibroblast growth factor 2, fibroblast growth factor 7, fibroblast growth factor 10, hepatocyte growth factor, transforming growth factor beta (TGF-beta), epidermal growth factor (EGF), heparin-binding EGF-like growth factor (HB-EGF), transforming growth factor-α (TGF-α), and platelet derived growth factor BB.

Preferably, said first, second, and third heterologous factor is a combination of
fibroblast growth factor 2, colony stimulating factor-1 and interleukin 4,
fibroblast growth factor 2, interleukin 34 and interleukin 4,
fibroblast growth factor 2, colony stimulating factor-1 and interleukin 13,
fibroblast growth factor 2, interleukin 34 and interleukin 13,
fibroblast growth factor 2, colony stimulating factor-1 and interleukin 10,
fibroblast growth factor 2, interleukin 34 and interleukin 10,
fibroblast growth factor 7, colony stimulating factor-1 and interleukin 4,
fibroblast growth factor 7, interleukin 34 and interleukin 4,
fibroblast growth factor 7, colony stimulating factor-1 and interleukin 13,
fibroblast growth factor 7, interleukin 34 and interleukin 13,
fibroblast growth factor 7, colony stimulating factor-1 and interleukin 10,
fibroblast growth factor 7, interleukin 34 and interleukin 10,
transforming growth factor beta, colony stimulating factor-1 and interleukin 4,
transforming growth factor beta, interleukin 34 and interleukin 4,
transforming growth factor beta, colony stimulating factor-1 and interleukin 13,
transforming growth factor beta, interleukin 34 and interleukin 13
transforming growth factor beta, colony stimulating factor-1 and interleukin 10,
transforming growth factor beta, interleukin 34 and interleukin 10,
transforming growth factor alpha, colony stimulating factor-1 and interleukin 4,
transforming growth factor alpha, interleukin 34 and interleukin 4,
transforming growth factor alpha, colony stimulating factor-1 and interleukin 13,
transforming growth factor alpha, interleukin 34 and interleukin 13
transforming growth factor alpha, colony stimulating factor-1 and interleukin 10,
transforming growth factor alpha, interleukin 34 and interleukin 10
platelet derived growth factor BB, colony stimulating factor-1 and interleukin 4,
platelet derived growth factor BB, interleukin 34 and interleukin 4, platelet derived growth factor BB, colony stimulating factor-1 and interleukin 13,
platelet derived growth factor BB, interleukin 34 and interleukin 13
platelet derived growth factor BB, colony stimulating factor-1 and interleukin 10, or
platelet derived growth factor BB, interleukin 34 and interleukin 10.

Further preferably, said first, second, and third heterologous factor is a combination of fibroblast growth factor 2, colony stimulating factor-1 and interleukin 4, functional analogs thereof, and biosimilars thereof.

Preferably, by release of two or more M2-polarizing factors from the probiotic bacteria of the present invention M2-polarization of unpolarized macrophages, M1-polarized macrophages as well as undifferentiated monocytes, and other macrophage progenitor cells is further fostered.

In an alternative embodiment, said first factor is a first growth factor selected from the group consisting from the above-mentioned growth factors, and said third factor is a second growth factor selected from the group consisting from the above-mentioned growth factors and which is functionally different from said first growth factor. Preferably, said second growth factor is transforming growth factor beta (TGF-beta).

Further preferred combinations of growth factors are:
fibroblast growth factor 1 and transforming growth factor beta,
fibroblast growth factor 2 and transforming growth factor beta,
fibroblast growth factor 7 and transforming growth factor beta,
fibroblast growth factor 10 and transforming growth factor beta,
platelet derived growth factor BB and transforming growth factor beta,
transforming growth factor alpha and transforming growth factor beta,
epidermal growth factor and transforming growth factor beta,
heparin-binding EGF-like growth factor and transforming growth factor beta,
hepatocyte growth factor and transforming growth factor beta, or
vascular endothelial growth factor A and transforming growth factor beta.

The above mentioned further preferred combinations of growth factors are preferably combined with a M2-polarizing factor selected from the group consisting of colony stimulating factor-1 (CSF-1), interleukin 34 (IL-34), interleukin 4 (IL-4), interleukin 10 (IL-10), interleukin 13 (IL-13), and mixtures thereof, preferably colony stimulating factor-1 (CSF-1), interleukin 34 (IL-34), interleukin 4 (IL-4), interleukin 13 (IL-13), and mixtures thereof.

The recombinant probiotic bacteria of the invention are to be used in the treatment of an inflammatory skin dysfunction, preferably a chronic inflammatory skin dysfunction.

In a preferred embodiment, said inflammatory skin dysfunction, preferably said chronic inflammatory skin dysfunction, is an inflammatory skin disease, preferably a chronic inflammatory skin disease, or an inflammatory connective tissue disease, preferably a chronic inflammatory connective tissue disease. Said inflammatory skin disease can be frostbite, eczema, psoriasis, dermatitis, ulcer, wound, lupus eritematosus, neurodermitis, and combinations thereof, preferably frostbites, dermatitis, ulcer, wound, and combinations thereof, further preferably wound, ulcer, and combinations thereof, further preferably ulcer.

Said inflammatory, preferably chronic inflammatory, skin disease can also include an inflammatory, preferably a chronic inflammatory, skin trauma, which may progress into a chronic inflammatory state.

Frostbite is the medical condition in which localized damage is caused to skin and other tissues due to freezing and can involve tissue destruction. Said frostbite can also be chilblains (perniones), which are superficial ulcers of the skin that result from exposure to cold and humidity. Damage to capillary beds in the skin causes redness, itching, inflammation, and sometimes blisters. Further preferably, said frostbites are chilblains.

Said wound can be a burn wound, a chemical wound, a radiation induced wound, an ischemic wound, or a mechanical wound.

Said ulcer can be a decubitus ulcer or an ulcus cruris. Said ulcer can also be a venous ulcer, an arterial ulcer, a diabetic ulcer, or a pressure ulcer.

Said ulcer can also be a preulceration stage of the above-mentioned ulcers without any visible sign of open skin wound. Without medical intervention, the preulceration stage may progress to ulceration.

Said wound can also be an acute wound or a chronic wound, preferably a chronic wound.

Chronic wounds are known to the skilled person and include, for example, chronic venous ulcers, chronic arterial ulcers, chronic diabetic ulcers, and chronic pressure ulcers. Chronic wounds may also be caused by radiation poisoning or ischemia. Preferably said chronic wound is at least one of a chronic venous ulcer, a chronic arterial ulcer, a chronic pressure ulcer and a chronic preulceration stage thereof, preferably a chronic venous ulcer, a chronic arterial ulcer and a chronic pressure ulcer.

Chronic venous ulcers usually may occur in the legs and account for about 70% to 90% of chronic wounds, mostly affecting elderly patients.

Another major cause of chronic wounds is diabetes. Patients suffering from diabetes have a 15% higher risk for amputation than the general population due to chronic ulcers. Diabetes causes neuropathy, which inhibits nociception and the perception of pain. Thus, patients may not notice small wounds to legs and feet and may therefore fail to prevent infection or repeated injury.

A further problem is that diabetes causes immune compromise and damage to small blood vessels resulting in a reduced oxygenation of tissue. Preventing adequate oxygenation of tissue significantly increase the prevalence for chronic wounds.

Pressure ulcers, which are also known as decubitus ulcers or bed sore, may occur with our without a diabetic condition. Pressure ulcers are localized injuries to the skin and/or underlying tissue that can occur over a bony prominence as a result of pressure, or pressure in combination with shear or friction.

Diabetes is a main endocrine metabolic disorder with an expanding proportion that has approached to a worldwide pandemic status. Lower extremity ulceration, for example diabetic foot ulcers, is one of the serious long-term complications associated with diabetes that may be sustained and amplified by the underlying failure of tissue regeneration.

There are approximately 13 million chronic wound patients in the USA, EU, and Japan, of which approximately 2.8 million suffer from lower extremity ulceration such as diabetic foot ulcers.

Lower extremity ulceration, for example diabetic foot ulcers, are challenging to treat with no definite conventional, non-invasive therapy existing. Lower extremity ulceration need a lot of medical attention and are extremely debilitating for the patients associated with substantial loss of quality of life.

Approximately, 24% of patients suffering from lower extremity ulceration will require amputation leading to long-term disability.

The annual healthcare cost for patients suffering from lower extremity ulceration is in the range of $ 100 billion USD. Furthermore, the five year mortality rate of patients suffering from lower extremity ulceration is about 45%, which is higher than that of many cancers.

Currently, the standard therapeutic management of chronic wounds including diabetic wounds such as lower extremity ulceration is focussed primarily on controlling infection and promoting revascularisation. Despite these strategies, the rate of amputation remains unacceptably high in patients suffering from lower extremity ulceration.

Furthermore, when an underlying disease condition or cause of an ulceration, such as diabetes mellitus or chronic venous insufficiency, is improved and/or treated, for example by controlling blood sugar levels or administering blood pressure medication, respectively, existing ulcers may still take a very long time to heal.

Thus, in order to overcome the lack of definitive, non-invasive treatments of chronic wounds including diabetic wounds such as lower extremity ulceration new strategies to reactivate and promote wound healing in patients suffering from chronic wounds are urgently needed.

Preferably, in case of a chronic wound, the unique combination of factors, preferably released from said probiotic bacteria, allows for a reprogramming of said chronic wound into an acute wound, which subsequently undergoes wound closure.

In a preferred embodiment, the recombinant probiotic bacteria are to be administered topically and/or by subcutaneous injection, further preferably topically.

The recombinant probiotic bacteria preferably are to be administered topically, to the inflammatory, preferably chronic inflammatory, skin dysfunction to be treated.

The recombinant probiotic bacteria can be administered topically to the inflammatory, preferably chronic inflammatory, skin dysfunction and/or by subcutaneous injection into the vicinity of the skin dysfunction, preferably into the edges or cavity of the inflammatory, preferably chronic inflammatory, skin dysfunction.

After application of the recombinant probiotic bacteria of the present invention, the bacteria express said first and second heterologous factor, preferably said first, second and third heterologous factor.

Furthermore, by topical application or subcutaneous injection of the recombinant probiotic bacteria of the present invention to and/or into the site of the preulceration a progression of the preulceration to an open wound can be avoided.

The recombinant probiotic bacteria are preferably obtained by transforming probiotic bacteria with at least one nucleic acid sequence encoding for said first heterologous factor and at least one nucleic acid sequence encoding for said second heterologous factor and, preferably with at least one nucleic acid sequence encoding for said third heterologous factor.

Suitable probiotic bacteria for obtaining the recombinant probiotic bacteria of the present invention are non-pathogenic bacteria. Preferably, the non-pathogenic bacteria are non-invasive bacteria. In a further preferred embodiment, the recombinant probiotic bacteria are gram-positive bacteria, preferably gram-positive non-sporulating bacteria. Further preferably, said probiotic bacteria are non-colonizing bacteria lacking the ability to multiply in human gastrointestinal tract.

In a further preferred embodiment, the recombinant probiotic bacteria comprise a gram-positive food grade bacterial strain.

According to a preferred embodiment of the present invention, the recombinant probiotic bacteria can be from the same bacterial strain or a mixture of different bacterial strains.

In another embodiment, the probiotic bacteria are classified as "generally recognized as safe" (GRAS) by the United States Food and Drug Administration (FDA).

In another embodiment, the probiotic bacteria have a "qualified presumption of safety" (QPS-status) as defined by the European Food Safety Authority (EFSA). An introduction of the qualified presumption of safety (QPS) approach for the assessment of selected microorganisms is described in the EFSA Journal, Vol. 587, 2007, pages 1-16.

In a further preferred embodiment, the probiotic bacteria are non-pathogenic bacteria belonging to the phylum firmicutes or actinobacteria. Preferably, the probiotic bacteria are non-pathogenic bacteria from at least one genus selected form the group consisting of *bifidobacterium, corynebacterium, enterococcus, lactobacillus, lactococcus, leuconostoc, pediococcus, propionibacterium*, and *streptococcus*.

In another preferred embodiment, the probiotic bacteria are lactic acid bacteria (LAB). Lactic acid bacteria are a Glade of gram-positive, acid-tolerant, generally non-sporulating, non-respiring bacteria that share common metabolic and physiological characteristics. These bacteria produce lactic acid as a major metabolic end product of carbohydrate formation.

Lactic acid bacteria are long known and are used, for example, in food fermentation. Furthermore, proteinaceous bacteriocins are produced by several lactic acid bacteria strains.

Furthermore, lactic acid bacteria have a generally recognized as safe (GRAS) status due to their ubiquitous appearance in food and their contribution to the healthy microflora of human mucosal surfaces.

In a further preferred embodiment, the probiotic bacteria exclude pathogenic and/or opportunistic bacteria.

In another embodiment, the probiotic bacteria are from the genus *Bifidobacterium* sp., including but not limited to, *Bifidobacterium actinocoloniiforme, Bifidobacterium adolescentis, Bifidobacterium aesculapii, Bifidobacterium angulatum, Bifidobacterium Bifidobacterium animalis*, for example *Bifidobacterium animalis* subsp. *animalis* or *Bifidobacterium animalis* subsp. *lactis, Bifidobacterium asteroides, Bifidobacterium biavatii, Bifidobacterium bifidum, Bifidobacterium bohemicum, Bifidobacterium bombi, Bifidobacterium boum, Bifidobacterium breve, Bifidobacterium callitrichos, Bifidobacterium catenulatum, Bifidobacterium choerinum, Bifidobacterium coryneforme, Bifidobacterium crudilactis, Bifidobacterium cuniculi, Bifidobacterium denticolens, Bifidobacterium dentium, Bifidobacterium faecale, Bifidobacterium gallicum, Bifidobacterium gallinarum, Bifidobacterium globosum, Bifidobacterium indicum, Bifidobacterium infantis, Bifidobacterium inopinatum, Bifidobacterium kashiwanohense, Bifidobacterium lactis, Bifidobacterium longum*, for example *Bifidobacterium longum* subsp. *infantis, Bifidobacterium longum* subsp. *longum*, or *Bifidobacterium longum* subsp. *suis, Bifidobac-* terium magnum, Bifidobacterium merycicum, Bifidobacterium minimum, Bifidobacterium mongoliense, Bifidobacterium moukalabense, Bifidobacterium pseudocatenulatum, Bifidobacterium pseudolongum, for example Bifidobacterium pseudolongum subsp. globosum or Bifidobacterium pseudolongum subsp. pseudolongum, Bifidobacterium psychraerophilum, Bifidobacterium pullorum, Bifidobacterium reuteri, Bifidobacterium ruminantium, Bifidobacterium saeculare, Bifidobacterium saguini, Bifidobacterium scardovii, Bifidobacterium stellenboschense, Bifidobacterium subtile, Bifidobacterium stercoris, Bifidobacterium suis, Bifidobacterium thermacidophilum, for example Bifidobacterium thermacidophilum subsp. porcinum or Bifidobacterium thermacidophilum subsp. thermacidophilum, Bifidobacterium thermophilum, or Bifidobacterium tsurumiense.

Preferably, the probiotic bacteria are not Bifidobacterium dentium.

Preferably, the probiotic bacteria are bacteria having a "Qualified Presumption of Safety" (QPS) status in the genus Bifidobacterium sp., including but not limited to, Bifidobacterium adolescentis, Bifidobacterium animalis, Bifidobacterium longum, Bifidobacterium breve, or Bifidobacterium bifidum.

In one embodiment, the probiotic bacteria are from the genus Corynebacterium sp., including but not limited to, Corynebacterium accolens, Corynebacterium afermentans, for example Corynebacterium afermentans subsp. afermentans or Corynebacterium afermentans subsp. lipophilum, Corynebacterium ammoniagenes, Corynebacterium amycolatum, Corynebacterium appendices, Corynebacterium aquatimens, Corynebacterium aquilae, Corynebacterium argentoratense, Corynebacterium atypicum, Corynebacterium aurimucosum, Corynebacterium auris, Corynebacterium auriscanis, Corynebacterium betae, Corynebacterium beticola, Corynebacterium bovis, Corynebacterium callunae, Corynebacterium camporealensis, Corynebacterium canis, Corynebacterium capitovis, Corynebacterium casei, Corynebacterium caspium, Corynebacterium ciconiae, Corynebacterium confusum, Corynebacterium coyleae, Corynebacterium cystitidis, Corynebacterium deserti, Corynebacterium diphtheriae, Corynebacterium doosanense, Corynebacterium durum, Corynebacterium efficiens, Corynebacterium epidermidicanis, Corynebacterium equi, Corynebacterium falsenii, Corynebacterium fascians, Corynebacterium felinum, Corynebacterium flaccumfaciens, for example Corynebacterium flaccumfaciens subsp. betae, Corynebacterium flaccumfaciens subsp. flaccumfaciens, Corynebacterium flaccumfaciens subsp. oortii, or Corynebacterium flaccumfaciens subsp. poinsettiae, Corynebacterium flavescens, Corynebacterium frankenforstense, Corynebacterium freiburgense, Corynebacterium freneyi, Corynebacterium glaucum, Corynebacterium glucuronolyticum, Corynebacterium glutamicum, Corynebacterium halotolerans, Corynebacterium hansenii, Corynebacterium hoagie, Corynebacterium humireducens, Corynebacterium ilicis, Corynebacterium imitans, Corynebacterium insidiosum, Corynebacterium iranicum, Corynebacterium jeikeium, Corynebacterium kroppenstedtii, Corynebacterium kutscheri, Corynebacterium lactis, Corynebacterium lilium, Corynebacterium lipophiloflavum, Corynebacterium liquefaciens, Corynebacterium lubricantis, Corynebacterium macginleyi, Corynebacterium marinum, Corynebacterium marls, Corynebacterium massiliense, Corynebacterium mastitidis, Corynebacterium matruchotii, Corynebacterium michiganense, for example Corynebacterium michiganense subsp. insidiosum, Corynebacterium michiganense subsp. michiganense, Corynebacterium michiganense subsp. nebraskense, Corynebacterium michiganense subsp. sepedonicum, or Corynebacterium michiganense subsp. tessellarius, Corynebacterium minutissimum, Corynebacterium mooreparkense, Corynebacterium mucifaciens, Corynebacterium mustelae, Corynebacterium mycetoides, Corynebacterium nebraskense, Corynebacterium nigricans, Corynebacterium nuruki, Corynebacterium oortii, Corynebacterium paurometabolum, Corynebacterium phocae, Corynebacterium pilbarense, Corynebacterium pilosum, Corynebacterium poinsettiae, Corynebacterium propinquum, Corynebacterium pseudodiphtheriticum, Corynebacterium pseudotuberculosis, Corynebacterium pyogenes, Corynebacterium pyruviciproducens, Corynebacterium rathayi, Corynebacterium renale, Corynebacterium resistens, Corynebacterium riegelii, Corynebacterium seminale, Corynebacterium sepedonicum, Corynebacterium simulans, Corynebacterium singulare, Corynebacterium sphenisci, Corynebacterium spheniscorum, Corynebacterium sputi, Corynebacterium stationis, Corynebacterium striatum, Corynebacterium suicordis, Corynebacterium sundsvallense, Corynebacterium terpenotabidum, Corynebacterium testudinoris, Corynebacterium thomssenii, Corynebacterium timonense, Corynebacterium tritici, Corynebacterium tuberculostearicum, Corynebacterium tuscaniense, Corynebacterium ulcerans, Corynebacterium ulceribovis, Corynebacterium urealyticum, Corynebacterium ureicelerivorans, Corynebacterium uterequi, Corynebacterium variabile, Corynebacterium vitaeruminis, or Corynebacterium xerosis.

Preferably, the probiotic bacteria are not Corynebacterium diphtheriae, Corynebacterium amicolatum, Corynebacterium striatum, Corynebacterium jeikeium, Corynebacterium urealyticum, Corynebacterium xerosis, Corynebacterium pseudotuberculosis, Corynebacterium tenuis, Corynebacterium striatum, or Corynebacterium minutissimum.

Preferably, the probiotic bacteria are bacteria classified as "generally regarded as safe" (GRAS) in the Corynebacterium genus, including but not limited to Corynebacterium ammoniagenes, Corynebacterium casei, Corynebacterium flavescens, or Corynebacterium variabile.

In another embodiment, the bacteria are from the genus Enterococcus sp., including but not limited to, Enterococcus alcedinis, Enterococcus aquimarinus, Enterococcus asini, Enterococcus avium, Enterococcus caccae, Enterococcus camelliae, Enterococcus canintestini, Enterococcus canis, Enterococcus casseliflavus, Enterococcus cecorum, Enterococcus columbae, Enterococcus devriesei, Enterococcus diestrammenae, Enterococcus dispar, Enterococcus durans, Enterococcus eurekensis, Enterococcus faecalis, Enterococcus faecium, Enterococcus flavescens, Enterococcus gallinarum, Enterococcus gilvus, Enterococcus haemoperoxidus, Enterococcus hermanniensis, Enterococcus hirae, Enterococcus italicus, Enterococcus lactis, Enterococcus lemanii, Enterococcus malodoratus, Enterococcus moraviensis, Enterococcus mundtii, Enterococcus olivae, Enterococcus pallens, Enterococcus phoeniculicola, Enterococcus plantarum, Enterococcus porcinus, Enterococcus pseudoavium, Enterococcus quebecensis, Enterococcus raffinosus, Enterococcus ratti, Enterococcus rivorum, Enterococcus rotai, Enterococcus saccharolyticus, for example Enterococcus saccharolyticus subsp. saccharolyticus or Enterococcus saccharolyticus subsp. taiwanensis, Enterococcus saccharominimus, Enterococcus seriolicida, Enterococcus silesiacus, Enterococcus solitarius, Enterococcus sulfureus, Enterococcus termitis, Enterococcus thailandicus, Enterococcus ureilyticus, Enterococcus viikkiensis, Enterococcus villorum, or Enterococcus xiangfangensis.

Preferably, the probiotic bacteria are bacteria classified as "generally regarded as safe" (GRAS) in the Enterococcus genus, including but not limited to Enterococcus durans, Enterococcus faecalis, or Enterococcus faecium.

In another embodiment, the probiotic bacteria are from the genus Lactobacillus sp., including but not limited to, Lactobacillus acetotolerans, Lactobacillus acidifarinae, Lactobacillus acidipiscis, Lactobacillus acidophilus, Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apinorum, Lactobacillus apis, Lactobacillus apodemi, Lactobacillus aquaticus, Lactobacillus arizonensis, Lactobacillus aviaries, for example Lactobacillus aviarius subsp. araffinosus or Lactobacillus aviarius subsp. aviarius, Lactobacillus backii, Lactobacillus bavaricus, Lactobacillus bifermentans, Lactobacillus bobalius, Lactobacillus bombi, Lactobacillus brantae, Lactobacillus brevis, Lactobacillus buchneri, Lactobacillus bulgaricus, Lactobacillus cacaonum, Lactobacillus camelliae, Lactobacillus capillatus, Lactobacillus carnis, Lactobacillus casei, for example Lactobacillus casei subsp. alactosus, Lactobacillus casei subsp. casei, Lactobacillus casei subsp. pseudoplantarum, Lactobacillus casei subsp. rhamnosus, or Lactobacillus casei subsp. tolerans, Lactobacillus catenaformis, Lactobacillus cellobiosus, Lactobacillus ceti, Lactobacillus coleohominis, Lactobacillus collinoides, Lactobacillus composti, Lactobacillus concavus, Lactobacillus confusus, Lactobacillus coryniformis, for example Lactobacillus coryniformis subsp. coryniformis or Lactobacillus coryniformis subsp. torquens, Lactobacillus crispatus, Lactobacillus crustorum, Lactobacillus curieae, Lactobacillus curvatus, for example Lactobacillus curvatus subsp. curvatus or Lactobacillus curvatus subsp. melibiosus, Lactobacillus cypricasei, Lactobacillus delbrueckii, for example Lactobacillus delbrueckii subsp. bulgaricus, Lactobacillus delbrueckii subsp. delbrueckii, Lactobacillus delbrueckii subsp. indicus, Lactobacillus delbrueckii subsp. jakobsenii, Lactobacillus delbrueckii subsp. lactis, or Lactobacillus delbrueckii subsp. sunkii, Lactobacillus dextrinicus, Lactobacillus diolivorans, Lactobacillus divergens, Lactobacillus durianis, Lactobacillus equi, Lactobacillus equicursoris, Lactobacillus equigenerosi, Lactobacillus fabifermentans, Lactobacillus faecis, Lactobacillus farciminis, Lactobacillus farraginis, Lactobacillus ferintoshensis, Lactobacillus fermentum, Lactobacillus floricola, Lactobacillus forum, Lactobacillus fornicalis, Lactobacillus fructivorans, Lactobacillus fructosus, Lactobacillus frumenti, Lactobacillus fuchuensis, Lactobacillus furfuricola, Lactobacillus futsaii, Lactobacillus gallinarum, Lactobacillus gasseri, Lactobacillus gastricus, Lactobacillus ghanensis, Lactobacillus gigeriorum, Lactobacillus graminis, Lactobacillus halotolerans, Lactobacillus hammesii, Lactobacillus hamsteri, Lactobacillus harbinensis, Lactobacillus hayakitensis, Lactobacillus heilongjiangensis, Lactobacillus helsingborgensis, Lactobacillus helveticus, Lactobacillus heterohiochii, Lactobacillus hilgardii, Lactobacillus hokkaidonensis, Lactobacillus hominis, Lactobacillus homohiochii, Lactobacillus hordei, Lactobacillus iners, Lactobacillus ingluviei, Lactobacillus intestinalis, Lactobacillus iwatensis, Lactobacillus jensenii, Lactobacillus johnsonii, Lactobacillus kalixensis, Lactobacillus kandleri, Lactobacillus kefiranofaciens, for example Lactobacillus kefiranofaciens subsp. kefiranofaciens or Lactobacillus kefiranofaciens subsp. kefirgranum, Lactobacillus kefiri, Lactobacillus kefirgranum, Lactobacillus kimbladii, Lactobacillus kimchicus, Lactobacillus kimchiensis, Lactobacillus kimchii, Lactobacillus kisonensis, Lactobacillus kitasatonis, Lactobacillus koreensis, Lactobacillus kullabergensis, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus mellifer, Lactobacillus mellis, Lactobacillus melliventris, Lactobacillus mindensis, Lactobacillus minor, Lactobacillus minutus, Lactobacillus mucosae, Lactobacillus murinus, Lactobacillus nagelii, Lactobacillus namurensis, Lactobacillus nantensis, Lactobacillus nasuensis, Lactobacillus nenjiangensis, Lactobacillus nodensis, Lactobacillus odoratitofui, Lactobacillus oeni, Lactobacillus oligofermentans, Lactobacillus oris, Lactobacillus oryzae, Lactobacillus otakiensis, Lactobacillus ozensis, Lactobacillus panis, Lactobacillus pantheris, Lactobacillus parabrevis, Lactobacillus parabuchneri, Lactobacillus paracasei, for example Lactobacillus paracasei subsp. paracasei or Lactobacillus paracasei subsp. tolerans, Lactobacillus paracollinoides, Lactobacillus parafarraginis, Lactobacillus parakefiri, Lactobacillus paralimentarius, Lactobacillus paraplantarum, Lactobacillus pasteurii, Lactobacillus paucivorans, Lactobacillus pentosus, Lactobacillus perolens, Lactobacillus piscicola, Lactobacillus plantarum, for example Lactobacillus plantarum subsp. argentoratensis or Lactobacillus plantarum subsp. plantarum, Lactobacillus pobuzihii, Lactobacillus pontis, Lactobacillus porcinae, Lactobacillus psittaci, Lactobacillus rapi, Lactobacillus rennini, Lactobacillus reuteri, Lactobacillus rhamnosus, Lactobacillus rimae, Lactobacillus rodentium, Lactobacillus rogosae, Lactobacillus rossiae, Lactobacillus ruminis, Lactobacillus saerimneri, Lactobacillus sakei, for example Lactobacillus sakei subsp. carnosus or Lactobacillus sakei subsp. sakei, Lactobacillus salivarius, for example Lactobacillus salivarius subsp. salicinius or Lactobacillus salivarius subsp. salivarius, Lactobacillus sanfranciscensis, Lactobacillus saniviri, Lactobacillus satsumensis, Lactobacillus secaliphilus, Lactobacillus selangorensis, Lactobacillus senioris, Lactobacillus senmaizukei, Lactobacillus sharpeae, Lactobacillus shenzhenensis, Lactobacillus sicerae, Lactobacillus silagei, Lactobacillus siliginis, Lactobacillus similes, Lactobacillus sobrius, Lactobacillus songhuajiangensis, Lactobacillus spicheri, Lactobacillus sucicola, Lactobacillus suebicus, Lactobacillus sunkii, Lactobacillus suntoryeus, Lactobacillus taiwanensis, Lactobacillus thailandensis, Lactobacillus thermotolerans, Lactobacillus trichodes, Lactobacillus tucceti, Lactobacillus uli, Lactobacillus ultunensis, Lactobacillus uvarum, Lactobacillus vaccinostercus, Lactobacillus vaginalis, Lactobacillus versmoldensis, Lactobacillus vini, Lactobacillus viridescens, Lactobacillus vitulinus, Lactobacillus xiangfangensis, Lactobacillus xylosus, Lactobacillus yamanashiensis, for example Lactobacillus yamanashiensis subsp. mali or Lactobacillus yamanashiensis subsp. yamanashiensis, Lactobacillus yonginensis, Lactobacillus zeae, or Lactobacillus zymae.

Prefereably, the probiotic bacteria are bacteria classified as "generally regarded as safe" (GRAS) in the genus Lactobacillus sp., including but not limited to, Lactobacillus acidophilus strain NP 28, Lactobacillus acidophilus strain NP51, Lactobacillus subsp. lactis strain NP7, Lactobacillus reuteri strain NCIMB 30242, Lactobacillus casei strain Shirota, Lactobacillus reuteri strain DSM 17938, Lactobacillus reuteri strain NCIMB 30242, Lactobacillus acidophilus strain NCFM, Lactobacillus rhamnosus strain HN001,

*Lactobacillus rhamnosus* strain HN001, *Lactobacillus reuteri* strain DSM 17938, *Lactobacillus casei* subsp. *rhamnosus* strain GG, *Lactobacillus acidophilus, Lactobacillus lactis, Lactobacillus acetotolerans, Lactobacillus acidifarinae, Lactobacillus acidipiscis, Lactobacillus acidophilus, Lactobacillus alimentarius, Lactobacillus amylolyticus, Lactobacillus amylovorus, Lactobacillus brevis, Lactobacillus buchneri, Lactobacillus cacaonum, Lactobacillus casei* subsp. *casei, Lactobacillus collinoides, Lactobacillus composti, Lactobacillus coryniformis* subsp. *coryniformis, Lactobacillus crispatus, Lactobacillus crustorum, Lactobacillus curvatus* subps. *curvatus, Lactobacillus delbrueckii* subsp. *bulgaricus, Lactobacillus delbrueckii* subsp. *delbrueckii, Lactobacillus delbrueckii* subsp. *lactis, Lactobacillus dextrinicus, Lactobacillus diolivorans, Lactobacillus fabifermentans, Lactobacillus farciminis, Lactobacillus fermentum, Lactobacillus fructivorans, Lactobacillus frumenti, Lactobacillus gasseri, Lactobacillus ghanensis, Lactobacillus hammesii, Lactobacillus harbinensis, Lactobacillus helveticus, Lactobacillus hilgardii, Lactobacillus homohiochii, Lactobacillus hordei, Lactobacillus jensenii, Lactobacillus johnsonii, Lactobacillus kefiri, Lactobacillus kefiranofadens* subsp. *kefiranofaciens, Lactobacillus kefiranofadens* subsp. *kefirgranum, Lactobacillus kimchii, Lactobacillus kisonensis, Lactobacillus mail, Lactobacillus manihotivorans, Lactobacillus mindensis, Lactobacillus mucosae, Lactobacillus nagelii, Lactobacillus namurensis, Lactobacillus nantensis, Lactobacillus nodensis, Lactobacillus oeni, Lactobacillus otakiensis, Lactobacillus panis, Lactobacillus parabrevis, Lactobacillus parabuchneri, Lactobacillus paracasei* subsp. *paracasei, Lactobacillus parakefiri, Lactobacillus paralimentarius, Lactobacillus paraplantarum, Lactobacillus pentosus, Lactobacillus perolens, Lactobacillus plantarum* subsp. *plantarum, Lactobacillus pobuzihii, Lactobacillus pontis, Lactobacillus rapi, Lactobacillus reuteri, Lactobacillus rhamnosus, Lactobacillus rossiae, Lactobacillus sakei* subsp *carnosus, Lactobacillus sakei* subsp. *sakei, Lactobacillus sali varius* subsp. *salivarius, Lactobacillus sanfranciscensis, Lactobacillus satsumensis, Lactobacillus secaliphilus, Lactobacillus senmaizukei, Lactobacillus siliginis, Lactobacillus spicheri, Lactobacillus suebicus, Lactobacillus sunkii, Lactobacillus tucceti, Lactobacillus vaccinostercus, Lactobacillus versmoldensis,* or *Lactobacillus yamanashiensis.*

Preferably, the probiotic bacteria are bacteria having a "Qualified Presumption of Safety" (QPS) status in the genus *Lactobacillus* sp., including but not limited to, *Lactobacillus acidophilus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus crispatus, Lactobacillus curvatus, Lactobacillus delbrueckii, Lactobacillus farciminis, Lactobacillus fermentum, Lactobacillus gallinarum, Lactobacillus gasseri, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus paracasei, Lactobacillus paraplantarum, Lactobacillus pentosus, Lactobacillus plantarum, Lactobacillus pontis, Lactobacillus reuteri, Lactobacillus rhamnosus, Lactobacillus sakei, Lactobacillus salivarius, Lactobacillus sanfranciscensis,* or *Lactobacillus zeae.*

In another embodiment, the probiotic bacteria are from the genus *Lactococcus* sp., including but not limited to *Lactococcus chungangensis, Lactococcus formosensis, Lactococcus fujiensis, Lactococcus garvieae, Lactococcus lactis,* for example *Lactococcus lactis* subsp. *cremoris, Lactococcus lactis* subsp. *hordniae, Lactococcus lactis* subsp. *lactis,* or *Lactococcus lactis* subsp. *tructae, Lactococcus piscium, Lactococcus plantarum, Lactococcus raffinolactis,* or *Lactococcus taiwanensis.*

Preferably, the probiotic bacteria are bacteria classified as "generally regarded as safe" (GRAS) in the genus *Lactococcus,* including but not limited to, *Lactococcus lactis* subsp. *cremoris, Lactococcus lactis* subsp. *lactis,* and *Lactococcus raffinolactis.*

Preferably, the probiotic bacteria are *Lactococcus lactis,* preferably *Lactococcus lactis* subsp. *lactis, Lactococcus lactis* subsp. *lactis biovariant diacetylactis,* or *Lactococcus lactis* subsp. *cremoris,* further preferably *Lactococcus lactis* subsp. *cremoris.*

In another embodiment, the probiotic bacteria are from the genus *Leuconostoc* sp., including but not limited to, *Leuconostoc amelibiosum, Leuconostoc argentinum, Leuconostoc carnosum, Leuconostoc citreum, Leuconostoc cremoris, Leuconostoc dextranicum, Leuconostoc durionis, Leuconostoc fallax, Leuconostoc ficulneum, Leuconostoc fructosum, Leuconostoc gasicomitatum, Leuconostoc gelidum,* for example *Leuconostoc gelidum* subsp. *aenigmaticum, Leuconostoc gelidum* subsp. *gasicomitatum,* or *Leuconostoc gelidum* subsp. *gelidum, Leuconostoc holzapfelii, Leuconostoc inhae, Leuconostoc kimchii, Leuconostoc lactis, Leuconostoc mesenteroides,* for example *Leuconostoc mesenteroides* subsp. *cremoris, Leuconostoc mesenteroides* subsp. *dextranicums, Leuconostoc mesenteroides* subsp. *mesenteroides,* or *Leuconostoc mesenteroides* subsp. *suionicum, Leuconostoc miyukkimchii, Leuconostoc oeni, Leuconostoc paramesenteroides, Leuconostoc pseudoficulneum,* or *Leuconostoc pseudomesenteroides.*

Preferably, the bacteria are bacteria classified as "generally regarded as safe" (GRAS) in the genus *Leuconostoc* sp., including but not limited to, *Leuconostoc carnosum, Leuconostoc citreum, Leuconostoc fallax, Leuconostoc holzapfelii, Leuconostoc inhae, Leuconostoc kimchii, Leuconostoc lactis, Leuconostoc mesenteroides* subsp. *cremoris, Leuconostoc mesenteroides* subsp. *dextranicums, Leuconostoc mesenteroides* subsp. *mesenteroides, Leuconostoc palmae,* or *Leuconostoc pseudomesenteroides.*

Preferably, the probiotic bacteria are bacteria having a "Qualified Presumption of Safety" (QPS) status in the genus *Leuconostoc* sp., including but not limited to, *Leuconostoc citreum, Leuconostoc lactis, Leuconostoc mesenteroides* subsp. *cremoris, Leuconostoc mesenteroides* subsp. *dextranicum,* or *Leuconostoc mesenteroides* subsp. *mesenteroides.*

In another embodiment, the bacteria are from the genus of *Pediococcus* sp., including but not limited to, *Pediococcus acidilactici, Pediococcus argentinicus, Pediococcus cellicola, Pediococcus claussenii, Pediococcus damnosus, Pediococcus dextrinicus. Pediococcus ethanolidurans, Pediococcus halophilus, Pediococcus inopinatus, Pediococcus lolii, Pediococcus parvulus, Pediococcus pentosaceus, Pediococcus siamensis, Pediococcus stilesii,* or *Pediococcus urinaeequi*

Preferably, the probiotic bacteria are bacteria having a "Qualified Presumption of Safety" (QPS) status in the genus *Pediococcus* sp., including but not limited to, *Pediococcus acidilactici, Pediococcus dextrinicus,* or *Pediococcus pentosaceus.*

In another embodiment, the probiotic bacteria are from the genus *Propionibacterium* sp., including but not limited to, *Propionibacterium acidifaciens, Propionibacterium acidipropionici, Propionibacterium acnes, Propionibacterium australiense, Propionibacterium avidum, Propionibacterium cyclohexanicum, Propionibacterium damnosum, Pro-* pionibacterium freudenreichii, for example *Propionibacterium freudenreichii* subsp. *freudenreichii* or *Propionibacterium freudenreichii* subsp. *shermanii*, *Propionibacterium granulosum*, *Propionibacterium innocuum*, *Propionibacterium jensenii*, *Propionibacterium lymphophilum*, *Propionibacterium microaerophilum*, *Propionibacterium olivae*, *Propionibacterium propionicum*, or *Propionibacterium thoenii*.

According to an embodiment, the probiotic bacteria are not *Propionibacterium acnes*.

Further preferably, the probiotic bacteria are bacteria classified as "generally regarded as safe" (GRAS) in the genus *Propionibacterium* sp., including but not limited to *Propionibacterium acidipropionici*, *Propionibacterium freudenreichii* subsp. *Freudenreichii*, *Propionibacterium freudenreichii* subsp. *shermanii*, *Propionibacterium jensenii*, or *Propionibacterium thoenii*.

Further preferably, the probiotic bacteria are *Propionibacterium freudenreichii*, further preferably *Propionibacterium freudenreichii* subsp. *freudenreichii* or *Propionibacterium freudenreichii* subsp. *shermanii*.

In another embodiment, the probiotic bacteria are from the genus *Streptococcus* sp., including but not limited to, *Streptococcus acidominimus*, *Streptococcus adjacens*, *Streptococcus agalactiae*, *Streptococcus alactolyticus*, *Streptococcus anginosus*, *Streptococcus australis*, *Streptococcus bovis*, *Streptococcus caballi*, *Streptococcus canis*, *Streptococcus caprinus*, *Streptococcus castoreus*, *Streptococcus cecorum*, *Streptococcus constellatus*, for example *Streptococcus constellatus* subsp. *constellatus*, *Streptococcus constellatus* subsp. *pharynges*, or *Streptococcus constellatus* subsp. *viborgensis*, *Streptococcus cremoris*, *Streptococcus criceti*, *Streptococcus cristatus*, *Streptococcus cuniculi*, *Streptococcus danieliae*, *Streptococcus defectivus*, *Streptococcus dentapri*, *Streptococcus dentirousetti*, *Streptococcus dentasini*, *Streptococcus dentisani*, *Streptococcus devriesei*, *Streptococcus didelphis*, *Streptococcus difficilis*, *Streptococcus downei*, *Streptococcus durans*, *Streptococcus dysgalactiae*, for example *Streptococcus dysgalactiae* subsp. *dysgalactiae* or *Streptococcus dysgalactiae* subsp. *equisimilis*, *Streptococcus entericus*, *Streptococcus equi*, for example *Streptococcus equi* subsp. *equi*, *Streptococcus equi* subsp. *ruminatorum*, or *Streptococcus equi* subsp. *zooepidemicus*, *Streptococcus equinus*, *Streptococcus faecalis*, *Streptococcus faecium*, *Streptococcus ferus*, *Streptococcus gallinaceus*, *Streptococcus gallinarum*, *Streptococcus gallolyticus*, for example *Streptococcus gallolyticus* subsp. *gallolyticus*, *Streptococcus gallolyticus* subsp. *macedonicus*, or *Streptococcus gallolyticus* subsp. *pasteurianus*, *Streptococcus garvieae*, *Streptococcus gordonii*, *Streptococcus halichoeri*, *Streptococcus hansenii*, *Streptococcus henryi*, *Streptococcus hongkongensis*, *Streptococcus hyointestinalis*, *Streptococcus hyovaginalis*, *Streptococcus ictaluri*, *Streptococcus infantarius*, for example *Streptococcus infantarius* subsp. *coli* or *Streptococcus infantarius* subsp. *infantarius*, *Streptococcus infantis*, *Streptococcus iniae*, *Streptococcus intermedius*, *Streptococcus intestinalis*, *Streptococcus lactarius*, *Streptococcus lactis*, for example *Streptococcus lactis* subsp. *cremoris*, *Streptococcus lactis* subsp. *diacetilactis*, or *Streptococcus lactis* subsp. *lactis*, *Streptococcus loxodontisalivarius*, *Streptococcus lutetiensis*, *Streptococcus macacae*, *Streptococcus macedonicus*, *Streptococcus marimammalium*, *Streptococcus massiliensis*, *Streptococcus merionis*, *Streptococcus minor*, *Streptococcus mitis*, *Streptococcus morbillorum*, *Streptococcus moroccensis*, *Streptococcus mutans*, *Streptococcus oligofermentans*, *Streptococcus oralis*, *Streptococcus orisasini*, *Streptococcus orisuis*, *Streptococcus ovis*, *Streptococcus parasanguinis*, *Streptococcus parauberis*, *Streptococcus parvulus*, *Streptococcus pasteurianus*, *Streptococcus peroris*, *Streptococcus phocae*, for example *Streptococcus phocae* subsp. *phocae* or *Streptococcus phocae* subsp. *salmonis*, *Streptococcus plantarum*, *Streptococcus pleomorphus*, *Streptococcus pluranimalium*, *Streptococcus plurextorum*, *Streptococcus pneumonia*, *Streptococcus porci*, *Streptococcus porcinus*, *Streptococcus porcorum*, *Streptococcus pseudopneumoniae*, *Streptococcus pseudoporcinus*, *Streptococcus pyogenes*, *Streptococcus raffinolactis*, *Streptococcus ratti*, *Streptococcus rifensis*, *Streptococcus rubneri*, *Streptococcus rupicaprae*, *Streptococcus saccharolyticus*, *Streptococcus salivarius*, for example *Streptococcus salivarius* subsp. *salivarius* or *Streptococcus salivarius* subsp. *thermophilus*, *Streptococcus saliviloxodontae*, *Streptococcus sanguinis*, *Streptococcus shiloi*, *Streptococcus sinensis*, *Streptococcus sobrinus*, *Streptococcus suis*, *Streptococcus thermophilus*, *Streptococcus thoraltensis*, *Streptococcus tigurinus*, *Streptococcus troglodytae*, *Streptococcus uberis*, *Streptococcus urinalis*, *Streptococcus ursoris*, *Streptococcus vestibularis*, or *Streptococcus waius*.

Preferably, the probiotic bacteria are a bacteria classified as "generally regarded as safe" (GRAS) in the genus *Streptococcus* sp., including but not limited to, *Streptococcus thermophilus* strain Th4, *Streptococcus gallolyticus* subsp. *macedonicus*, *Streptococcus salivarius* subsp. *salivarius*, or *Streptococrus salivarius* subsp. *thermophilus*.

Preferably, the probiotic bacteria are bacteria having a "Qualified Presumption of Safety" (QPS) status in the genus *Streptococcus* sp., including but not limited to, *Streptococcus thermophilus*.

In a preferred embodiment, said probiotic bacteria produce no endotoxins or other potentially toxic substances. Thereby, said probiotic bacteria are safe to use and are not harmful to a subject after application.

Preferably, said probiotic bacteria produce no spores. Bacterial spores are not part of a sexual cycle but are resistant structures used for survival under unfavourable conditions. Since said probiotic bacteria preferably produce no spores, said recombinant probiotic bacteria can not survive, for example, without nutrients or if an auxotrophic factor is missing.

Preferably, said probiotic bacteria produce no inclusion bodies. Inclusion bodies often contain over-expressed proteins and aggregation of said over-expressed proteins in inclusion bodies can be irreversible.

Since said probiotic bacteria preferably produce no inclusion bodies, the amount of said first, second, and third heterologous factor after transcribing and translating the respective nucleic acid sequences is not diminished by intracellular accumulation in inclusion bodies.

Further preferably, said probiotic bacteria produce also no extracellular proteinases. Extracellular proteinases may be secreted from bacteria to destroy extracellular structures, such as proteins, to generate nutrients, such as carbon, nitrogen, or sulfur. Extracellular proteinases may also act as an exotoxin and be an example of a virulence factor in bacterial pathogenesis.

Due to the absence of extracellular proteinases the safety of said probiotic bacteria after application to a subject is preferably increased. Furthermore, said probiotic bacteria preferably do not degrade the respective first, second, and third heterologous factor after release from said recombinant probiotic bacteria.

Preferably, said probiotic bacteria are devoid of all naturally occurring plasmids. Due to the absence of all naturally occurring plasmids, said probiotic bacteria preferably possess no antibiotic resistance.

Further preferably, said probiotic bacteria lack host factors required for conjugative transposition.

Naturally occurring plasmids can be broadly classified into conjugative plasmids and non-conjugative plasmids. Conjugative plasmids contain a set of transfer or tra genes which promote sexual conjugation between different cells. In the complex process of conjugation, plasmid may be transferred from one bacterium to another via sex pili encoded by some of the tra genes. Non-conjugative plasmids are incapable of initiating conjugation, hence they can be transferred only with the assistance of host factors required for conjugative transposition, such as conjugative plasmids.

Due to the absence of host factors required for conjugative transposition, gene transfer of said nucleic acid(s) encoding the respective first, second, and third heterologous factor from said probiotic bacteria to other microorganisms is highly unlikely, preferably gene transfer is suppressed.

In a further preferred embodiment, said recombinant probiotic bacteria are lactic acid bacteria, preferably a lactobacillus or a *lactococcus* species. In a further preferred embodiment, said *lactococcus* species is *Lactococcus lactis* subsp. *cremoris*.

Lactic acid bacteria further release lactic acid as the major metabolic end-product of carbohydrate fermentation. Lactic acid is known to also stimulate endothelial growth and proliferation. Furthermore, lactic acid has an antibacterial effect which reduces the probability of a bacterial infection at the site of the skin dysfunction.

Techniques for transforming the above-mentioned probiotic bacteria are known to the skilled person, and, for example, are described in Green and Sambrook (2012): "Molecular cloning: a laboratory manual", fourth edition, Cold Spring Harbour Laboratory Press (Cold Spring Harbor, N.Y., USA).

After transformation the recombinant probiotic bacteria comprise at least one nucleic acid sequence encoding for said first heterologous factor and at least one nucleic acid sequence encoding for said second heterologous factor, and preferably at least one nucleic acid sequence encoding for said third heterologous factor.

In an embodiment, the at least one nucleic acid sequence encoding for said first heterologous factor and the at least one nucleic acid sequence encoding said second heterologous factor, preferably and the at least one nucleic acid sequence encoding for said third heterologous factor, are located in different sub-populations of the recombinant probiotic bacteria.

For example, the respective nucleic acid sequences are each located in separate sub-populations of the probiotic bacteria, which are combined to obtain the recombinant probiotic bacteria of the present invention.

The respective individual sub-population comprising the respective nucleic acid sequences can, for example, be from the same species or from different species of the above mentioned probiotic bacteria.

For example, different species of recombinant probiotic bacteria expressing different heterologous factors can be used to adapt the expression and, preferably the release, of the respective heterologous factors from the probiotic bacteria.

In a preferred embodiment of the present invention, the respective nucleic acid sequences are present in the recombinant probiotic bacteria in various numbers of copies. For example, the recombinant probiotic bacteria comprise at least one copy of the respective nucleic acid sequences encoding for said first, said second, and/or preferably said third factor.

The numbers of copies of the respective nucleic acid sequence can be increased in order to enhance the expression of the respective heterologous factor.

Preferably, the ratio of copies of the respective nucleic acid sequences encoding for said first, said second, and/or said third factor is 1:1:1.

The translation efficiency can be enhanced by providing additional copies of a nucleic acid sequence to be transcribed by the recombinant probiotic bacteria.

In a further embodiment of the present invention, a sub-population of the recombinant probiotic bacteria comprises at least one nucleic acid sequence encoding for two of the three heterologous factors wherein preferably the third heterologous factor is encoded by a nucleic acid sequence located in a second sub-population of the recombinant probiotic bacteria.

In a preferred embodiment, the nucleic acid sequences encoding for all three heterologous factors are located in one population of the recombinant probiotic bacteria.

In a further preferred embodiment, the respective nucleic acid sequences are located on at least one of a chromosome and a plasmid of said recombinant probiotic bacteria.

Locating nucleic acid sequence on a chromosome of the recombinant probiotic bacteria or on a plasmid of said recombinant probiotic bacteria determines inter alia the amount of protein translated by the bacteria, since expression levels on a plasmid are higher compared to expression levels on a chromosome.

In a further preferred embodiment of the present invention, at least one nucleic acid sequence encoding for the respective heterologous factor is provided on a chromosome of the bacteria and at least one nucleic acid sequence encoding for another heterologous factor is provided on a plasmid of said recombinant probiotic bacteria.

The respective nucleic acid sequence encoding for the third factor might then either be provided on a chromosome or on a plasmid of the recombinant probiotic bacteria.

In an alternative embodiment of the present invention, the respective nucleic acid sequences are either provided on individual portions of the chromosome of the recombinant probiotic bacteria or on different plasmids of said recombinant probiotic bacteria.

In particular preferred embodiment of the invention, all nucleic acid sequences encoding for said heterologous factors are provided on a single plasmid, for example, each controlled and functionally coupled to a distinct promoter.

In another particular preferred embodiment of the invention, the respective nucleic acid sequences encoding for the respective heterologous factors are located in a single operon which is operatively linked to and controlled by a single promoter.

An operon is a functioning unit of DNA containing a cluster of genes under the control of a single promoter. The genes are transcribed together in mRNA strands and are either translated together in the cytoplasm, or undergo trans-splicing to create monocistronic mRNAs that are translated separately.

Preferably, the respective nucleic acid sequences encoding for the respective heterologous factors located in said single operon are provided with a nucleic acid sequences encoding a ribosome binding site for translational initiation.

Preferably, the nucleic acid sequences encoding a ribosome binding site is located upstream of the start codon, which is towards the 5' region of the same strand which is to be transcribed. The sequence is preferably complementary to the 3' end of the 16S ribosomal RNA.

Preferably, the respective nucleic acid sequences encoding for the respective heterologous factors located in said single operon are provided with a nucleic acid sequence encoding for a secretory signal sequence at the 5'-end of the open reading frame (ORF) of the heterologous factor generating a fusion protein comprising the secretory signal sequence and the heterologous factor.

In a further preferred embodiment, the nucleic acid sequences are controlled by and functionally coupled to a constitutive promoter or an inducible promoter, preferably to an inducible promoter.

For example, the nucleic acid sequences encoding for the respective heterologous factors can be controlled by and functionally coupled to individual promoters, which could either be a constitutive promoter or an inducible promoter, further preferably an inducible promoter.

A constitutive promoter is active in a cell in all circumstances, while an inducible promoter becomes active in response to specific inducer.

A promoter is a nucleic acid sequence that initiates transcription of a particular gene. Promoters are located near the transcription start side of the gene, on the same strand and upstream of the DNA, which is towards the 5' region of the same strand which is to be transcribed.

Preferably, the respective promoter used is an autologous promoter from the probiotic bacteria, which expresses the respective nucleic acid sequence.

Alternatively, the respective promoter is a heterologous promoter, preferably a prokaryotic promoter, further preferably a promoter from bacteria.

In a further preferred embodiment, the expression of at least one nucleic acid sequence is controlled by an inducible promoter, said at least one nucleic acid sequence being expressible in the presence of at least one inducer.

Preferably, said inducible promoter, which is inducible by inducer, is a promoter for at least one microbial gene which encodes for a lantibiotic peptide.

Lantibiotic peptides are known to the skilled person. Lantibiotics are a class of peptides that contain the characteristic polycyclic thioether amino acid lanthionine as well as the unsaturated amino acids dehydroalanine and 2-aminoisobutyric acid.

Lanthionine, for example, is a monosulfide analogue of a cysteine and is composed of two alanine residues that are cross-linked on their beta-carbon atoms by a thioether linkage.

Lantibiotics are produced by a large number of gram-positive bacteria.

In a preferred embodiment, said inducible promoter is a nisin promoter from *Lactococcus lactis*, a bisin promoter from *Bifidobacterium longum*, an optiline promoter from *Bacillus subtilis*, a salvarizine promoter from *Streptococcus salivarius*, an epidermin promoter from *Staphylococcus epidermidis*, a gallidermin promoter from *staphylococcus gallinarum*, a mutacin promoter from *Streptococcus mutans*, a streptin promoter from *Streptococcus pyogenes*, a streptococcinum promoter from *Streptococcus pyogenes*, a lacticin promoter from *Lactococcus lactis*, an epidermin promoter from *staphylococcis epidermidis*, a epilanzine promoter from *Staphylococcus epidermidis*, a pep5 promoter from *staphylococcus* epidermidis, a lactocin-s promoter from *lactobacillus sakei*, a salvaricin promoter from *streptococcus salivarius*, or *Streptococcus pyogenes*, a plantarizine promoter from *Lactobacillus plantarum*, a thermophilin promoter from *streptococcus*, a bovicine promoter from *streptococcus* or combinations thereof.

Further preferably, said inducible promoter is PnisA, PnisZ, PnisQ, PnisF, PnisU or combinations thereof of *Lactococcus lactis*.

In a preferred embodiment, the inducer is at least one lantibiotic peptide or functional analogue thereof, preferably selected from the group consisting of nisin A, nisin Z, nisin Q, nisin F, nisin U, functional analogues thereof and mixtures thereof.

A nisin controlled gene expression system is, for example, commercially available from MoBiTec GmbH (Göttingen, Germany) under the trade name NICE®, which was developed at NIZO Food Research (Ede, Netherlands).

Nisin, which is well known to the skilled person, is a 34 amino acid lantibiotic peptide with a broad host spectrum. For example, nisin from *Lactococcus lactis* is commercially available from Sigma-Aldrich Chemie GmbH (Munich, Germany).

Nisin is widely used as a preservative in food. Initially, nisin is ribosomally synthesized as precursor. After subsequent enzymatic modifications, the modified molecule is translocated across the cytoplasmic membrane and processed into its mature form.

Nisin induces its own expression. Expression of a nucleic acid sequence of interest can be induced by addition of a sub-inhibitory amount of nisin, which is preferably of from 0.01 to 50 ng/ml culture medium, further preferably from 0.1 to 5 ng/ml culture medium, when the gene of interest is subsequently based behind the inducible promoters of the nisin system.

Furthermore, the NICE system has been transferred to other gram-positive bacteria, for example, *leuconostoc lactis, Lactobacillus brevis, lactobacillus helveticus, Lactobacillus plantarum, Streptococcus pyogenes, Streptococcus agalactiae, Streptococcus pneumoniae, streptococcus zooepidemicus, Enterococcus faecalis* or *lactoBacillus subtilis*.

An inducible nisin promoter, which preferably is selected from PnisA, PnisZ, PnisQ, PnisF, PnisU, and combinations thereof, can be integrated into a chromosome of the probiotic bacteria used together with at least one nucleic acid sequence encoding for said first heterologous factor, said second heterologous factor, and/or preferably said third heterologous factor.

Preferably, said inducible promoter is PnisA.

Alternatively, the respective promoters together with at least one nucleic acid sequence are provided on a plasmid which is then transformed into the probiotic bacteria.

The respective nucleic acid sequence is expressible in the presence of nisin.

Suitable plasmids are commercially available, for example, from MoBiTec GmbH, (Göttingen, Germany) such as pNZ8008, pNZ8148, pNZ8149, and pNZ8150.

In a further preferred embodiment, the genes NisR and NisK are also provided on either a chromosome or a plasmid of the probiotic bacteria used. The respective protein NisR and NisK belong to the family of bacterial two-component signal transduction systems. NisK is a histidine-protein kinase that resides in the cytoplasmic membrane where it preferably acts as a receptor for the mature nisin molecule. Upon binding of nisin to NisK, it autophosphorylates and transfers the phosphate group to NisR, which is the response regulator that becomes activated upon phosphorylation by NisK.

Activated NisR induces transcription from the PnisA promoter, the PnisF promoter, the PnisZ promoter, PnisQ promoter, and/or the PnisU promoter.

The respective regulators of the expression of the nisin genes NisR and NisK can, for example, be provided on a chromosome of the probiotic bacteria and/or on a plasmid.

Suitable plasmids are commercially available and include, for example, the plasmid pNZ9530 (MoBiTec GmbH, Göttingen, Germany). The plasmid pNZ9530 carries the NisR and NisK genes and is preferably used for cloning in *lactococcus* strains and in strains of other lactic acid bacteria genera that do not have the regulatory genes integrated into the chromosome. For example, for nisin induced expression in *Enterococcus faecalis*, a plasmid pMSP3535 has been described by Brian et al. (2000) and which is, for example, available from AddGene, a non-profit plasmid repository (Plasmid No. 46886).

The nucleic acid sequence of the plasmid pMSP3535 is available under the NCBI accession number AY303239.1.

In a further preferred embodiment, probiotic bacteria are used, which contain the regulatory genes for nisin controlled gene expression NisR and NisK.

Suitable strains are commercially available, for example, from MoBiTec GmbH (Göttingen, Germany). Suitable strains are, for example, *Lactococcus lactis* strain NZ9000, *Lactococcus lactis* strain NZ9100, *Lactococcus lactis* strain NZ3900.

A suitable strain is also *Lactococcus lactis* strain NZ3000, which is commercially available, for example, from MoBiTec GmbH. *Lactococcus lactis* strain NZ3000 is a strain without NisR and NisK. *Lactococcus lactis* strain NZ3000 can be used, when expression of said nucleic acid sequence(s) is/are controlled by a constitutive promoter.

In a further preferred embodiment the probiotic bacteria are *Lactococcus lactis* strain NZ3900, which is a food grade strain. *Lactococcus lactis* strain NZ3900 includes a plasmid selection system which is not based on antibiotic resistance but on the ability to grow on lactose.

*Lactococcus lactis* strain NZ3900 produces no endotoxins or other potentially toxic substances. Furthermore, *Lactococcus lactis* strain NZ3900 produces no inclusion bodies and no spores. Moreover, *Lactococcus lactis* strain NZ3900 produces no extracellular proteinases.

In a further preferred embodiment, the nucleic acid sequences encoding for the respective heterologous factors are modified in order to increase expression, secretion and/or stability of the encoded heterologous factor.

Suitable modifications are known to the skilled person and include, for example, adapting the codon usage of the at least one nucleic acid sequence to the probiotic bacteria used.

For example, the at least one nucleic acid sequence can be designed to fit the codon usage pattern of the probiotic bacteria used. Furthermore, in addition to a general codon optimization, specific codon tables can be used, such as a codon table for the highly expressed ribosomal protein genes of the respective probiotic bacteria, to further increase translation of the encoded factors.

Suitable modifications include also, for example, the incorporation of a nucleic acid sequence encoding for a secretory signal sequence at the 5'-end of the open reading frame (ORF) of the heterologous factor generating a fusion protein comprising the secretory signal sequence and the heterologous factor. The secretory signal sequence is preferably arranged at the N-terminal side of the respective heterologous factor.

The secretory signal sequence preferably directs the newly synthesized protein to the plasma membrane. At the end of the secretory signal sequence, preferably signal peptide or propeptide, there is preferably a stretch of amino acids that is recognized and cleaved by a signal peptidase in order to generate a free secretory signal sequence, preferably signal peptide or propeptide, and the mature heterologous factor, which is secreted extracellularly.

In bacteria, two major pathways exist to secrete proteins across the cytoplasmic membrane. The general secretion route, termed Sec-pathway, catalyses the transmembrane translocation of proteins in their unfolded conformation, whereupon they fold into their native structure at the trans-side of the membrane.

The twin-arginine translocation pathway, termed Tat-pathway, catalyses translocation of secretory proteins in their folded state.

Suitable secretory signal sequences include, for example, a signal peptide.

Preferably, the secretory signal sequence is the native signal peptide or propeptide of the respective heterologous factor encoded by the nucleic acid sequence, which preferably is a precursor and/or preproprotein of the respective factor.

In a further preferred embodiment, said secretory signal sequence is a homologous secretory sequence from said recombinant probiotic bacteria, preferably said secretory signal sequence is the ubiquitin specific peptidase 45 (Usp 45) signal sequence of *Lactococcus* sp. The Usp 45 secretion signal has very high secretion efficiency. Other secretion signals are known to the skilled person and include, for example, SP310, SPEXP4 and AL9 of *Lactococcus* sp.

For example, the native signal peptide of the heterologous factor can be replaced by a homologous secretory signal sequence from the probiotic bacteria used to express said heterologous factor.

A secretory signal sequence preferably improves the secretion efficiency of the respective heterologous factor. For example, in *Lactococcus lactis*, most proteins are secreted via the Sec-pathway. Proteins are synthesized as precursors containing the mature moiety of the proteins with an N-terminal signal peptide. The signal peptide targets the protein to the cyctoplasmic membrane. Following cleavage of the signal peptide, the mature protein is released extracellularly.

Further preferably, the secretory signal comprises the amino acid sequence of SEQ ID No. 34.

In a further preferred embodiment, the respective heterologous factor is expressed as a propeptide with or without a secretion enhancing factor. The propeptide can be cleaved by proteases to release the mature heterologous factor.

In a further preferred embodiment, the recombinant probiotic bacteria comprise at least one inactivated gene encoding for an essential protein necessary for viability of said probiotic bacteria.

In a preferred embodiment, the essential protein necessary for viability of said probiotic bacteria is a protein, further preferably an enzyme, necessary for synthesis of an organic compound necessary for viability of said probiotic bacteria.

After inactivation of said essential protein, preferably enzyme, the respective organic compound is an auxotrophic factor required for the viability of the recombinant probiotic bacteria and which has to be supplemented in order to sustain the viability of the recombinant probiotic bacteria.

Preferably, said auxotrophic factor is a vitamin, amino acid, nucleic acid, and/or a fatty acid.

For example, amino acids and nucleotides are biologically important organic compounds, which are precursors to proteins and nucleic acids, respectively.

In a further preferred embodiment, the at least one gene necessary for viability of the probiotic bacteria is selected from the group consisting of alanine racemase (alaR), thymidylate synthase (thyA), asparagine synthase (asnH), CTP synthase (pyrG), tryptophan synthase (trbBA), and combinations thereof.

For example, alanine racemase is an enzyme that catalyzes the conversion of L-alanine into D-alanine. D-alanine produced by alanine racemase is used for peptidoglycan synthesis. Peptidoglycan is found in the cell walls of all bacteria.

It is known to the skilled person that inactivating the alanine racemase (alaR) gene in bacteria results in the need of the bacteria to use an external source of D-alanine in order to maintain cell wall integrity.

It is known to the skilled person that, for example, *Lactococcus lactis* and *Lactobacillus plantarum* contain a single alaR gene. Inactivation of the gene effects the incorporation of D-alanine into the cell wall.

*Lactococcus lactis* bacteria, for example, with an inactivated alanine racemase (alaR) gene are dependent on external supply of D-alanine to be able to synthesize peptidoglycan and to incorporate D-alanine in the lipoteichoic acid (LTA). These bacteria lyses rapidly when D-alanine is removed, for example, at mid-exponential growth.

Alanine racemase deficient strains of lactic acid bacteria could, for example, be generated by methods known in the art.

Thymidylate synthase is an enzyme that catalyzes the conversion of deoxyuridine monophosphate (dUMP) to deoxythymidylate monophosphate (dTMP). dTPM is one of the three nucleotides that form thymine (dTMP, dTDP, and dTTP). Thymidine is a nucleic acid in DNA.

It is known to the skilled person that thymidylate synthase plays a crucial role in the early stage of DNA biosynthesis. For example, DNA damage or deletion occurs on a daily basis as a result of endogenous and environmental factors.

Furthermore, for proliferation of the probiotic bacteria it is necessary to synthesize DNA.

Inactivation of the thymidylate synthase (thyA) gene in bacteria results in the need of the bacteria to use an external source of thymidine in order to maintain DNA integrity.

Asparagine synthetase is an enzyme that generates the amino acid asparagine from aspartate. Inactivation of the asparagines synthetase (asnH) gene results in an inability to synthesize the respective amino acid, which becomes an auxotrophic factor.

CTP-synthase is an enzyme involved in pyrimidine synthesis. CTP synthase interconverts uridine-5'-triphosphate (UTP) and cytidine triphosphate (CTP). Inactivation of the CTP-synthase (pyrG) gene renders the bacteria unable to synthesize cytosine nucleotides from both the de novo synthesis as well as the uridine cell wall pathway.

CTP becomes an auxotrophic factor, which has to be supplemented for the synthesis of RNA and DNA.

Tryptophan synthase is an enzyme that catalyzes the final two steps in the biosynthesis of the amino acid tryptophan. Inactivation of the tryptophan synthase (trpBA) gene renders the bacteria unable to synthesize the respective amino acid, which becomes an auxotrophic factor.

Methods for inactivation of said gene necessary for the viability of the probiotic bacteria are known to the skilled person and include deletion of the gene, mutation of the gene, epigenetic modification of said gene, RNA interference (RNAi) mediated gene silencing of said gene, translational inhibition of said gene, or combinations thereof.

In a further preferred embodiment, the respective auxotrophic factor is provided together with said probiotic bacteria.

In a further preferred embodiment of the invention, said inactivated gene necessary for viability of the probiotic bacteria is used for environmental containment.

After application of the recombinant probiotic bacteria comprising at least one inactivated gene necessary for viability of said probiotic bacteria, the respective auxotrophic factor has to be provided externally, for example, with an application medium or a growth medium.

In case the recombinant probiotic bacteria are released into the environment, the auxotrophic factor is missing and, preferably, the recombinant probiotic bacteria die.

Furthermore, application of the externally supplemented auxotrophic factor enables for a control of the biosynthesis and release of the respective heterologous factors.

Preferably, at least one of said first factor, said second factor and said third factor is releasable from said recombinant probiotic bacteria. Further preferably, at least one of said first factor, said second factor and said third factor is secreted from said recombinant probiotic bacteria.

For example, in gram-positive bacteria, such as lactic acid bacteria, proteins to be secreted from the bacteria are preferably synthesized as a precursor containing an N-terminal signal peptide and the mature moiety of the protein. Precursors are recognized by the secretion machinery of the bacteria and are translocated across the cytoplasmic membrane. The signal peptide is then cleaved and degraded and the mature protein is secreted from the bacteria, for example, into the culture supernatant or into the area of an inflammatory skin dysfunction.

For example, *Lactococcus lactis* is able to secrete proteins ranging from low molecular mass, for example smaller than 10 kDa, to high molecular mass, for example molecular weight above 160 kDa, through a Sec-dependent pathway.

Alternatively, at least one of said first factor, said second factor, and said third factor is released from said recombinant probiotic bacteria through a leaky cytoplasmic membrane.

For example, when using nisin as an inducer for protein synthesis in said recombinant probiotic bacteria, nisin also forms pores within the cytoplasmic membrane through which at least one of said first factor, said second factor, and said third factor is released from the probiotic bacteria.

Alternatively, the cytoplasmic membrane of said recombinant probiotic bacteria becomes leaky due to an impaired synthesis of cell wall components.

For example, said recombinant probiotic bacteria comprise an inactivated alanine racemase (alaR) gene. In the absence of D-alanine, said recombinant probiotic bacteria cannot maintain the integrity of the cytoplasmic membrane and, subsequently, at least one of said first factor, said second factor and said third factor is released from said recombinant probiotic bacteria.

During the healing process of said inflammatory skin dysfunction, the released first heterologous factor, second heterologous factor and/or third heterologous factor can undergo degradation, for example by protease cleavage, which may lead to a loss of the biological activity of said heterologous factors.

The degradation or depletion of said heterologous factors can be compensated by a sustained release of said heterologous factors from said recombinant probiotic bacteria. Preferably, said recombinant probiotic bacteria express at least one of said first heterologous factor, said second heterologous factor and said third heterologous factor in a constant manner. Preferably, said recombinant probiotic bacteria release said heterologous factors constantly.

In a preferred embodiment, said probiotic bacteria are provided in a pharmaceutical composition for use in the treatment of said inflammatory skin dysfunction.

Preferably, said pharmaceutical composition comprises at least one pharmaceutically acceptable carrier or excipient which, further preferably, is suitable for the intended route of administration.

Preferably, said pharmaceutically acceptable carrier or said pharmaceutically acceptable excipient comprises at least one polymeric carrier, preferably selected from the group consisting of polysaccharides, polyesters, polymethacrylamide, and mixtures thereof. For example, said pharmaceutically acceptable carrier is a hydrogel, which, for example, provide additionally optimal moisture environment for promoting wound healing. Furthermore, the pharmaceutically acceptable carrier assists in the adhesion of said recombinant probiotic bacteria to the site of said inflammatory skin dysfunction after application.

Preferably, said pharmaceutical composition further comprises at least one nutrient for said recombinant probiotic bacteria, preferably selected from the group consisting of carbohydrates, vitamins, minerals, amino acids, trace elements and mixtures thereof.

Further preferably, said pharmaceutical composition further comprises at least one component for stabilizing at least one of said first factor, said second factor and said third factor.

Said stabilizing compound is preferably selected from the group consisting of anti-microbial agents, cryoprotectants, protease inhibitors, reducing agents, metal chelators, and mixtures thereof.

In a further preferred embodiment, said recombinant probiotic bacteria are in a solution, frozen or dried, preferably lyophilized or spray dried.

Preferably, said recombinant probiotic bacteria are to be applied in a solution, for example, in form of said pharmaceutical composition.

In an alternative embodiment, said recombinant probiotic bacteria are frozen or dried, preferably lyophilized or spray dried. The recombinant probiotic bacteria might be reconstituted prior to use.

After application, the recombinant probiotic bacteria might be contacted with said at least one inducer, preferably to induce expression of at least one of said first factor, said second factor, and said third factor.

Further preferably, after induction of the expression, at least one of said first factor, said second factor and said third factor is released from said bacteria.

LITERATURE

Brian et al. (2000): "Improved vector for nisin-controlled expression in gram-positive bacteria", plasmid 44 (2), 2000, pages 183 to 190.

Davis et al. (2013): Macrophage M1/M2 polarization dynamically adapts to changes in cytokine microenvironments in *cryptococcus neoformans* infection, mbio. 4(3), 2013, e00264-13. doi:10.1128/mBio.00264-13.

de Ruyter et al. (1996): Functional analysis of promoters in the nisin gene cluster of *Lactococcus lactis*. J. Bacteriol. 178 (12), 1996, pages 3434 to 3439.

Duluc et al. (2007): Tumor-associated leukemia inhibitory factor and IL-6 skew monocyte differentiation into tumor-associated macrophage-like cells, Blood 110(13), 2007, pages 4319 to 4330.

Hao et al. (2012): Macrophages in tumor microenvironments and the progression of Tumors: Clin. Dev. Immunol. 2012, pages 1 to 11 van Asseldonk et al. (1993): Functional analysis of the *Lactococcus lactis* usp45 secretion signal in the secretion of a homologous proteinase and a heterologous alpha-amylase. Mol. Gen. Genet. 240 (3), 1993, pages 428-434.

van Asseldonk et al. (1990): Cloning of usp45, a gene encoding a secreted protein from *Lactococcus lactis* subsp. *lactis* MG1363. Gene 95 (1), 1990, pages 155 to 160.

Richard et al. (1995): Effect of topical basic fibroblast growth factor on the healing of chronic diabetic neuropathic ulcer of the foot. A pilot, randomized, double-blind, placebo-controlled study; Diabetes Care 18 (1), 1995, page 64 to 69.

SEQUENCES

SEQ ID Nos. 1 to 3 correspond to human CSF-1 isoform 1 to 3 precursor, respectively, including a signal peptide.

SEQ ID No. 4 corresponds to the mature human CSF-1.

SEQ ID No. 5 corresponds to the synthetic construct of CSF-1 used in Example 1, including the Usp45 secretion signal from *Lactococcus lactis*, which spans the amino acids 1 to 27 of the protein, and mature human CSF-1, which spans the amino acids 28 to 185 of the protein.

SEQ ID No. 6 corresponds to the synthetic construct of CSF-1 generated after secretion from *Lactococcus lactis* expressing pCSF1.

SEQ ID Nos. 7 and 8 correspond to human IL-34 isoform 1 and 2 precursor, respectively, including a signal peptide.

SEQ ID No. 9 corresponds to the mature human IL-34.

SEQ ID Nos. 10 and 11 correspond to human IL-4 isoform 1 and 2 precursor, respectively, including a signal peptide.

SEQ ID No. 12 corresponds to the mature human IL-4.

SEQ ID No. 13 corresponds to the synthetic construct of human IL-4 used in Example 1, including the Usp45 secretion signal from *Lactococcus lactis*, which spans the amino acids 1 to 27 of the protein, and mature human IL-4, which spans the amino acids 28 to 185 of the protein.

SEQ ID No. 14 corresponds to the synthetic construct of IL-4 generated after secretion from *Lactococcus lactis* expressing pIL4.

SEQ ID No. 15 corresponds to human IL-10 precursor including a signal peptide.

SEQ ID No. 16 corresponds to the mature human IL-10.

SEQ ID No. 17 corresponds to human IL-13 precursor including a signal peptide.

SEQ ID No. 18 corresponds to the mature human IL-13.

SEQ ID No. 19 corresponds to human TGF-$\beta$1 precursor including a signal peptide.

SEQ ID No. 20 corresponds to the mature human TGF-$\beta$1.

SEQ ID Nos. 21 and 22 correspond to human TGF-$\beta$2 isoform 1 and 2 precursor, respectively, including a signal peptide.

SEQ ID No. 23 corresponds to the mature human TGF-$\beta$2.

SEQ ID No. 24 corresponds to human TGF-$\beta$3 preprotein including a signal peptide.

SEQ ID No. 25 corresponds to the mature human TGF-$\beta$3.

SEQ ID No. 26 corresponds to human FGF-2 preproprotein, including a propeptide.

SEQ ID No. 27 corresponds to the mature human FGF-2 after secretion (hFGF2-155).

SEQ ID No. 28 corresponds to the partial sequence of the mature human FGF-2.

SEQ ID No. 29 corresponds to the synthetic construct of human FGF-2 used in Example 1, including the Usp45 secretion signal from *Lactococcus lactis*, which spans the amino acids 1 to 27 of the protein, and mature human FGF-2, which corresponds to the amino acids 136 to 288 of SEQ ID No. 26.

SEQ ID No. 30 corresponds to the human FGF-2 variant hFGF2-153 used in Example 1 after secretion from *Lactococcus lactis* expressing pFGF.

SEQ ID No. 31 corresponds to human HGF.

SEQ ID No. 32 corresponds to human HGF alpha chain.

SEQ ID No. 33 corresponds to human HGF beta chain.

SEQ ID No. 34 corresponds to the Usp45 secretion signal from *Lactococcus lactis*.

SEQ ID No. 35 corresponds to the nucleic acid sequence of the plasmid pNZ8149.

SEQ ID Nos. 36 to 43 correspond to primers used in the Examples.

SEQ ID No. 44 corresponds to the nucleic acid sequence of nisin A promoter of *Lactococcus lactis*.

SEQ ID No. 45 corresponds to the nucleic acid sequence of the synthetic construct ssUsp45-FGF2-153 containing the nisinA promoter, the Usp45 signal sequence and the hFGF2-153 gene.

SEQ ID No. 46 corresponds to the nucleic acid sequence of the plasmid pFGF2.

SEQ ID No. 47 corresponds to the nucleic acid sequence of the synthetic construct ssUsp45-hIL4 containing the nisinA promoter, the Usp45 signal sequence and the hIL4 gene.

SEQ ID No. 48 corresponds to the nucleic acid sequence of the plasmid pIL4.

SEQ ID No. 49 corresponds to the nucleic acid sequence of the synthetic construct ssUsp45-hCSF1 containing the nisinA promoter, the Usp45 signal sequence and the hCSF1 gene.

SEQ ID No. 50 corresponds to the nucleic acid sequence of the plasmid pCSF1.

SEQ ID No. 51 to SEQ ID No. 53 correspond to nucleic acid sequences providing the respective ribosome binding sites including the start codon (ATG) of the respective open reading frame used in the Examples.

SEQ ID No. 54 corresponds to the nucleic acid sequence of the 3' end of 16S ribosomal RNA (rRNA) of *Lactococcus lactis*.

Figure 24B:
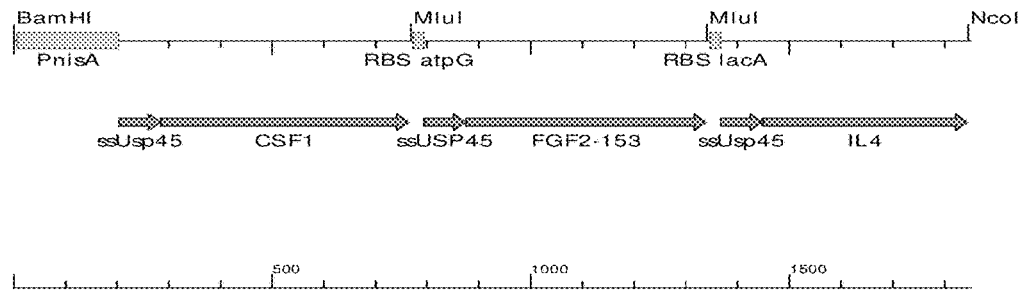
FIG. 24a shows an overview of the three ribosome binding sites used in Example 2d. The respective sequences of the synthesized DNA sequences CSF-RBS1-FGF-RBS2-IL4, FGF-RBS1-IL4-RBS2-CSF, and IL4-RBS-CSF-RBS2-FGF used in Example 2d are depicted in FIGS. 24b to 24d, respectively, as well as in SEQ ID No. 55, SEQ ID No. 56, and SEQ ID No. 57, respectively.
FIGS. 24*e* to 24*g* show respective SDS-PAGE gels as well as Western blots obtained with the single operon constructs used in Example 2d).

SEQ ID No. 55 corresponds to the nucleic acid sequence of the synthetic construct CSF-RBS1-FGF-RBS2-IL4 depicted in FIG. 24B. SEQ ID No. 56 corresponds to the nucleic acid sequence of the synthetic construct FGF-RBS1-IL4-RBS2-CSF depicted in FIG. 24C. SEQ ID No. 57 corresponds to the nucleic acid sequence of the synthetic construct IL4-RBS1-CSF-RBS2-FGF depicted in FIG. 24D.

SEQ ID No. 58 corresponds to the amino acid sequence of epidermal growth factor isoform 1 preproprotein from *Homo sapiens*. SEQ ID No. 59 corresponds to the amino acid sequence of epidermal growth factor isoform 2 preproprotein from *Homo sapiens*. SEQ ID No. 60 corresponds to the amino acid sequence of epidermal growth factor isoform 3 preproprotein from *Homo sapiens*. SEQ ID No. 61 corresponds to the amino acid sequence of the mature epidermal growth factor from *Homo sapiens*. SEQ ID No. 62 corresponds to the amino acid sequence of the heparin-binding EGF-like growth factor precursor from *Homo sapiens*. SEQ ID No. 63 corresponds to the amino acid sequence of the mature heparin-binding EGF-like growth factor from *Homo sapiens*.

SEQ ID No. 64 corresponds to the amino acid sequence of transforming growth factor alpha isoform 1 preproprotein from *Homo sapiens*. SEQ ID No. 65 corresponds to the amino acid sequence of transforming growth factor alpha isoform 2 preproprotein from *Homo sapiens*. SEQ ID No. 66 corresponds to the amino acid sequence of transforming growth factor alpha isoform 3 preproprotein from *Homo sapiens*. SEQ ID No. 67 corresponds to the amino acid sequence of transforming growth factor alpha isoform 4 preproprotein from *Homo sapiens*. SEQ ID No. 68 corresponds to the amino acid sequence of transforming growth factor alpha isoform 5 preproprotein from *Homo sapiens*. SEQ ID No. 69 corresponds to the amino acid sequence of the mature transforming growth factor alpha from *Homo sapiens*.

SEQ ID No. 70 corresponds to the amino acid sequence of amphiregulin preproprotein from *Homo sapiens*. SEQ ID No. 71 corresponds to the amino acid sequence of the mature amphiregulin from *Homo sapiens*.

SEQ ID No. 72 corresponds to the amino acid sequence of epiregulin preproprotein from *Homo sapiens*. SEQ ID No. 73 corresponds to the amino acid sequence of the mature epiregulin from *Homo sapiens*.

SEQ ID No. 74 corresponds to the amino acid sequence of the epigen isoform 1 precursor from *Homo sapiens*. SEQ ID No. 75 corresponds to the amino acid sequence of the epigen isoform 2 precursor from *Homo sapiens*. SEQ ID No. 76 corresponds to the amino acid sequence of the epigen isoform 3 precursor from *Homo sapiens*. SEQ ID No. 77 corresponds to the amino acid sequence of the epigen isoform 4 precursor from *Homo sapiens*. SEQ ID No. 78 corresponds to the amino acid sequence of the epigen isoform 5 precursor from *Homo sapiens*. SEQ ID No. 79 corresponds to the amino acid sequence of the epigen isoform 6 precursor from *Homo sapiens*. SEQ ID No. 80 corresponds to the amino acid sequence of the epigen isoform 7 precursor from *Homo sapiens*. SEQ ID No. 81 corresponds to the amino acid sequence of the mature epigen from *Homo sapiens*.

SEQ ID No. 82 corresponds to the amino acid sequence of the betacellulin precursor from *Homo sapiens*. SEQ ID No. 83 corresponds to the amino acid sequence of the mature betacellulin from *Homo sapiens*.

The following Figures and Examples are given for illustrative purpose only. The invention is not to be construed to be limited to the following examples:

FIGURES

FIG. 1 shows a SDS-PAGE of a human FGF2 reference protein.

Figure 2A:
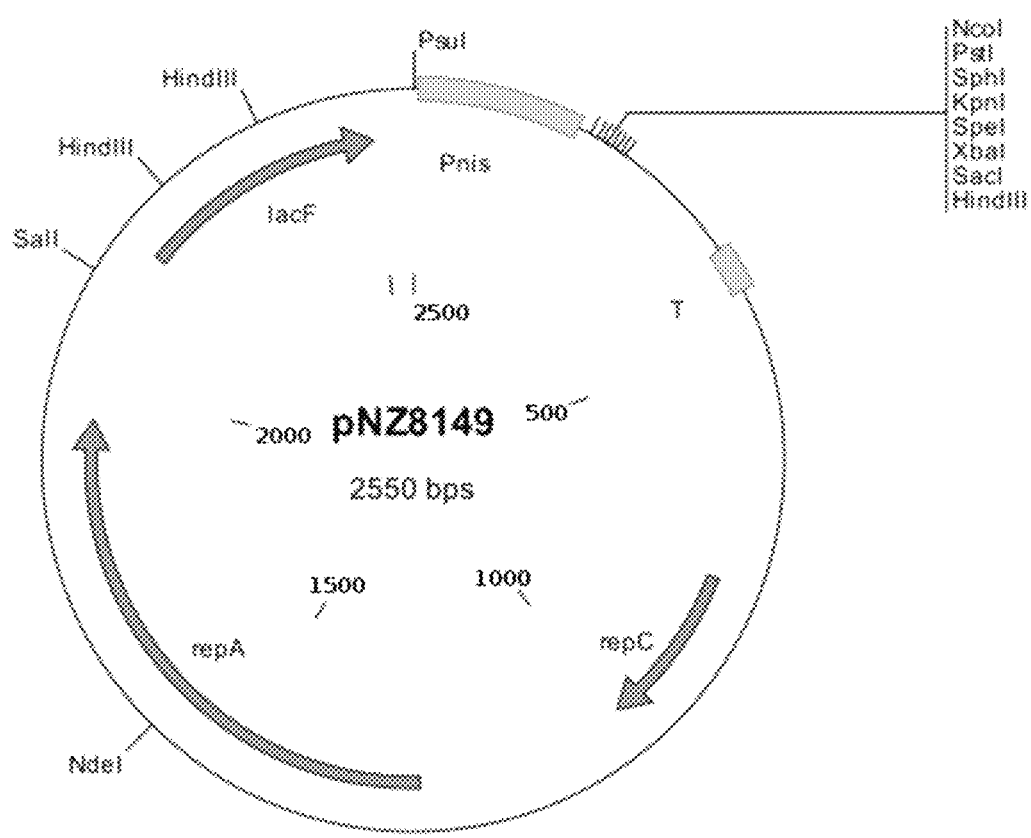
FIG. 2 shows a plasmid map of expression vector pNZ8149. "lacF" is a selection marker for growth of the host strain NZ3900 on lactose; "Pnis" is the nisin A promoter of the nisin operon of *Lactococcus lactis*; "T" is a terminator; "repC" and "repA" are replication genes. The nucleic acid sequence is also shown in SEQ ID No. 35.

FIG. 2A shows a plasmid map of expression vector pNZ8149. "lacF" is a selection marker for growth of the host strain NZ3900 on lactose; "Pnis" is the nisin A promoter of the nisin operon of *Lactococcus lactis*; "T" is a terminator; "repC" and "repA" are replication genes. The nucleic acid sequence (FIG. 2B) is also shown in SEQ ID No. 35.

FIG. 3 shows the nucleic acid sequence of the nisinA promoter of *L. lactis*, which is also shown in SEQ ID No. 44.

Figure 4A:
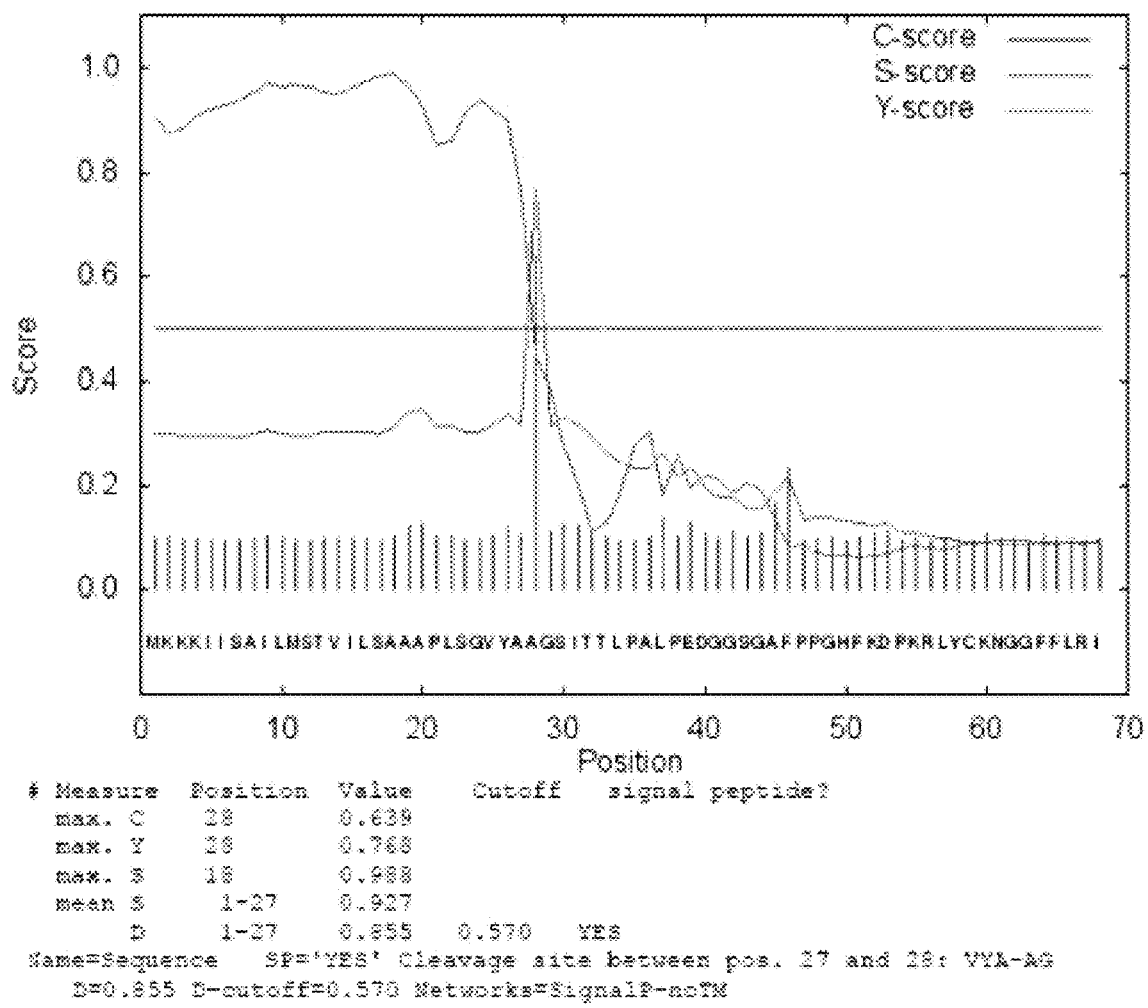
FIGS. 4a, 4b, and 4c show readouts of SignalP 4.1 obtained with the amino acid sequence depicted in SEQ ID No. 29, SEQ ID No. 13, and SEQ ID No.5, respectively.
Figure 4B:
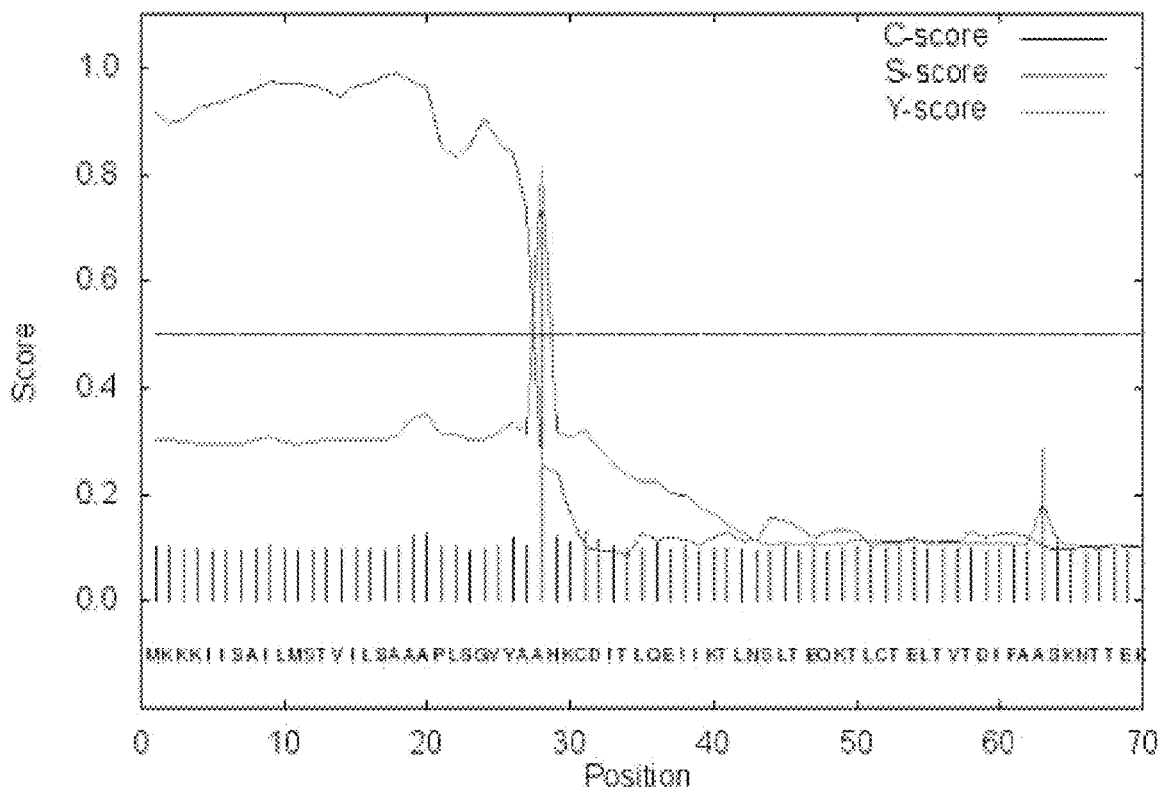
Figure 4C:
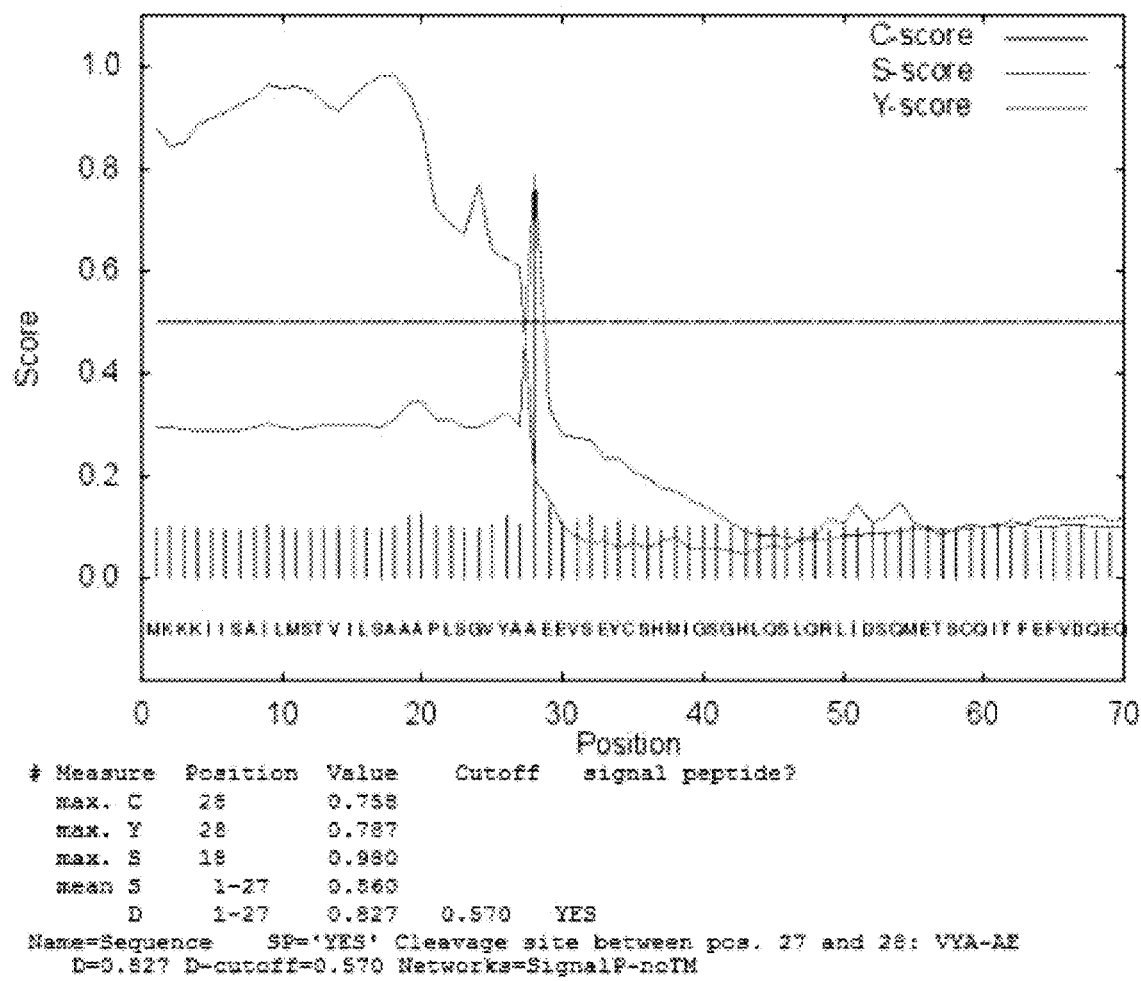

FIGS. 4A, 4B, and 4C show readouts of SignalP 4.1 obtained with the amino acid sequence depicted in SEQ ID No. 29, SEQ ID No. 13, and SEQ ID No. 5, respectively.

FIGS. 5A, 5B, and 5C show the synthesized inserts used in Example 1 as well as the corresponding amino acid sequence. "FGF2-153" denotes the human FGF-2 coding insert. "hIL4" denotes the human IL4 coding insert. "hCSF1" denotes the human CSF1 coding insert. "PnisA" denotes the nisinA promoter of the *Lactococcus lactis* nisin operon. "ssUsp45" denotes the signal sequence of the usp45 gene of *Lactococcus lactis*. An asterisk denotes a stop codon. The respective nucleic acid sequences are also depicted in SEQ ID No. 45, SEQ ID No. 47, and SEQ ID No. 49.

Figure 6A:
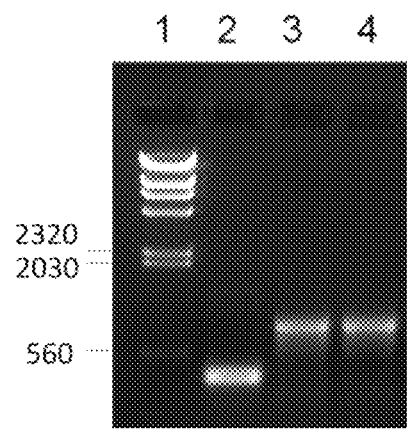
FIGS. 6a, 6b, and 6c show the results of colony PCR analysis of potential colonies of *Lactococcus lactis* NZ3900 with pFGF2, pIL4, and pCSF1, respectively.
Figure 6B:
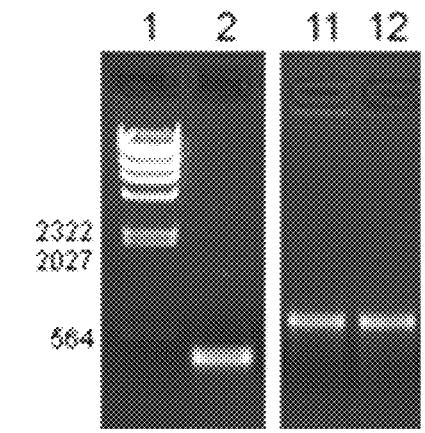
Figure 6C:
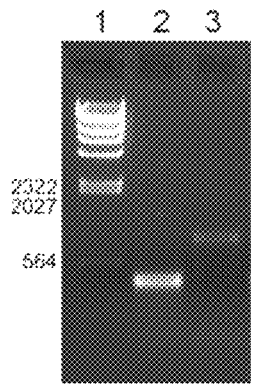

FIGS. 6A, 6B, and 6C show the results of colony PCR analysis of potential colonies of *Lactococcus lactis* NZ3900 with pFGF2, pIL4, and pCSF1, respectively.

FIGS. 7A-7F show plasmid maps (FIGS. 7A, 7C, and 7E) as well as the nucleic acid sequence (FIGS. 7B, 7D, and 7F) of the plasmids pFGF2, pIL4, and pCSF1, respectively, for the expression and secretion of hFGF2, hIL4, and hCSF1, respectively, in *Lactococcus lactis*. "Pnis" is the nisin A promoter of the nisin operon of *Lactococcus lactis*; "T" is a terminator; "repC" and "repA" are replication genes. The nucleic acid sequences of the plasmids pFGF2, pIL4, and pCSF1, are depicted in SEQ ID No. 46, SEQ ID No. 48, and SEQ ID No. 50, respectively.

Figure 8:
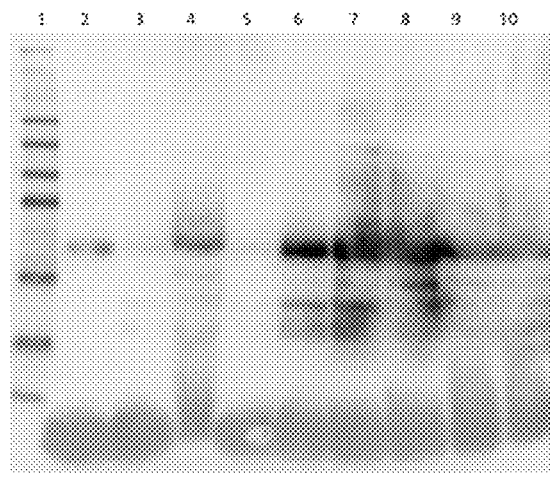
FIG. 8 shows a Western blot analysis of fermentation samples of *Lactococcus* expressing NZ3900(pFGF2) under different induction conditions. "0.5/5" denotes induction at OD 600=0.5 with 5 ng/mL nisin; "3/5" denotes induction at OD 600=3 with 5 ng/mL nisin, "T" denotes the time point, at which a sample was taken from the fermentation.

FIG. 8 shows a Western blot analysis of fermentation samples of *Lactococcus* expressing NZ3900(pFGF2) under different induction conditions. "0.5/5" denotes induction at OD 600=0.5 with 5 ng/mL nisin; "3/5" denotes induction at OD 600=3 with 5 ng/mL nisin, "T" denotes the time point, at which a sample was taken from the fermentation.

Figure 9:
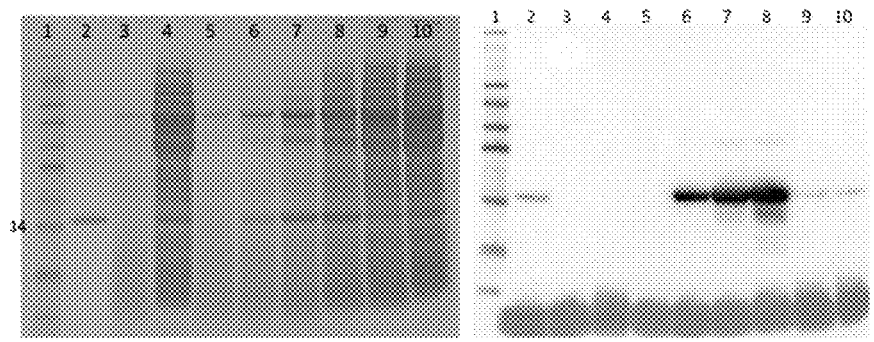
FIG. 9 shows a SDS-PAGE analysis of supernatant (Sup) samples from controlled fermentation runs after Coomassie (Coom) staining and a Western blot (WB) analysis of fermentation samples of *Lactococcus* expressing NZ3900 (pIL4). 0.⅝" denotes induction at OD 600=0.5 with 5 ng/mL nisin; "3/5" denotes induction at OD 600=3 with 5 ng/mL nisin, "T" denotes the time point, at which a sample was taken from the fermentation.

FIG. 9 shows a SDS-PAGE analysis of supernatant (Sup) samples from controlled fermentation runs after Coomassie (Coom) staining and a Western blot (WB) analysis of fermentation samples of *Lactococcus* expressing NZ3900 (pIL4). 0.5/5" denotes induction at OD 600=0.5 with 5 ng/mL nisin; "3/5" denotes induction at OD 600=3 with 5 ng/mL nisin, "T" denotes the time point, at which a sample was taken from the fermentation.

Figure 10:
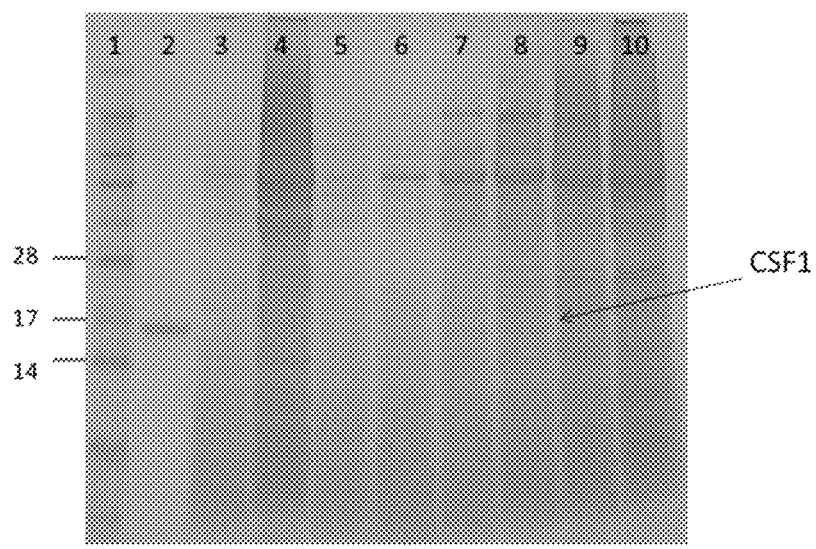
FIG. 10 shows a SDS-PAGE analysis of supernatant (Sup) samples from controlled fermentation runs after Coomassie (Coom) staining of fermentation samples of *Lactococcus* expressing NZ3900(pCSF1). 0.⅝" denotes induction at OD 600=0.5 with 5 ng/mL nisin; "3/5" denotes induction at OD 600=3 with 5 ng/mL nisin, "T" denotes the time point, at which a sample was taken from the fermentation.

FIG. 10 shows a SDS-PAGE analysis of supernatant (Sup) samples from controlled fermentation runs after Coomassie (Coom) staining of fermentation samples of *Lactococcus* expressing NZ3900(pCSF1). 0.5/5" denotes induction at OD 600=0.5 with 5 ng/mL nisin; "3/5" denotes induction at OD 600=3 with 5 ng/mL nisin, "T" denotes the time point, at which a sample was taken from the fermentation.

Figure 11:
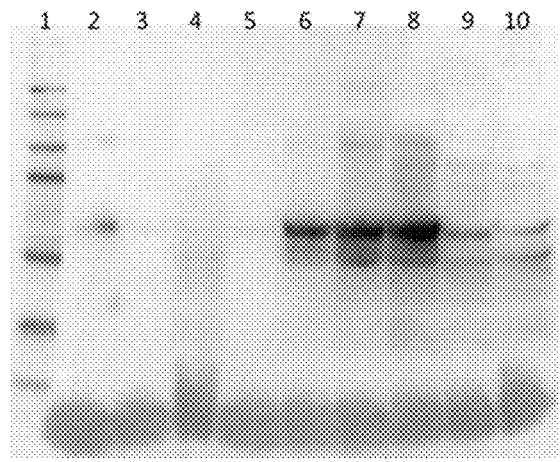
FIG. 11 shows a Western blot (WB) analysis of fermentation samples of *Lactococcus* expressing NZ3900(pCSF1). 0.⅝" denotes induction at OD 600=0.5 with 5 ng/mL nisin; "3/5" denotes induction at OD 600=3 with 5 ng/mL nisin, "T" denotes the time point, at which a sample was taken from the fermentation.

FIG. 11 shows a Western blot (WB) analysis of fermentation samples of *Lactococcus* expressing NZ3900(pCSF1). 0.5/5" denotes induction at OD 600=0.5 with 5 ng/mL nisin; "3/5" denotes induction at OD 600=3 with 5 ng/mL nisin, "T" denotes the time point, at which a sample was taken from the fermentation.

Figure 12:
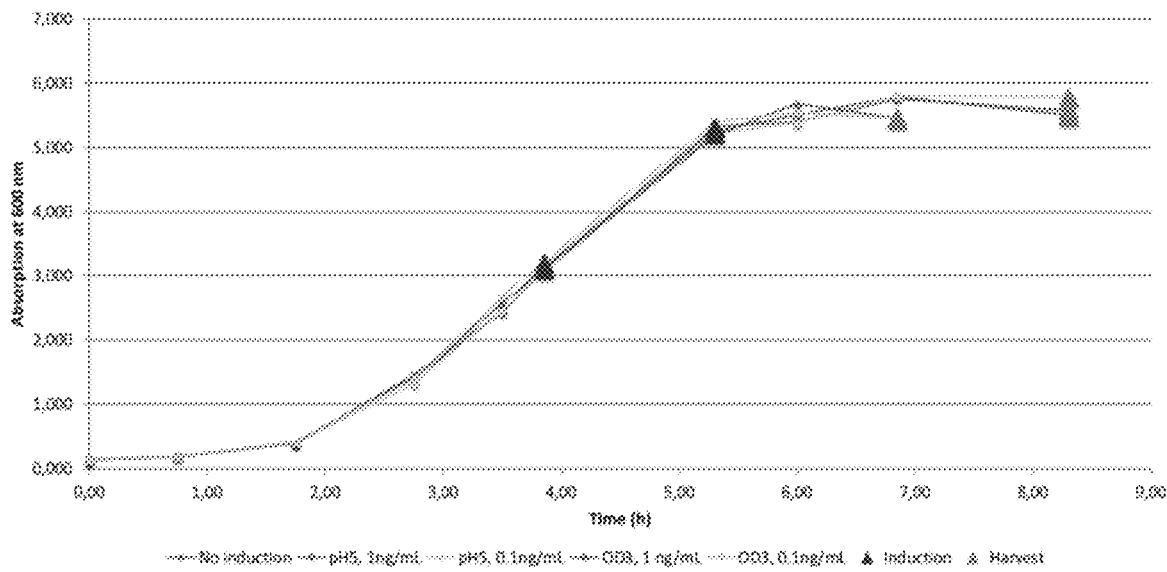
FIG. 12 shows the growth of acidifying cultures for induction experiment under conditions that resemble wound healing circumstances.

FIG. 12 shows the growth of acidifying cultures for induction experiment under conditions that resemble wound healing circumstances.

Figure 13:
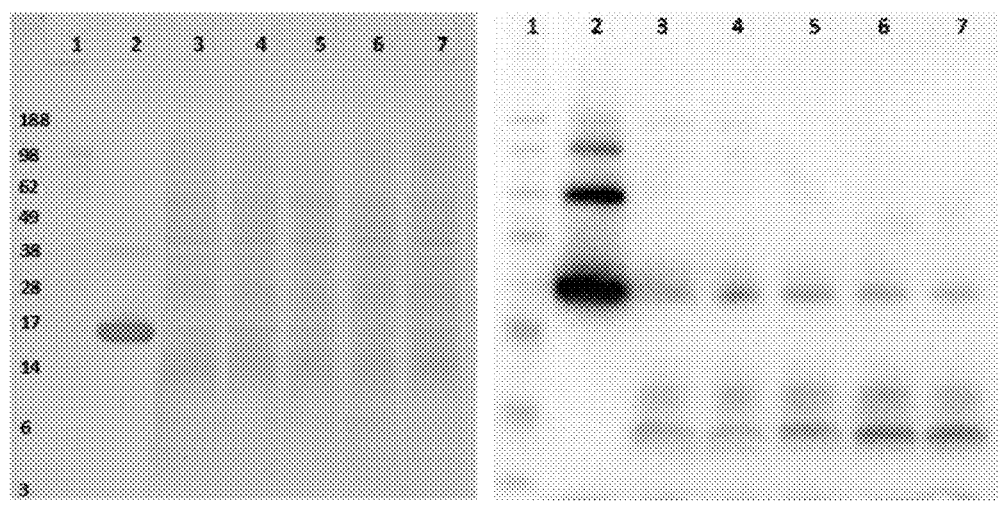
FIG. 13 shows SDS-PAGE and Western blot analysis of hFGF2 production in the supernatant after induction at pH 5 or at OD 600=3.

FIG. 13 shows SDS-PAGE and Western blot analysis of hFGF2 production in the supernatant after induction at pH 5 or at OD 600=3.

Figure 14A:
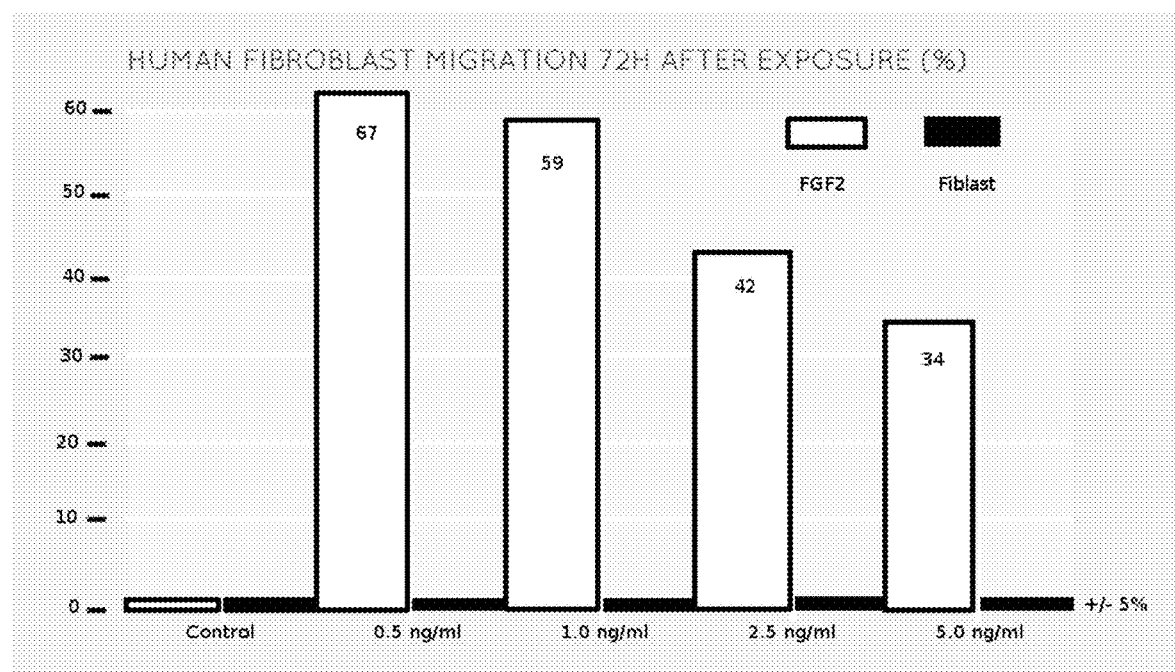
FIG. 14a shows the result of a human fibroblast migration assay described in Example 4a after 72 h exposure with recombinant probiotic bacteria expressing hFGF2 or the commercially available product Fiblast.

FIG. 14A shows the result of a human fibroblast migration assay described in Example 4a after 72 h exposure with recombinant probiotic bacteria expressing hFGF2 or the commercially available product Fiblast.

Figure 14B:
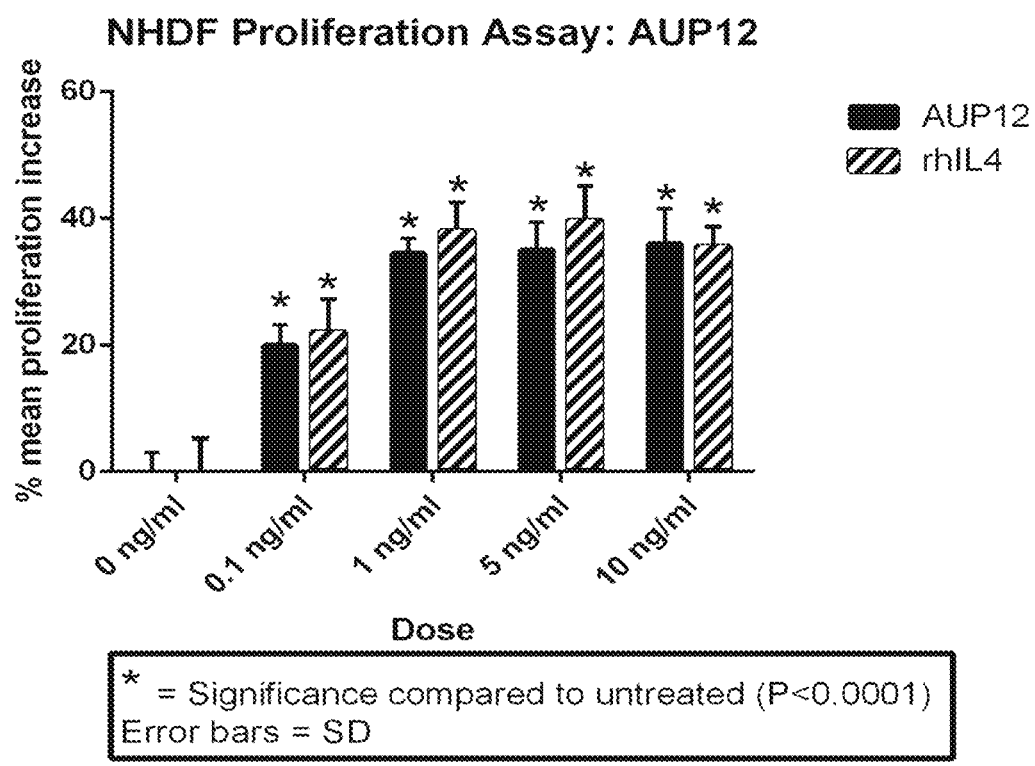
FIG. 14b shows the result of a human fibroblast migration assay described in Example 4a after 72 h exposure with recombinant probiotic bacteria expressing hIL4 or recombinant human IL4.

FIG. 14B shows the result of a human fibroblast migration assay described in Example 4a after 72 h exposure with recombinant probiotic bacteria expressing hIL4 or recombinant human IL4.

Figure 14C:
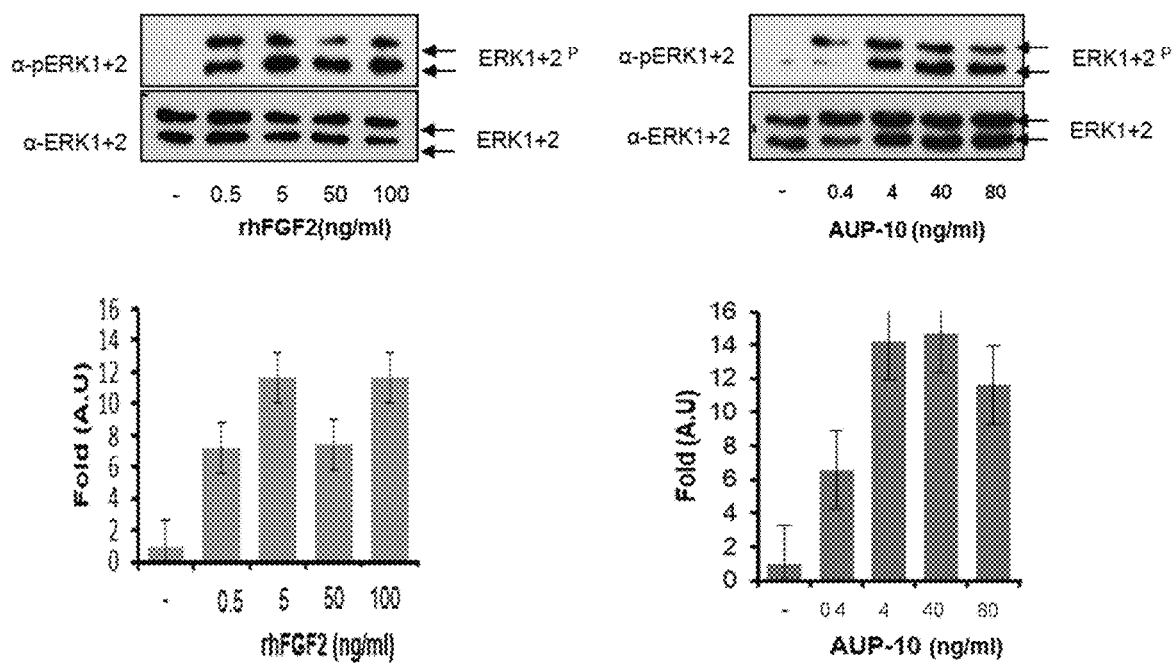
FIG. 14c shows the result of the induction of ERK 1+2 phosphorylation in NHDF cells by AUP-10 culture medium containing 0.4-80 ng/ml FGF2 and by rhFGF2.

FIG. 14C shows the result of the induction of ERK 1+2 phosphorylation in NHDF cells by AUP-10 culture medium containing 0.4-80 ng/ml FGF2 and by rhFGF2.

Figure 14D:
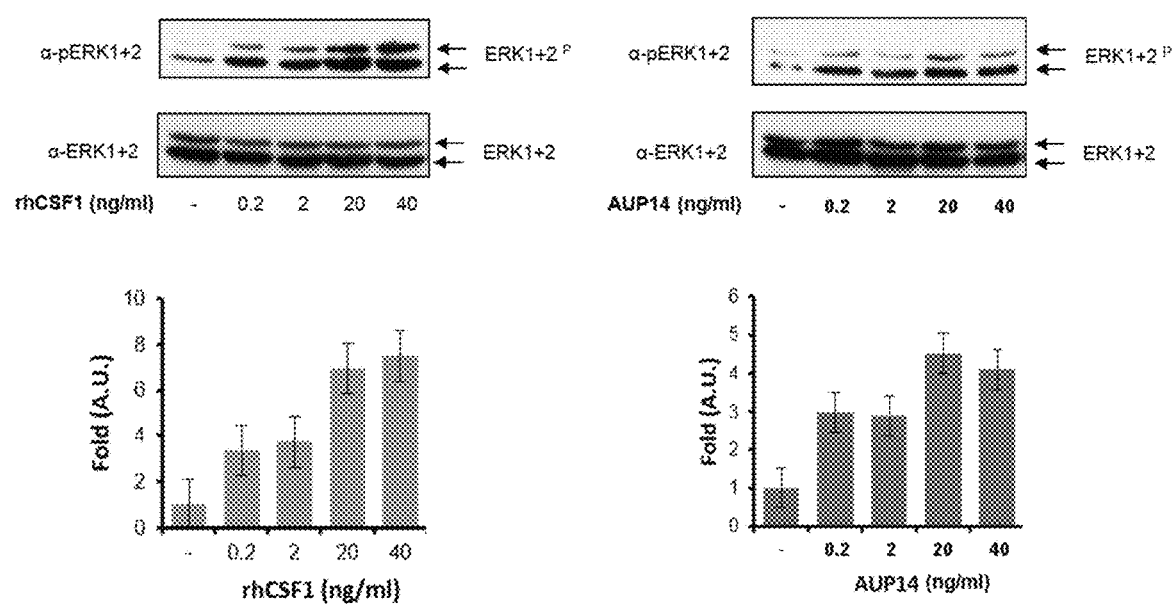
FIG. 14d shows the result of the induction of ERK 1+2 phosphorylation in M-NFS-60 cells by AUP-14 culture medium containing 0.2-40 ng/ml of CSF1 and by rhCSFI.

FIG. 14D shows the result of the induction of ERK 1+2 phosphorylation in M-NFS-60 cells by AUP-14 culture medium containing 0.2-40 ng/ml of CSF1 and by rhCSF1.

Figure 14E:
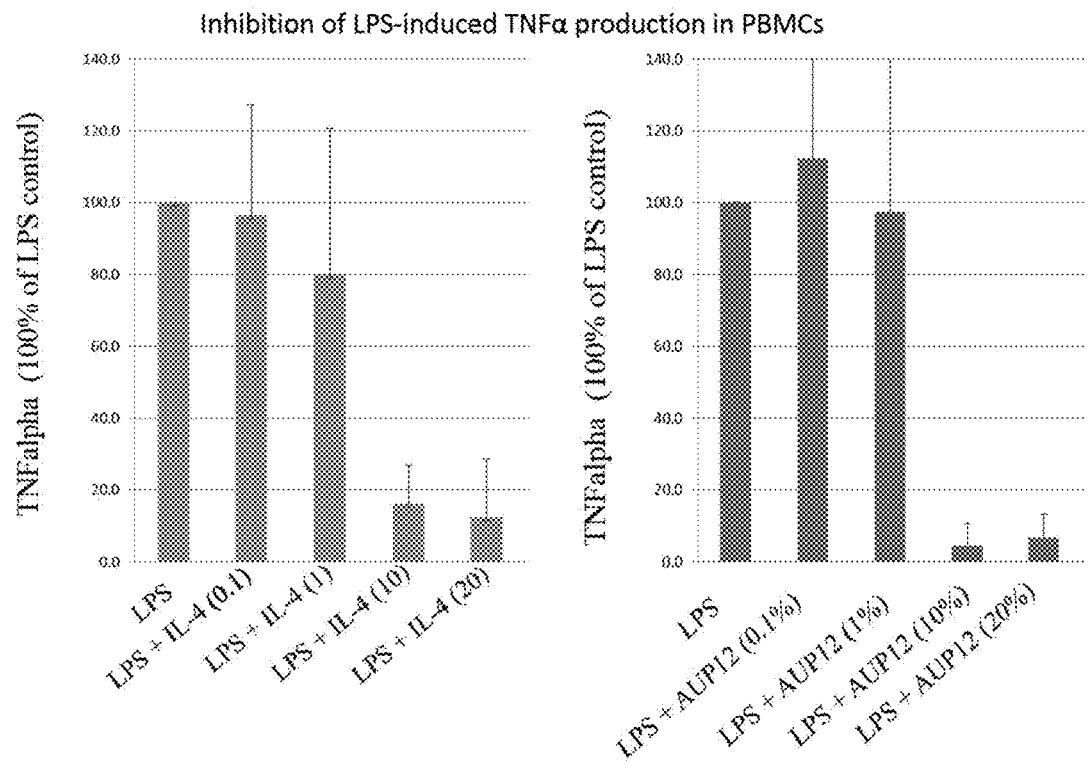
FIG. 14e shows the inhibition of LPS-induced TNFalpha mRNA production in human THP-1 cells described in Example 4c.

FIG. 14E shows the inhibition of LPS-induced TNFalpha mRNA production in human THP-1 cells described in Example 4c.

Figure 14F:
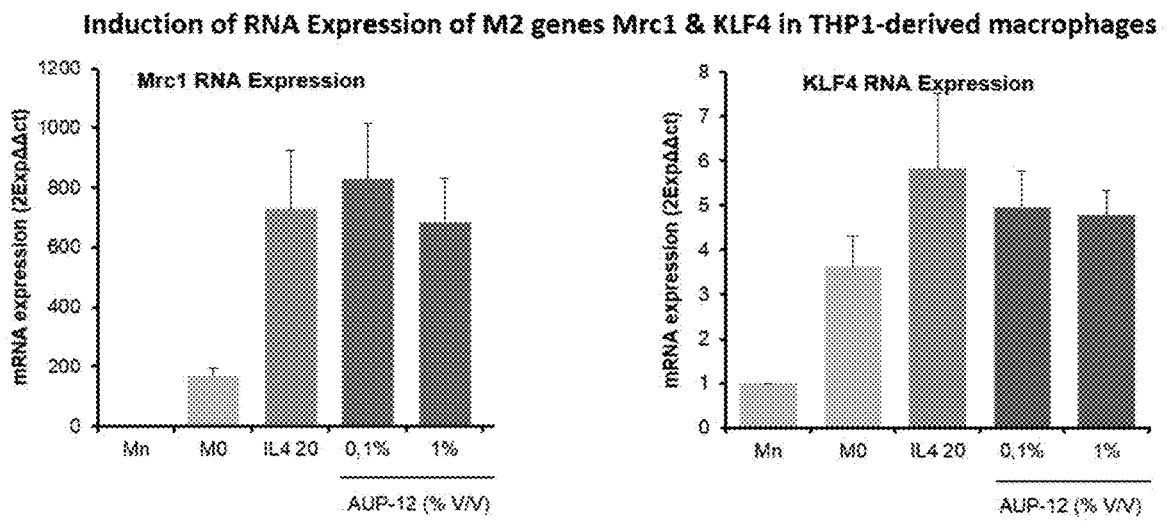
FIG. 14f shows the induction of RNA expression of M2 genes for the macrophage mannose receptor 1 (Mrcl) and Kruppel-like factor 4 (KLF4) in THP1-derived macrophages as described in Example 4d.

FIG. 14F shows the induction of RNA expression of M2 genes for the macrophage mannose receptor 1 (Mrc1) and Kruppel-like factor 4 (KLF4) in THP1-derived macrophages as described in Example 4d.

Figure 14G:
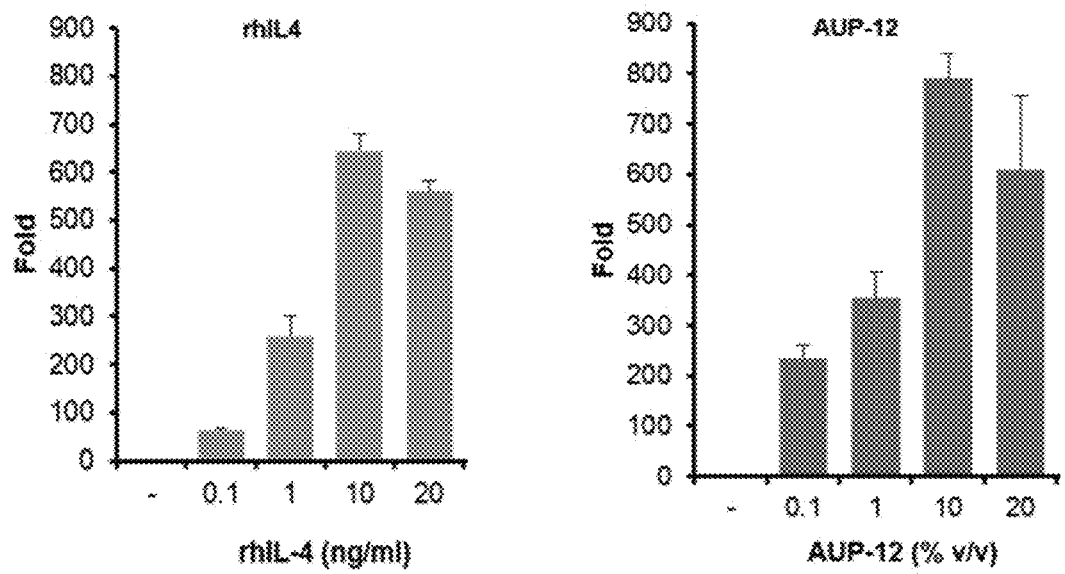
FIG. 14g shows the STAT-6 transcriptional Activity of AUP-12 and rhIL-4 in Human Glial Hybrid Cell Line M03.13 as described in Example 4e.

FIG. 14G shows the STAT-6 transcriptional Activity of AUP-12 and rhIL-4 in Human Glial Hybrid Cell Line M03.13 as described in Example 4e.

Figure 14H:
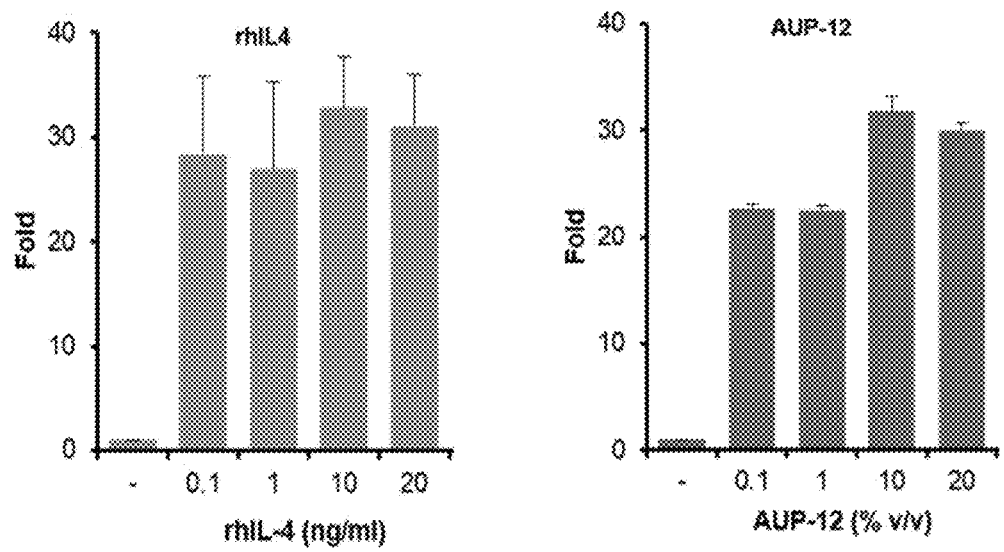
FIG. 14h shows the STAT-6 Transcriptional Activity of AUP-12 and rhIL-4 in Human Embryonic Kidney 293T Cells as described in Example 4e.

FIG. 14H shows the STAT-6 Transcriptional Activity of AUP-12 and rhIL-4 in Human Embryonic Kidney 293T Cells as described in Example 4e.

Figure 15A:
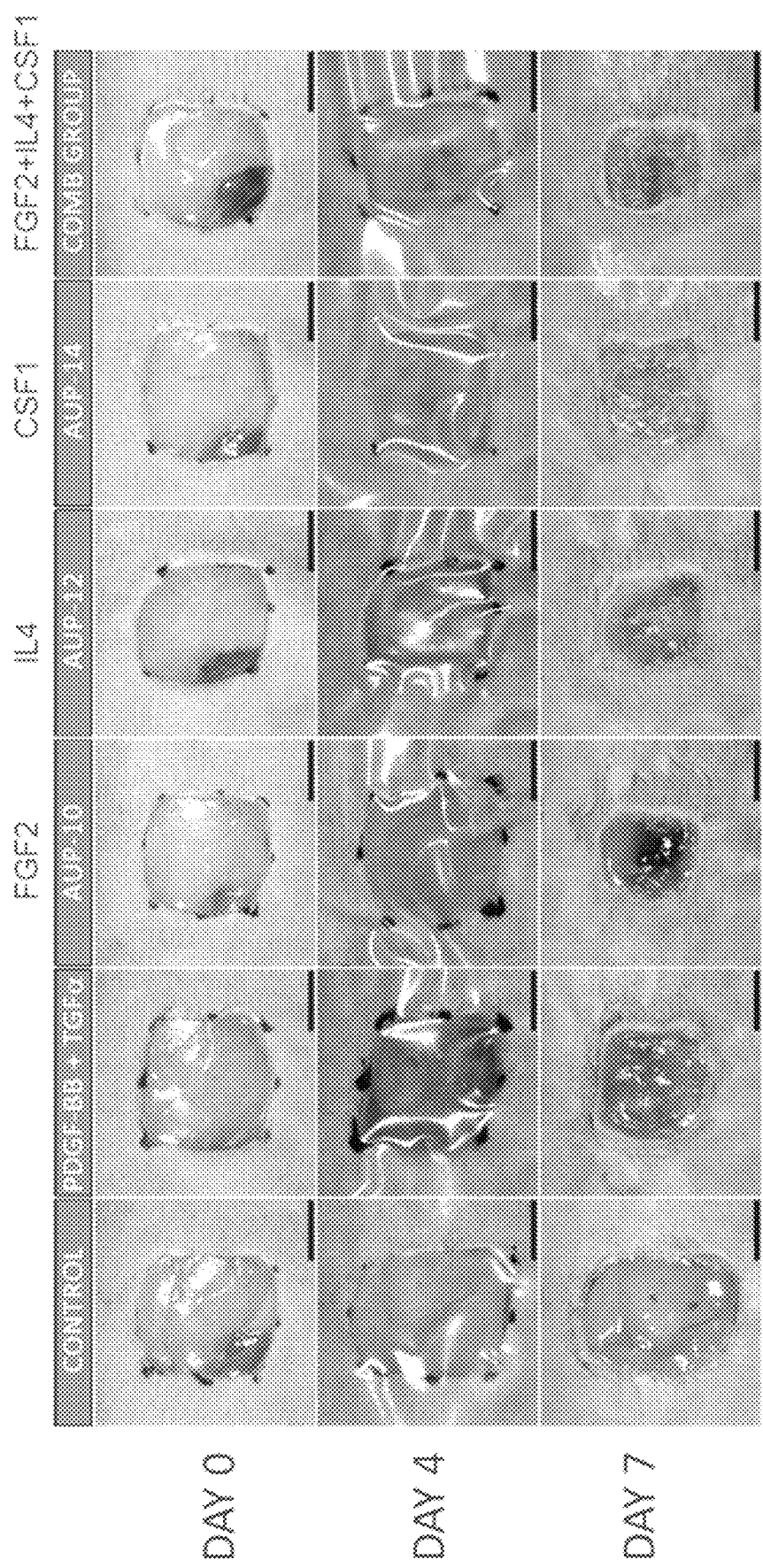
FIG. 15a shows results of wound healing experiments described in Example 5.

FIG. 15A shows results of wound healing experiments described in Example 5.

Figure 15B:
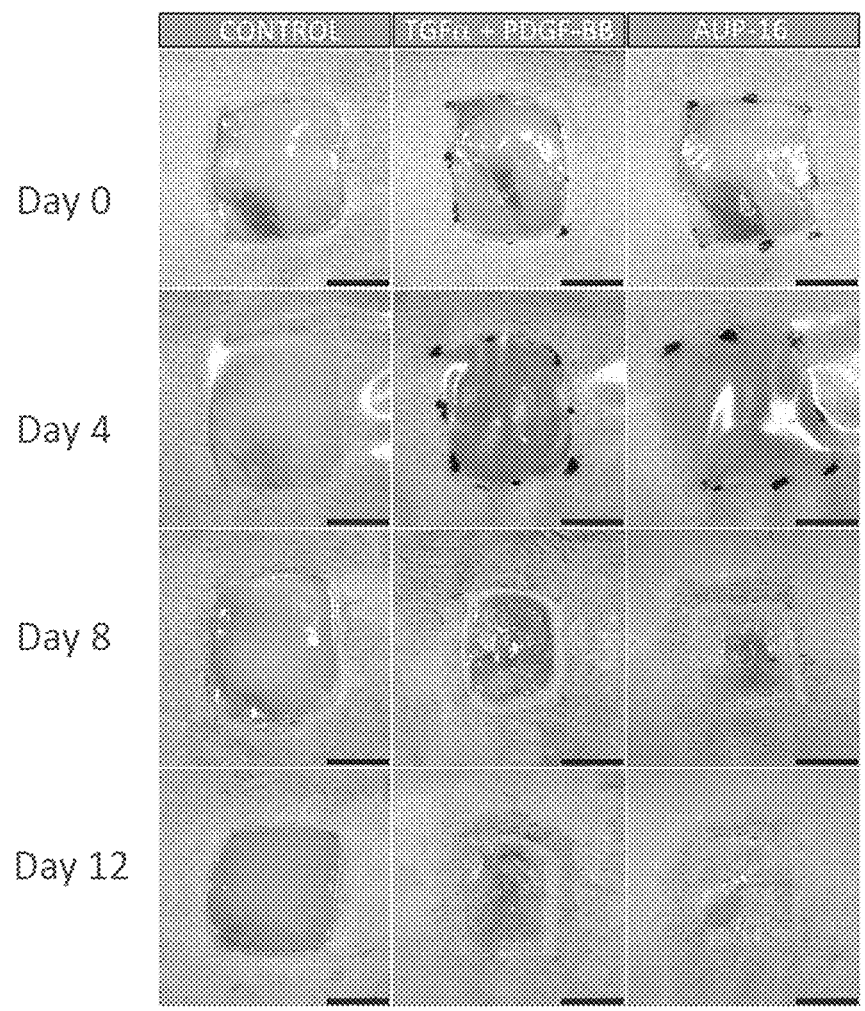
FIG. 15b shows a comparison of wound-healing status of control, positive control and AUP-16 treated tissue after the indicated time points described in Example 5.

FIG. 15B shows a comparison of wound-healing status of control, positive control and AUP-16 treated tissue after the indicated time points described in Example 5.

Figure 15C:
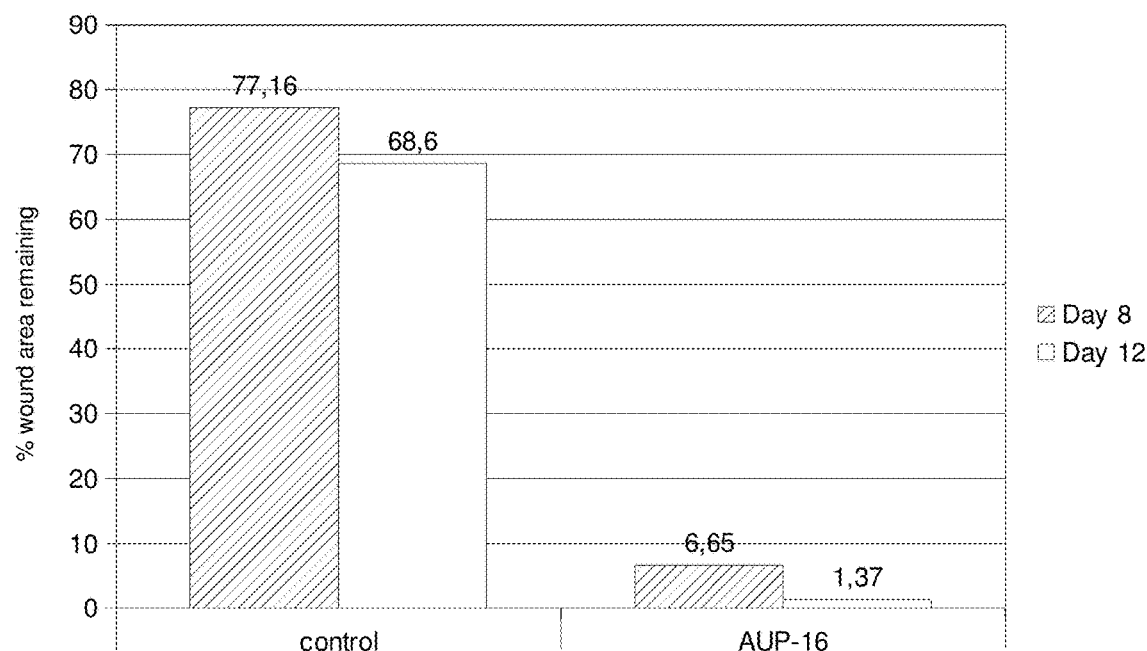
FIG. 15c shows a comparison of the remaining wound area after day 8 and day 12 of the positive control (treatment group 17) and AUP-16 treated tissue (treatment group 18) described in Example 5.

FIG. 15C shows a comparison of the remaining wound area after day 8 and day 12 of the positive control (treatment group 17) and AUP-16 treated tissue (treatment group 18) described in Example 5.

FIG. 16A shows the amino acid sequence of macrophage colony-stimulating factor 1 isoform a precursor from *Homo sapiens* (SEQ ID NO: 1). FIG. 16B shows the amino acid sequence of macrophage colony-stimulating factor 1 isoform b precursor from *Homo sapiens* (SEQ ID NO: 2). FIG. 16C shows the amino acid sequence of macrophage colony-stimulating factor 1 isoform c precursor from *Homo sapiens* (SEQ ID NO: 3). FIG. 16D shows the amino acid sequence of the mature human macrophage colony-stimulating factor 1 (SEQ ID NO: 4).

FIG. 17A shows the amino acid sequence of interleukin-34 isoform 1 precursor from *Homo sapiens* (SEQ ID NO: 7). FIG. 17B shows the amino acid sequence of interleukin-34 isoform 2 precursor from *Homo sapiens* (SEQ ID NO: 8). FIG. 17C shows the amino acid sequence of interleukin-34 from *Homo sapiens* (SEQ ID NO: 9).

FIG. 18A shows the amino acid sequence of interleukin-4 isoform 1 precursor from *Homo sapiens* (SEQ ID NO: 10). FIG. 18B shows the amino acid sequence of interleukin-4 isoform 2 precursor from *Homo sapiens* (SEQ ID NO: 11). FIG. 18C shows the amino acid sequence of interleukin-4 from *Homo sapiens* (SEQ ID NO: 12).

FIG. 19A shows the amino acid sequence of interleukin-10 precursor from *Homo sapiens* (SEQ ID NO: 15). FIG. 19B shows the amino acid sequence of interleukin-10 from *Homo sapiens* (SEQ ID NO: 16).

FIG. 20A shows the amino acid sequence of interleukin-13 precursor from *Homo sapiens* (SEQ ID NO: 17). FIG. 20B shows the amino acid sequence of interleukin-13 from *Homo sapiens* (SEQ ID NO: 18).

FIG. 21A shows the amino acid sequence of transforming growth factor beta-1 precursor from *Homo sapiens* (SEQ ID NO: 18). FIG. 21B shows the amino acid sequence of transforming growth factor beta-1 from *Homo sapiens* (SEQ ID NO: 20). FIG. 21C shows the amino acid sequence of transforming growth factor beta-2 isoform 1 precursor from *Homo sapiens* (SEQ ID NO: 21). FIG. 21D shows the amino acid sequence of transforming growth factor beta-2 isoform 2 precursor from *Homo sapiens* (SEQ ID NO: 22).

FIG. 21E shows the amino acid sequence of transforming growth factor beta-2 from *Homo sapiens* (SEQ ID NO: 23). FIG. 21F shows the amino acid sequence of transforming growth factor beta-3 preproprotein from *Homo sapiens* (SEQ ID NO: 24). FIG. 21G shows the amino acid sequence of transforming growth factor beta-3 from *Homo sapiens* (SEQ ID NO: 25).

FIG. 22A shows the amino acid sequence of fibroblast growth factor 2 precursor from *Homo sapiens* (SEQ ID NO: 26). FIG. 22B shows the amino acid sequence of a fragment of fibroblast growth factor 2 from *Homo sapiens* (SEQ ID NO: 28).

FIG. 23A: Amino acid sequence of hepatocyte growth factor from *Homo sapiens* (SEQ ID NO: 31). FIG. 23B: Amino acid sequence of hepatocyte growth factor alpha chain from *Homo sapiens* (SEQ ID NO: 32). FIG. 23C: Amino acid sequence of hepatocyte growth factor beta chain from *Homo sapiens* (SEQ ID NO: 33).

Figure 24E:
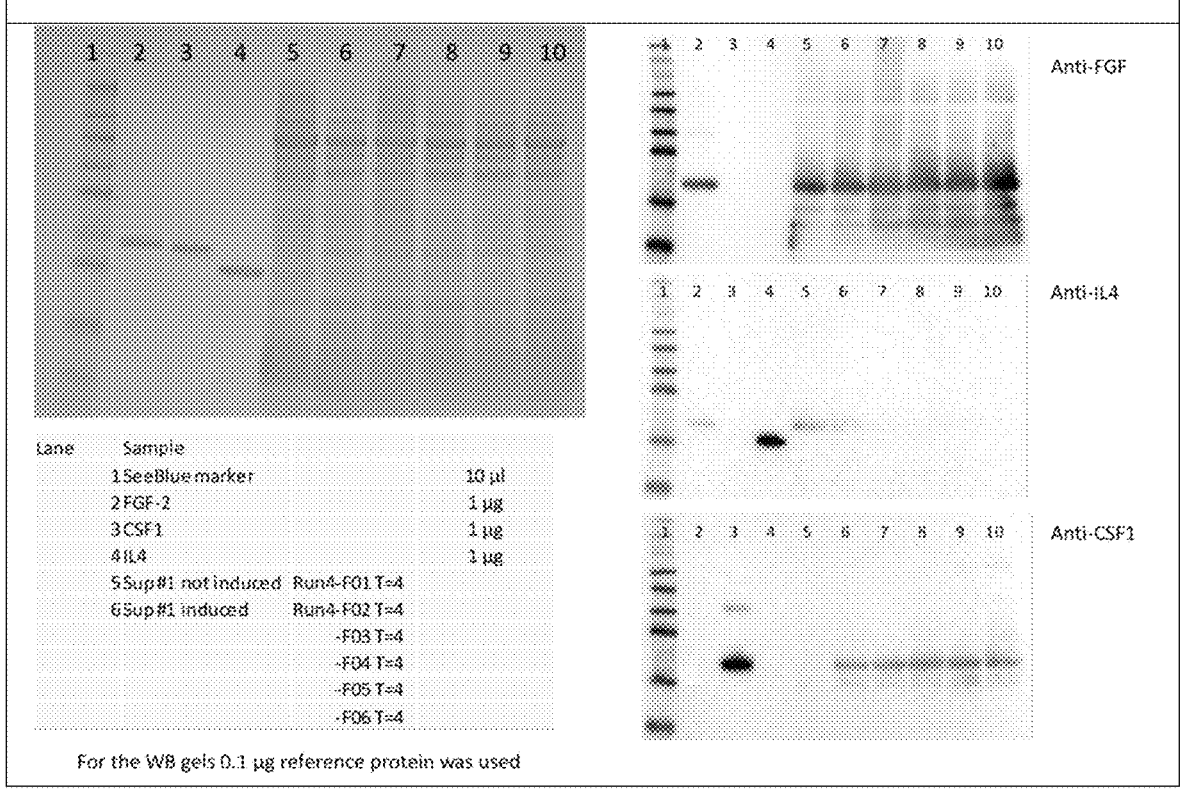

FIG. 24A shows an overview of the three ribosome binding sites used in Example 2d (SEQ ID NOS: 51-54). The respective sequences of the synthesized DNA sequences CSF-RBS1-FGF-RBS2-IL4, FGF-RBS1-IL4-RBS2-CSF, and IL4-RBS—CSF-RBS2-FGF used in Example 2d are depicted in FIGS. 24B to 24D, respectively, as well as in SEQ ID No. 55, SEQ ID No. 56, and SEQ ID No. 57, respectively. FIGS. 24E to 24G show respective SDS-PAGE gels as well as Western blots obtained with the single operon constructs used in Example 2d.

FIG. 25A shows the amino acid sequence of epidermal growth factor isoform 1 preproprotein from *Homo sapiens* (SEQ ID NO: 58). FIG. 25B shows the amino acid sequence of epidermal growth factor isoform 2 preproprotein from *Homo sapiens* (SEQ ID NO: 59). FIG. 25C shows the amino acid sequence of epidermal growth factor isoform 3 preproprotein from *Homo sapiens* (SEQ ID NO: 60). FIG. 25d shows the amino acid sequence of the mature epidermal growth factor from *Homo sapiens* (SEQ ID NO: 61).

FIG. 26A shows the amino acid sequence of the heparin-binding EGF-like growth factor precursor from *Homo sapiens* (SEQ ID NO: 62). FIG. 26B shows the amino acid sequence of the mature heparin-binding EGF-like growth factor from *Homo sapiens* (SEQ ID NO: 63).

FIG. 27A shows the amino acid sequence of transforming growth factor alpha isoform 1 preproprotein from *Homo sapiens* (SEQ ID NO: 64). FIG. 27B shows the amino acid sequence of transforming growth factor alpha isoform 2 preproprotein from *Homo sapiens* (SEQ ID NO: 65). FIG. 27C shows the amino acid sequence of transforming growth factor alpha isoform 3 preproprotein from *Homo sapiens* (SEQ ID NO: 66). FIG. 27D shows the amino acid sequence of transforming growth factor alpha isoform 4 preproprotein from *Homo sapiens* (SEQ ID NO: 67). FIG. 27E shows the amino acid sequence of transforming growth factor alpha isoform 5 preproprotein from *Homo sapiens* (SEQ ID NO: 68). FIG. 27F shows the amino acid sequence of the mature transforming growth factor alpha from *Homo sapiens* (SEQ ID NO: 69).

FIG. 28A shows the amino acid sequence of amphiregulin preproprotein from *Homo sapiens* (SEQ ID NO: 70). FIG. 28B shows the amino acid sequence of the mature amphiregulin from *Homo sapiens* (SEQ ID NO: 71).

FIG. 29A shows the amino acid sequence of epiregulin preproprotein from *Homo sapiens* (SEQ ID NO: 72). FIG. 29B shows the amino acid sequence of the mature epiregulin from *Homo sapiens* (SEQ ID NO: 73).

FIG. 30A shows the amino acid sequence of the human epigen isoform 1 precursor from *Homo sapiens* (SEQ ID NO: 74). FIG. 30B shows the amino acid sequence of the human epigen isoform 2 precursor from *Homo sapiens* (SEQ ID NO: 75). FIG. 30C shows the amino acid sequence of the human epigen isoform 3 precursor from *Homo sapiens* (SEQ ID NO: 76).

FIG. 30D shows the amino acid sequence of the human epigen isoform 4 precursor from *Homo sapiens* (SEQ ID NO: 77). FIG. 30E shows the amino acid sequence of the human epigen isoform 5 precursor from *Homo sapiens* (SEQ ID NO: 78). FIG. 30F shows the amino acid sequence of the human epigen isoform 6 precursor from *Homo sapiens* (SEQ ID NO: 79). FIG. 30G shows the amino acid sequence of the human epigen isoform 7 precursor from *Homo sapiens* (SEQ ID NO: 80). FIG. 30H shows the amino acid sequence of the mature epigen from *Homo sapiens* (SEQ ID NO: 81).

FIG. 31A shows the amino acid sequence of the betacellulin precursor from *Homo sapiens* (SEQ ID NO: 82). FIG. 31B shows the amino acid sequence of the mature betacellulin from *Homo sapiens* (SEQ ID NO: 83).

FIG. 32A shows the amino acid sequence of the mature fibroblast growth factor 2 from *Homo sapiens* (SEQ ID NO: 27). FIG. 32B shows the amino acid sequence of the fibroblast growth factor 2 variant hFGF2-153 used in the Examples (SEQ ID NO: 30).

FIG. 33 shows the amino acid sequence of the human interleukin 4 (hIL-4) variant used in the Examples (SEQ ID NO: 14).

FIG. 34 shows the amino acid sequence of the human colony stimulating factor 1 (hCSF-1) variant used in the Examples (SEQ ID NO: 6).

FIG. 35 shows the amino acid sequence of the secretion signal of the *Lactococcus* protein Usp45 used in the Examples (SEQ ID NO: 34).

EXAMPLES

1. General Experimental Procedures

Unless otherwise stated, Examples were carried out following the protocol of the manufacturer of the analytical systems. Unless otherwise stated, indicated chemicals were commercially obtained from Sigma-Aldrich Chemie Gmbh (Munich, Del.), Merck KGaA (Darmstadt, Del.), Thermo Fisher Scientific Inc. (Waltham, Mass., USA) or Becton, Dickinson and Company (Franklin Lakes, N.J., USA).

1.1 Growth Media

For different purposes cells were grown in different media. For general cloning procedures M17 medium (Oxoid Deutschland GmbH, Wesel, Del.) was used containing 0.5% glucose or lactose.

In order to monitor food grade selection the Elliker medium was used, on which lactococcal colonies colour yellow when they grow on lactose. The yellow colouring is a pH effect that changes the colour of the indicator dye bromocresol purple in the vicinity of a growing colony and of the colony itself.

The recipe of the Elliker medium is as follows:

| | |
|---|---|
| 20 g/L | tryptone |
| 5 g/L | yeast extract |
| 4 g/L | NaCl |
| 1.5 g/L | Na-acetate (water free) |
| 0.5 g/L | L(+)Ascorbic acid |
| 15 g/L | agar |
| pH 6.8 | |

Sterilization: 15 min at 121° C.

After sterilization and cooling 1% lactose was added from 20% heat- or filter-sterilized stock and 0.004% bromocresol purple (0.4% stock solution, filter sterilized).

For fermentations and other functional growth experiments the IM1 medium was used, which is free from animal derived ingredients. Lactose, the only remaining animal derived ingredient, can be obtained in pharmaceutical quality.

The recipe for the IM1 medium is as follows:

| | |
|---|---|
| 5% | Lactose monohydrate (Scharlab S.L., Barcelona, ES) |
| 1.5% | Soy peptone |
| 1% | Yeast extract |
| 1 mM | $MgSO_4 \times 7 H_2O$ |
| 0.1 mM | $MnSO_4 \times 4 H_2O$ |
| pH 6.7 | |

Sterilisation: 110° C. 15 min

During fermentation no buffer is added since the pH was automatically regulated using 2.5 M NaOH. For acidifying test tube cultivations 2% Na-beta-glycerophosphate was added to the medium.

This buffer neutralizes the produced lactate and allows the culture to reach a cell density of $OD_{600}$=4-5.

Stocks of the final constructs NZ3900(pFGF2), NZ3900 (pIL4), and NZ3900(pCSF1) were prepared after growth in IM1 medium with lactose and Na-beta-glycerophosphate by the addition of glycerol to a final concentration of 20%. Stocks were stored at −80° C.

1.2 Induction of Protein Production using the NICE System

The NICE system was induced using nisin concentrations between 0.1-10 ng/ml nisin. Nisin from *Lactococcus lactis* was obtained from Sigma (product number N5764).

1.3 Molecular Cloning Techniques

For molecular cloning standard techniques were used as, for example, described in Green and Sambrook (2012): "Molecular cloning: a laboratory manual", fourth edition, Cold Spring Harbour Laboratory Press (Cold Spring Harbor, N.Y., USA).

Nucleotide sequencing, gene synthesis and primer synthesis was outsourced to BaseClear (Leiden, NL).

1.4 Fermentations

Fermentations were carried out in a 0.5-L Multifors 6-fermenter array (Infors Benelux, Velp, NL). Inoculation was carried out with 1% pre-culture in IM-1 medium; stirrer speed was 200 rpm and the incubation temperature was 30° C. During the runs pH was controlled using 2.5 M NaOH. pH, temperature and the addition of NaOH were continuously monitored.

Induction with nisin was carried out at different time points of the growth cycle with different amounts of nisin as indicated in the results section. Samples were taken also as indicated in the results section.

1.5 Cinac Fermentations

For the monitoring of acidifying cultures the Cinac pH monitoring unit (AMS France, Frepillion, FR) was used for continuous measurement of pH changes. In order to ensure homogeneous pH the cultures were mixed with a magnetic stirrer at 200 rpm.

1.6 Sample Treatment

For SDS-PAGE and Western blotting, samples were processed to produce three fractions: (i) supernatant fraction, (ii) total cell extract (containing cell free extract, cell wall fragments and other particulate matter) and (iii) cell free extract.

The supernatant fraction was prepared by mixing 1 mL fermentation supernatant with 150 μL TCA and incubated at 4° C. for at least 1 h. The precipitate was collected by centrifugation at 20,000×g. The pellet was either used immediately or stored at −20° C.; after an additional centrifugation step to remove traces of TCA it was re-suspended in 15 μL 5 mM Tris-HCl pH 7.5.

Subsequently, 5 μL 4× sample buffer (containing 75 mM DTT) was added and the suspension was heated for 20 min at 70° C. In all cases, volumes of 20 μL were applied to the gel.

Total cell extracts were prepared as follows: the pellet of 10 mL of sample of a batch culture or 1 ml of a fermentation culture was dissolved in 1 mL 5 mM Tris-HCl pH7.5 and transferred to a bead beating tube with 500 mg zirconium beads and frozen at −20° C. until further processing. After thawing, this suspension was shaken with a FastPrep (MP Biomedicals LLP, Santa Ana, Calif., USA) bead-beater 4×30 seconds at speed 4 with intermittent cooling for 1 min on ice. After beads had settled for 1 min 15 μL supernatant were mixed with 5 μL loading buffer and treated as mentioned above.

Cell free extract was prepared by centrifuging the total cell extract for 1 min at 20,000×g. Further preparation for SDS-PAGE was carried out as described above.

1.7 Sodium Dodecyl Sulfate Polyacrylamide Gel Electrophoresis (SDS-PAGE)

SDS-PAGE was carried out with the commercially available NuPage system (Life Technologies GmbH, Darmstadt, Del.) following the protocol of the manufacturer.

Human FGF2 reference protein was obtained from Sigma Aldrich. 50 μg were dissolved in 25 μl of 5 mM Tris pH 7.5 to give a final concentration of 2 μg/μl. In a test run 5 and 10 μg were applied to the SDS-PAGE gel after mixing with 4× concentrated loading buffer resulting in 1× loading buffer concentration.

As depicted in FIG. 1, the gel shows monomers, a small amount of dimer and a very small amount of trimer of hFGF2. Lanes 1 and 4=SeeBlue marker; lane=25 μg FGF2 and lane 3=10 μg hFGF2. This gel was run without the addition of DTT to the loading buffer and the gel buffer.

Human IL4 reference protein was obtained from R&D systems (Minneapolis, Minn., USA). Human IL4 was dissolved in PBS (5.8 mM $Na_2HPO_4$, 4.2 mM $NaH_2PO_4$, 145 mM NaCl) to give a final concentration of 100 μg/mL. As reference 1 μg was applied per lane for Coomassie staining and 0.1 μg for silver staining and Western blots.

Human CSF1 reference protein was obtained from Abcam PLC (Cambridge, GB). Human CSF1 was dissolved in sterile water to give a final concentration of 100 μg/mL. As reference 1 μg was applied per lane for Coomassie staining and 0.1 μg for silver staining and Western blots.

1.8 Western Blots

Protein blotting was also carried out using the NuPage system (XCell Blot Module) according to the protocol of LifeTechnologies. The blotting membranes were pre-cut nitrocellulose membranes from Thermo Fisher Scientific Inc. The transfer buffer was NuPage Transfer buffer (20×) from Life Technologies. Transfer of the proteins was carried out at 35 V for 1 h.

For detection of human FGF2 a purified mouse anti-human FGF2 monoclonal antibody (BD Transduction laboratories, Heidelberg, Del.) was used at a dilution of 1:250. The second antibody was horseradish peroxidase (HRP)-linked antibody anti-mouse IgG at a dilution of 1:10,000 obtained from Bioké B.V. (Leiden, NL).

For detection of human IL4 a monoclonal mouse anti-human IL4 IgG1 from R&D systems (clone #3007) was used at a dilution of 1:500. The second antibody was HRP-linked antibody anti-mouse IgG at a dilution of 1:10,000 obtained from Bioké B.V. (Leiden, NL).

For detection of human CSF1 a rabbit polyclonal antibody to human MCSF from Abcam PLC (clone ab9693) was used at a dilution of 1:2,000. The second antibody was HRP-linked anti-rabbit IgG antibody at a dilution of 1:2,000 obtained from Bioké B.V. (Leiden, NL).

Western blots were developed with SuperSignal West Pico Chemiluminescent substrate obtained from Thermo Fisher Scientific Inc.

1.9 N-Terminal Amino Acid Sequencing

For N-terminal amino-acid sequencing of hFGF2, hIL4, and hCSF1 from the supernatant of controlled fermentation cultures the bands of two lanes of a Coomassie stained SDS-PAGE were cut out and sent to Eurosequence (Groningen, NL).

Example 1: Generation of Expression Plasmids 1.1 Sequencing of Plasmid pNZ8149

Plasmid pNZ8149 was used as vector for the expression of human fibroblast growth factor 2 (hFGF2), human interleukin 4 (hIL4), and human colony stimulating factor 1 (hCSF1) in *L. lactis*. Plasmid pNZ8149 is selected in the host cells via a food grade mechanism based on growth on lactose.

For reference purposes plasmid DNA was isolated and sequenced (for primers see Table 1). No differences were found in relation to the currently available sequence. The sequence of pNZ8149 is provided in SEQ ID No.35.

1.1.1 Human Fibroblast Growth Factor 2 (hFGF-2)

The mature form of hFGF-2 contains 155 amino acids and is designated in the following as hFGF2-155. It has a molecular weight of 17.3 kDa and a pI of 9.85. The molecule contains 4 cysteine residues.

The hFGF-2 variant used for cloning and expression in *L. lactis* is lacking the first two amino acids methionine and alanine and thus contains 153 amino acids. Thus, this variant is designated in the following as hFGF2-153. hFGF2-153 has a molecular weight of 17.1 kDa and a pI of 9.85. This variant also contains four cysteine residues.

The corresponding amino acid sequence of the human FGF2-155 is shown below, in FIG. 32A and in SEQ ID No. 27:

```
MAAGSITTLP ALPEDGGSGA FPPGHFKDPK RLYCKNGGFF

LRIHPDGRVD GVREKSDPHI KLQLQAEERG VVSIKGVCAN

RYLAMKEDGR LLASKCVTDE CFFFERLESN NYNTYRSRKY

TSWYVALKRT GQYKLGSKTG PGQKAILFLP MSAKS
```

The underlined amino acids denote the first two amino acids methionine and alanine which are missing in the variant hFGF2-153. The amino acid sequence of the variant hFGF2-153 is depicted in FIG. 32B and in SEQ ID No. 30.

The sequence of FGF2-155 is the mature human FGF2 sequence after secretion. In vivo this sequence is further processed. However, various existing recombinant products have used this 155 amino acid sequence with or without the N-terminal methionine residue.

1.1.2 Human Interleukin 4 (hIL-4)

The mature protein of hIL-4 contains 129 amino acids, which correspond to the amino acids 25 to 153 of the amino acid sequence available under the NCBI accession number NP_000580.1. The mature protein has a molecular weight of 14.96 kDa and a pI of 9.36. The molecule contains 6 cysteine residues.

The amino acid sequence of the mature human IL-4 is shown below, in FIG. 18C, and in SEQ ID No. 12:

```
HKCDITLQEI IKTLNSLTEQ KTLCTELTVT DIFAASKNTT

EKETFCRAAT VLRQFYSHHE KDTRCLGATA QQFHRHKQLI

RFLKRLDRNL WGLAGLNSCP VKEANQSTLE NFLERLKTIM

REKYSKCSS
```

The hIL-4 variant that is used for cloning and expression in *L. lactis* contains an additional alanine residue at the N-terminus of the mature protein and thus contains 130 amino acids. It has a molecular weight of 15.03 kDa and a pI of 9.36. This variant also contains 6 cysteine residues.

The corresponding amino acid sequence of the human hIL-4 variant that is used for cloning and expression is shown below, in FIG. 33 and in SEQ ID No. 14:

```
AHKCDITLQE IIKTLNSLTE QKTLCTELTV TDIFAASKNT

TEKETFCRAA TVLRQFYSHH EKDTRCLGAT AQQFHRHKQL

IRFLKRLDRN LWGLAGLNSC PVKEANQSTL ENFLERLKTI

MREKYSKCSS
```

The additional alanine residue at the N-terminus is underlined in the above amino acid sequence.

1.1.3 Human Colony Stimulating Factor 1 (hCSF1)

The amino acid sequence used for expression is derived from the 554 amino acid sequence of the human CSF1 precursor available under the NCBI accession number NP_000748.3. The sequence used starts at amino acid 33 (E), which is the first amino acid of the mature hCSF1, and ends at amino acid 181 (Q).

Furthermore an additional 9 amino acids have been added at the C-terminus that occupy in the native protein the positions 480-488 (GHERQSEGS). In order to improve the removal of the signal peptide by the signal peptidase an additional alanine residue was added at the N-terminus. The resulting amino acid sequence is shown below, in FIG. 34, and in SEQ ID No. 6:

```
AEEVSEYCSH MIGSGHLQSL QRLIDSQMET SCQITFEFVD

QEQLKDPVCY LKKAFLLVQD IMEDTMRFRD NTPNAIAIVQ

LQELSLRLKS CFTKDYEEHD KACVRTFYET PLQLLEKVKN

VFNETKNLLD KDWNIFSKNC NNSFAECSSQ GHERQSEGS
```

The additional alanine residue at the N-terminus is underlined in the above amino acid sequence. The additional 9 amino acids added at the C-terminus are depicted in bold. The protein encoded by this sequence contains 159 amino acids, has a molecular weight of 18.5 kDa and an pI of 4.72. The protein contains 7 cysteine residues.

1.2 Construction of a Plasmid for the Expression of hFGF2, hIL4, and hCSF1 in *Lactococcus lactis*

For *L. lactis* the aim was to express and secrete hFGF2, hIL4, and hCSF1, for example, into the supernatant of the growth medium. For that signals for transcription, translation and protein secretion were used. The signals for transcription and translation were present in the NICE expression system of *L. lactis* and originating from the nisinA promoter of *L. lactis*. The nisinA promoter of *L. lactis* is depicted in FIG. 3 and SEQ ID No. 44 and is, for example, described in de Ruyter et al. (1996).

FIG. 3 further shows the −10 element and the −35 element of the promoter as well as the ribosomal binding site (RBS). The ATG start codon of the respective target protein follows directly the two Cysteine residues at the 3'-end of the sequence.

The secretion signal was derived from the *Lactococcus* protein Usp45, which is described, for example, in van Asseldonk et al. (1993) and van Asseldonk et al. (1990).

The secretion signal of the *Lactococcus* protein Usp45 is shown below, in FIG. 35, and in SEQ ID No. 34:

```
MKKKIISAIL MSTVILSAAA PLSGVYA
```

In the cell a mechanism exists that ensures that after the secretion of a protein this signal sequence is cleaved off from the target protein. This reaction is catalysed by the signal peptidase which has a specific preference for certain amino acids in the positions around the cleavage site.

In order to optimize the cleavage site the web based program SignalP 4.1 (www.cbs.dtu.dk/services/SignalP/) was used.

For the amino acid sequence of hFGF2 this program showed that optimum cleavage occurs when the first two amino acids of hFGF2-155 are removed, leaving an hFGF2-155 protein starting with an Ala residue and a total length of 153 amino acids (Variant hFGF2-153).

The respective amino acid sequence of the hFGF2-153 precursor protein used for analysis with the program SignalP 4.1 is shown below and in SEQ ID No. 29:

```
MKKKIISAIL MSTVILSAAA PLSGVYAAGS ITTLPALPED

GGSGAFPPGH FKDPKRLYCK NGGFFLRIHP DGRVDGVREK

SDPHIKLQLQ AEERGVVSIK GVCANRYLAM KEDGRLLASK

CVTDECFFFE RLESNNYNTY RSRKYTSWYV ALKRTGQYKL

GSKTGPGQKA ILFLPMSAKS
```

The underlined amino acids denote the secretion signal of the *Lactococcus* protein Usp45.

For the amino acid sequence of hIL4 this program showed that optimum cleavage occurs when an alanine residue is added to the N-terminus of the mature IL4 protein, resulting in a protein of 130 amino acids.

The respective amino acid sequence of the hIL4 precursor protein used for analysis with the program SignalP 4.1 is shown below and in SEQ ID No. 13:

```
MKKKIISAIL MSTVILSAAA PLSGVYAAHK CDITLQEIIK

TLNSLTEQKT LCTELTVTDI FAASKNTTEK ETFCRAATVL

RQFYSHHEKD TRCLGATAQQ FHRHKQLIRF LKRLDRNLWG

LAGLNSCPVK EANQSTLENF LERLKTIMRE KYSKCSS
```

The underlined amino acids denote the secretion signal of the *Lactococcus* protein Usp45.

For the amino acid sequence of hCSF1 this program showed that optimum cleavage occurs when an alanine residue is added to the N-terminus of the mature hCSF1 protein resulting in a protein of 159 amino acids.

The respective amino acid sequence of the hCSF1 precursor protein used for analysis with the program SignalP 4.1 is shown below and in SEQ ID No. 5:

```
MKKKIISAIL MSTVILSAAA PLSGVYAAEE VSEYCSHMIG

SGHLQSLQRL IDSQMETSCQ ITFEFVDQEQ LKDPVCYLKK

AFLLVQDIME DTMRFRDNTP NAIAIVQLQE LSLRLKSCFT

KDYEEHDKAC VRTFYETPLQ LLEKVKNVFN ETKNLLDKDW

NIFSKNCNNS FAECSSQGHE RQSEGS
```

The underlined amino acids denote the secretion signal of the *Lactococcus* protein Usp45.

FIG. 4A shows a readout of SignalP 4.1 obtained with the amino acid sequence depicted in SEQ ID No. 29, in which the secretory signal of the Usp45 protein is fused to the N-Terminus of hFGF2-153. The readout shows a clear cleavage site between amino acids 27 and 28 of the hFGF2-153 precursor and scores for this cleavage site.

FIG. 4B shows a readout of SignalP 4.1 obtained with the amino acid sequence depicted in SEQ ID No. 13, in which the secretory signal of the Usp45 protein is fused to the N-Terminus of hIL4. The readout shows a clear cleavage site between amino acids 27 and 28 of the hIL4 precursor and scores for this cleavage site.

FIG. 4C shows a readout of SignalP 4.1 obtained with the amino acid sequence depicted in SEQ ID No. 5, in which the secretory signal of the Usp45 protein is fused to the N-Terminus of hCSF1. The readout shows a clear cleavage site between amino acids 27 and 28 of the hCSF1 precursor and scores for this cleavage site.

The codon usage for the respective genes, coding for hFGF2-153, hIL4, and hCSF1 were adapted to the general codon usage of *L. lactis*. This is a routine procedure of the supplier of the gene synthesis.

Furthermore, the same Usp45 signal sequence was used for all three proteins. Thereby, expression of all three proteins and posttranslational processing of the signal peptide in the same bacterial cell was improved.

For hFGF2 a fragment was synthesized that contained the nisinA promoter, the Usp45 signal sequence and the hFGF2-153 gene. The nucleic sequence of the artificial construct ssUsp45-FGF2-153 is depicted in SEQ ID No. 45 and FIG. 5A. The codon usage was optimized to the general codon usage of *L. lactis*.

FIG. 5A shows the synthesized insert as well as the corresponding amino acid sequence obtained after transcription and translation. FGF2-153 denotes the human FGF-2 coding insert. PnisA denotes the nisinA promoter of the *Lactococcus lactis* nisin operon. ssUsp45 denotes the signal sequence of the usp45 gene of *Lactococcus lactis*. An asterisk denotes a stop codon. Furthermore, in the nucleic acid sequence, the restriction recognition sites for endonucleases BamHI (position 1 to 6) and XbaI (position 751 to 756) are denoted by underlining.

For hIL4 a fragment was synthesized that contained the nisinA promoter, the Usp45 signal sequence and the hIL4 gene. The nucleic sequence of the artificial construct ssUsp45-hIL4 is depicted in SEQ ID No. 47 and FIG. 5B. The codon usage was optimized to the general codon usage of *L. lactis*.

FIG. 5B shows the synthesized insert as well as the corresponding amino acid sequence obtained after transcription and translation. hIL4 denotes the human IL4 coding insert. PnisA denotes the nisinA promoter of the *Lactococcus lactis* nisin operon. ssUsp45 denotes the signal sequence of the usp45 gene of *Lactococcus lactis*. An asterisk denotes a stop codon. Furthermore, in the nucleic acid sequence, the restriction recognition sites for endonucleases BamHI (position 1 to 6) and XbaI (position 682 to 687) are denoted by underlining.

For hCSF1 a fragment was synthesized that contained the nisinA promoter, the Usp45 signal sequence and the hCSF1 gene. The nucleic sequence of the artificial construct ssUsp45-hCSF2 is depicted in SEQ ID No. 49 and in FIG. 5C. The codon usage was optimized to the general codon usage of *L. lactis*.

FIG. 5C shows the synthesized insert as well as the corresponding amino acid sequence obtained after transcription and translation. hCSF1 denotes the human CSF1 coding insert. PnisA denotes the nisinA promoter of the *Lactococcus lactis* nisin operon. ssUsp45 denotes the signal sequence of the usp45 gene of *Lactococcus lactis*. An asterisk denotes a stop codon. Furthermore, in the nucleic acid sequence, the restriction recognition sites for endonucleases BamHI (position 1 to 6) and XbaI (position 769 to 774) are denoted by underlining.

The finished gene synthesis products were obtained from BaseClear each as a fragment cloned in the *E. coli* vector pUC57.

The fragments were cloned into the plasmid pNZ8149 by digesting the pUC57 plasmids with the respective gene synthesis products with the restriction enzymes BamHI and XbaI. The BamHI and XbaI fragments containing the respective gene synthesis products were isolated and ligated into PsuI and XbaI cut plasmid pNZ8149 to result in the respective plasmids pFGF2, pIL4, and pCSF1. The respective restriction endonucleases were obtained from Thermo Fisher Scientific Inc.

The respective ligation mix was transformed into strain *L. lactis* NZ3900. Verification of the plasmid was carried out by colony PCR analysis. The respective nucleic acid sequences of the primers used are depicted in Table 1 below. The results are shown in FIGS. 6A-6C.

FIG. 6A shows the result of a colony PCR analysis of potential colonies of *L. lactis* strain NZ3900 with pFGF2. Lane 1: lambda DNA digested with HindIII; lane 2: pNZ8149 (empty vector) amplified with primers nis2 and seqlacF (expected fragment size 391 bp); lanes 3 and 4 isolated colonies amplified with primers nis2 and seqlacF (expected fragment size 907 bp).

FIG. 6B shows the result of a colony PCR analysis of potential colonies of *L. lactis* strain NZ3900 with pIL4. Lane 1: lambda DNA digested with HindIII; lane 2: pNZ8149 (empty vector) amplified with primers nis2 and seqlacF (expected fragment size 391 bp); lanes 11 and 12 isolated colonies amplified with primers nis2 and seqlacF (expected fragment size 838 bp).

FIG. 6C shows the result of a colony PCR analysis of potential colonies of *L. lactis* strain NZ3900 with pCSF1. Lane 1: lambda DNA digested with HindIII; lane 2: pNZ8149 (empty vector) amplified with primers nis2 and seqlacF (expected fragment size 391 bp); lane 3: isolated colony amplified with primers nis2 and seqlacF (expected fragment size 925 bp).

TABLE 1

Primers used.

| Primers | Sequence | SEQ ID No. |
|---|---|---|
| seq1acF | 5' TGTGATTCATCACCTCATCG 3' | 36 |
| seq2F | 5' CGTGGCTTTGCAGCGAAGATG 3' | 37 |
| seq3F | 5' GACTCAATTCCTAATGATTGG 3' | 38 |
| seq4F | 5' TCAGTGTGGATATAGAGCAAG 3' | 39 |
| seq6R | 5' CTGTAATTTGTTTAATTGCC 3' | 40 |
| seq7R | 5' TTGAGCCAGTTGGGATAGAG 3' | 41 |
| seq8R | 5' GTATCTCAACATGAGCAACTG 3' | 42 |
| nis2 | 5' CAATTGAACGTTTCAAGCCTTGG 3' | 43 |

Figure 7A:
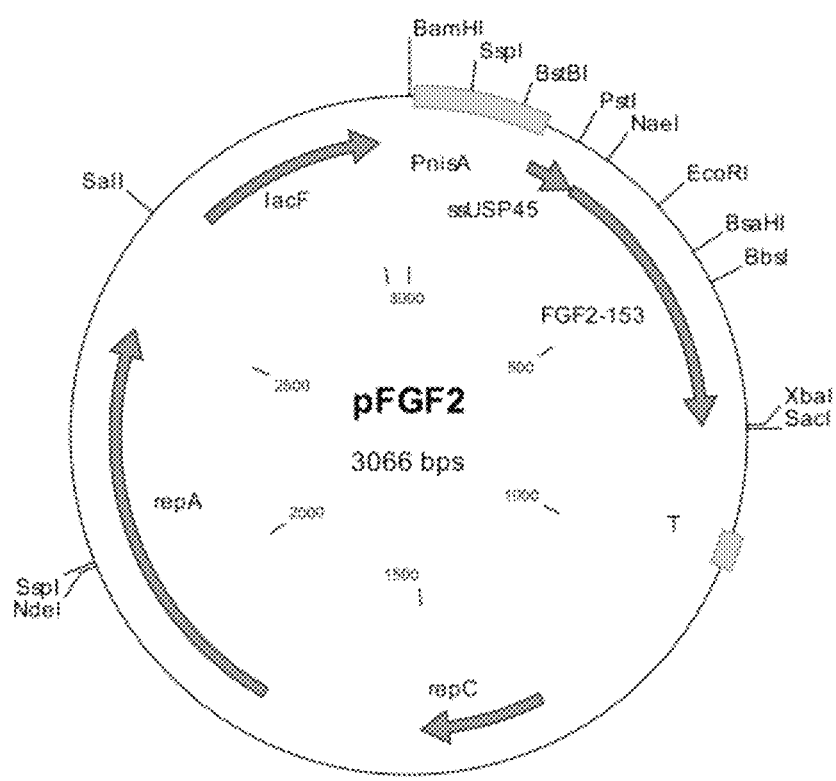
FIGS. 7a, 7b, and 7c show plasmid maps as well as the nucleic acid sequence of the plasmids pFGF2, pIL4, and pCSF1, respectively, for the expression and secretion of hFGF2, hIL4, and hCSF1, respectively, in *Lactococcus lactis*. "Pnis" is the nisin A promoter of the nisin operon of *Lactococcus lactis*; "T" is a terminator; "repC" and "repA" are replication genes. The nucleic acid sequences of the plasmids pFGF2, pIL4, and pCSF1, are depicted in SEQ ID No. 46, SEQ ID No. 48, and SEQ ID No. 50, respectively.

FIG. 7A shows a plasmid map and FIG. 7B shows a nucleic acid sequence of the plasmid pFGF2 for the expression and secretion of hFGF2 in *Lactococcus lactis*. lacF denotes a selection marker for growth of the host strain NZ3900 on lactose; PnisA denotes a nisin A promoter of the nisin operon of *Lactococcus lactis*; ssUSP45 denotes a signal sequence of the usp45 gene of *L. lactis*. T denotes a terminator; repC and repA denotes replication genes. The nucleic acid sequence of the plasmid pFGF2 is also depicted in SEQ ID No. 46.

Figure 7C:
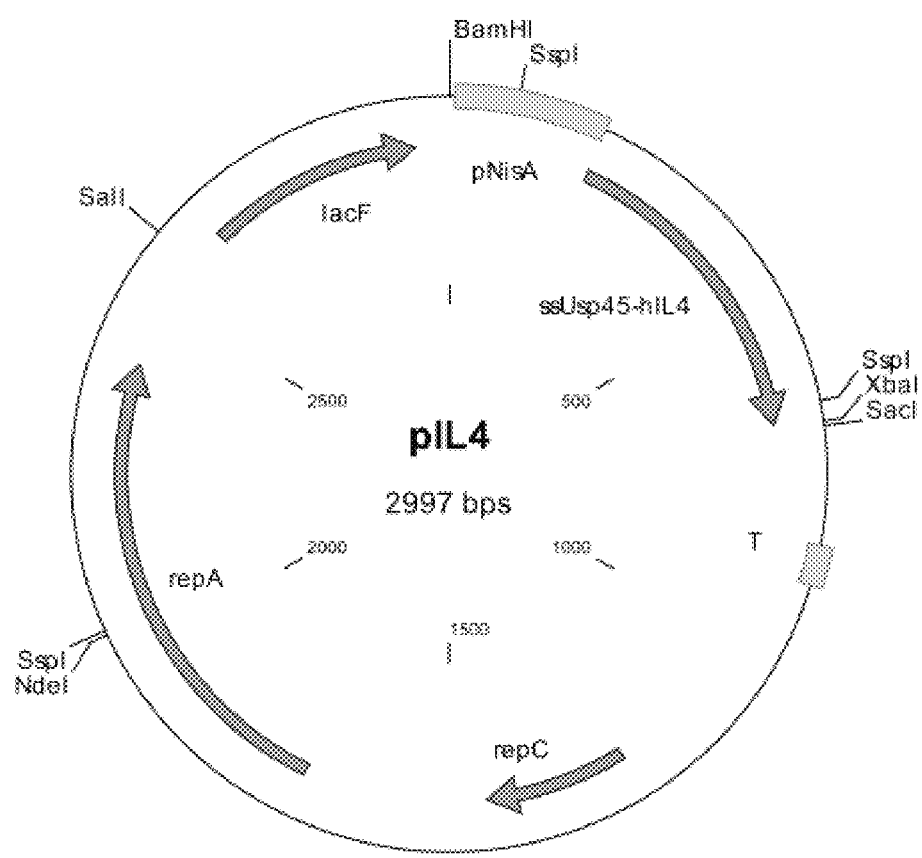

FIG. 7C shows a plasmid map and FIG. 7D shows a nucleic acid sequence of the plasmid pIL4 for the expression and secretion of hIL4 in *Lactococcus lactis*. lacF denotes a selection marker for growth of the host strain NZ3900 on lactose; PnisA denotes a nisin A promoter of the nisin operon of *Lactococcus lactis*; ssUSP45 denotes a signal sequence of the usp45 gene of *L. lactis*. T denotes a terminator; repC and repA denotes replication genes. The nucleic acid sequence of the plasmid pIL4 is also depicted in SEQ ID No. 48.

Figure 7E:
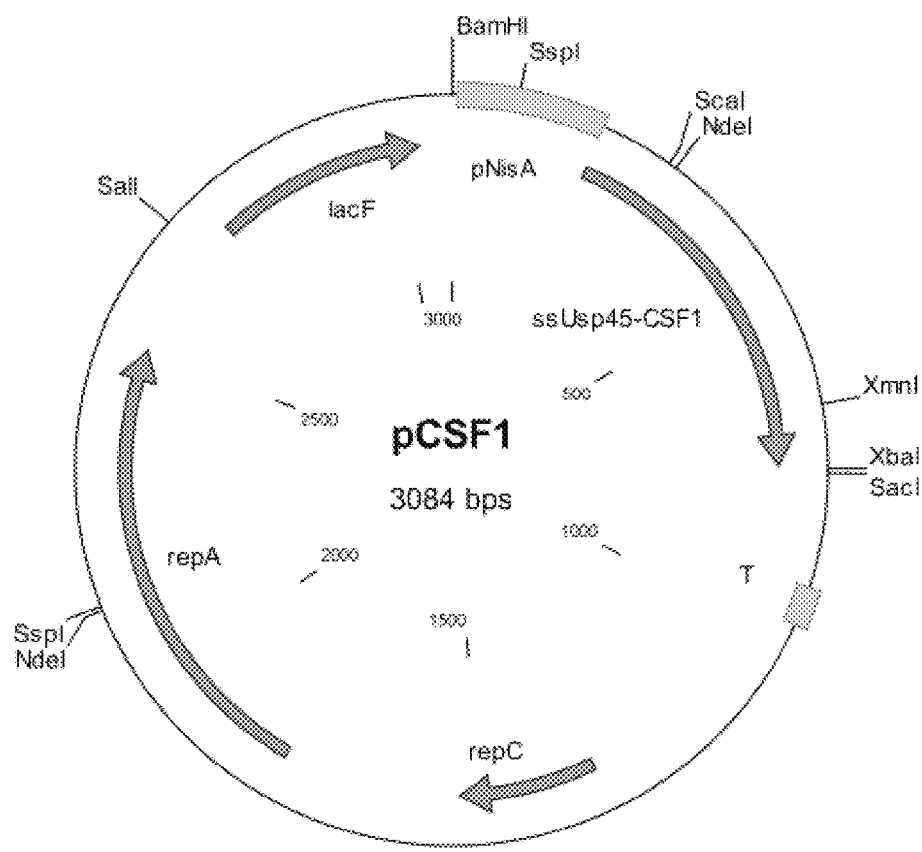

FIG. 7E shows a plasmid map and FIG. 7F shows a nucleic acid sequence of the plasmid pCSF1 for the expression and secretion of hCSF1 in *Lactococcus lactis*. lacF denotes a selection marker for growth of the host strain NZ3900 on lactose; PnisA denotes a nisin A promoter of the nisin operon of *Lactococcus lactis*; ssUSP45 denotes a signal sequence of the usp45 gene of *L. lactis*. T denotes a terminator; repC and repA denotes replication genes. The nucleic acid sequence of the plasmid pCSF1 is also depicted in SEQ ID No. 50.

Example 2: Testing Production of Recombinant Factors in *Lactococcus lactis*

In order to test whether the respective recombinant factors hFGF2, hIL4, or hCSF1 are produced in and secreted from *Lactococcus lactis*, five colonies of the initial transformation were chosen for further analysis. These colonies were first purified by plating and single colony isolation. The five colonies were individually inoculated into M17 lactose medium and grown to an OD 600≈0.5 and induced with 1 ng/ml nisin.

The cultures were terminated and harvested 2 h after the addition of nisin. All cultures showed the same behaviour after the addition of nisin and a certain amount of growth retardation (Data not shown).

a) Production of hFGF2 in *L. lactis* NZ3900(pFGF2) Under Controlled Fermentation Conditions In order to establish the yield of a NZ3900(pFGF2) culture, controlled fermentation runs were carried out.

The following five fermentation runs were carried out:
1. NZ3900(pFGF2) not induced
2. NZ3900(pFGF2) induced at OD 600=0.5 with 5 ng/mL nisin
3. NZ3900(pFGF2) induced at OD 600=3 with 5 ng/mL nisin
4. NZ3900(pNZ8149) induced at OD 600=0.5 with 5 ng/mL nisin
5. NZ3900(pNZ8149) induced at OD 600=3 with 5 ng/mL nisin Samples were taken at t=0 (before induction), t=2 hrs, t=4 hrs and t=6 hrs after induction with the indicated amount of nisin.

Cultures 4 and 5 were performed to establish whether 5 ng/mL nisin has an effect on the growth of a culture because of the activation of the nisin promoter, which is in this case is not followed by a target gene. No effect on growth was observed (Data not shown).

Western blots have been carried out with samples of both induction conditions. Detection of hFGF2 was performed with the antibodies described above under item 1.8.

FIG. 8 shows in the Western blot in lanes 3 and 4 the baseline expression of FGF2 without induction by nisin.

Furthermore, FIG. 8 shows that after induction of the culture at OD 600=0.5 hFGF2 production is strongly induced and increases up to 6 hours after the moment of induction.

hFGF2 bands from an SDS-PAGE gel (induction at OD 600=0.5 with 5 ng/mL nisin, time points t=4 and t=6) were isolated and shipped to Eurosequence B.V. (Groningen, NL) for N-terminal amino acid sequencing.

After clean-up of the samples a tentative N-terminal amino acid sequence was determined. The determined sequence is: Ala-Gly-Ser-Ile-Thr-Thr.

This sequence exactly matches the expected sequence after the signal sequence is cleaved off. The expected sequence is: AGSITTLPAL. This means that hFGF2 is expressed, secreted and correctly processed in *L. lactis*.

The culture supernatant of NZ3900(pFGF2) induced at OD 600=0.5 with 5 ng/mL nisin was used in the following Examples. The culture was designated AUP-10.

b) Production of hIL4 in *L. lactis* NZ3900(pIL4) Under Controlled Fermentation Conditions In order to establish the yield of a NZ3900(pIL4) culture, controlled fermentation runs were carried out with the following fermentations runs:
1. NZ3900(pIL4) not induced
2. NZ3900(pIL4) induced at OD 600=0.5 with 5 ng/mL nisin
3. NZ3900(pIL4) induced at OD 600=3 with 5 ng/mL nisin Samples were taken at t=0 (before induction), t=2 hrs, t=4 hrs and t=6 hrs after induction with the indicated amount of nisin.

The production of hIL4 was analysed by SDS-PAGE of the supernatant fraction and the cell free extract in combination with Western blotting. Detection of hIL4 was performed with the antibodies described above under item 1.8.

During SDS-PAGE DTT was added to the sample buffer and the running buffer in order to facilitate the dissociation of disulphide bridges. These same SDS-PAGE gel were also used to run a Western blot for the specific detection of hIL4.

The effect of the addition of DTT is that hIL4 forms a single protein band in the Coomassie stained gel and in the Western blot (see FIG. 9).

Furthermore, an hIL4 reference protein preparation was used without a carrier protein. The reference protein band is at the same height as the protein produced by *L. lactis* NZ3900(pIL4) cells.

The Western blot shows further detail on the expression of hIL4 in *L. lactis* NZ3900(pIL4).

Induction takes place when the culture is induced at OD 600=0.5 with 5 ng/mL nisin but not when induced at OD 600=3 with 5 ng/mL nisin. The production of hIL4 continues up to at least 6 h. In this period the IL4 concentration in the supernatant increases.

hIL4 bands from an SDS-PAGE gel (induction at OD 600=0.5 with 5 ng/mL nisin, time points t=4 and t=6) were isolated and shipped to Eurosequence B.V. for N-terminal amino acid sequencing.

After clean-up of the samples a tentative N-terminal amino acid sequence was determined. The determined sequence is: Ala-His-Lys-Cys.

This sequence exactly matches the expected sequence after the signal sequence is cleaved off. The expected sequence is: AHKCDITLQE.

This means that hIL4 is expressed, secreted and correctly processed in *L. lactis*. The culture supernatant of NZ3900 (pIL4) induced at OD 600=0.5 with 5 ng/mL nisin was used in the following Examples. The culture was designated AUP-12.

c) Production of hCSF1 in *L. lactis* NZ3900(pCSF1) Under Controlled Fermentation Conditions In order to establish the yield of a NZ3900(pCSF1) culture, controlled fermentation runs were carried out. The following three fermentations were carried out.
1. NZ3900(pCSF1) not induced
2. NZ3900(pCSF1) induced at OD 600=0.5 with 5 ng/mL nisin
3. NZ3900(pCSF1) induced at OD 600=3 with 5 ng/mL nisin The NZ3900(pCSF1) culture was designated AUP-14.

Samples were taken at t=0 (before induction), t=2 hrs, t=4 hrs and t=6 hrs after induction with the indicated amount of nisin.

The production of hCSF1 was analysed by SDS-PAGE of the supernatant fraction and the cell free extract in combination with Western blotting. Detection of hCSF1 was performed with the antibodies described above under item 1.8.

During SDS-PAGE DTT was added to the sample buffer and the running buffer in order to facilitate the dissociation of disulphide bridges. These same SDS-PAGE gel were also used to run a Western blot for the specific detection of hCSF1.

In the Western blot (see FIG. 11) the lane with the reference protein still shows a small amount of dimer. Furthermore, the Coomassie stained gel (see FIG. 10) also shows bands of the same size as the reference protein.

In uninduced cultures hardly any baseline production can be detected. In the cultures induced at OD 600=0.5 with 5 ng/mL nisin CSF1 production increases over time up to at least 6 h. Only a small amount of degradation products could be observed.

hCSF1 bands from an SDS-PAGE gel (induction at OD 600=0.5 with 5 ng/mL nisin, time points t=4 and t=6) were isolated and subjected to N-terminal amino acid sequencing.

After clean-up of the samples a tentative N-terminal amino acid sequence was determined. The determined sequence is: Ala-Glu-Glu-Val-Ser.

This sequence exactly matches the expected sequence after the signal sequence is cleaved off. The expected sequence is: AEEVSEYCSH.

This means that hCSF1 is expressed, secreted and correctly processed in *L. lactis*.

The culture supernatant of NZ3900(pCSF1) induced at OD 600=0.5 with 5 ng/mL nisin was used in the following Examples. The culture was designated AUP-14.

d) Production of hFGF2, hIL4 and hCSF1 in *L. lactis* NZ3900 from a Single Operon Under Controlled Fermentation Conditions 3 constructs were made with 3 of the 6 permutation of the three genes (FGF2, IL4, CSF1):
  a) hFGF2, hIL4, hCSF1,
  b) hCSF1, hFGF2, hIL4,
  c) hIL4, hCSF1, hFGF2.

For the design of the operons each gene was provided with its own ribosome binding site for translational initiation and its own signal peptide for protein secretion. In relation to the signal peptide it had been decided earlier to use for all three genes the same signal sequence (ssUsp45). In order to avoid large identical nucleotide regions on the plasmid in close proximity (possibility of intra-plasmid recombination/deletions) the same signal peptide was coded by different codons on the basis of codon degeneration and the codon usage of *L. lactis*.

For each of the first genes of the 3 constructs the ribosome binding site of the Nisin A (nisA) gene was used. For the other two genes of each of the 3 constructs the ribosome binding sites of the ATP synthase subunit gamma (atpG) gene and the galactoside O-acetyltransferase (lacA) gene were chosen on the basis of good fits with the 3'-end of the 16S rRNA of *L. lactis*, as described in Bolotin et al. (2001) ("The complete genome sequence of the lactic acid bacterium *Lactococcus lactis* ssp. *lactis* IL1403", Genome Res. Volume 11, pages 731 to 753). The nucleotide sequence of the *L. lactis* IL1403 genome is available from NCBI with accession no. AE005176.1.

An overview of all three ribosome binding sites is provided in FIG. 24A. Furthermore, nucleic acid sequences providing the respective ribosome binding sites including the start codon (ATG) of the respective open reading frame are also shown in SEQ ID No. 51 to SEQ ID No. 53.

The 3' end of 16S rRNA of *L. lactis* (5' GGAUCACCUC-CUUUCU 3') is shown in SEQ ID No. 54. In FIG. 24A the 16S rRNA is shown as 16S rDNA, in which uracil (U) was replaced by thymidin (T).

FIG. 24A also shows the six-base consensus sequence of the Shine-Dalgarno sequence (5' AGGAGG 3'). The Shine-Dalgarno sequence is a ribosomal binding site in prokaryotic messenger RNA, generally located around 8 bases upstream of the start codon. The RNA sequence helps recruit the ribosome to the mRNA to initiate protein synthesis by aligning the ribosome with the start codon.

The three operons were designed in such a way that the synthesized sequences can be cloned in one step into plasmid pNZ8149 using the PsuI and NcoI sites of the vector (BamHI and PsuI are compatible). Furthermore, MluI sites were introduced in front of the ribosome binding sites in front of genes two and three. Thereby creation of the remaining three operons was enabled by deletion of the middle gene and cloning of the third gene by PCR using the NcoI and XbaI sites of the plasmid.

The respective sequences of the synthesized nucleic acids are depicted in FIGS. 24B-24D and in SEQ ID No. 55 to SEQ ID No. 57. The codon usage of the three genes has been adapted for *L. lactis*.

Expression from the 3 constructs are each controlled by a single nisinA promoter followed by the above indicated nucleic acid sequences coding for the hFGF2-153 precursor protein, hIL4 precursor protein, and hCSF1 precursor protein obtained in Example 1.

The finished gene synthesis products were obtained from BaseClear each as a fragment cloned in the *E. coli* vector pUC57.

The fragments were cloned into the plasmid pNZ8149 by digesting the pUC57 plasmids containing the respective gene synthesis products with the restriction enzymes BamHI and NcoI. The BamHI/NcoI fragments containing the respective gene synthesis products were isolated and ligated into PsuI and NcoI cut plasmid pNZ8149 to result in the respective plasmids
  pC-F-I (containing the BamHI/NcoI fragment of the CSF-RBS1-FGF-RBS2-IL4 gene synthesis product),
  pF-I-C (containing the BamHI/NcoI fragment of the FGF-RBS1-IL4-RBS2-CSF gene synthesis product), and
  pI-C-F (containing the BamHI/NcoI fragment of the IL4-RBS-CSF-RBS2-FGF gene synthesis product).

The respective restriction endonucleases used were obtained from Thermo Fisher Scientific Inc.

The respective constructs were transformed *L. lactis* NZ3900.

Each 5 colonies of the three constructs were grown in pH regulated fermentation runs and induced at OD600=0.5 with 5 ng/ml nisin and harvested after 4 hours.

1 ml of the supernatant was precipitated with TCA and applied to one well of the SDS-PAGE gel. One gel was stained with Coomassie blue and the other as Western blots for the three target proteins.

The respective SDS-PAGE gels as well as Western blots were processed as outlined above and are depicted in FIGS. 24E-24G.

As can be seen from FIG. 24E construct a) pF-I-C (FGF2, hIL4, hCSF1) resulted in the expression and secretion of much FGF2, little IL4 as well as little CSF1.

As can be seen from FIG. 24F construct b) pC-F-I (hCSF1, hFGF2, hIL4) resulted in the expression and secretion of much CSF1 and FGF2 as well as medium IL4.

As can be seen from FIG. 24G construct c) pI-C-F (hIL4, hCSF1, hFGF2) resulted in the expression and secretion of much IL4 and little less CSF1 and FGF2. The coomassie stained gel showed best production and induction of all three proteins.

The three target proteins can be cloned in and expressed from an operon structure resulting in the release of the respective proteins hIL4, hCSF1, and hFGF2 into the supernatant.

Example 3: Induction of FGF2 Production Under Conditions that Resemble Wound Healing Circumstances The physiological conditions in a wound are different from those in a test tube or fermenter.

Therefore an experiment was set up to test the induction of the NICE system and thus production of hFGF2 under conditions in which strain NZ3900 does not grow or grows only minimally. These conditions are present when the pH of a culture has reached 5.0 and when the culture is going into the stationary phase.

The experiment was carried out in 200 mL bottles with stirring and pH monitoring. As growth medium IM1 medium with 2% weight by volume Na-beta-glycerophosphate and 0.5% weight by volume lactose was used. The following fermentations were carried out:
1. NZ3900(pFGF2)—no induction
2. NZ3900(pFGF2)—induction when culture reaches pH=5 with 1 ng/mL nisin
3. NZ3900(pFGF2)—induction when culture reaches pH=5 with 0.1 ng/mL nisin
4. NZ3900(pFGF2)—induction when culture reaches OD 600=3 with 1 ng/mL nisin
5. NZ3900(pFGF2)—induction when culture reaches OD 600=3 with 0.1 ng/mL nisin.

The cultures were harvested 3 h after induction. The control culture was harvested at the same time as the cultures that were induced at pH 5.0. The results are depicted in FIG. 11.

FIG. 12 shows that growth and pH development are identical in all five cultures and that induction with nisin has no effect on either growth or pH development.

Formation of hFGF2 was measured in 1 ml culture supernatant using SDS-PAGE and Western blotting. FIG. 13 shows that under conditions where the cells do not grow or are in the slowing down phase of growth, nisin does not induce gene expression. In relation to the background production of FGF2 (without induction) there is little or no increase in the amount of FGF2 in the culture supernatant.

Western blot analysis shows that hFGF2 is detectable in the culture supernatant of all five cultures. Furthermore, two breakdown products of hFGF2 are detectable.

This means that all FGF2 with signal sequence that is produced in the cell is processed and secreted.

The gene for human FGF2 has been cloned into a food-grade NICE expression vector for *Lactococcus lactis*.

The expression of the FGF2 gene can be induced by the addition of nisin. hFGF2 is secreted into the supernatant at about 100-200 ng/mL. Determination of the N-terminal amino acid sequence of the secreted FGF2 has shown that the protein is processed correctly Induction of the production of FGF2 leads to a limited growth retardation, but not to arrest of growth.

In a controlled fermentation FGF2 production has been induced at a wide window in the growth curve (between OD 600=0.5-3). The highest FGF2 production has been observed after induction at OD 600=0.5 with 5 ng/ml nisin.

Plasmid pFGF2 is stable for at least 100 generations in strain NZ3900 also under non-selective conditions, such as growth on glucose.

Example 4a: Human Fibroblast Migration Assay

The biological activity of FGF2 released from *Lactococcus lactis* NZ3900(pFGF2) and of IL4 released from *Lactococcus lactis* NZ3900(pIL4) on wound healing was assessed by measuring the migration of normal human dermal fibroblasts (NHDF) into an artificial migration zone. The effect of the test compound was evaluated using an image analysis of the wound recovery.

*Lactococcus lactis* NZ3900(pFGF2) from Example 2a and *Lactococcus lactis* NZ3900(pIL4) from Example 2b were each induced at OD 600=0.5 with 5 ng/mL nisin. After 6 h fermentation, the respective culture supernatants were isolated, freeze dried and stored at −20° C. as described above.

For further testing stock solutions from the freeze-dried supernatants were prepared in a concentration of 1 mg/ml by reconstituting the powder with tris HCl (5 mM, pH 7.6). The AUP-10 stock solution was obtained from the culture supernatant of *Lactococcus lactis* NZ3900(pFGF2) from Example 2a. The AUP-12 stock solution was obtained from the culture supernatant of *Lactococcus lactis* NZ3900(pIL4) from Example 2b.

The stock solutions were diluted with assay medium no 1 to the final concentration of 0.5 ng/ml, 1 ng/ml, 2.5 ng/ml, and 5 ng/ml, respectively, for AUP-10 (FGF2) and to the final concentration of 0.1 ng/ml, 1 ng/ml, 5 ng/ml, and 10 ng/ml, respectively, for AUP-12 (IL4).

The indicated concentrations for the stock solutions as well as dilutions refer to the total amount of protein, which is present in respective solution and which mainly corresponds to the amount of FGF2 and IL4 into the culture supernatants of *Lactococcus lactis* NZ3900(pFGF2) from Example 2a and *Lactococcus lactis* NZ3900(pIL4) from Example 2b, respectively.

Furthermore, recombinant human bFGF (Fiblast), which was purchased from Kaken Pharmaceutical Co., Inc (Tokyo, Japan), was diluted with assay medium no 1 to the final concentration of 0.5 ng/ml, 1 ng/ml, 2.5 ng/ml, and 5 ng/ml, respectively.

Recombinant human IL4, which was purchased from R&D systems (Minneapolis, Minn., USA), was diluted with tris HCl (5 mM, pH 7.6) to the final concentration of 0.1 ng/ml, 1 ng/ml, 5 ng/ml, and 10 ng/ml, respectively.

Normal human dermal fibroblasts (NHDF) were obtained from Lonza Group AG (Basel, CH).

Fibroblasts were seeded in 96-well microplates dedicated to migration analysis and incubated for 24 hours.
  Culture conditions: 37° C., 5% $CO_2$.
  Culture medium: Dulbecco's modified Eagle's medium (DMEM) supplemented with L-glutamine 2 mM, penicillin 50 U/ml, streptomycin 50 μg/ml, and fetal calf serum (FCS) 10% by volume.

In these plates, wells were coated with a collagen solution and a cell seeding stopper was placed in the center of the well in order to restrict cell seeding to the outer annular regions of the wells, thus creating an artificial wound (migration zone). The cells were then labeled using calcein-AM obtained from Thermo Fisher Scientific.

Calcein-AM is a cell-permeant dye that can be used to determine cell viability in most eukaryotic cells. In live cells the nonfluorescent calcein AM is converted to a green-fluorescent calcein after acetoxymethyl ester hydrolysis by intracellular esterases.

After 30 minutes of incubation, the stoppers were removed and culture medium was replaced by assay medium no 1 containing the test compounds (FGF2, Fiblast, IL4 or recombinant hIL4) or only assay medium no 1 (control) or the reference (FCS at 10%). Cells were then incubated for 72 hours. All experimental conditions were performed in n=5.
  Assay medium no 1: DMEM supplemented with L-glutamine 2 mM, penicillin 50 U/ml, and streptomycin 50 μg/ml.

Cell migration into the migration zone was observed after 0, 24, 48 and 72 hours of incubation, using a NIKON Diaphot 300 microscope (lens×4) and images were captured using a NIKON DX-1200 camera.

The surface of the artificial wound was measured at each time point and compared to the pre-migration area measured at T0 in order to visualize and quantify the wound recovery. The effects of the test compounds on cell migration were compared to the untreated control.

The respective concentrations applied were 0.5 ng/ml, 1.0 ng/ml, 2.5 ng/ml, and 5.0 ng/ml for hFGF2 and 0.1 ng/ml, 1 ng/ml, 5 ng/ml, and 10 ng/ml for hIL4. After 72 h exposure migration of the fibroplasts were compared to fibroblast incubated with growth medium (control).

The %-recovery of the area of the artificial wound is shown in FIGS. 14A and 14B.

FIG. 14A shows a significant increase of migrating fibroblasts after incubation with hFGF2 expressing recombinant probiotic bacteria. Under the experimental conditions of the assay, recombinant human bFGF (Fiblast) purchased from Kaken Pharmaceutical Co., Inc (Tokyo, Japan), did not modulate NHDF migration and proliferation.

hFGF2 expressed in recombinant probiotic bacteria AUP-10 obtained in Example 2a posses biological activity.

FIG. 14B shows that AUP-12 culture medium containing 0.1-10 ng/ml of hIL4 induces NHDF proliferation similar to rhIL4.

hIL4 expressed in recombinant probiotic bacteria AUP-12 obtained in Example 2b posses biological activity.

Example 4b: ERK1- and ERK2-phosphorylation in Normal Human Dermal Fibroblasts and in Mouse Lymphoblasts The biological activity of FGF2 released from *Lactococcus lactis* NZ3900(pFGF2) was further assessed by measuring the phosporylation of extracellular signal-regulated kinase 1 (ERK1) and extracellular signal-regulated kinase 2 (ERK2) in normal human dermal fibroblasts (NHDF).

The biological activity of CSF1 released from *Lactococcus lactis* NZ3900(pCSF1) was assessed by measuring the phosporylation of extracellular signal-regulated kinase 1 (ERK1) and extracellular signal-regulated kinase 2 (ERK2) in mouse lymphoblasts M-NFS-60 cells.

The AUP-10 stock solution was prepared as described above in Example 4a.

Furthermore, *Lactococcus lactis* NZ3900(pCSF1) from Example 2c (AUP-14) was induced at OD 600=0.5 with 5 ng/mL nisin. After 6 h fermentation, the culture supernatant was isolated, freeze dried and stored at −20° C. For further testing a stock solution from the freeze-dried supernatant was prepared in a concentration of 1 mg/ml total protein by reconstituting the powder with tris HCl (5 mM, pH 7.6) obtaining the AUP-14 stock solution.

The stock solutions were further diluted with the respective serum free medium to a final concentration of 0.4 ng/ml, 4 ng/ml, 40 ng/ml, and 80 ng/ml, respectively, for AUP-10 (FGF2) and to the final concentration of 0.2 ng/ml, 2 ng/ml, 20 ng/ml, and 40 ng/ml, respectively, for AUP-14 (CSF1).

Recombinant human bFGF from Kaken Pharmaceutical Co. was diluted with serum free medium (Assay medium no 1) to a final concentration of 0.5 ng/ml, 5 ng/ml, 50 ng/ml, and 100 ng/ml, respectively.

Recombinant human CSF1, which was purchased from Abcam PLC (Cambridge, GB), was diluted with serum free medium (Assay medium no 2) to a final concentration of 0.2 ng/ml, 2 ng/ml, 20 ng/ml, and 40 ng/ml, respectively.

Normal human dermal fibroblasts (NHDF) were seeded in 96-well microplates and incubated for 24 hours under the conditions described above under Example 4a.

Mouse M-NFS-60 cells (ATCC® CRL-1838™) were obtained from LGC Standards GmbH (Wesel, Germany). The cells were seeded in 96-well microplates and incubated for 24 hours under the following conditions:

Culture conditions: 37° C.

Culture medium: RPMI-1640 Medium (Life Technologies Corporation, Carlsbad, Calif., USA) supplemented with 0.05 mM 2-mercaptoethanol, 62 ng/ml human recombinant macrophage colony stimulating factor (M-CSF), penicillin 50 U/ml, streptomycin 50 μg/ml, and fetal calve serum to a final concentration of 10% by volume.

Assay medium no 2: RPMI-1640 Medium, supplemented with 0.05 mM 2-mercaptoethanol, penicillin 50 U/ml and streptomycin 50 μg/ml, Exponentially growing NHDF were incubated in serum free medium (Assay medium no 1) for 24 hours, transferred to eppendorf tubes ($0.5 \times 10^5$ cells/tube) and incubated for 15 min at 37° C. in serum free medium (Assay medium no 1) containing 0.5 ng/ml, 5 ng/ml, 50 ng/ml, and 100 ng/ml of rhFGF2 or dilutions of the AUP-10 stock solution at final concentrations as indicated above. Cells were then washed with PBS and resuspended in lysis buffer.

Exponentially growing Mouse M-NFS-60 cells were incubated in serum free medium (Assay medium no 2) for 24 hours, transferred to eppendorf tubes ($2 \times 10^6$ cells/tube) and incubated with Ki-20227 at a concentration of 1 μM for 1 hour. The c-fms inhibitor Ki-20227, which was obtained from Abcam PLC, was included as a control for CSF-1 receptor (CSF-1R) specificity.

After 1 h preincubation with Ki-20227 cells were incubated for 15 min at 37° C. in Assay medium no 2 containing 0.2, 2, 20, and 40 ng/ml of rhCSF1 or dilutions of the AUP-14 stock solution at final concentrations as indicated above. Cells were then washed with PBS and resuspended in lysis buffer.

The recipe for the lysis buffer is as follows: 0.5% by volume Surfact-Amps NP-40 (Pierce Biotechnology, Rockford, Ill., USA), 20 mM Hepes (pH 8.0), 0.35 M NaCl, 0.1 mM EGTA, 0.5 mM EDTA, 1 mM $MgCl_2$, 20% by volume Glycerol, 1 mM DTT, 1 μg/ml leupeptin, 0.5 μg/ml pepstatin, 0.5 μg/ml apronitin, and 1 mM phenylmethylsulfonyl fluoride.

Cells were each incubated for 15 min in ice, and cellular proteins were obtained by centrifugation. Protein concentration was determined by Bradford assay (Bio-Rad), and 50 μg of proteins were boiled in Laemmli buffer and electrophoresed in 10% sodium dodecyl sulfate-polyacrylamide gel. Separated proteins were transferred to nitrocellulose membranes (24V) for 30 min. Blots were blocked in Tris-buffered saline solution containing 0.1% Tween 20 and 5% nonfat dry milk, and the expression of phosphorylated ERK 1+2 and total ERK 1+2 were determined by using the following specifics antibodies.

For detection of ERK1 and ERK2 a rabbit anti-human ERK1 and ERK2 polyclonal antibody (whole antiserum, obtained from Sigma-Aldrich Chemie GmbH, Munich, Germany, product no. M5670) was used at a dilution of 1:10000. The second antibody was horseradish peroxidase (HRP)-linked antibody anti-rabbit IgG at a dilution of 1:10,000 obtained from Bioké B.V. (Leiden, NL).

For detection of phosphorylated ERK1 and ERK2 a purified mouse anti-human P-ERK (E-4) monoclonal antibody (Santa Cruz Biotechnology, Inc., Heidelberg, Germany, product no. sc-7383) was used at a dilution of 1:1000. p-ERK (E-4) is a mouse monoclonal antibody epitope corresponding to a sequence containing Tyr 204 phosphorylated ERK of human origin. The monoclonal antibody detects ERK 1 phosphorylated at Tyr 204 and correspondingly phosphorylated ERK 2 of mouse, rat and human origin.

The second antibody was horseradish peroxidase (HRP)-linked antibody anti-mouse IgG at a dilution of 1:10,000 obtained from Bioké B.V. (Leiden, NL).

The induction of ERK1+2 phosphorylation was quantified using Image J software (National Institutes of Health, Bethesda, Md., USA).

As can be seen from FIG. 14C AUP-10 culture medium containing 0.4-80 ng/ml of FGF2 induce ERK 1+2 phosphorylation in NHDF similar to rhFGF2.

As can be seen from FIG. 14D AUP-14 culture medium containing 0.2-40 ng/ml of CSF1 induce ERK 1+2 phosphorylation in mouse M-NFS-60 cells similar to rhCSF1.

Example 4c: Inhibition of Lipopolysaccharide (LPS) Induced M1-Activation of Human Peripheral Blood Mononuclear Cells (PBMCs)

Human THP-1 cells (ATCC® TIB-202™) were obtained from LGC Standards GmbH. The cells were seeded in 96-well microplates and incubated for 24 hours under the following conditions:
  Culture conditions: 37° C., 5% $CO_2$.
  Culture medium: RPMI-1640 Medium (Life Technologies Corporation, Carlsbad, Calif., USA) supplemented with 0.05 mM 2-mercaptoethanol, penicillin 50 U/ml, streptomycin 50 μg/ml, and fetal calve serum to a final concentration of 10% by volume.
  Assay medium no 2: RPMI-1640 Medium, supplemented with 0.05 mM 2-mercaptoethanol, penicillin 50 U/ml and streptomycin 50 μg/ml,
THP1 is a human monocytic cell line derived from an acute monocytic leukemia patient. THP-1 cells were differentiated to macrophage cells and polarized according to established protocols. *Escheria coli*-derived lipopolysaccharide (LPS) (serotype 026:B6—obtained from Sigma-Aldrich) and Interferon gamma (IFN-γ) obtained from U-Cytech (Utrecht, The Netherlands) was used for polarization.

Briefly, 1 million THP1 cells were plated in 6-well plates in 3-mL DMEM media plus 100 ng/mL phorbol-12-myristate-13-acetate (PMA), which was obtained from Sigma-Aldrich, for 24 hours to induce differentiation to unpolarized macrophages (unpolarized THP-1 derived macrophages).

After differentiation, unpolarized THP-1 derived macrophages were treated in DMEM media for 48 hours with LPS (1 μg/ml) and IFN-γ (100 U/ml) to induce M1 phenotype resulting in the generation of M1 polarized THP-1 derived macrophages.

For inhibition of M1 polarization, unpolarized THP-1 macrophages were first incubated with dilutions of the AUP-12 stock solution obtained in Example 4a or with dilutions of a stock solution of recombinant human IL4 (rhIL4) for 18 hours and then stimulated as described above with LPS and IFN-γ for an additional 48 hours.

The AUP-12 stock solution, having a total protein concentration of 1 mg/ml, was diluted to concentrations of 0.1%, 1%, 10% and 20% by volume with DMEM medium. The stock solution of rhIL4 was diluted to concentrations of 0.1 ng/ml, 1 ng/ml, 10 ng/ml and 20 ng/ml by volume with DMEM medium.

The cells were collected and total RNA was extracted using the High Pure RNA Isolation kit (Roche Diagnostics). Total RNA (1 μg) was retrotranscribed using the iScript™ cDNA Synthesis Kit (Bio-Rad; Hercules, Calif., USA), and the cDNA generated was analyzed by real-time PCR, using the iQ™ SYBR Green Supermix (Bio-Rad; Hercules, Calif., USA). Real-time PCR was performed using a CFX96 Real-time PCR Detection System (Bio-Rad; Hercules, Calif., USA). The HPRT gene was used to standardize mRNA expression in each sample and gene expression was quantified using the 2-ΔΔCt method. A Marker for M1 polarization was tumor necrosis factor alpha (TNF-α) mRNA production.

FIG. 14E shows the inhibition of LPS-induced TNFalpha mRNA production in human THP-1 cells.

As can be seen from FIG. 14E AUP-12 culture medium inhibit LPS-induced TNFalpha mRNA production in human THP-1 cells similar to rhIL4. The effective dose of rhIL4 is between 1-20 ng/ml.

An * in FIG. 14E means a p-value P<0.05 compared to LPS alone. Error bars represent the standard deviation.

Example 4d: Induction of M2-Polarization in Thp1-Derived Macrophages

In order to induce M2 polarization, unpolarizied THP-1 derived macrophages obtained in Example 4c were incubated with dilutions of the AUP-12 stock solution obtained in Example 4a or with dilutions of a stock solution of recombinant human IL4 (rhIL4) having a final concentration of 20 ng/ml for 18 hours.

The AUP-12 stock solution, having a total protein concentration of 1 mg/ml, was diluted to concentrations of 0.1% and 1% by volume with DMEM medium.

Cells were analysed as described above. After polarization cells were collected and total RNA was extracted. Total RNA was retrotranscribed and the cDNA generated was analyzed by real-time PCR. Real-time PCR was performed using a CFX96 Real-time PCR Detection System. The HPRT gene was used to standardize mRNA expression in each sample and gene expression was quantified using the 2-ΔΔCt method. Markers for M2 polarization were macrophage mannose receptor 1 (Mrc1) and Kruppel-like factor 4 (KLF4).

FIG. 14F shows the induction of RNA expression of M2 genes for the macrophage mannose receptor 1 (Mrc1) and Kruppel-like factor 4 (KLF4) in THP1-derived macrophages.

As can be seen from FIG. 14F AUP-12 culture medium induces RNA expression of M2 genes for the macrophage mannose receptor 1 (Mrc1) and Kruppel-like factor 4 (KLF4) in THP1-derived macrophages similar to rhIL4. The effective dose of rhIL4 is between 2-20 ng/ml.

An * in FIG. 14F means a p-value P<0.05 compared to M0 (M0=PMA induced THP1) and Mn=Non-induced THP1. An  in FIG. 14F** means a p-value P<0.05 compared to Mn=Non-induced THP1. Error bars represent the standard deviation.

Example 4e: STAT-6 Transcriptional Activity of AUP-12 in Various Cell Lines

To determine the biological activity of recombinant IL-4 and AUP-12 on STAT6 transcriptional activity MO3.13 (human) and HEK293T (human) cells transiently co-transfected with the STAT-6 and STAT6-Luc plasmids (Addgene Inc, Cambridge, Mass., USA) were used.

Human embryonic kidney 293T cells HEK293T (ATCC® CRL-3216™) were obtained from LGC Standards GmbH.

The cells were seeded in 96-well microplates and incubated for 24 hours under the following conditions:

Culture conditions: 37° C., 5% $CO_2$.

Culture medium: DMEM medium, penicillin 50 U/ml, streptomycin 50 µg/ml, and fetal calve serum to a final concentration of 10% by volume.

Human Glial (Oligodendrocytic) Hybrid Cell Line MO3.13 was obtained from tebu-bio GmbH (Offenbach, Germany). The cells were seeded in 96-well microplates and incubated for 24 hours under the following conditions:

Culture conditions: 37° C.

Culture medium: DMEM medium, penicillin 50 U/ml, streptomycin 50 µg/ml, and fetal calve serum to a final concentration of 10% by volume.

The transfections with the STAT-6 and STAT6-Luc plasmids were performed using RotiFect™ reagent (Carl Roth GmbH+Co. KG, Karlsruhe, Germany) according to the manufacturer's recommendations. The cells were treated with 0.1 ng/ml, 1 ng/ml, 10 ng/ml, 20 ng/ml and 100 ng/ml of recombinant human IL4 (rhIL-4) and dilutions of the AUP-12 stock solution for 6 hours. The AUP-12 stock solution was diluted to concentrations of 0.1%, 1%, 10% and 20% by volume with DMEM medium.

Then the cells were lysed in 25 mM Tris-phosphate pH 7.8, 8 mM MgCl2, 1 mM DTT, 1% Triton X-100, and 7% glycerol.

Luciferase activity was measured using an Autolumat LB 953 (EG&G Berthold, USA) following the instructions of the luciferase assay kit (Promega, Madison, Wis., USA). The results of the specific transactivation are expressed as a fold induction over untreated cells FIG. 14G shows the STAT-6 transcriptional Activity of AUP-12 and rhIL-4 in Human Glial Hybrid Cell Line (MO3.13).

FIG. 14H shows the STAT-6 Transcriptional Activity of AUP-12 and rhIL-4 in Human Embryonic Kidney 293 Cells.

As can be seen from FIGS. 14G and 14H AUP-12 culture medium induces STAT-6 transcriptional Activity in a Human Glial Hybrid Cell Line (MO3.13) as well as 4 in Human Embryonic Kidney 293 Cells similar to rhIL4. The effective dose of rhIL4 is between 0.1 and 20 ng/ml.

Example 5: Wound Closure Experiments

The consequence of application of probiotic bacteria expressing human FGF-2, CSF-1 and IL-4 alone or in combination to full-thickness excisional wounds on db/db diabetic mice was examined in a combined pharmacokinetic (PK)/pharmacodynamic (PD)–efficacy study. Therein, bacteria expressing FGF2 (AUP-10), IL4 (AUP-12) and CSF1 (AUP-14) was evaluated alone or combined as three part combination (i.e. AUP-10+AUP-12+AUP14) and compared in respect of efficacy to a positive control (i.e. a combination of recombinant protein TGF-alpha+PDGF-BB). Furthermore, bacteria expressing FGF2, IL4 and CSF1 in a single bacterial cell (AUP-16) was evaluated and compared to a vehicle treatment (i.e. saline+film dressing or IM1 medium+film dressing) and the positive control (TGF-alpha+PDGF-BB).

Patients with diabetes are prone to impaired wound healing, with foot ulceration being particularly prevalent. This delay in wound healing also extends to diabetic animals, including the spontaneously diabetic (db/db) mouse—which was commercially obtained from The Jackson Laboratory (Bar Harbor, Me., USA).

99 diabetic mice (strain name BKS.Cg-Dock$^{7m}$+/+Lepr$^{db}$/J-Stock Code 00642), all male and aged approximately 10 weeks were used in a first study and a subsequent second study.

Recombinant probiotic bacteria expressing human FGF-2, CSF-1 or IL-4 alone or as a three part combination as well as recombinant probiotic bacteria expressing FGF2, IL4 and CSF1 in a single bacterial cell were applied to wounds on the day of wounding (day 0) and their survival was examined 6 hours after application. In order to facilitate determination of the production of FGF-2, CSF-1 and/or IL-4 by bacteria applied to wounds, wound fluid samples were taken from wounds after 6 hours, and 1, 2 & 7 days. Systemic blood and key organs were harvested after 6 & 24 hours and 7 days to facilitate PK/PD analysis. Wounds in receipt of IM1 medium alone were used as controls for the PK/PD component of this study.

In order to examine the impact of these recombinant probiotic bacteria on the process of wound healing, bacteria expressing human FGF-2, CSF-1 and IL-4, as well as bacteria expressing human FGF-2, CSF-1 or IL-4 alone were applied to wounds on the day of wounding (day 0) and daily thereafter until post-wounding day 6. The healing of wounds in receipt of these recombinant probiotic bacteria was compared to that of similar wounds exposed to fresh IM1 medium only.

Furthermore, recombinant human platelet-derived growth factor-BB (rh-PDGF-BB) in combination with recombinant human Transforming Growth Factor-alpha (rh-TGF-α) was used as the "positive control" in this study. The positive control was prepared in a 0.25% Hydroxypropyl methylcellulose (HPMC) vehicle, which was prepared by dissolving 0.5 g of Hydroxypropyl methylcellulose, obtained from Sigma Aldrich (St. Louis, Mo., USA) in 100 ml distilled water and adding sodium hydroxide to bring the pH up to 7.0.

The combination of PDGF-BB and TGF is based on a study done by Brown R L et al. (Brown R L, Breeden M P, Greenhalgh D G.: "PDGF and TGF-alpha act synergistically to improve wound healing in the genetically diabetic mouse. J. Surg. Res. 56(6), 1994, pages 562 to 570). Brown et al. describe that improvements in wound closure were observed with a combination of PDGF-BB and TGF-alpha when compared to treatment with the individual growth factors.

Wound healing was studied at both the macroscopic and histological levels. Wound healing was studied at the macroscopic level in terms of (i) initiation of neo-dermal repair responses, and (ii) wound closure.

Wound closure, and its components wound contraction and wound re-epithelialisation, were determined from digital photographs taken on post-wounding days 0, 4 & 7 post-wounding. Histological assessments of granulation tissue formation (depth) and wound width (cranio-caudal contraction) were undertaken on routine (H&E) stained sections. These histological assessments were undertaken on tissues harvested on post-wounding day 7.

The development of adverse effects were monitored and fully documented.

Creation of Full-Thickness Experimental Wounds and Application of Treatments

After experimental wounding, animals were housed in individual cages (cage size 500 $cm^2$ with sawdust bedding, changed three times per week), in an environment maintained at an ambient temperature of 23° C. with 12-hour light/dark cycles. They were provided with food (CRM-P, product code 801722, SDS diets, UK) and water ad libitum. To acclimatise the animals to their surroundings, prior to experimentation, they were housed for a period of 5-7 days without disturbance, other than to refresh their bedding and to replenish their food and water provisions. Following all anaesthetic events, animals were placed in a warm environment and were monitored until they have fully recovered from the procedure. All animals received appropriate analgesia (buprenorphine) after surgery and received additional analgesics as required.

All animal procedures were carried out in a UK Home Office licensed establishment under UK Home Office Licences (PCD: 50/2505; PPL: 40/3614; PIL: IBCEFDF55; PIL: 134817249). The health of animals was monitored on a daily basis throughout the study.

Animals were randomized to one of the 18 treatment regimes according to Tables 2a and 2b.

On day 0, animals were anaesthetised (isofluorane & air) and the dorsum was shaved and cleaned with saline-soaked gauze. The skin was then be swabbed with 70% EtOH and wiped dry with sterile gauze. A single standardised full-thickness wound (10.0 mm×10.0 mm) was created in the left dorsal flank skin of each experimental animal.

Wounds on animals in all groups were then be dressed with a circumferential band of the transparent film dressing Bioclusive (Systagenix Wound Management, Gatwick, UK); after which they received one of the treatments described below (see Table 2a and 2b) which was applied by injection through the Bioclusive film using a 27-gauge needle.

For each treatment the respective un-induced recombinant probiotic bacteria were provided in 10 ml IM1 medium having the following cell density (colony forming units (CFU) per ml medium):

| Designation | Sample | CFU/ml |
|---|---|---|
| AUP-10 | Un-induced NZ3900(pFGF2) obtained in Example 2a | $3 \times 10^8$ |
| AUP-14 | Un-induced NZ3900(pCSF1) obtained in Example 2c | $3 \times 10^8$ |
| AUP-12 | Un-induced NZ3900(pIL4) obtained in Example 2b | $3 \times 10^8$ |
| Combination | Un-induced NZ3900(pFGF2) obtained in Example 2a | $1 \times 10^8$ |
| | Un-induced NZ3900(pCSF1) obtained in Example 2c | $1 \times 10^8$ |
| | Un-induced NZ3900(pIL4) obtained in Example 2b | $1 \times 10^8$ |
| AUP-16 | Un-induced NZ3900(pC-F-I) cells obtained in Example 2d | $3 \times 10^8$ |

The treatment scheme "Combination" represents a three part combination resulting from a mixture of un-induced NZ3900(pFGF2) obtained in Example 2a, un-induced NZ3900(pCSF1) obtained in Example 2c, and un-induced NZ3900(pIL4) obtained in Example 2b. The mixture has a total cell density of $3 \times 10^8$ CFU/ml.

Before application of treatment, the respective un-induced recombinant probiotic bacteria provided in 10 ml IM1 medium were incubated at 30° C. without shaking and the optical density was determined spectrophotometrically at a wavelength of 600 nm (0D600).

At an OD600 of 0.5 nisin was added to a final concentration of 5 ng/ml. After additional incubation for 30 min. at 30° C. the induced culture was transferred to 10° C. Subsequently, the respective induced culture was applied by injection through the Bioclusive film using a 27-gauge needle.

Treatments were applied according to the scheme described in Table 2a and 2b. The animals of treatment groups 1 to 9 received a single application of 50 μl at day 0. The animals of treatment groups 10 to 18 received seven consecutive applications divided as a single application of 50 μl per day at days 0, 1, 2, 3, 4, 5, and 6.

Six hours after the first application of treatment, wound fluid was harvested from all animals in groups 1 through 4. The wound fluid harvested from the combination group (grp 1) was processed in such a manner to permit CFU counting of the recombinant probiotic bacteria. The fluid taken from wounds in the remaining groups was held on wet ice prior to transfer to −80° C. for longer term storage. After wound fluid collection, all animals in these groups were terminated (by a UK Home Office approved method). Prior to termination, systemic blood was taken by cardiac puncture into EDTA treated tubes. One half of the blood sample was centrifuged to derive plasma; the remaining half was held at 4° C. overnight prior to shipment to Langford Veterinary Services Ldt. (Bristol, UK), where full and differential blood counts were undertaken. Post-mortem samples of liver, kidney, spleen, heart, lung tissue and draining lymph nodes were harvested from all animals (plasma and tissues was be placed in cryovials which were snap-frozen in liquid nitrogen—after which they were stored at −80° C.).

24 hours after the first application of treatment, wound fluid were harvested from all animals in groups 5 through 9 and were stored as described above. Blood was collected and stored and animals were then be terminated. Wound fluid, whole blood, plasma and tissue samples were harvested and stored as described above.

One day after the first application and at daily intervals thereafter until day 6, treatments were re-applied to all wounds in groups 10 through 15.

2 days after the first application of treatment (1 day after second application), wound fluid was harvested from all animals in groups 10 through 15 and was stored as described above.

7 days after the first application of treatment (one day after the final application of treatment on day 6), wound fluid was harvested from all animals in groups 10 through 15 and was stored as described above. Blood was collected and stored and animals were then be terminated. Following termination, wound and marginal tissue was harvested and processed for histological investigation (see section 3.7). Wound fluid, whole blood, plasma and tissue samples were harvested and stored as described above.

On post-wounding days 4 and 7, animals in groups 10 to 15 were re-anaesthetised and their wounds were assessed and digitally photographed together with a calibration/identity plate. On day 4 this was undertaken with the Bioclusive film dressing in place. On day 7, dressings and any free debris was removed and wounds were then be cleaned using saline-soaked sterile gauze and mopped dry with sterile gauze. Wounds were assessed and digitally photographed together with a calibration/identity plate.

TABLE 2a

Experimental groups of study 1

| Tx Group | Treatment (BFD = Bioclusive Film Dressing) PK/PD STUDY | Application of treatment | Time of termination | Fluid sample | Group name | "n" |
|---|---|---|---|---|---|---|
| 1 | combination (FGF2, IL4, CSF1) OD 0.5 CFU + BFD (1 × 50 μl) (for CFU count) | Day 0 | +6 h | — | COMBO-6 h | 5 |
| 2 | single (FGF2) OD0.5 + BFD (1 × 50 μl) | Day 0 | +6 h | 50 μl | FGF-6 h | 5 |
| 3 | single (IL4) OD 0.5 + BFD (1 × 50 μl) | Day 0 | +6 h | 50 μl | IL4-6 h | 5 |
| 4 | Vehicle (IM1 medium) + BFD (1 × 50 μl) | Day 0 | +6 h | 50 μl | VEH-6 h | 5 |
| 5 | combination (FGF2, IL4, CSF1) OD 0.5 + BFD (1 × 50 μl) | Day 0 | +1 | 50 μl | COMBO-24 h | 5 |
| 6 | single (FGF2) OD 0.5 + BFD (1 × 50 μl) | Day 0 | +1 | 50 μl | FGF-24 h | 5 |
| 7 | single (IL4) OD 0.5 + BFD (1 × 50 μl) | Day 0 | +1 | 50 μl | IL4-24 h | 5 |
| 8 | single (CSF1) OD0.5 + BFD (1 × 50 μl) | Day 0 | +1 | 50 μl | CSF1-24 h | 5 |
| 9 | Vehicle (IM1 medium) + BFD (1 × 50 μl) | Day 0 | +1 | 50 μl | VEH-24 h | 5 |
| 10 | combination (FGF2, IL4, CSF1) OD0.5 + BFD (7 × 50 μl) | Days 0, 1, 2, 3, 4, 5, 6 | +7 | 50 μl on days 2 and 7 | COMBO-7 d | 5 |
| 11 | single (FGF2) OD0.5 + BFD (7 × 50 μl) | Days 0, 1, 2, 3, 4, 5, 6 | +7 | 50 μl on days 2 and 7 | FGF-7 d | 5 |
| 12 | single (IL4) OD0.5 + BFD (7 × 50 μl) | Days 0, 1, 2, 3, 4, 5, 6 | +7 | 50 μl on days 2 and 7 | IL4-7 d | 5 |
| 13 | single (CSF1) OD0.5 + BFD (7 × 50 μl) | Days 0, 1, 2, 3, 4, 5, 6 | +7 | 50 μl on days 2 and 7 | CSF1-7 d | 5 |
| 14 | Vehicle (IM1 medium) + BFD (7 × 50 μl) | Days 0, 1, 2, 3, 4, 5, 6 | +7 | 50 μl on days 2 and 7 | VEH-7 d | 5 |
| 15 | rh-PDGF-BB [10 μg] + rh-TGF-α [1 ug] – (7 × 50 μl) in 0.5% HMPC + BFD | Days 0, 1, 2, 3, 4, 5, 6 | +7 | 50 μl on days 2 and 7 | +ve-7 d | 5 |

TABLE 2b

Experimental groups of study 2

| | | | | | |
|---|---|---|---|---|---|
| 16 | Saline + BFD (7 × 50 μl) | Days 0, 1, 2, 3, 4, 5, 6 | +12 | VEH-12 d | 8 |
| 17 | rh-PDGF-BB [10 μg] + rh-TGF-α [1 ug] – (7 × 50 μl) in 0.5% HMPC + BFD | Days 0, 1, 2, 3, 4, 5, 6 | +12 | +ve-12 d | 8 |
| 18 | AUP-16 (FGF2, IL4, CSF1) OD0.5 + BFD (7 × 50 μl) | Days 0, 1, 2, 3, 4, 5, 6 | +12 | COMBO-12 d | 8 |

TABLE 3

Results of the CFU counting

| Wound number | Colony count | Dilution | Cfu/ml | Average count |
|---|---|---|---|---|
| 1 | 342 | $10^{-4}$ | $3.42 \times 10^7$ | $3.76 \times 10^7$ |
| | 41 | $10^{-5}$ | $4.10 \times 10^7$ | |
| 2 | 141 | $10^{-4}$ | $1.41 \times 10^7$ | — |
| 3 | 346 | $10^{-4}$ | $3.46 \times 10^7$ | $3.13 \times 10^7$ |
| | 28 | $10^{-5}$ | $2.80 \times 10^7$ | |
| 4 | 78 | $10^{-2}$ | $7.80 \times 10^4$ | — |
| 5 | 287 | $10^{-1}$ | $2.87 \times 10^4$ | $2.93 \times 10^4$ |

Image Analysis of Wound Closure

Image Pro image analysis software (version 4.1.0.0, Media Cybernetics, USA) was used to measure wound closure from images of wounds in groups 10 through 15 and 16 through 18 over time. For each wound at each time point (days 4 & 7 for groups 10 through 15 and days 4, 7, 8, and 12 for groups 16 through 18), open wound area was measured and expressed in terms of % wound area relative to day 0.

Survival of Recombinant Probiotic Bacteria After 6 Hours After Application.

Six hours after introducing the combination of FGF2, IL4 and CSF1 expressing bacteria into the wound, wound fluid was extracted and a bacterial colony forming unit (CFU) counting was performed. The results of the CFU counting from 5 wounds are given in Table 3.

The result confirms that the bacteria are viable in the wound and were still capable of proliferating, after being in the wound for 6 hours, highlighting the fact that the above mentioned recombinant probiotic bacteria can be used to deliver therapeutic protein combinations to the wounds.

Wound Healing Response in the Different Treatment Groups

The wound healing response in the different treatment groups on post-wounding was evaluated by visual inspection 4 and 7 days after starting treatment.

Visual inspection by naked eye as well as quantitative analysis by Image Pro image analysis software of groups 10 through 15 reveals that wound healing occurs even as early as four days after starting treatment. Moreover, on day seven the mice treated with the three part combination of recombinant probiotic bacteria expressing FGF2, IL4, and CSF1 (treatment groups 1, 5, and 10) demonstrate a superior healing response (demonstrating pink/red granulation tissue deposition as well as epithelialization of the wound) compared to the individual treatment groups of FGF2 expressing probiotic bacteria (AUP-10), IL4 expressing probiotic bacteria (AUP-12) and CSF1 expressing probiotic bacteria (AUP-14), as well as compared to the positive control (i.e. TGF-alpha and PDGF-BB). The results are depicted in FIG. 15A.

FIG. 15A illustrates the wound healing response in different treatment groups.

The individual treatments groups show a comparable healing response, which is superior to the IM1 medium treated group (vehicle treated group). The results showed the synergistic effect of combining FGF2, IL4 and CSF1 in wound healing.

FGF2 (AUP-10) treated mice further showed granulation tissue formation, as well as vascularization, but not epithelialization. It can also be seen that there is leakiness from the blood vessels when FGF2 expressing probiotic bacteria was used alone. IL4 expressing probiotic bacteria (AUP-12) and CSF1 expressing probiotic bacteria (AUP-14) showed mainly epithelialization of the wound, but not granulation, whereas wounds treated with the three part combination of recombinant probiotic bacteria (AUP-10+AUP-12+AUP-14) demonstrate granulation tissue formation as well as epithelialization of the wound. No leakiness of blood vessels can be seen.

It is important to know that in diabetic foot ulcers (in humans) epithelialization is dependent on granulation tissue formation. Without granulation tissue formation, epithelialization can not occur and the wound does not close.

In the groups 16 through 18 AUP-16 (recombinant bacteria expressing FGF2, IL4 and CSF1 in a single bacterial cell) was compared to vehicle treatment (saline+dressing) and positive control (i.e. TGF-alpha+PDGF-BB). Throughout the days 4, 8 and 12 AUP-16 demonstrated superiority in wound healing compared to the positive control group (TGF-alpha+PDGF-BB). The results are depicted in FIG. 15B.

A comparison of the wound-healing status of control (saline treated group 16), positive control (treatment group 17) and AUP-16 treated tissue (treatment group 18) after post-wounding and after 4, 8 and 12 days is shown in FIG. 15B.

Day 0 represents the original wound immediately post-wounding. The same wound is also shown at days 4, 8 and 12. The respective photographs were approximately equally scaled to visualise wound closure. The black bar in each photograph represents 1 cm.

A comparison of the remaining wound area after day 8 and day 12 of the positive control (treatment group 17) and AUP-16 treated tissue (treatment group 18) is depicted in FIG. 15C.

The remaining wound area was measured with Image Pro image analysis software in images of wounds and expressed in terms of % wound area relative to day 0.

At day 12 almost full closure of the wound was observed in wounds treated with the combination (AUP-16). This is reflected by a remaining wound area of 1.37% relative to the wound area at day 0 immediately post-wounding.

Furthermore, it can be seen from FIGS. 15A and 15B that in wounds treated with the three part combination as well as AUP-16 a significant better wound closure was observed compared to the wounds treated with recombinant human platelet-derived growth factor-BB in combination with recombinant human transforming growth factor-alpha (positive control), especially at day 12.

All bacterial treatment regimes investigated in this experiment, AUP-10, AUP-12 and AUP-14—applied alone or as a three part combination as well as AUP-16, were found to promote wound repair in the diabetic db/db mouse, which is a widely accepted and one of the best validated animal model of delayed wound healing in humans.

Excisional wounds in db/db mice show a statistically significant delay in wound closure, decreased granulation tissue formation, decreased wound bed vascularity, and markedly diminished proliferation, as for example described in Michaels et al. (2007) ("db/db mice exhibit severe wound-healing impairments compared with other murine diabetic strains in a silicone-splinted excisional wound model", Wound Rep. Reg. 15, pages 665 to 670).

The experimental results clearly show that application of recombinant probiotic bacteria of the present invention provides a significant improvement in the treatment of wounds in humans, especially of chronic wounds.

Application of recombinant probiotic bacteria of the present invention induces granulation tissue formation, increased wound bed vascularity and proliferation, thus leading to an improved and accelerated wound closure even in a model exhibiting severe wound-healing impairments.

These results, thus, show that inflammatory, preferably chronic inflammatory, skin dysfunctions such as frostbite, eczema, psoriasis, dermatitis, ulcer, wound, lupus eritematosus, neurodermitis, and combinations thereof, preferably dermatitis, ulcer, wound, and combinations thereof, further preferably ulcer, benefit from the application of recombinant probiotic bacteria of the present invention.

For example, chronic wounds such as chronic venous ulcers, chronic arterial ulcers, chronic diabetic ulcers, and chronic pressure ulcers, can be treated by application of the recombinant probiotic bacteria of the present invention, since the wound-healing impairments observed in the respective chronic wounds are overcome after application of the recombinant probiotic bacteria of the present invention.

The invention claimed is:

1. A recombinant probiotic bacteria expressing nucleic acid sequence(s) encoding for a first heterologous factor, and nucleic acid sequence(s) encoding for a second heterologous factor, wherein said first factor and said second factor are functionally different from each other, wherein said first factor is a fibroblast growth factor (FGF), wherein said second factor is an M2-polarizing factor selected from the group consisting of interleukin 4 (IL-4), interleukin 10 (IL-10), interleukin 13 (IL-13), colony stimulating factor-1 (CSF-1), interleukin 34 (IL-34), and mixtures thereof, and wherein said probiotic bacteria further comprises at least one inactivated gene selected from the group consisting of alanine racemase (alaR), thymidylate synthase (thyA), asparagine synthase (asnH), CTP synthase (pyrG), tryptophan synthase (trpBA), and combinations thereof.

2. The recombinant probiotic bacteria according to claim 1, wherein said nucleic acid sequence(s) is/are located on at least one of a chromosome and a plasmid of said recombinant probiotic bacteria.

3. The recombinant probiotic bacteria according to claim 1, wherein an expression of said nucleic acid sequence(s) is/are controlled by a constitutive promoter or an inducible promoter.

4. The recombinant probiotic bacteria according to claim 3, wherein the expression of said nucleic acid sequence(s) is/are controlled by an inducible promoter, said nucleic acid sequence(s) being expressible in the presence of at least one inducer.

5. The recombinant probiotic bacteria according to claim 3, wherein said inducible promoter, which is inducible by an inducer, is a promoter for a microbial gene which encodes for a lantibiotic peptide.

6. The recombinant probiotic bacteria according to claim 4, wherein the inducer is at least one lantibiotic peptide.

7. The recombinant probiotic bacteria according to claim 1, wherein said probiotic bacteria further comprises at least one inactivated gene encoding for an essential protein necessary for viability of said probiotic bacteria.

8. The recombinant probiotic bacteria according to claim 7, wherein said gene is inactivated by deletion of said gene, mutation of said gene, epigenetic modification of said gene, RNA interference (RNAi) mediated gene silencing of said gene, translational inhibition of said gene, or combinations thereof.

9. The recombinant probiotic bacteria according to claim 8, wherein said recombinant probiotic bacteria comprises lactic acid bacteria.

10. The recombinant probiotic bacteria according to claim 9, wherein said lactic acid bacteria comprises *Lactococcus lactis*.

11. The recombinant probiotic bacteria according to claim 8, wherein said recombinant probiotic bacteria are in a solution, frozen or dried.

12. The recombinant probiotic bacteria according to claim 8, wherein said recombinant probiotic bacteria are to be administered by at least one of topical administration or by subcutaneous injection.

13. A pharmaceutical composition for treating an inflammatory skin dysfunction, wherein the composition comprises a recombinant probiotic bacteria expressing nucleic acid sequence(s) encoding fibroblast growth factor 2, colony stimulating factor 1, and interleukin 4, wherein said probiotic bacteria further comprises at least one inactivated gene selected from the group consisting of alanine racemase (alaR), thymidylate synthase (thyA), asparagine synthase (asnH), CTP synthase (pyrG), tryptophan synthase (trpBA), and combinations thereof, and wherein the inflammatory skin dysfunction is a chronic wound.

14. A method for treating an inflammatory skin dysfunction, wherein said method comprises the step of administering recombinant probiotic bacteria expressing nucleic acid sequence(s) encoding fibroblast growth factor 2, colony stimulating factor 1, and interleukin 4, and wherein said probiotic bacteria further comprises at least one inactivated gene selected from the group consisting of alanine racemase (alaR), thymidylate synthase (thyA), asparagine synthase (asnH), CTP synthase (pyrG), tryptophan synthase (trpBA), and combinations thereof, to an individual suffering from said inflammatory skin dysfunction, wherein the inflammatory skin dysfunction is a chronic wound.

15. The recombinant probiotic bacteria according to claim 1, further expressing nucleic acid sequence(s) encoding for a third heterologous factor.

16. The recombinant probiotic bacteria according to claim 15, wherein said third factor is releasable from said recombinant probiotic bacteria.

17. The recombinant probiotic bacteria according to claim 15, wherein said first factor, said second factor, and said third factor are functionally different from each other, and wherein said third factor is selected from the group consisting of M2-polarizing factors and growth factors.

18. The recombinant probiotic bacteria according to claim 5, wherein said inducible promoter is a *Lactococcus lactis* promoter chosen from PnisA, PnisZ, PnisQ, PnisF, PnisU, or a combination thereof.

19. The recombinant probiotic bacteria according to claim 6, wherein the inducer is selected from the group consisting of nisin A, nisin Z, nisin Q, nisin F, nisin U, and mixtures thereof.

20. The recombinant probiotic bacteria according to claim 1, wherein said fibroblast growth factor comprises fibroblast growth factor 2 (FGF-2).

21. The recombinant probiotic bacteria according to claim 9, wherein said lactic acid bacteria comprises *Lactobacillus* species.

22. The recombinant probiotic bacteria according to claim 9, wherein said lactic acid bacteria comprises *Lactococcus* species.

23. The recombinant probiotic bacteria according to claim 10, wherein said lactic acid bacteria comprises *Lactococcus lactis* subspecies *cremoris*.

24. The pharmaceutical composition of claim 13, wherein the chronic wound is a chronic venous ulcer, a chronic arterial ulcer, a chronic pressure ulcer, or a chronic preulceration stage thereof.

25. The method of claim 14, wherein the chronic wound is a chronic venous ulcer, a chronic arterial ulcer, a chronic pressure ulcer, or a chronic preulceration stage thereof.

26. A pharmaceutical composition comprising recombinant probiotic bacteria, expressing: nucleic acid sequence(s) encoding for a first heterologous factor, and nucleic acid sequence(s) encoding for a second heterologous factor, wherein said first factor and said second factor are functionally different from each other, wherein said first factor is a fibroblast growth factor (FGF), wherein said second factor is an M2-polarizing factor selected from the group consisting of interleukin 4 (IL-4), interleukin 10 (IL-10), interleukin 13 (IL-13), colony stimulating factor-1 (CSF-1), and wherein said probiotic bacteria comprises at least one inactivated gene selected from the group consisting of alanine racemase (alaR), thymidylate synthase (thyA), asparagine synthase (asnH), CTP synthase (pyrG), tryptophan synthase (trpBA), and combinations thereof, and a pharmaceutically-acceptable carrier or excipient.

27. The recombinant probiotic bacteria according to claim 1, wherein the M2-polarizing factor is a colony stimulating factor-1 receptor ligand.

\* \* \* \* \*

UNITED STATES PATENT AND TRADEMARK OFFICE
CERTIFICATE OF CORRECTION

PATENT NO. : 10,738,315 B2
APPLICATION NO. : 15/548558
DATED : August 11, 2020
INVENTOR(S) : Thomas Wirth et al.

Page 1 of 1

It is certified that error appears in the above-identified patent and that said Letters Patent is hereby corrected as shown below:

In the Claims

Column 183, Line 18, Claim 1, delete "expressing" and insert -- expressing: --

Column 183, Lines 62-63, Claim 9, delete "claim 8," and insert -- claim 1, --

Column 184, Lines 17-18, Claim 11, delete "claim 8," and insert -- claim 1, --

Column 184, Lines 20-21, Claim 12, delete "claim 8," and insert -- claim 1, --

Column 186, Line 2, Claim 26, delete "bacteria," and insert -- bacteria --

Signed and Sealed this
Fifteenth Day of December, 2020

Andrei Iancu
*Director of the United States Patent and Trademark Office*

SEQUENCE LISTING

```
<160> NUMBER OF SEQ ID NOS: 83

<210> SEQ ID NO 1
<211> LENGTH: 554
<212> TYPE: PRT
<213> ORGANISM: Homo sapiens

<400> SEQUENCE: 1

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45
```

-continued

```
Gln Ser Leu Gln Arg Leu Ile Asp Ser Gln Met Glu Thr Ser Cys Gln
     50                  55                  60
Ile Thr Phe Glu Phe Val Asp Gln Glu Gln Leu Lys Asp Pro Val Cys
 65                  70                  75                  80
Tyr Leu Lys Lys Ala Phe Leu Leu Val Gln Asp Ile Met Glu Asp Thr
                 85                  90                  95
Met Arg Phe Arg Asp Asn Thr Pro Asn Ala Ile Ala Ile Val Gln Leu
            100                 105                 110
Gln Glu Leu Ser Leu Arg Leu Lys Ser Cys Phe Thr Lys Asp Tyr Glu
        115                 120                 125
Glu His Asp Lys Ala Cys Val Arg Thr Phe Tyr Glu Thr Pro Leu Gln
    130                 135                 140
Leu Leu Glu Lys Val Lys Asn Val Phe Asn Glu Thr Lys Asn Leu Leu
145                 150                 155                 160
Asp Lys Asp Trp Asn Ile Phe Ser Lys Asn Cys Asn Asn Ser Phe Ala
                165                 170                 175
Glu Cys Ser Ser Gln Asp Val Val Thr Lys Pro Asp Cys Asn Cys Leu
            180                 185                 190
Tyr Pro Lys Ala Ile Pro Ser Ser Asp Pro Ala Ser Val Ser Pro His
        195                 200                 205
Gln Pro Leu Ala Pro Ser Met Ala Pro Val Ala Gly Leu Thr Trp Glu
    210                 215                 220
Asp Ser Glu Gly Thr Glu Gly Ser Ser Leu Leu Pro Gly Glu Gln Pro
225                 230                 235                 240
Leu His Thr Val Asp Pro Gly Ser Ala Lys Gln Arg Pro Pro Arg Ser
                245                 250                 255
Thr Cys Gln Ser Phe Glu Pro Pro Glu Thr Pro Val Val Lys Asp Ser
            260                 265                 270
Thr Ile Gly Gly Ser Pro Gln Pro Arg Pro Ser Val Gly Ala Phe Asn
        275                 280                 285
Pro Gly Met Glu Asp Ile Leu Asp Ser Ala Met Gly Thr Asn Trp Val
    290                 295                 300
Pro Glu Glu Ala Ser Gly Glu Ala Ser Glu Ile Pro Val Pro Gln Gly
305                 310                 315                 320
Thr Glu Leu Ser Pro Ser Arg Pro Gly Gly Gly Ser Met Gln Thr Glu
                325                 330                 335
Pro Ala Arg Pro Ser Asn Phe Leu Ser Ala Ser Ser Pro Leu Pro Ala
            340                 345                 350
Ser Ala Lys Gly Gln Gln Pro Ala Asp Val Thr Gly Thr Ala Leu Pro
        355                 360                 365
Arg Val Gly Pro Val Arg Pro Thr Gly Gln Asp Trp Asn His Thr Pro
    370                 375                 380
Gln Lys Thr Asp His Pro Ser Ala Leu Leu Arg Asp Pro Pro Glu Pro
385                 390                 395                 400
Gly Ser Pro Arg Ile Ser Ser Leu Arg Pro Gln Gly Leu Ser Asn Pro
                405                 410                 415
Ser Thr Leu Ser Ala Gln Pro Gln Leu Ser Arg Ser His Ser Ser Gly
            420                 425                 430
Ser Val Leu Pro Leu Gly Glu Leu Gly Arg Arg Ser Thr Arg Asp
        435                 440                 445
Arg Arg Ser Pro Ala Glu Pro Glu Gly Gly Pro Ala Ser Glu Gly Ala
    450                 455                 460
Ala Arg Pro Leu Pro Arg Phe Asn Ser Val Pro Leu Thr Asp Thr Gly
```

```
                        465                 470                 475                 480
His Glu Arg Gln Ser Glu Gly Ser Ser Pro Gln Leu Gln Glu Ser
                    485                 490                 495

Val Phe His Leu Leu Val Pro Ser Val Ile Leu Val Leu Ala Val
                500                 505                 510

Gly Gly Leu Leu Phe Tyr Arg Trp Arg Arg Ser His Gln Glu Pro
                515                 520                 525

Gln Arg Ala Asp Ser Pro Leu Glu Gln Pro Glu Gly Ser Pro Leu Thr
530                 535                 540

Gln Asp Asp Arg Gln Val Glu Leu Pro Val
545                 550

<210> SEQ ID NO 2
<211> LENGTH: 438
<212> TYPE: PRT
<213> ORGANISM: Homo sapiens

<400> SEQUENCE: 2

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
                20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
        50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285
```

-continued

Pro Gly Met Glu Asp Ile Leu Asp Ser Ala Met Gly Thr Asn Trp Val
290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
            325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly His Glu Arg Gln
            355                 360                 365

Ser Glu Gly Ser Ser Ser Pro Gln Leu Gln Glu Ser Val Phe His Leu
            370                 375                 380

Leu Val Pro Ser Val Ile Leu Val Leu Leu Ala Val Gly Gly Leu Leu
385                 390                 395                 400

Phe Tyr Arg Trp Arg Arg Ser His Gln Glu Pro Gln Arg Ala Asp
                405                 410                 415

Ser Pro Leu Glu Gln Pro Glu Gly Ser Pro Leu Thr Gln Asp Asp Arg
            420                 425                 430

Gln Val Glu Leu Pro Val
            435

<210> SEQ ID NO 3
<211> LENGTH: 256
<212> TYPE: PRT
<213> ORGANISM: Homo sapiens

<400> SEQUENCE: 3

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Gly His Glu Arg Gln Ser Glu Gly Ser Ser Ser
            180                 185                 190

Pro Gln Leu Gln Glu Ser Val Phe His Leu Leu Val Pro Ser Val Ile
        195                 200                 205

Leu Val Leu Leu Ala Val Gly Gly Leu Leu Phe Tyr Arg Trp Arg Arg
    210                 215                 220

```
Arg Ser His Gln Glu Pro Gln Arg Ala Asp Ser Pro Leu Glu Gln Pro
225                 230                 235                 240

Glu Gly Ser Pro Leu Thr Gln Asp Asp Arg Gln Val Glu Leu Pro Val
            245                 250                 255

<210> SEQ ID NO 4
<211> LENGTH: 149
<212> TYPE: PRT
<213> ORGANISM: Homo sapiens

<400> SEQUENCE: 4

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
130                 135                 140

Glu Cys Ser Ser Gln
145

<210> SEQ ID NO 5
<211> LENGTH: 186
<212> TYPE: PRT
<213> ORGANISM: Artificial Sequence
<220> FEATURE:
<223> OTHER INFORMATION: synthetic construct hCSF1

<400> SEQUENCE: 5

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Ala Glu Glu Val Ser
            20                  25                  30

Glu Tyr Cys Ser His Met Ile Gly Ser Gly His Leu Gln Ser Leu Gln
        35                  40                  45

Arg Leu Ile Asp Ser Gln Met Glu Thr Ser Cys Gln Ile Thr Phe Glu
50                  55                  60

Phe Val Asp Gln Glu Gln Leu Lys Asp Pro Val Cys Tyr Leu Lys Lys
65                  70                  75                  80

Ala Phe Leu Leu Val Gln Asp Ile Met Glu Asp Thr Met Arg Phe Arg
                85                  90                  95

Asp Asn Thr Pro Asn Ala Ile Ala Ile Val Gln Leu Gln Glu Leu Ser
            100                 105                 110

Leu Arg Leu Lys Ser Cys Phe Thr Lys Asp Tyr Glu Glu His Asp Lys
        115                 120                 125
```

```
Ala Cys Val Arg Thr Phe Tyr Glu Thr Pro Leu Gln Leu Leu Glu Lys
    130                 135                 140

Val Lys Asn Val Phe Asn Glu Thr Lys Asn Leu Leu Asp Lys Asp Trp
145                 150                 155                 160

Asn Ile Phe Ser Lys Asn Cys Asn Asn Ser Phe Ala Glu Cys Ser Ser
                165                 170                 175

Gln Gly His Glu Arg Gln Ser Glu Gly Ser
            180                 185
```

<210> SEQ ID NO 6
<211> LENGTH: 159
<212> TYPE: PRT
<213> ORGANISM: Artificial Sequence
<220> FEATURE:
<223> OTHER INFORMATION: synthetic construct hCSF1

<400> SEQUENCE: 6

```
Ala Glu Glu Val Ser Glu Tyr Cys Ser His Met Ile Gly Ser Gly His
1               5                   10                  15

Leu Gln Ser Leu Gln Arg Leu Ile Asp Ser Gln Met Glu Thr Ser Cys
                20                  25                  30

Gln Ile Thr Phe Glu Phe Val Asp Gln Glu Gln Leu Lys Asp Pro Val
            35                  40                  45

Cys Tyr Leu Lys Lys Ala Phe Leu Leu Val Gln Asp Ile Met Glu Asp
50                  55                  60

Thr Met Arg Phe Arg Asp Asn Thr Pro Asn Ala Ile Ala Ile Val Gln
65                  70                  75                  80

Leu Gln Glu Leu Ser Leu Arg Leu Lys Ser Cys Phe Thr Lys Asp Tyr
                85                  90                  95

Glu Glu His Asp Lys Ala Cys Val Arg Thr Phe Tyr Glu Thr Pro Leu
            100                 105                 110

Gln Leu Leu Glu Lys Val Lys Asn Val Phe Asn Glu Thr Lys Asn Leu
        115                 120                 125

Leu Asp Lys Asp Trp Asn Ile Phe Ser Lys Asn Cys Asn Asn Ser Phe
130                 135                 140

Ala Glu Cys Ser Ser Gln Gly His Glu Arg Gln Ser Glu Gly Ser
145                 150                 155
```

<210> SEQ ID NO 7
<211> LENGTH: 242
<212> TYPE: PRT
<213> ORGANISM: Homo sapiens

<400> SEQUENCE: 7

```
Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
                20                  25                  30

Glu Glu Cys Thr Val Thr Gly Phe Leu Arg Asp Lys Leu Gln Tyr Arg
            35                  40                  45

Ser Arg Leu Gln Tyr Met Lys His Tyr Phe Pro Ile Asn Tyr Lys Ile
50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
```

```
            100                 105                 110
His Pro Ser Trp Lys Tyr Leu Gln Glu Val Glu Thr Leu Leu Leu Asn
    115                 120                 125
Val Gln Gln Gly Leu Thr Asp Val Glu Val Ser Pro Lys Val Glu Ser
130                 135                 140
Val Leu Ser Leu Leu Asn Ala Pro Gly Pro Asn Leu Lys Leu Val Arg
145                 150                 155                 160
Pro Lys Ala Leu Leu Asp Asn Cys Phe Arg Val Met Glu Leu Leu Tyr
                165                 170                 175
Cys Ser Cys Cys Lys Gln Ser Ser Val Leu Asn Trp Gln Asp Cys Glu
                180                 185                 190
Val Pro Ser Pro Gln Ser Cys Ser Pro Glu Pro Ser Leu Gln Tyr Ala
                195                 200                 205
Ala Thr Gln Leu Tyr Pro Pro Pro Trp Ser Pro Ser Ser Pro Pro
    210                 215                 220
His Ser Thr Gly Ser Val Arg Pro Val Arg Ala Gln Gly Glu Gly Leu
225                 230                 235                 240
Leu Pro

<210> SEQ ID NO 8
<211> LENGTH: 241
<212> TYPE: PRT
<213> ORGANISM: Homo sapiens

<400> SEQUENCE: 8

Met Pro Arg Gly Phe Thr Trp Leu Arg Tyr Leu Gly Ile Phe Leu Gly
1               5                   10                  15
Val Ala Leu Gly Asn Glu Pro Leu Glu Met Trp Pro Leu Thr Gln Asn
                20                  25                  30
Glu Glu Cys Thr Val Thr Gly Phe Leu Arg Asp Lys Leu Gln Tyr Arg
            35                  40                  45
Ser Arg Leu Gln Tyr Met Lys His Tyr Phe Pro Ile Asn Tyr Lys Ile
    50                  55                  60
Ser Val Pro Tyr Glu Gly Val Phe Arg Ile Ala Asn Val Thr Arg Leu
65                  70                  75                  80
Arg Ala Gln Val Ser Glu Arg Glu Leu Arg Tyr Leu Trp Val Leu Val
                85                  90                  95
Ser Leu Ser Ala Thr Glu Ser Val Gln Asp Val Leu Leu Glu Gly His
                100                 105                 110
Pro Ser Trp Lys Tyr Leu Gln Glu Val Glu Thr Leu Leu Leu Asn Val
            115                 120                 125
Gln Gln Gly Leu Thr Asp Val Glu Val Ser Pro Lys Val Glu Ser Val
    130                 135                 140
Leu Ser Leu Leu Asn Ala Pro Gly Pro Asn Leu Lys Leu Val Arg Pro
145                 150                 155                 160
Lys Ala Leu Leu Asp Asn Cys Phe Arg Val Met Glu Leu Leu Tyr Cys
                165                 170                 175
Ser Cys Cys Lys Gln Ser Ser Val Leu Asn Trp Gln Asp Cys Glu Val
                180                 185                 190
Pro Ser Pro Gln Ser Cys Ser Pro Glu Pro Ser Leu Gln Tyr Ala Ala
            195                 200                 205
Thr Gln Leu Tyr Pro Pro Pro Trp Ser Pro Ser Ser Pro Pro His
    210                 215                 220
Ser Thr Gly Ser Val Arg Pro Val Arg Ala Gln Gly Glu Gly Leu Leu
```

```
          225                 230                 235                 240
Pro

<210> SEQ ID NO 9
<211> LENGTH: 222
<212> TYPE: PRT
<213> ORGANISM: Homo sapiens

<400> SEQUENCE: 9

Asn Glu Pro Leu Glu Met Trp Pro Leu Thr Gln Asn Glu Glu Cys Thr
1               5                   10                  15
Val Thr Gly Phe Leu Arg Asp Lys Leu Gln Tyr Arg Ser Arg Leu Gln
            20                  25                  30
Tyr Met Lys His Tyr Phe Pro Ile Asn Tyr Lys Ile Ser Val Pro Tyr
        35                  40                  45
Glu Gly Val Phe Arg Ile Ala Asn Val Thr Arg Leu Gln Arg Ala Gln
    50                  55                  60
Val Ser Glu Arg Glu Leu Arg Tyr Leu Trp Val Leu Val Ser Leu Ser
65                  70                  75                  80
Ala Thr Glu Ser Val Gln Asp Val Leu Leu Glu Gly His Pro Ser Trp
                85                  90                  95
Lys Tyr Leu Gln Glu Val Glu Thr Leu Leu Leu Asn Val Gln Gln Gly
            100                 105                 110
Leu Thr Asp Val Glu Val Ser Pro Lys Val Glu Ser Val Leu Ser Leu
        115                 120                 125
Leu Asn Ala Pro Gly Pro Asn Leu Lys Leu Val Arg Pro Lys Ala Leu
    130                 135                 140
Leu Asp Asn Cys Phe Arg Val Met Glu Leu Leu Tyr Cys Ser Cys Cys
145                 150                 155                 160
Lys Gln Ser Ser Val Leu Asn Trp Gln Asp Cys Glu Val Pro Ser Pro
                165                 170                 175
Gln Ser Cys Ser Pro Glu Pro Ser Leu Gln Tyr Ala Ala Thr Gln Leu
            180                 185                 190
Tyr Pro Pro Pro Pro Trp Ser Pro Ser Ser Pro Pro His Ser Thr Gly
        195                 200                 205
Ser Val Arg Pro Val Arg Ala Gln Gly Glu Gly Leu Leu Pro
    210                 215                 220

<210> SEQ ID NO 10
<211> LENGTH: 153
<212> TYPE: PRT
<213> ORGANISM: Homo sapiens

<400> SEQUENCE: 10

Met Gly Leu Thr Ser Gln Leu Leu Pro Pro Leu Phe Phe Leu Leu Ala
1               5                   10                  15
Cys Ala Gly Asn Phe Val His Gly His Lys Cys Asp Ile Thr Leu Gln
            20                  25                  30
Glu Ile Ile Lys Thr Leu Asn Ser Leu Thr Glu Gln Lys Thr Leu Cys
        35                  40                  45
Thr Glu Leu Thr Val Thr Asp Ile Phe Ala Ala Ser Lys Asn Thr Thr
    50                  55                  60
Glu Lys Glu Thr Phe Cys Arg Ala Ala Thr Val Leu Arg Gln Phe Tyr
65                  70                  75                  80
Ser His His Glu Lys Asp Thr Arg Cys Leu Gly Ala Thr Ala Gln Gln
                85                  90                  95
```

Phe His Arg His Lys Gln Leu Ile Arg Phe Leu Lys Arg Leu Asp Arg
              100                 105                 110

Asn Leu Trp Gly Leu Ala Gly Leu Asn Ser Cys Pro Val Lys Glu Ala
          115                 120                 125

Asn Gln Ser Thr Leu Glu Asn Phe Leu Glu Arg Leu Lys Thr Ile Met
      130                 135                 140

Arg Glu Lys Tyr Ser Lys Cys Ser Ser
145                 150

<210> SEQ ID NO 11
<211> LENGTH: 137
<212> TYPE: PRT
<213> ORGANISM: Homo sapiens

<400> SEQUENCE: 11

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
              20                  25                  30

Glu Ile Ile Lys Thr Leu Asn Ser Leu Thr Glu Gln Lys Asn Thr Thr
          35                  40                  45

Glu Lys Glu Thr Phe Cys Arg Ala Ala Thr Val Leu Arg Gln Phe Tyr
      50                  55                  60

Ser His His Glu Lys Asp Thr Arg Cys Leu Gly Ala Thr Ala Gln Gln
65                  70                  75                  80

Phe His Arg His Lys Gln Leu Ile Arg Phe Leu Lys Arg Leu Asp Arg
                  85                  90                  95

Asn Leu Trp Gly Leu Ala Gly Leu Asn Ser Cys Pro Val Lys Glu Ala
              100                 105                 110

Asn Gln Ser Thr Leu Glu Asn Phe Leu Glu Arg Leu Lys Thr Ile Met
          115                 120                 125

Arg Glu Lys Tyr Ser Lys Cys Ser Ser
      130                 135

<210> SEQ ID NO 12
<211> LENGTH: 129
<212> TYPE: PRT
<213> ORGANISM: Homo sapiens

<400> SEQUENCE: 12

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
              20                  25                  30

Phe Ala Ala Ser Lys Asn Thr Thr Glu Lys Glu Thr Phe Cys Arg Ala
          35                  40                  45

Ala Thr Val Leu Arg Gln Phe Tyr Ser His His Glu Lys Asp Thr Arg
      50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                  85                  90                  95

Asn Ser Cys Pro Val Lys Glu Ala Asn Gln Ser Thr Leu Glu Asn Phe
              100                 105                 110

Leu Glu Arg Leu Lys Thr Ile Met Arg Glu Lys Tyr Ser Lys Cys Ser
          115                 120                 125

Ser

<210> SEQ ID NO 13
<211> LENGTH: 157
<212> TYPE: PRT
<213> ORGANISM: Artificial Sequence
<220> FEATURE:
<223> OTHER INFORMATION: synthetic construct hIL4 precursor protein

<400> SEQUENCE: 13

```
Met Lys Lys Lys Ile Ile Ser Ala Ile Leu Met Ser Thr Val Ile Leu
1               5                   10                  15

Ser Ala Ala Ala Pro Leu Ser Gly Val Tyr Ala His Lys Cys Asp
                20                  25                  30

Ile Thr Leu Gln Glu Ile Ile Lys Thr Leu Asn Ser Leu Thr Glu Gln
            35                  40                  45

Lys Thr Leu Cys Thr Glu Leu Thr Val Thr Asp Ile Phe Ala Ala Ser
        50                  55                  60

Lys Asn Thr Thr Glu Lys Glu Thr Phe Cys Arg Ala Ala Thr Val Leu
65                  70                  75                  80

Arg Gln Phe Tyr Ser His His Glu Lys Asp Thr Arg Cys Leu Gly Ala
                85                  90                  95

Thr Ala Gln Gln Phe His Arg His Lys Gln Leu Ile Arg Phe Leu Lys
            100                 105                 110

Arg Leu Asp Arg Asn Leu Trp Gly Leu Ala Gly Leu Asn Ser Cys Pro
        115                 120                 125

Val Lys Glu Ala Asn Gln Ser Thr Leu Glu Asn Phe Leu Glu Arg Leu
    130                 135                 140

Lys Thr Ile Met Arg Glu Lys Tyr Ser Lys Cys Ser Ser
145                 150                 155
```

<210> SEQ ID NO 14
<211> LENGTH: 130
<212> TYPE: PRT
<213> ORGANISM: Artificial Sequence
<220> FEATURE:
<223> OTHER INFORMATION: synthetic construct hIL4

<400> SEQUENCE: 14

```
Ala His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
                20                  25                  30

Ile Phe Ala Ala Ser Lys Asn Thr Thr Glu Lys Glu Thr Phe Cys Arg
            35                  40                  45

Ala Ala Thr Val Leu Arg Gln Phe Tyr Ser His His Glu Lys Asp Thr
        50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130
```

<210> SEQ ID NO 15
<211> LENGTH: 178
<212> TYPE: PRT
<213> ORGANISM: Homo sapiens

<400> SEQUENCE: 15

Met His Ser Ser Ala Leu Leu Cys Cys Leu Val Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 16
<211> LENGTH: 160
<212> TYPE: PRT
<213> ORGANISM: Homo sapiens

<400> SEQUENCE: 16

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
        50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 17
<211> LENGTH: 146
<212> TYPE: PRT
<213> ORGANISM: Homo sapiens

<400> SEQUENCE: 17

Met His Pro Leu Leu Asn Pro Leu Leu Ala Leu Gly Leu Met Ala
1               5                   10                  15

Leu Leu Leu Thr Thr Val Ile Ala Leu Thr Cys Leu Gly Phe Ala
                20                  25                  30

Ser Pro Gly Pro Val Pro Pro Ser Thr Ala Leu Arg Glu Leu Ile Glu
            35                  40                  45

Glu Leu Val Asn Ile Thr Gln Asn Gln Lys Ala Pro Leu Cys Asn Gly
50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
                100                 105                 110

Phe Ser Ser Leu His Val Arg Asp Thr Lys Ile Glu Val Ala Gln Phe
            115                 120                 125

Val Lys Asp Leu Leu Leu His Leu Lys Lys Leu Phe Arg Glu Gly Arg
130                 135                 140

Phe Asn
145

<210> SEQ ID NO 18
<211> LENGTH: 112
<212> TYPE: PRT
<213> ORGANISM: Homo sapiens

<400> SEQUENCE: 18

Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
                100                 105                 110

<210> SEQ ID NO 19
<211> LENGTH: 390
<212> TYPE: PRT
<213> ORGANISM: Homo sapiens

<400> SEQUENCE: 19

Met Pro Pro Ser Gly Leu Arg Leu Leu Pro Leu Leu Leu Pro Leu Leu

-continued

```
1               5                   10                  15
  Trp Leu Val Leu Thr Pro Gly Arg Pro Ala Ala Gly Leu Ser Thr
             20                  25                  30

Cys Lys Thr Ile Asp Met Glu Leu Val Lys Arg Lys Arg Ile Glu Ala
             35                  40                  45

Ile Arg Gly Gln Ile Leu Ser Lys Leu Arg Leu Ala Ser Pro Pro Ser
   50                  55                  60

Gln Gly Glu Val Pro Pro Gly Pro Leu Pro Glu Ala Val Leu Ala Leu
   65                  70                  75                  80

Tyr Asn Ser Thr Arg Asp Arg Val Ala Gly Glu Ser Ala Glu Pro Glu
                     85                  90                  95

Pro Glu Pro Glu Ala Asp Tyr Tyr Ala Lys Glu Val Thr Arg Val Leu
                 100                 105                 110

Met Val Glu Thr His Asn Glu Ile Tyr Asp Lys Phe Lys Gln Ser Thr
                 115                 120                 125

His Ser Ile Tyr Met Phe Phe Asn Thr Ser Glu Leu Arg Glu Ala Val
             130                 135                 140

Pro Glu Pro Val Leu Leu Ser Arg Ala Glu Leu Arg Leu Leu Arg Leu
  145                 150                 155                 160

Lys Leu Lys Val Glu Gln His Val Glu Leu Tyr Gln Lys Tyr Ser Asn
                 165                 170                 175

Asn Ser Trp Arg Tyr Leu Ser Asn Arg Leu Leu Ala Pro Ser Asp Ser
             180                 185                 190

Pro Glu Trp Leu Ser Phe Asp Val Thr Gly Val Val Arg Gln Trp Leu
             195                 200                 205

Ser Arg Gly Gly Glu Ile Glu Gly Phe Arg Leu Ser Ala His Cys Ser
  210                 215                 220

Cys Asp Ser Arg Asp Asn Thr Leu Gln Val Asp Ile Asn Gly Phe Thr
  225                 230                 235                 240

Thr Gly Arg Arg Gly Asp Leu Ala Thr Ile His Gly Met Asn Arg Pro
                 245                 250                 255

Phe Leu Leu Leu Met Ala Thr Pro Leu Glu Arg Ala Gln His Leu Gln
             260                 265                 270

Ser Ser Arg His Arg Arg Ala Leu Asp Thr Asn Tyr Cys Phe Ser Ser
             275                 280                 285

Thr Glu Lys Asn Cys Cys Val Arg Gln Leu Tyr Ile Asp Phe Arg Lys
             290                 295                 300

Asp Leu Gly Trp Lys Trp Ile His Glu Pro Lys Gly Tyr His Ala Asn
  305                 310                 315                 320

Phe Cys Leu Gly Pro Cys Pro Tyr Ile Trp Ser Leu Asp Thr Gln Tyr
                 325                 330                 335

Ser Lys Val Leu Ala Leu Tyr Asn Gln His Asn Pro Gly Ala Ser Ala
             340                 345                 350

Ala Pro Cys Cys Val Pro Gln Ala Leu Glu Pro Leu Pro Ile Val Tyr
             355                 360                 365

Tyr Val Gly Arg Lys Pro Lys Val Glu Gln Leu Ser Asn Met Ile Val
             370                 375                 380

Arg Ser Cys Lys Cys Ser
  385                 390
```

<210> SEQ ID NO 20
<211> LENGTH: 112
<212> TYPE: PRT
<213> ORGANISM: Homo sapiens

<400> SEQUENCE: 20

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
            85                  90                  95

Lys Val Glu Gln Leu Ser Asn Met Ile Val Arg Ser Cys Lys Cys Ser
            100                 105                 110
```

<210> SEQ ID NO 21
<211> LENGTH: 442
<212> TYPE: PRT
<213> ORGANISM: Homo sapiens

<400> SEQUENCE: 21

```
Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
            85                  90                  95

Glu Tyr Tyr Ala Lys Glu Val Tyr Lys Ile Asp Met Pro Pro Phe Phe
            100                 105                 110

Pro Ser Glu Thr Val Cys Pro Val Val Thr Thr Pro Ser Gly Ser Val
            115                 120                 125

Gly Ser Leu Cys Ser Arg Gln Ser Gln Val Leu Cys Gly Tyr Leu Asp
        130                 135                 140

Ala Ile Pro Pro Thr Phe Tyr Arg Pro Tyr Phe Arg Ile Val Arg Phe
145                 150                 155                 160

Asp Val Ser Ala Met Glu Lys Asn Ala Ser Asn Leu Val Lys Ala Glu
                165                 170                 175

Phe Arg Val Phe Arg Leu Gln Asn Pro Lys Ala Arg Val Pro Glu Gln
            180                 185                 190

Arg Ile Glu Leu Tyr Gln Ile Leu Lys Ser Lys Asp Leu Thr Ser Pro
        195                 200                 205

Thr Gln Arg Tyr Ile Asp Ser Lys Val Val Lys Thr Arg Ala Glu Gly
    210                 215                 220

Glu Trp Leu Ser Phe Asp Val Thr Asp Ala Val His Glu Trp Leu His
225                 230                 235                 240

His Lys Asp Arg Asn Leu Gly Phe Lys Ile Ser Leu His Cys Pro Cys
                245                 250                 255
```

-continued

```
Cys Thr Phe Val Pro Ser Asn Asn Tyr Ile Ile Pro Asn Lys Ser Glu
            260                 265                 270

Glu Leu Glu Ala Arg Phe Ala Gly Ile Asp Gly Thr Ser Thr Tyr Thr
                275                 280                 285

Ser Gly Asp Gln Lys Thr Ile Lys Ser Thr Arg Lys Lys Asn Ser Gly
            290                 295                 300

Lys Thr Pro His Leu Leu Leu Met Leu Leu Pro Ser Tyr Arg Leu Glu
305                 310                 315                 320

Ser Gln Gln Thr Asn Arg Arg Lys Arg Ala Leu Asp Ala Ala Tyr
                    325                 330                 335

Cys Phe Arg Asn Val Gln Asp Asn Cys Cys Leu Arg Pro Leu Tyr Ile
                340                 345                 350

Asp Phe Lys Arg Asp Leu Gly Trp Lys Trp Ile His Glu Pro Lys Gly
                355                 360                 365

Tyr Asn Ala Asn Phe Cys Ala Gly Ala Cys Pro Tyr Leu Trp Ser Ser
370                 375                 380

Asp Thr Gln His Ser Arg Val Leu Ser Leu Tyr Asn Thr Ile Asn Pro
385                 390                 395                 400

Glu Ala Ser Ala Ser Pro Cys Cys Val Ser Gln Asp Leu Glu Pro Leu
                    405                 410                 415

Thr Ile Leu Tyr Tyr Ile Gly Lys Thr Pro Lys Ile Glu Gln Leu Ser
                420                 425                 430

Asn Met Ile Val Lys Ser Cys Lys Cys Ser
                435                 440

<210> SEQ ID NO 22
<211> LENGTH: 414
<212> TYPE: PRT
<213> ORGANISM: Homo sapiens

<400> SEQUENCE: 22

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
                20                  25                  30

Met Arg Lys Arg Ile Glu Ala Ile Arg Gly Gln Ile Leu Ser Lys Leu
            35                  40                  45

Lys Leu Thr Ser Pro Pro Glu Asp Tyr Pro Glu Pro Glu Glu Val Pro
        50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
                100                 105                 110

Pro Ser Glu Asn Ala Ile Pro Pro Thr Phe Tyr Arg Pro Tyr Phe Arg
            115                 120                 125

Ile Val Arg Phe Asp Val Ser Ala Met Glu Lys Asn Ala Ser Asn Leu
        130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
```

```
                180               185               190
Arg Ala Glu Gly Glu Trp Leu Ser Phe Asp Val Thr Asp Ala Val His
            195                 200                 205
Glu Trp Leu His His Lys Asp Arg Asn Leu Gly Phe Lys Ile Ser Leu
            210                 215                 220
His Cys Pro Cys Cys Thr Phe Val Pro Ser Asn Asn Tyr Ile Ile Pro
225                 230                 235                 240
Asn Lys Ser Glu Glu Leu Glu Ala Arg Phe Ala Gly Ile Asp Gly Thr
                245                 250                 255
Ser Thr Tyr Thr Ser Gly Asp Gln Lys Thr Ile Lys Ser Thr Arg Lys
                260                 265                 270
Lys Asn Ser Gly Lys Thr Pro His Leu Leu Met Leu Leu Pro Ser
            275                 280                 285
Tyr Arg Leu Glu Ser Gln Gln Thr Asn Arg Arg Lys Lys Arg Ala Leu
            290                 295                 300
Asp Ala Ala Tyr Cys Phe Arg Asn Val Gln Asp Asn Cys Cys Leu Arg
305                 310                 315                 320
Pro Leu Tyr Ile Asp Phe Lys Arg Asp Leu Gly Trp Lys Trp Ile His
                325                 330                 335
Glu Pro Lys Gly Tyr Asn Ala Asn Phe Cys Ala Gly Ala Cys Pro Tyr
            340                 345                 350
Leu Trp Ser Ser Asp Thr Gln His Ser Arg Val Leu Ser Leu Tyr Asn
            355                 360                 365
Thr Ile Asn Pro Glu Ala Ser Ala Ser Pro Cys Cys Val Ser Gln Asp
370                 375                 380
Leu Glu Pro Leu Thr Ile Leu Tyr Tyr Ile Gly Lys Thr Pro Lys Ile
385                 390                 395                 400
Glu Gln Leu Ser Asn Met Ile Val Lys Ser Cys Lys Cys Ser
                405                 410

<210> SEQ ID NO 23
<211> LENGTH: 112
<212> TYPE: PRT
<213> ORGANISM: Homo sapiens

<400> SEQUENCE: 23

Ala Leu Asp Ala Ala Tyr Cys Phe Arg Asn Val Gln Asp Asn Cys Cys
1               5                   10                  15
Leu Arg Pro Leu Tyr Ile Asp Phe Lys Arg Asp Leu Gly Trp Lys Trp
            20                  25                  30
Ile His Glu Pro Lys Gly Tyr Asn Ala Asn Phe Cys Ala Gly Ala Cys
        35                  40                  45
Pro Tyr Leu Trp Ser Ser Asp Thr Gln His Ser Arg Val Leu Ser Leu
    50                  55                  60
Tyr Asn Thr Ile Asn Pro Glu Ala Ser Ala Ser Pro Cys Cys Val Ser
65                  70                  75                  80
Gln Asp Leu Glu Pro Leu Thr Ile Leu Tyr Tyr Ile Gly Lys Thr Pro
                85                  90                  95
Lys Ile Glu Gln Leu Ser Asn Met Ile Val Lys Ser Cys Lys Cys Ser
            100                 105                 110

<210> SEQ ID NO 24
<211> LENGTH: 412
<212> TYPE: PRT
<213> ORGANISM: Homo sapiens
```

```
<400> SEQUENCE: 24

Met Lys Met His Leu Gln Arg Ala Leu Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Arg Val Glu Ala Ile Arg Gly Gln Ile Leu
            35                  40                  45

Ser Lys Leu Arg Leu Thr Ser Pro Glu Pro Thr Val Met Thr His
50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Thr
    290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410
```

<210> SEQ ID NO 25
<211> LENGTH: 112
<212> TYPE: PRT
<213> ORGANISM: Homo sapiens

<400> SEQUENCE: 25

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 26
<211> LENGTH: 288
<212> TYPE: PRT
<213> ORGANISM: Homo sapiens

<400> SEQUENCE: 26

```
Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220
```

```
Leu Ala Ser Lys Cys Val Thr Asp Glu Cys Phe Phe Glu Arg Leu
225                 230                 235                 240

Glu Ser Asn Asn Tyr Asn Thr Tyr Arg Ser Arg Lys Tyr Thr Ser Trp
            245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285
```

<210> SEQ ID NO 27
<211> LENGTH: 155
<212> TYPE: PRT
<213> ORGANISM: Homo sapiens

<400> SEQUENCE: 27

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 28
<211> LENGTH: 146
<212> TYPE: PRT
<213> ORGANISM: Homo sapiens

<400> SEQUENCE: 28

```
Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110
```

```
Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
130                 135                 140

Lys Ser
145

<210> SEQ ID NO 29
<211> LENGTH: 180
<212> TYPE: PRT
<213> ORGANISM: Artificial Sequence
<220> FEATURE:
<223> OTHER INFORMATION: sythetic construct hFGF2-153 precursor protein

<400> SEQUENCE: 29

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Ala Gly Ser Ile Thr
            20                  25                  30

Thr Leu Pro Ala Leu Pro Glu Asp Gly Gly Ser Gly Ala Phe Pro Pro
        35                  40                  45

Gly His Phe Lys Asp Pro Lys Arg Leu Tyr Cys Lys Asn Gly Gly Phe
    50                  55                  60

Phe Leu Arg Ile His Pro Asp Gly Arg Val Asp Gly Val Arg Glu Lys
65                  70                  75                  80

Ser Asp Pro His Ile Lys Leu Gln Leu Gln Ala Glu Glu Arg Gly Val
                85                  90                  95

Val Ser Ile Lys Gly Val Cys Ala Asn Arg Tyr Leu Ala Met Lys Glu
            100                 105                 110

Asp Gly Arg Leu Leu Ala Ser Lys Cys Val Thr Asp Glu Cys Phe Phe
        115                 120                 125

Phe Glu Arg Leu Glu Ser Asn Asn Tyr Asn Thr Tyr Arg Ser Arg Lys
    130                 135                 140

Tyr Thr Ser Trp Tyr Val Ala Leu Lys Arg Thr Gly Gln Tyr Lys Leu
145                 150                 155                 160

Gly Ser Lys Thr Gly Pro Gly Gln Lys Ala Ile Leu Phe Leu Pro Met
                165                 170                 175

Ser Ala Lys Ser
            180

<210> SEQ ID NO 30
<211> LENGTH: 153
<212> TYPE: PRT
<213> ORGANISM: Artificial Sequence
<220> FEATURE:
<223> OTHER INFORMATION: synthetic construct hFGF2-153

<400> SEQUENCE: 30

Ala Gly Ser Ile Thr Thr Leu Pro Ala Leu Pro Glu Asp Gly Gly Ser
1               5                   10                  15

Gly Ala Phe Pro Pro Gly His Phe Lys Asp Pro Lys Arg Leu Tyr Cys
            20                  25                  30

Lys Asn Gly Gly Phe Phe Leu Arg Ile His Pro Asp Gly Arg Val Asp
        35                  40                  45

Gly Val Arg Glu Lys Ser Asp Pro His Ile Lys Leu Gln Leu Gln Ala
    50                  55                  60

Glu Glu Arg Gly Val Val Ser Ile Lys Gly Val Cys Ala Asn Arg Tyr
```

```
                65                  70                  75                  80

Leu Ala Met Lys Glu Asp Gly Arg Leu Leu Ala Ser Lys Cys Val Thr
                    85                  90                  95

Asp Glu Cys Phe Phe Phe Glu Arg Leu Glu Ser Asn Asn Tyr Asn Thr
                    100                 105                 110

Tyr Arg Ser Arg Lys Tyr Thr Ser Trp Tyr Val Ala Leu Lys Arg Thr
                    115                 120                 125

Gly Gln Tyr Lys Leu Gly Ser Lys Thr Gly Pro Gly Gln Lys Ala Ile
                    130                 135                 140

Leu Phe Leu Pro Met Ser Ala Lys Ser
145                 150

<210> SEQ ID NO 31
<211> LENGTH: 728
<212> TYPE: PRT
<213> ORGANISM: Homo sapiens

<400> SEQUENCE: 31

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
                35                  40                  45

Thr Leu Ile Lys Ile Asp Pro Ala Leu Lys Ile Lys Thr Lys Lys Val
            50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                    85                  90                  95

Leu Trp Phe Pro Phe Asn Ser Met Ser Ser Gly Val Lys Lys Glu Phe
                    100                 105                 110

Gly His Glu Phe Asp Leu Tyr Glu Asn Lys Asp Tyr Ile Arg Asn Cys
                    115                 120                 125

Ile Ile Gly Lys Gly Arg Ser Tyr Lys Gly Thr Val Ser Ile Thr Lys
                    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                    165                 170                 175

Cys Arg Asn Pro Arg Gly Glu Glu Gly Pro Trp Cys Phe Thr Ser
                    180                 185                 190

Asn Pro Glu Val Arg Tyr Glu Val Cys Asp Ile Pro Gln Cys Ser Glu
                    195                 200                 205

Val Glu Cys Met Thr Cys Asn Gly Glu Ser Tyr Arg Gly Leu Met Asp
                    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                    245                 250                 255

Asp Asn Tyr Cys Arg Asn Pro Asp Gly Gln Pro Arg Pro Trp Cys Tyr
                    260                 265                 270

Thr Leu Asp Pro His Thr Arg Trp Glu Tyr Cys Ala Ile Lys Thr Cys
                    275                 280                 285
```

-continued

```
Ala Asp Asn Thr Met Asn Asp Thr Asp Val Pro Leu Glu Thr Thr Glu
    290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
            340                 345                 350
Tyr Cys Arg Asn Pro Asp Gly Ser Glu Ser Pro Trp Cys Phe Thr Thr
        355                 360                 365
Asp Pro Asn Ile Arg Val Gly Tyr Cys Ser Gln Ile Pro Asn Cys Asp
370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Ala His
        435                 440                 445
Gly Pro Trp Cys Tyr Thr Gly Asn Pro Leu Ile Pro Trp Asp Tyr Cys
450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
        515                 520                 525
Val Leu Thr Ala Arg Gln Cys Phe Pro Ser Arg Asp Leu Lys Asp Tyr
530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
        595                 600                 605
Lys Thr Ser Cys Ser Val Tyr Gly Trp Gly Tyr Thr Gly Leu Ile Asn
610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
            660                 665                 670
Tyr Gly Gly Pro Leu Val Cys Glu Gln His Lys Met Arg Met Val Leu
        675                 680                 685
Gly Val Ile Val Pro Gly Arg Gly Cys Ala Ile Pro Asn Arg Pro Gly
690                 695                 700
Ile Phe Val Arg Val Ala Tyr Tyr Ala Lys Trp Ile His Lys Ile Ile
```

```
                705                 710                 715                 720
Leu Thr Tyr Lys Val Pro Gln Ser
                725

<210> SEQ ID NO 32
<211> LENGTH: 463
<212> TYPE: PRT
<213> ORGANISM: Homo sapiens

<400> SEQUENCE: 32

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
    130                 135                 140

Tyr Cys Arg Asn Pro Arg Gly Glu Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
            180                 185                 190

Asp His Thr Glu Ser Gly Lys Ile Cys Gln Arg Trp Asp His Gln Thr
        195                 200                 205

Pro His Arg His Lys Phe Leu Pro Glu Arg Tyr Pro Asp Lys Gly Phe
    210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
            260                 265                 270

Glu Cys Ile Gln Gly Gln Gly Glu Gly Tyr Arg Gly Thr Val Asn Thr
        275                 280                 285

Ile Trp Asn Gly Ile Pro Cys Gln Arg Trp Asp Ser Gln Tyr Pro His
    290                 295                 300

Glu His Asp Met Thr Pro Glu Asn Phe Lys Cys Lys Asp Leu Arg Glu
305                 310                 315                 320

Asn Tyr Cys Arg Asn Pro Asp Gly Ser Glu Ser Pro Trp Cys Phe Thr
                325                 330                 335

Thr Asp Pro Asn Ile Arg Val Gly Tyr Cys Ser Gln Ile Pro Asn Cys
            340                 345                 350
```

```
Asp Met Ser His Gly Gln Asp Cys Tyr Arg Gly Asn Gly Lys Asn Tyr
            355                 360                 365

Met Gly Asn Leu Ser Gln Thr Arg Ser Gly Leu Thr Cys Ser Met Trp
370                 375                 380

Asp Lys Asn Met Glu Asp Leu His Arg His Ile Phe Trp Glu Pro Asp
385                 390                 395                 400

Ala Ser Lys Leu Asn Glu Asn Tyr Cys Arg Asn Pro Asp Asp Ala
                405                 410                 415

His Gly Pro Trp Cys Tyr Thr Gly Asn Pro Leu Ile Pro Trp Asp Tyr
            420                 425                 430

Cys Pro Ile Ser Arg Cys Glu Gly Asp Thr Thr Pro Thr Ile Val Asn
            435                 440                 445

Leu Asp His Pro Val Ile Ser Cys Ala Lys Thr Lys Gln Leu Arg
        450                 455                 460
```

<210> SEQ ID NO 33
<211> LENGTH: 234
<212> TYPE: PRT
<213> ORGANISM: Homo sapiens

<400> SEQUENCE: 33

```
Val Val Asn Gly Ile Pro Thr Arg Thr Asn Ile Gly Trp Met Val Ser
1               5                   10                  15

Leu Arg Tyr Arg Asn Lys His Ile Cys Gly Gly Ser Leu Ile Lys Glu
                20                  25                  30

Ser Trp Val Leu Thr Ala Arg Gln Cys Phe Pro Ser Arg Asp Leu Lys
            35                  40                  45

Asp Tyr Glu Ala Trp Leu Gly Ile His Asp Val His Gly Arg Gly Asp
50                  55                  60

Glu Lys Cys Lys Gln Val Leu Asn Val Ser Gln Leu Val Tyr Gly Pro
65                  70                  75                  80

Glu Gly Ser Asp Leu Val Leu Met Lys Leu Ala Arg Pro Ala Val Leu
                85                  90                  95

Asp Asp Phe Val Ser Thr Ile Asp Leu Pro Asn Tyr Gly Cys Thr Ile
                100                 105                 110

Pro Glu Lys Thr Ser Cys Ser Val Tyr Gly Trp Gly Tyr Thr Gly Leu
            115                 120                 125

Ile Asn Tyr Asp Gly Leu Leu Arg Val Ala His Leu Tyr Ile Met Gly
        130                 135                 140

Asn Glu Lys Cys Ser Gln His His Arg Gly Lys Val Thr Leu Asn Glu
145                 150                 155                 160

Ser Glu Ile Cys Ala Gly Ala Glu Lys Ile Gly Ser Gly Pro Cys Glu
                165                 170                 175

Gly Asp Tyr Gly Gly Pro Leu Val Cys Glu Gln His Lys Met Arg Met
            180                 185                 190

Val Leu Gly Val Ile Val Pro Gly Arg Gly Cys Ala Ile Pro Asn Arg
        195                 200                 205

Pro Gly Ile Phe Val Arg Val Ala Tyr Tyr Ala Lys Trp Ile His Lys
    210                 215                 220

Ile Ile Leu Thr Tyr Lys Val Pro Gln Ser
225                 230
```

<210> SEQ ID NO 34
<211> LENGTH: 27
<212> TYPE: PRT
<213> ORGANISM: Lactococcus lactis

<400> SEQUENCE: 34

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala
            20                  25

<210> SEQ ID NO 35
<211> LENGTH: 2550
<212> TYPE: DNA
<213> ORGANISM: Artificial Sequence
<220> FEATURE:
<223> OTHER INFORMATION: plasmid pNZ8149

<400> SEQUENCE: 35

| | | | | | |
|---|---|---|---|---|---|
| ggatctagtc | ttataactat | actgacaata | gaaacattaa | caaatctaaa | acagtcttaa | 60 |
| ttctatcttg | agaaagtatt | ggtaataata | ttattgtcga | taacgcgagc | ataataaacg | 120 |
| gctctgatta | aattctgaag | tttgttagat | acaatgattt | cgttcgaagg | aactacaaaa | 180 |
| taaattataa | ggaggcactc | accatgggta | ctgcaggcat | gcggtaccac | tagttctaga | 240 |
| gagctcaagc | tttctttgaa | ccaaaattag | aaaaccaagg | cttgaaacgt | tcaattgaaa | 300 |
| tggcaattaa | acaaattaca | gcacgtgttg | ctttgattga | tagccaaaaa | gcagcagttg | 360 |
| ataaagcaat | tactgatatt | gctgaaaaat | tgtaatttat | aaataaaaat | cacctttag | 420 |
| aggtggtttt | tttatttata | aattattcgt | ttgatttcgc | tttcgataga | acaatcaaat | 480 |
| cgtttctgag | acgttttagc | gtttatttcg | tttagttatc | ggcataatcg | ttaaaacagg | 540 |
| cgttatcgta | gcgtaaaagc | ccttgagcgt | agcgtggctt | tgcagcgaag | atgttgtctg | 600 |
| ttagattatg | aaagccgatg | actgaatgaa | ataataagcg | cagcgtcctt | ctatttcggt | 660 |
| tggaggaggc | tcaagggagt | tgagggaat | gaaattccct | catgggtttg | attttaaaaa | 720 |
| ttgcttgcaa | ttttgccgag | cggtagcgct | ggaaaatttt | tgaaaaaaat | ttggaatttg | 780 |
| gaaaaaaatg | gggggaaagg | aagcgaattt | tgcttccgta | ctacgacccc | ccattaagtg | 840 |
| ccgagtgcca | ttttttgtgc | caaaaacgct | ctatcccaac | tggctcaagg | gtttgagggg | 900 |
| ttttcaatc | gccaacgaat | cgccaacgtt | tcgccaacg | tttttataa | atctatattt | 960 |
| aagtagcttt | attttttgttt | ttatgattac | aaagtgatac | actaattta | taaaattatt | 1020 |
| tgattggagt | ttttaaatg | gtgatttcag | aatcgaaaaa | aagagttatg | atttctctga | 1080 |
| caaaagagca | agataaaaaa | ttaacagata | tggcgaaaca | aaaagatttt | tcaaaatctg | 1140 |
| cggttgcggc | gttagctata | gaagaatatg | caagaaagga | atcagaacaa | aaaaaataag | 1200 |
| cgaaagctcg | cgtttttaga | aggatacgag | ttttcgctac | ttgttttga | taaggtaatt | 1260 |
| atatcatggc | tattaaaaat | actaaagcta | gaaatttgg | atttttatta | tatcctgact | 1320 |
| caattcctaa | tgattggaaa | gaaaaattag | agagtttggg | cgtatctatg | gctgtcagtc | 1380 |
| ctttacacga | tatggacgaa | aaaaagata | agatacatg | gaatagtagt | gatgttatac | 1440 |
| gaaatggaaa | gcactataaa | aaaccacact | atcacgttat | atatattgca | cgaaatcctg | 1500 |
| taacaataga | aagcgttagg | aacaagatta | agcgaaaatt | ggggaatagt | tcagttgctc | 1560 |
| atgttgagat | acttgattat | atcaaggtt | catatgaata | tttgactcat | gaatcaaagg | 1620 |
| acgctattgc | taagaataaa | catatatacg | acaaaaaaga | tattttgaac | attaatgatt | 1680 |
| ttgatattga | ccgctatata | acacttgatg | aaagccaaaa | aagagaattg | aagaatttac | 1740 |
| ttttagatat | agtggatgac | tataatttgg | taaatacaaa | agatttaatg | gcttttattc | 1800 |

-continued

```
gccttagggg agcggagttt ggaattttaa atacgaatga tgtaaaagat attgtttcaa    1860
caaactctag cgcctttaga ttatggtttg agggcaatta tcagtgtgga tatagagcaa    1920
gttatgcaaa ggttcttgat gctgaaacgg gggaaataaa atgacaaaca agaaaaaga    1980
gttatttgct gaaatgagg aattaaaaaa agaaattaag gacttaaaag agcgtattga    2040
aagatacaga gaaatggaag ttgaattaag tacaacaata gatttattga gaggagggat    2100
tattgaataa ataaaagccc ccctgacgaa agtcgacatg gactgataaa gtatagtaaa    2160
aacataaaac ggaggatatt gttgtgaaca gagaagagat gactctctta gggtttgaaa    2220
ttgttgctta tgctggagat gctcgctcta agcttttaga agcgcttaaa gcggctgaaa    2280
atggtgattt cgctaaggca gatagtcttg tagtagaagc aggaagctgt attgcagagg    2340
ctcacagttc tcagacaggt atgttggctc gagaagcttc tggggaggaa cttccataca    2400
gtgttactat gatgcatggt caggatcact tgatgactac gatcttatta aaagatgtga    2460
ttcatcacct catcgaactt tataaaagag gagcaaagta attaatgcat aaactcattg    2520
aacttattga gaaagggaaa cgacggatca                                     2550
```

<210> SEQ ID NO 36
<211> LENGTH: 20
<212> TYPE: DNA
<213> ORGANISM: Artificial Sequence
<220> FEATURE:
<223> OTHER INFORMATION: sequencing Primer seqlacF

<400> SEQUENCE: 36
tgtgattcat cacctcatcg        20

<210> SEQ ID NO 37
<211> LENGTH: 21
<212> TYPE: DNA
<213> ORGANISM: Artificial Sequence
<220> FEATURE:
<223> OTHER INFORMATION: Sequencing primer seq2F

<400> SEQUENCE: 37
cgtggctttg cagcgaagat g       21

<210> SEQ ID NO 38
<211> LENGTH: 21
<212> TYPE: DNA
<213> ORGANISM: Artificial Sequence
<220> FEATURE:
<223> OTHER INFORMATION: sequencing primer seq3F

<400> SEQUENCE: 38
gactcaattc ctaatgattg g       21

<210> SEQ ID NO 39
<211> LENGTH: 21
<212> TYPE: DNA
<213> ORGANISM: Artificial Sequence
<220> FEATURE:
<223> OTHER INFORMATION: sequencing primer seq4F

<400> SEQUENCE: 39
tcagtgtgga tatagagcaa g       21

<210> SEQ ID NO 40
<211> LENGTH: 20
<212> TYPE: DNA
<213> ORGANISM: Artificial Sequence

```
<220> FEATURE:
<223> OTHER INFORMATION: sequencing primer seq6R

<400> SEQUENCE: 40
ctgtaatttg tttaattgcc                                              20

<210> SEQ ID NO 41
<211> LENGTH: 20
<212> TYPE: DNA
<213> ORGANISM: Artificial Sequence
<220> FEATURE:
<223> OTHER INFORMATION: sequencing primer seq7R

<400> SEQUENCE: 41
ttgagccagt tgggatagag                                              20

<210> SEQ ID NO 42
<211> LENGTH: 21
<212> TYPE: DNA
<213> ORGANISM: Artificial Sequence
<220> FEATURE:
<223> OTHER INFORMATION: sequencing primer seq8R

<400> SEQUENCE: 42
gtatctcaac atgagcaact g                                            21

<210> SEQ ID NO 43
<211> LENGTH: 23
<212> TYPE: DNA
<213> ORGANISM: Artificial Sequence
<220> FEATURE:
<223> OTHER INFORMATION: nis2 sequencing primer

<400> SEQUENCE: 43
caattgaacg tttcaagcct tgg                                          23

<210> SEQ ID NO 44
<211> LENGTH: 198
<212> TYPE: DNA
<213> ORGANISM: Lactococcus lactis

<400> SEQUENCE: 44
tagtcttata actatactga caatagaaac attaacaaat ctaaaacagt cttaattcta    60
tcttgagaaa gtattggtaa taatattatt gtcgataacg cgagcataat aaacggctct   120
gattaaattc tgaagtttgt tagatacaat gatttcgttc gaaggaacta caaataaat    180 tataaggagg cactcacc                                                198

<210> SEQ ID NO 45
<211> LENGTH: 756
<212> TYPE: DNA
<213> ORGANISM: Artificial Sequence
<220> FEATURE:
<223> OTHER INFORMATION: synthetic construct ssUsp45-FGF2-153

<400> SEQUENCE: 45
ggatcctagt cttataacta tactgacaat agaaacatta acaaatctaa aacagtctta    60
attctatctt gagaaagtat tggtaataat attattgtcg ataacgcgag cataataaac   120
ggctctgatt aaattctgaa gtttgttaga tacaatgatt tcgttcgaag gaactacaaa   180
ataaattata aggaggcact caccatgaaa aaaagatta tctcagctat tttaatgtct   240
acagtgatac tttctgctgc agccccgttg tcaggtgttt acgctgctgg ttccattacg   300
```

| | |
|---|---|
| accttgccgg ctttaccaga ggacggaggt tcaggagcct ttccaccagg gcactttaaa | 360 |
| gatcccaaac gtctatattg taaaaatgga ggcttctttc tgcgaattca tcctgatgga | 420 |
| cgtgtagatg gtgtgcgtga gaaaagtgat cctcatatca aactccaact tcaggcagaa | 480 |
| gaaagaggcg tcgtaagtat aaaaggagtt tgcgcgaatc gttacttagc tatgaaagaa | 540 |
| gacggtcgat tattggcctc taagtgtgtt actgatgaat gttttttttt tgaacggctt | 600 |
| gaatctaata attataacac ttatagaagc agaaaatata catcatggta cgttgcactt | 660 |
| aaaaggacag gtcaatataa attagggtct aagacaggac ctggtcaaaa agcaattttg | 720 |
| ttcttaccaa tgtcggctaa agttaataa tctaga | 756 |

<210> SEQ ID NO 46
<211> LENGTH: 3066
<212> TYPE: DNA
<213> ORGANISM: Artificial Sequence
<220> FEATURE:
<223> OTHER INFORMATION: Plasmid pFGF2

<400> SEQUENCE: 46

| | |
|---|---|
| ggatcctagt cttataacta tactgacaat agaaacatta acaaatctaa aacagtctta | 60 |
| attctatctt gagaaagtat tggtaataat attattgtcg ataacgcgag cataataaac | 120 |
| ggctctgatt aaattctgaa gtttgttaga tacaatgatt tcgttcgaag gaactacaaa | 180 |
| ataaattata aggaggcact caccatgaaa aaaaagatta tctcagctat tttaatgtct | 240 |
| acagtgatac tttctgctgc agccccgttg tcaggtgttt acgctgctgg ttccattacg | 300 |
| accttgccgg ctttaccaga ggacggaggt tcaggagcct ttccaccagg gcactttaaa | 360 |
| gatcccaaac gtctatattg taaaaatgga ggcttctttc tgcgaattca tcctgatgga | 420 |
| cgtgtagatg gtgtgcgtga gaaaagtgat cctcatatca aactccaact tcaggcagaa | 480 |
| gaaagaggcg tcgtaagtat aaaaggagtt tgcgcgaatc gttacttagc tatgaaagaa | 540 |
| gacggtcgat tattggcctc taagtgtgtt actgatgaat gttttttttt tgaacggctt | 600 |
| gaatctaata attataacac ttatagaagc agaaaatata catcatggta cgttgcactt | 660 |
| aaaaggacag gtcaatataa attagggtct aagacaggac ctggtcaaaa agcaattttg | 720 |
| ttcttaccaa tgtcggctaa agttaataa tctagagagc tcaagctttc tttgaaccaa | 780 |
| aattagaaaa ccaaggcttg aaacgttcaa ttgaaatggc aattaaacaa attacagcac | 840 |
| gtgttgcttt gattgatagc caaaaagcag cagttgataa agcaattact gatattgctg | 900 |
| aaaaattgta atttataaat aaaaatcacc ttttagaggt ggttttttta tttataaatt | 960 |
| attcgtttga tttcgctttc gatagaacaa tcaaatcgtt tctgagacgt tttagcgttt | 1020 |
| atttcgttta gttatcggca taatcgttaa aacaggcgtt atcgtagcgt aaaagccctt | 1080 |
| gagcgtagcg tggctttgca gcgaagatgt tgtctgttag attatgaaag ccgatgactg | 1140 |
| aatgaaataa taagcgcagc gtccttctat ttcggttgga ggaggctcaa gggagtttga | 1200 |
| gggaatgaaa ttccctcatg ggtttgattt taaaaattgc ttgcaatttt gccgagcggt | 1260 |
| agcgctggaa aattttgaa aaaaatttgg aatttggaaa aaatggggg gaaaggaagc | 1320 |
| gaattttgct tccgtactac gaccccccat taagtgccga gtgccaattt ttgtgccaaa | 1380 |
| aacgctctat cccaactggc tcaagggttt gagggttttt tcaatcgcca acgaatcgcc | 1440 |
| aacgttttcg ccaacgtttt ttataaatct atatttaagt agctttattt ttgttttttat | 1500 |
| gattacaaag tgatacacta attttataaa attatttgat tggagttttt taaatggtga | 1560 |
| tttcagaatc gaaaaaaaga gttatgattt ctctgacaaa agagcaagat aaaaaattaa | 1620 |

```
cagatatggc gaaacaaaaa gatttttcaa aatctgcggt tgcggcgtta gctatagaag    1680
aatatgcaag aaaggaatca gaacaaaaaa aataagcgaa agctcgcgtt tttagaagga    1740
tacgagtttt cgctacttgt ttttgataag gtaattatat catggctatt aaaaatacta    1800
aagctagaaa ttttggattt ttattatatc ctgactcaat tcctaatgat tggaaagaaa    1860
aattagagag tttgggcgta tctatggctg tcagtccttt acacgatatg gacgaaaaaa    1920
aagataaaga tacatggaat agtagtgatg ttatacgaaa tggaaagcac tataaaaaac    1980
cacactatca cgttatatat attgcacgaa atcctgtaac aatagaaagc gttaggaaca    2040
agattaagcg aaaattgggg aatagttcag ttgctcatgt tgagatactt gattatatca    2100
aaggttcata tgaatatttg actcatgaat caaaggacgc tattgctaag aataaacata    2160
tatacgacaa aaaagatatt ttgaacatta atgattttga tattgaccgc tatataacac    2220
ttgatgaaag ccaaaaaaga gaattgaaga atttactttt agatatagtg gatgactata    2280
atttggtaaa tacaaaagat ttaatggctt ttattcgcct taggggagcg gagtttggaa    2340
ttttaaatac gaatgatgta aaagatattg tttcaacaaa ctctagcgcc tttagattat    2400
ggtttgaggg caattatcag tgtggatata gagcaagtta tgcaaaggtt cttgatgctg    2460
aaacggggga aataaaatga caaacaaaga aaaagagtta tttgctgaaa atgaggaatt    2520
aaaaaaagaa attaaggact taaaagagcg tattgaaaga tacagagaaa tggaagttga    2580
attaagtaca acaatagatt tattgagagg agggattatt gaataaataa aagccccct    2640 gacgaaagtc gacatggact gataaagtat agtaaaaaca taaacggag gatattgttg    2700 tgaacagaga agagatgact ctcttagggt ttgaaattgt tgcttatgct ggagatgctc    2760
gctctaagct tttagaagcg cttaaagcgg ctgaaaatgg tgatttcgct aaggcagata    2820
gtcttgtagt agaagcagga agctgtattg cagaggctca cagttctcag acaggtatgt    2880
tggctcgaga agcttctggg gaggaacttc catacagtgt tactatgatg catggtcagg    2940
atcacttgat gactacgatc ttattaaaag atgtgattca tcacctcatc gaactttata    3000
aaagaggagc aaagtaatta atgcataaac tcattgaact tattgagaaa gggaaacgac    3060
ggatca                                                              3066
```

<210> SEQ ID NO 47
<211> LENGTH: 687
<212> TYPE: DNA
<213> ORGANISM: Artificial Sequence
<220> FEATURE:
<223> OTHER INFORMATION: synthetic construct ssUsp45-hIL4

<400> SEQUENCE: 47

```
ggatcctagt cttataacta tactgacaat agaaacatta acaaatctaa aacagtctta     60
attctatctt gagaaagtat tggtaataat attattgtcg ataacgcgag cataataaac    120
ggctctgatt aaattctgaa gtttgttaga tacaatgatt tcgttcgaag gaactacaaa    180
ataaattata aggaggcact caccatgaag aaaaagatta ttagtgcaat ttaatgtca    240 acggtcatct taagcgctgc tgccccattg tcaggtgttt atgcagcaca taagtgtgat    300
ataacattac aagaaattat caaaaccctt aatagtttaa ctgaacagaa gactttgtgt    360
accgaattaa ctgtaactga tattttttgct gcttctaaaa atacaactga aaaagagaca    420
ttttgtcgag ctgccacagt gttaagacaa ttttacagtc atcatgaaaa agacacaaga    480
tgtcttggtg ctacggcaca acaatttcat agacacaaac aacttatccg ttttcttaaa    540
```

```
cgtttggatc gtaatctgtg gggcttggca ggattgaaca gttgtcctgt taaagaagcc      600
aatcaatcta ctcttgaaaa tttcttagag agattgaaaa caattatgcg agaaaaatat      660
tctaagtgtt catcttaata atctaga                                          687

<210> SEQ ID NO 48
<211> LENGTH: 2997
<212> TYPE: DNA
<213> ORGANISM: Artificial Sequence
<220> FEATURE:
<223> OTHER INFORMATION: Plasmid pIL4

<400> SEQUENCE: 48
ggatcctagt cttataacta tactgacaat agaaacatta acaaatctaa acagtctta       60 attctatctt gagaaagtat tggtaataat attattgtcg ataacgcgag cataataaac      120
ggctctgatt aaattctgaa gtttgttaga tacaatgatt tcgttcgaag gaactacaaa      180
ataaattata aggaggcact caccatgaag aaaaagatta ttagtgcaat tttaatgtca      240
acggtcatct taagcgctgc tgccccattg tcaggtgttt atgcagcaca taagtgtgat      300
ataacattac aagaaattat caaaacccctt aatagtttaa ctgaacagaa gactttgtgt      360
accgaattaa ctgtaactga tatttttgct gcttctaaaa atacaactga aaagagaca       420 ttttgtcgag ctgccacagt gttaagacaa ttttacagtc atcatgaaaa agacacaaga      480
tgtcttggtg ctacggcaca acaatttcat agacacaaac aacttatccg ttttcttaaa      540
cgtttggatc gtaatctgtg gggcttggca ggattgaaca gttgtcctgt taaagaagcc      600
aatcaatcta ctcttgaaaa tttcttagag agattgaaaa caattatgcg agaaaaatat      660
tctaagtgtt catcttaata atctagagag ctcaagcttt ctttgaacca aaattagaaa      720
accaaggctt gaaacgttca attgaaatgg caattaaaca aattacagca cgtgttgctt      780
tgattgatag ccaaaaagca gcagttgata agcaattac tgatattgct gaaaaattgt      840
aatttataaa taaaaatcac cttttagagg tggttttttt attataaaat tattcgtttg      900
atttcgcttt cgatagaaca atcaaatcgt ttctgagacg ttttagcgtt tatttcgttt      960
agttatcggc ataatcgtta aaacaggcgt tatcgtagcg taaaagccct tgagcgtagc      1020
gtggctttgc agcgaagatg ttgtctgtta gattatgaaa gccgatgact gaatgaaata      1080
ataagcgcag cgtccttcta tttcggttgg aggaggctca agggagtttg agggaatgaa      1140
attccctcat gggtttgatt ttaaaaattg cttgcaattt tgccgagcgg tagcgctgga      1200 aaattttga aaaaatttg gaatttggaa aaaaatgggg ggaaaggaag cgaatttgc         1260 ttccgtacta cgaccccca ttaagtgccg agtgccaatt tttgtgccaa aaacgctcta      1320
tcccaactgg ctcaagggtt tgaggggttt tcaatcgcc aacgaatcgc caacgttttc       1380
gccaacgttt tttataaatc tatatttaag tagctttatt tttgttttta tgattacaaa      1440
gtgatacact aattttataa aattatttga ttggagtttt ttaaatggtg atttcagaat      1500
cgaaaaaaag agttatgatt tctctgacaa aagagcaaga taaaaaatta acagatatgg      1560
cgaaacaaaa agattttca aaatctgcgg ttgcggcgtt agctatagaa gaatatgcaa       1620
gaaaggaatc agaacaaaaa aataagcga agctcgcgt ttttagaagg atacgagttt       1680
tcgctacttg ttttttgataa ggtaattata tcatggctat taaaaatact aaagctagaa      1740
attttggatt tttattatat cctgactcaa ttcctaatga ttggaaagaa aaattagaga      1800
gtttgggcgt atctatggct gtcagtcctt tacacgatat ggacgaaaaa aaagataaag      1860
atacatggaa tagtagtgat gttatacgaa atggaaagca ctataaaaaa ccacactatc      1920
```

```
acgttatata tattgcacga aatcctgtaa caatagaaag cgttaggaac aagattaagc    1980
gaaaattggg gaatagttca gttgctcatg ttgagatact tgattatatc aaaggttcat    2040
atgaatattt gactcatgaa tcaaaggacg ctattgctaa gaataaacat atatacgaca    2100
aaaaagatat tttgaacatt aatgattttg atattgaccg ctatataaca cttgatgaaa    2160
gccaaaaaag agaattgaag aatttacttt tagatatagt ggatgactat aatttggtaa    2220
atacaaaaga tttaatggct tttattcgcc ttaggggagc ggagtttgga atttttaaata   2280 cgaatgatgt aaaagatatt gtttcaacaa actctagcgc ctttagatta tggtttgagg    2340
gcaattatca gtgtggatat agagcaagtt atgcaaaggt tcttgatgct gaaacggggg    2400
aaataaaatg acaaacaaag aaaaagagtt atttgctgaa aatgaggaat taaaaaaaga    2460
aattaaggac ttaaaagagc gtattgaaag atacagagaa atggaagttg aattaagtac    2520
aacaatagat ttattgagag gagggattat tgaataaata aaagcccccc tgacgaaagt    2580
cgacatggac tgataaagta tagtaaaaac ataaaacgga ggatattgtt gtgaacagag    2640
aagagatgac tctcttaggg tttgaaattg ttgcttatgc tggagatgct cgctctaagc    2700
ttttagaagc gcttaaagcg gctgaaaatg gtgatttcgc taaggcagat agtcttgtag    2760
tagaagcagg aagctgtatt gcagaggctc acagttctca gacaggtatg ttggctcgag    2820
aagcttctgg ggaggaactt ccatacagtg ttactatgat gcatggtcag gatcacttga    2880
tgactacgat cttattaaaa gatgtgattc atcacctcat cgaactttat aaaagaggag    2940
caaagtaatt aatgcataaa ctcattgaac ttattgagaa agggaaacga cggatca      2997

<210> SEQ ID NO 49
<211> LENGTH: 774
<212> TYPE: DNA
<213> ORGANISM: Artificial Sequence
<220> FEATURE:
<223> OTHER INFORMATION: synthetic construct ssUsp45-hCSF1

<400> SEQUENCE: 49
ggatcctagt cttataacta tactgacaat agaaacatta acaaatctaa acagtctta      60 attctatctt gagaaagtat tggtaataat attattgtcg ataacgcgag cataataaac    120
ggctctgatt aaattctgaa gtttgttaga tacaatgatt tcgttcgaag gaactacaaa    180
ataaattata aggaggcact caccatgaaa aagaaaatca tttcagcgat tttgatgtca    240
acggttattt taagcgcagc agctccatta tctggagttt atgcagcaga agaagttagt    300
gagtactgta gtcatatgat tggttctgga cacttacaat cacttcagcg tcttattgat    360
agtcaaatgg aaacctcttg tcaaattaca tttgaatttg tagaccaaga acaacttaaa    420
gatccagtat gttatcttaa gaaagctttt cttttagtcc aagacataat ggaagataca    480
atgagattca gagacaatac tcctaacgct atcgccattg tccaattaca agaactttct    540
ttaagattga aagttgcttt cactaaagat tatgaggaac atgataaagc ttgtgttcga    600 acatttatg aaactccttt gcaattattg gaaaaagtga aaaatgtttt caatgagacg    660
aagaatttgt tggataaaga ttggaatata ttcagtaaga attgtaataa ctcatttgcc    720
gaatgttcaa gccagggtca tgaacgtcaa tcagaaggct cttaataatc taga          774

<210> SEQ ID NO 50
<211> LENGTH: 3084
<212> TYPE: DNA
<213> ORGANISM: Artificial Sequence
<220> FEATURE:
```

<223> OTHER INFORMATION: Plasmid pCSF1

<400> SEQUENCE: 50

```
ggatcctagt cttataacta tactgacaat agaaacatta acaaatctaa acagtctta      60
attctatctt gagaaagtat tggtaataat attattgtcg ataacgcgag cataataaac    120
ggctctgatt aaattctgaa gtttgttaga tacaatgatt tcgttcgaag gaactacaaa    180
ataaattata aggaggcact caccatgaaa agaaaatca tttcagcgat tttgatgtca    240
acggttattt taagcgcagc agctccatta tctggagttt atgcagcaga agaagttagt    300
gagtactgta gtcatatgat tggttctgga cacttacaat cacttcagcg tcttattgat    360
agtcaaatgg aaacctcttg tcaaattaca tttgaatttg tagaccaaga acaacttaaa    420
gatccagtat gttatcttaa gaaagctttt cttttagtcc aagacataat ggaagataca    480
atgagattca gagacaatac tcctaacgct atcgccattg tccaattaca agaactttct    540
ttaagattga aaagttgctt cactaaagat tatgaggaac atgataaagc ttgtgttcga    600
acatttatg aaactccttt gcaattattg gaaaagtga aaaatgtttt caatgagacg    660
aagaatttgt tggataaaga ttggaatata ttcagtaaga attgtaataa ctcatttgcc    720
gaatgttcaa gccagggtca tgaacgtcaa tcagaaggct cttaataatc tagagagctc    780
aagcttctt tgaaccaaaa ttagaaaacc aaggcttgaa acgttcaatt gaatggcaa    840
ttaaacaaat tacagcacgt gttgctttga ttgatagcca aaaagcagca gttgataaag    900
caattactga tattgctgaa aaattgtaat ttataaataa aaatcaccct ttagaggtgg    960
ttttttatt tataaattat tcgtttgatt tcgctttcga tagaacaatc aaatcgtttc    1020
tgagacgttt tagcgtttat ttcgtttagt tatcggcata atcgttaaaa caggcgttat    1080
cgtagcgtaa aagcccttga gcgtagcgtg gctttgcagc gaagatgttg tctgttagat    1140
tatgaaagcc gatgactgaa tgaaataata agcgcagcgt ccttctattt cggttggagg    1200
aggctcaagg gagtttgagg gaatgaaatt ccctcatggg tttgatttta aaaattgctt    1260
gcaattttgc cgagcggtag cgctggaaaa ttttgaaaa aaatttggaa tttggaaaaa    1320
aatgggggga aaggaagcga attttgcttc cgtactacga ccccccatta agtgccgagt    1380
gccaattttt gtgccaaaaa cgctctatcc caactggctc aagggtttga ggggttttc    1440
aatcgccaac gaatcgccaa cgttttcgcc aacgtttttt ataaatctat atttaagtag    1500
ctttattttt gttttatga ttacaaagtg atacactaat tttataaaat tatttgattg    1560
gagttttta aatggtgatt tcagaatcga aaaaagagt tatgatttct ctgacaaaag    1620
agcaagataa aaaattaaca gatatggcga aacaaaaaga ttttttcaaaa tctgcggttg    1680
cggcgttagc tatagaagaa tatgcaagaa aggaatcaga acaaaaaaaa taagcgaaag    1740
ctcgcgtttt tagaaggata cgagttttcg ctacttgttt ttgataaggt aattatatca    1800
tggctattaa aaatactaaa gctagaaatt ttggattttt attatatcct gactcaattc    1860
ctaatgattg gaagaaaaa ttagagagtt tgggcgtatc tatggctgtc agtcctttac    1920
acgatatgga cgaaaaaaaa gataagata catggaatag tagtgatgtt atacgaaatg    1980
gaaagcacta taaaaaacca cactatcacg ttatatatat tgcacgaaat cctgtaacaa    2040
tagaaagcgt taggaacaag attaagcgaa aattggggaa tagttcagtt gctcatgttg    2100
agatacttga ttatatcaaa ggttcatatg aatatttgac tcatgaatca aaggacgcta    2160
ttgctaagaa taaacatata tacgacaaaa aagatatttt gaacattaat gattttgata    2220
ttgaccgcta tataacactt gatgaaagcc aaaaaagaga attgaagaat ttacttttag    2280
```

```
atatagtgga tgactataat ttggtaaata caaaagattt aatggctttt attcgcctta    2340
ggggagcgga gtttggaatt ttaaatacga atgatgtaaa agatattgtt tcaacaaact    2400
ctagcgcctt tagattatgg tttgagggca attatcagtg tggatataga gcaagttatg    2460
caaaggttct tgatgctgaa acggggaaa taaaatgaca aacaaagaaa aagagttatt     2520
tgctgaaaat gaggaattaa aaaagaaat taaggactta aaagagcgta ttgaaagata    2580
cagagaaatg gaagttgaat taagtacaac aatagattta ttgagaggag ggattattga    2640
ataaataaaa gcccccctga cgaaagtcga catggactga taaagtatag taaaaacata    2700
aaacggagga tattgttgtg aacagagaag agatgactct cttagggttt gaaattgttg    2760
cttatgctgg agatgctcgc tctaagcttt tagaagcgct taaagcggct gaaaatggtg    2820
atttcgctaa ggcagatagt cttgtagtag aagcaggaag ctgtattgca gaggctcaca    2880
gttctcagac aggtatgttg gctcgagaag cttctgggga ggaacttcca tacagtgtta    2940
ctatgatgca tggtcaggat cacttgatga ctacgatctt attaaaagat gtgattcatc    3000
acctcatcga actttataaa agaggagcaa agtaattaat gcataaactc attgaactta    3060
ttgagaaagg gaaacgacgg atca                                           3084
```

```
<210> SEQ ID NO 51
<211> LENGTH: 27
<212> TYPE: DNA
<213> ORGANISM: Artificial Sequence
<220> FEATURE:
<223> OTHER INFORMATION: nisA ribosome binding site

<400> SEQUENCE: 51
ataaattata aggaggcact caccatg                                          27

<210> SEQ ID NO 52
<211> LENGTH: 24
<212> TYPE: DNA
<213> ORGANISM: Artificial Sequence
<220> FEATURE:
<223> OTHER INFORMATION: atpG ribosome binding site

<400> SEQUENCE: 52
tattaataag gaggctaact aatg                                             24

<210> SEQ ID NO 53
<211> LENGTH: 23
<212> TYPE: DNA
<213> ORGANISM: Artificial Sequence
<220> FEATURE:
<223> OTHER INFORMATION: lacA ribosome binding site

<400> SEQUENCE: 53
aaatttagga ggtagtccaa atg                                              23

<210> SEQ ID NO 54
<211> LENGTH: 16
<212> TYPE: RNA
<213> ORGANISM: Artificial Sequence
<220> FEATURE:
<223> OTHER INFORMATION: 3 prime end of 16S ribosomal DNA

<400> SEQUENCE: 54
ggaucaccuc cuuucu                                                      16

<210> SEQ ID NO 55
```

<211> LENGTH: 1850
<212> TYPE: DNA
<213> ORGANISM: Artificial Sequence
<220> FEATURE:
<223> OTHER INFORMATION: synthetic construct CSF-RBS1-FGF-RBS2-IL4

<400> SEQUENCE: 55

| | | | | | |
|---|---|---|---|---|---|
| ggatcctagt | cttataacta | tactgacaat | agaaacatta | acaaatctaa | aacagtctta | 60 |
| attctatctt | gagaaagtat | tggtaataat | attattgtcg | ataacgcgag | cataataaac | 120 |
| ggctctgatt | aaattctgaa | gtttgttaga | tacaatgatt | tcgttcgaag | gaactacaaa | 180 |
| ataaattata | aggaggcact | caccatgaaa | aagaaaatca | tttcagcgat | tttgatgtca | 240 |
| acggttattt | taagcgcagc | agctccatta | tctggagttt | atgcagcaga | agaagttagt | 300 |
| gagtactgta | gtcatatgat | tggttctgga | cacttacaat | cacttcagcg | tcttattgat | 360 |
| agtcaaatgg | aaacctcttg | tcaaattaca | tttgaatttg | tagaccaaga | acaacttaaa | 420 |
| gatccagtat | gttatcttaa | gaaagctttt | cttttagtcc | aagacataat | ggaagataca | 480 |
| atgagattca | gagacaatac | tcctaacgct | atcgccatta | tccaattaca | agaactttct | 540 |
| ttaagattga | aaagttgctt | cactaaagat | tatgaggaac | atgataaagc | ttgtgttcga | 600 |
| acattttatg | aaactccttt | gcaattattg | gaaaaagtga | aaaatgtttt | caatgagacg | 660 |
| aagaatttgt | tggataaaga | ttggaatata | ttcagtaaga | attgtaataa | ctcatttgcc | 720 |
| gaatgttcaa | gccagggtca | tgaacgtcaa | tcagaaggct | cttaataaac | gcgtattaat | 780 |
| aaggaggcta | actaatgaaa | aaaagatta | tctcagctat | tttaatgtct | acagtgatac | 840 |
| tttctgctgc | agccccgttg | tcaggtgttt | acgctgctgg | ttccattacg | accttgccgg | 900 |
| ctttaccaga | ggacggaggt | tcaggagcct | ttccaccagg | gcactttaaa | gatcccaaac | 960 |
| gtctatattg | taaaaatgga | ggcttctttc | tgcgaattca | tcctgatgga | cgtgtagatg | 1020 |
| gtgtgcgtga | gaaaagtgat | cctcatatca | aactccaact | tcaggcagaa | gaaagaggcg | 1080 |
| tcgtaagtat | aaaaggagtt | tgcgcgaatc | gttacttagc | tatgaaagaa | gacggtcgat | 1140 |
| tattggcctc | taagtgtgtt | actgatgaat | gtttttttt | tgaacggctt | gaatctaata | 1200 |
| attataacac | ttatagaagc | agaaaatata | catcatggta | cgttgcactt | aaaaggacag | 1260 |
| gtcaatataa | attagggtct | aagacaggac | ctggtcaaaa | agcaatttg | ttcttaccaa | 1320 |
| tgtcggctaa | aagttaataa | acgcgtgaaa | tttaggaggt | agtccaaatg | aagaaaaaga | 1380 |
| ttattagtgc | aattttaatg | tcaacggtca | tcttaagcgc | tgctgcccca | ttgtcaggtg | 1440 |
| tttatgcagc | acataagtgt | gatataacat | tacaagaaat | tatcaaaacc | cttaatagtt | 1500 |
| taactgaaca | gaagactttg | tgtaccgaat | taactgtaac | tgatattttt | gctgcttcta | 1560 |
| aaaatacaac | tgaaaagag | acattttgtc | gagctgccac | agtgttaaga | caattttaca | 1620 |
| gtcatcatga | aaaagacaca | agatgtcttg | gtgctacggc | acaacaattt | catagacaca | 1680 |
| aacaacttat | ccgttttctt | aaacgtttgg | atcgtaatct | gtggggcttg | gcaggattga | 1740 |
| acagttgtcc | tgttaaagaa | gccaatcaat | ctactcttga | aaatttctta | gagagattga | 1800 |
| aaacaattat | gcgagaaaaa | tattctaagt | gttcatctta | ataaccatgg | | 1850 |

<210> SEQ ID NO 56
<211> LENGTH: 1850
<212> TYPE: DNA
<213> ORGANISM: Artificial Sequence
<220> FEATURE:
<223> OTHER INFORMATION: synthetic construct FGF-RBS1-IL4-RBS2-CSF

<400> SEQUENCE: 56

```
ggatcctagt cttataacta tactgacaat agaaacatta acaaatctaa aacagtctta      60
attctatctt gagaaagtat tggtaataat attattgtcg ataacgcgag cataataaac     120
ggctctgatt aaattctgaa gtttgttaga tacaatgatt tcgttcgaag gaactacaaa     180
ataaattata aggaggcact caccatgaaa aaaagatta tctcagctat tttaatgtct      240
acagtgatac tttctgctgc agccccgttg tcaggtgttt acgctgctgg ttccattacg     300
accttgccgg ctttaccaga ggacggaggt tcaggagcct ttccaccagg cactttaaa     360
gatcccaaac gtctatattg taaaaatgga ggcttctttc tgcgaattca tcctgatgga     420
cgtgtagatg gtgtgcgtga gaaagtgat cctcatatca aactccaact tcaggcagaa     480
gaaagaggcg tcgtaagtat aaaaggagtt tgcgcgaatc gttacttagc tatgaaagaa     540
gacggtcgat tattggcctc taagtgtgtt actgatgaat gttttttttt tgaacggctt     600
gaatctaata attataacac ttatagaagc agaaaatata catcatggta cgttgcactt     660
aaaaggacag gtcaatataa attagggtct aagacaggac ctggtcaaaa agcaattttg     720
ttcttaccaa tgtcggctaa aagttaataa acgcgtatta ataaggaggc taactaatga     780
agaaaaagat tattagtgca attttaatgt caacggtcat cttaagcgct gctgccccat     840
tgtcaggtgt ttatgcagca cataagtgtg atataacatt acaagaaatt atcaaaaccc     900
ttaatagttt aactgaacag aagactttgt gtaccgaatt aactgtaact gatatttttg     960
ctgcttctaa aaatacaact gaaaagagaa cattttgtcg agctgccaca gtgttaagac    1020
aattttacag tcatcatgaa aaagacacaa gatgtcttgg tgctacggca caacaatttc    1080
atagacacaa acaacttatc cgttttctta aacgtttgga tcgtaatctg tggggcttgg    1140
caggattgaa cagttgtcct gttaaagaag ccaatcaatc tactcttgaa aatttcttag    1200
agagattgaa aacaattatg cgagaaaaat attctaagtg ttcatcttaa taaacgcgtg    1260
aaatttagga ggtagtccaa atgaaaaaga aaatcatttc agcgattttg atgtcaacgg    1320
ttatttttaag cgcagcagct ccattatctg gagtttatgc agcagaagaa gttagtgagt    1380
actgtagtca tatgattggt tctggacact acaatcact tcagcgtctt attgatagtc    1440
aaatggaaac ctcttgtcaa attacatttg aatttgtaga ccaagaacaa cttaaagatc    1500
cagtatgtta tcttaagaaa gcttttcttt tagtccaaga cataatggaa gatacaatga    1560
gattcagaga caatactcct aacgctatcg ccattgtcca attacaagaa ctttctttaa    1620
gattgaaaag ttgcttcact aaagattatg aggaacatga taagcttgt gttcgaacat    1680
tttatgaaac tcctttgcaa ttattggaaa agtgaaaaa tgttttcaat gagacgaaga    1740
atttgttgga taaagattgg aatatattca gtaagaattg taataactca tttgccgaat    1800
gttcaagcca gggtcatgaa cgtcaatcag aaggctctta taaccatgg               1850
```

<210> SEQ ID NO 57
<211> LENGTH: 1850
<212> TYPE: DNA
<213> ORGANISM: Artificial Sequence
<220> FEATURE:
<223> OTHER INFORMATION: synthetic construct IL4-RBS1-CSF-RBS2-FGF

<400> SEQUENCE: 57

```
ggatcctagt cttataacta tactgacaat agaaacatta acaaatctaa aacagtctta      60
attctatctt gagaaagtat tggtaataat attattgtcg ataacgcgag cataataaac     120
ggctctgatt aaattctgaa gtttgttaga tacaatgatt tcgttcgaag gaactacaaa     180
```

```
ataaattata aggaggcact caccatgaag aaaaagatta ttagtgcaat tttaatgtca    240
acggtcatct taagcgctgc tgccccattg tcaggtgttt atgcagcaca taagtgtgat    300
ataacattac aagaaattat caaaaccctt aatagtttaa ctgaacagaa gactttgtgt    360
accgaattaa ctgtaactga tattttgct gcttctaaaa atacaactga aaaagagaca    420
ttttgtcgag ctgccacagt gttaagacaa ttttacagtc atcatgaaaa agacacaaga    480
tgtcttggtg ctacggcaca acaatttcat agacacaaac aacttatccg ttttcttaaa    540
cgtttggatc gtaatctgtg gggcttggca ggattgaaca gttgtcctgt taagaagcc    600 aatcaatcta ctcttgaaaa tttcttagag agattgaaaa caattatgcg agaaaaatat    660
tctaagtgtt catcttaata aacgcgtatt aataaggagg ctaactaatg aaaaagaaaa    720
tcatttcagc gattttgatg tcaacggtta ttttaagcgc agcagctcca ttatctggag    780
tttatgcagc agaagaagtt agtgagtact gtagtcatat gattggttct ggacacttac    840
aatcacttca gcgtcttatt gatagtcaaa tggaacctc ttgtcaaatt acatttgaat    900
ttgtagacca agaacaactt aaagatccag tatgttatct taagaaagct tttcttttag    960
tccaagacat aatggaagat acaatgagat cagagacaa tactcctaac gctatcgcca   1020
ttgtccaatt acaagaactt tctttaagat tgaaaagttg cttcactaaa gattatgagg   1080
aacatgataa agcttgtgtt cgaacatttt atgaaactcc tttgcaatta ttggaaaaag   1140
tgaaaaatgt tttcaatgag acgaagaatt tgttggataa agattggaat atattcagta   1200
agaattgtaa taactcattt gccgaatgtt caagccaggg tcatgaacgt caatcagaag   1260
gctcttaata aacgcgtgaa atttaggagg tagtccaaat gaaaaaaaag attatctcag   1320 ctatttaat gtctacagtg atactttctg ctgcagcccc gttgtcaggt gtttacgctg   1380
ctggttccat tacgaccttg ccggctttac cagaggacgg aggttcagga gcctttccac   1440
cagggcactt taaagatccc aaacgtctat attgtaaaaa tggaggcttc tttctgcgaa   1500
ttcatcctga tggacgtgta gatggtgtgc gtgagaaaaa tgatcctcat atcaaactcc   1560
aacttcaggc agaagaaaga ggcgtcgtaa gtataaaagg agtttgcgcg aatcgttact   1620
tagctatgaa agaagacggt cgattattgg cctctaagtg tgttactgat gaatgttttt   1680
tttttgaacg gcttgaatct aataattata acacttatag aagcagaaaa tatacatcat   1740
ggtacgttgc acttaaaagg acaggtcaat ataaattagg gtctaagaca ggacctggtc   1800
aaaaagcaat tttgttctta ccaatgtcgg ctaaaagtta ataaccatgg                1850
```

<210> SEQ ID NO 58
<211> LENGTH: 1207
<212> TYPE: PRT
<213> ORGANISM: Homo sapiens

<400> SEQUENCE: 58

```
Met Leu Leu Thr Leu Ile Ile Leu Leu Pro Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80
```

-continued

```
Phe His Tyr Asn Glu Lys Arg Ile Tyr Trp Val Asp Leu Glu Arg Gln
             85                  90                  95

Leu Leu Gln Arg Val Phe Leu Asn Gly Ser Arg Gln Glu Arg Val Cys
        100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
        130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
                180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
        210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
                260                 265                 270

Asn Lys His Thr Gly Lys Asp Met Val Arg Ile Asn Leu His Ser Ser
                275                 280                 285

Phe Val Pro Leu Gly Glu Leu Lys Val Val His Pro Leu Ala Gln Pro
        290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
                340                 345                 350

Tyr Cys Glu Asp Val Asn Glu Cys Ala Phe Trp Asn His Gly Cys Thr
        355                 360                 365

Leu Gly Cys Lys Asn Thr Pro Gly Ser Tyr Tyr Cys Thr Cys Pro Val
        370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
        435                 440                 445

Gln Leu Cys Val Pro Leu Ser Pro Val Ser Trp Glu Cys Asp Cys Phe
        450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
```

```
            500                 505                 510
Met Val Tyr Ala Leu Asp His Asp Pro Val Glu Asn Lys Ile Tyr Phe
            515                 520                 525

Ala His Thr Ala Leu Lys Trp Ile Glu Arg Ala Asn Met Asp Gly Ser
            530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                    565                 570                 575

Ser Leu Ile Gly Arg Ser Asp Leu Asn Gly Lys Arg Ser Lys Ile Ile
            580                 585                 590

Thr Lys Glu Asn Ile Ser Gln Pro Arg Gly Ile Ala Val His Pro Met
            595                 600                 605

Ala Lys Arg Leu Phe Trp Thr Asp Thr Gly Ile Asn Pro Arg Ile Glu
            610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                    645                 650                 655

Tyr Trp Cys Asp Ala Lys Gln Ser Val Ile Glu Met Ala Asn Leu Asp
                    660                 665                 670

Gly Ser Lys Arg Arg Leu Thr Gln Asn Asp Val Gly His Pro Phe
            675                 680                 685

Ala Val Ala Val Phe Glu Asp Tyr Val Trp Phe Ser Asp Trp Ala Met
            690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val Val His Pro
                    725                 730                 735

Leu Ala Lys Pro Gly Ala Asp Pro Cys Leu Tyr Gln Asn Gly Gly Cys
                    740                 745                 750

Glu His Ile Cys Lys Lys Arg Leu Gly Thr Ala Trp Cys Ser Cys Arg
            755                 760                 765

Glu Gly Phe Met Lys Ala Ser Asp Gly Lys Thr Cys Leu Ala Leu Asp
            770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                    805                 810                 815

Thr Glu Ser Gln His Met Leu Val Ala Glu Ile Met Val Ser Asp Gln
            820                 825                 830

Asp Asp Cys Ala Pro Val Gly Cys Ser Met Tyr Ala Arg Cys Ile Ser
            835                 840                 845

Glu Gly Glu Asp Ala Thr Cys Gln Cys Leu Lys Gly Phe Ala Gly Asp
850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                    885                 890                 895

Cys Arg Cys Ser Glu Gly Tyr Gln Gly Asp Gly Ile His Cys Leu Asp
                    900                 905                 910

Ile Asp Glu Cys Gln Leu Gly Glu His Ser Cys Gly Glu Asn Ala Ser
            915                 920                 925
```

Cys Thr Asn Thr Glu Gly Gly Tyr Thr Cys Met Cys Ala Gly Arg Leu
         930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
                965                 970                 975

Pro Leu Ser His Asp Gly Tyr Cys Leu His Asp Gly Val Cys Met Tyr
            980                 985                 990

Ile Glu Ala Leu Asp Lys Tyr Ala Cys Asn Cys Val Val Gly Tyr Ile
        995                 1000                1005

Gly Glu Arg Cys Gln Tyr Arg Asp Leu Lys Trp Trp Glu Leu Arg
    1010                1015                1020

His Ala Gly His Gly Gln Gln Gln Lys Val Ile Val Val Ala Val
    1025                1030                1035

Cys Val Val Val Leu Val Met Leu Leu Leu Ser Leu Trp Gly
    1040                1045                1050

Ala His Tyr Tyr Arg Thr Gln Lys Leu Leu Ser Lys Asn Pro Lys
    1055                1060                1065

Asn Pro Tyr Glu Glu Ser Ser Arg Asp Val Arg Ser Arg Arg Pro
    1070                1075                1080

Ala Asp Thr Glu Asp Gly Met Ser Ser Cys Pro Gln Pro Trp Phe
    1085                1090                1095

Val Val Ile Lys Glu His Gln Asp Leu Lys Asn Gly Gly Gln Pro
    1100                1105                1110

Val Ala Gly Glu Asp Gly Gln Ala Ala Asp Gly Ser Met Gln Pro
    1115                1120                1125

Thr Ser Trp Arg Gln Glu Pro Gln Leu Cys Gly Met Gly Thr Glu
    1130                1135                1140

Gln Gly Cys Trp Ile Pro Val Ser Ser Asp Lys Gly Ser Cys Pro
    1145                1150                1155

Gln Val Met Glu Arg Ser Phe His Met Pro Ser Tyr Gly Thr Gln
    1160                1165                1170

Thr Leu Glu Gly Gly Val Glu Lys Pro His Ser Leu Leu Ser Ala
    1175                1180                1185

Asn Pro Leu Trp Gln Gln Arg Ala Leu Asp Pro Pro His Gln Met
    1190                1195                1200

Glu Leu Thr Gln
    1205

<210> SEQ ID NO 59
<211> LENGTH: 1165
<212> TYPE: PRT
<213> ORGANISM: Homo sapiens

<400> SEQUENCE: 59

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp

```
            65                  70                  75                  80
        Phe His Tyr Asn Glu Lys Arg Ile Tyr Trp Val Asp Leu Glu Arg Gln
                        85                  90                  95

Leu Leu Gln Arg Val Phe Leu Asn Gly Ser Arg Gln Glu Arg Val Cys
                        100                 105                 110

Asn Ile Glu Lys Asn Val Ser Gly Met Ala Ile Asn Trp Ile Asn Glu
                        115                 120                 125

Glu Val Ile Trp Ser Asn Gln Gln Glu Gly Ile Ile Thr Val Thr Asp
                        130                 135                 140

Met Lys Gly Asn Asn Ser His Ile Leu Leu Ser Ala Leu Lys Tyr Pro
        145                 150                 155                 160

Ala Asn Val Ala Val Asp Pro Val Glu Arg Phe Ile Phe Trp Ser Ser
                        165                 170                 175

Glu Val Ala Gly Ser Leu Tyr Arg Ala Asp Leu Asp Gly Val Gly Val
                        180                 185                 190

Lys Ala Leu Leu Glu Thr Ser Glu Lys Ile Thr Ala Val Ser Leu Asp
                        195                 200                 205

Val Leu Asp Lys Arg Leu Phe Trp Ile Gln Tyr Asn Arg Glu Gly Ser
        210                 215                 220

Asn Ser Leu Ile Cys Ser Cys Asp Tyr Asp Gly Gly Ser Val His Ile
        225                 230                 235                 240

Ser Lys His Pro Thr Gln His Asn Leu Phe Ala Met Ser Leu Phe Gly
                        245                 250                 255

Asp Arg Ile Phe Tyr Ser Thr Trp Lys Met Lys Thr Ile Trp Ile Ala
                        260                 265                 270

Asn Lys His Thr Gly Lys Asp Met Val Arg Ile Asn Leu His Ser Ser
                        275                 280                 285

Phe Val Pro Leu Gly Glu Leu Lys Val Val His Pro Leu Ala Gln Pro
        290                 295                 300

Lys Ala Glu Asp Asp Thr Trp Glu Pro Asp Val Asn Glu Cys Ala Phe
        305                 310                 315                 320

Trp Asn His Gly Cys Thr Leu Gly Cys Lys Asn Thr Pro Gly Ser Tyr
                        325                 330                 335

Tyr Cys Thr Cys Pro Val Gly Phe Val Leu Leu Pro Asp Gly Lys Arg
                        340                 345                 350

Cys His Gln Leu Val Ser Cys Pro Arg Asn Val Ser Glu Cys Ser His
                        355                 360                 365

Asp Cys Val Leu Thr Ser Glu Gly Pro Leu Cys Phe Cys Pro Glu Gly
                        370                 375                 380

Ser Val Leu Glu Arg Asp Gly Lys Thr Cys Ser Gly Cys Ser Ser Pro
        385                 390                 395                 400

Asp Asn Gly Gly Cys Ser Gln Leu Cys Val Pro Leu Ser Pro Val Ser
                        405                 410                 415

Trp Glu Cys Asp Cys Phe Pro Gly Tyr Asp Leu Gln Leu Asp Glu Lys
                        420                 425                 430

Ser Cys Ala Ala Ser Gly Pro Gln Pro Phe Leu Leu Phe Ala Asn Ser
                        435                 440                 445

Gln Asp Ile Arg His Met His Phe Asp Gly Thr Asp Tyr Gly Thr Leu
                        450                 455                 460

Leu Ser Gln Gln Met Gly Met Val Tyr Ala Leu Asp His Asp Pro Val
        465                 470                 475                 480

Glu Asn Lys Ile Tyr Phe Ala His Thr Ala Leu Lys Trp Ile Glu Arg
                        485                 490                 495
```

```
Ala Asn Met Asp Gly Ser Gln Arg Glu Arg Leu Ile Glu Glu Gly Val
            500                 505                 510

Asp Val Pro Glu Gly Leu Ala Val Asp Trp Ile Gly Arg Arg Phe Tyr
        515                 520                 525

Trp Thr Asp Arg Gly Lys Ser Leu Ile Gly Arg Ser Asp Leu Asn Gly
    530                 535                 540

Lys Arg Ser Lys Ile Ile Thr Lys Glu Asn Ile Ser Gln Pro Arg Gly
545                 550                 555                 560

Ile Ala Val His Pro Met Ala Lys Arg Leu Phe Trp Thr Asp Thr Gly
                565                 570                 575

Ile Asn Pro Arg Ile Glu Ser Ser Leu Gln Gly Leu Gly Arg Leu
            580                 585                 590

Val Ile Ala Ser Ser Asp Leu Ile Trp Pro Ser Gly Ile Thr Ile Asp
        595                 600                 605

Phe Leu Thr Asp Lys Leu Tyr Trp Cys Asp Ala Lys Gln Ser Val Ile
    610                 615                 620

Glu Met Ala Asn Leu Asp Gly Ser Lys Arg Arg Leu Thr Gln Asn
625                 630                 635                 640

Asp Val Gly His Pro Phe Ala Val Ala Val Phe Glu Asp Tyr Val Trp
                645                 650                 655

Phe Ser Asp Trp Ala Met Pro Ser Val Met Arg Val Asn Lys Arg Thr
            660                 665                 670

Gly Lys Asp Arg Val Arg Leu Gln Gly Ser Met Leu Lys Pro Ser Ser
        675                 680                 685

Leu Val Val Val His Pro Leu Ala Lys Pro Gly Ala Asp Pro Cys Leu
    690                 695                 700

Tyr Gln Asn Gly Gly Cys Glu His Ile Cys Lys Lys Arg Leu Gly Thr
705                 710                 715                 720

Ala Trp Cys Ser Cys Arg Glu Gly Phe Met Lys Ala Ser Asp Gly Lys
                725                 730                 735

Thr Cys Leu Ala Leu Asp Gly His Gln Leu Leu Ala Gly Gly Glu Val
            740                 745                 750

Asp Leu Lys Asn Gln Val Thr Pro Leu Asp Ile Leu Ser Lys Thr Arg
        755                 760                 765

Val Ser Glu Asp Asn Ile Thr Glu Ser Gln His Met Leu Val Ala Glu
    770                 775                 780

Ile Met Val Ser Asp Gln Asp Cys Ala Pro Val Gly Cys Ser Met
785                 790                 795                 800

Tyr Ala Arg Cys Ile Ser Glu Gly Glu Asp Ala Thr Cys Gln Cys Leu
                805                 810                 815

Lys Gly Phe Ala Gly Asp Gly Lys Leu Cys Ser Asp Ile Asp Glu Cys
            820                 825                 830

Glu Met Gly Val Pro Val Cys Pro Ala Ser Ser Lys Cys Ile Asn
                835                 840                 845

Thr Glu Gly Gly Tyr Val Cys Arg Cys Ser Glu Gly Tyr Gln Gly Asp
        850                 855                 860

Gly Ile His Cys Leu Asp Ile Asp Glu Cys Gln Leu Gly Glu His Ser
865                 870                 875                 880

Cys Gly Glu Asn Ala Ser Cys Thr Asn Thr Glu Gly Gly Tyr Thr Cys
                885                 890                 895

Met Cys Ala Gly Arg Leu Ser Glu Pro Gly Leu Ile Cys Pro Asp Ser
            900                 905                 910
```

Thr Pro Pro Pro His Leu Arg Glu Asp Asp His His Tyr Ser Val Arg
                915                 920                 925

Asn Ser Asp Ser Glu Cys Pro Leu Ser His Asp Gly Tyr Cys Leu His
    930                 935                 940

Asp Gly Val Cys Met Tyr Ile Glu Ala Leu Asp Lys Tyr Ala Cys Asn
945                 950                 955                 960

Cys Val Val Gly Tyr Ile Gly Glu Arg Cys Gln Tyr Arg Asp Leu Lys
                965                 970                 975

Trp Trp Glu Leu Arg His Ala Gly His Gly Gln Gln Lys Val Ile
                980                 985                 990

Val Val Ala Val Cys Val Val Val Leu Val Met Leu Leu Leu Leu Ser
                995                 1000                1005

Leu Trp Gly Ala His Tyr Tyr Arg Thr Gln Lys Leu Leu Ser Lys
    1010                1015                1020

Asn Pro Lys Asn Pro Tyr Glu Glu Ser Ser Arg Asp Val Arg Ser
    1025                1030                1035

Arg Arg Pro Ala Asp Thr Glu Asp Gly Met Ser Ser Cys Pro Gln
    1040                1045                1050

Pro Trp Phe Val Val Ile Lys Glu His Gln Asp Leu Lys Asn Gly
    1055                1060                1065

Gly Gln Pro Val Ala Gly Glu Asp Gly Gln Ala Ala Asp Gly Ser
    1070                1075                1080

Met Gln Pro Thr Ser Trp Arg Gln Glu Pro Gln Leu Cys Gly Met
    1085                1090                1095

Gly Thr Glu Gln Gly Cys Trp Ile Pro Val Ser Ser Asp Lys Gly
    1100                1105                1110

Ser Cys Pro Gln Val Met Glu Arg Ser Phe His Met Pro Ser Tyr
    1115                1120                1125

Gly Thr Gln Thr Leu Glu Gly Gly Val Glu Lys Pro His Ser Leu
    1130                1135                1140

Leu Ser Ala Asn Pro Leu Trp Gln Gln Arg Ala Leu Asp Pro Pro
    1145                1150                1155

His Gln Met Glu Leu Thr Gln
    1160                1165

<210> SEQ ID NO 60
<211> LENGTH: 1166
<212> TYPE: PRT
<213> ORGANISM: Homo sapiens

<400> SEQUENCE: 60

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
                20                  25                  30

Leu Ala Gly Asn Gly Asn Ser Thr Cys Val Gly Pro Ala Pro Phe Leu
            35                  40                  45

Ile Phe Ser His Gly Asn Ser Ile Phe Arg Ile Asp Thr Glu Gly Thr
        50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
                100                 105                 110

Asn Ile Glu Lys Asn Val Ser Gly Met Ala Ile Asn Trp Ile Asn Glu
            115                 120                 125

Glu Val Ile Trp Ser Asn Gln Gln Glu Gly Ile Ile Thr Val Thr Asp
        130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
                180                 185                 190

Lys Ala Leu Leu Glu Thr Ser Glu Lys Ile Thr Ala Val Ser Leu Asp
                195                 200                 205

Val Leu Asp Lys Arg Leu Phe Trp Ile Gln Tyr Asn Arg Glu Gly Ser
        210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
                260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
        290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
                340                 345                 350

Tyr Cys Glu Asp Val Asn Glu Cys Ala Phe Trp Asn His Gly Cys Thr
        355                 360                 365

Leu Gly Cys Lys Asn Thr Pro Gly Ser Tyr Tyr Cys Thr Cys Pro Val
        370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
        435                 440                 445

Gln Leu Cys Val Pro Leu Ser Pro Val Ser Trp Glu Cys Asp Cys Phe
        450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
                500                 505                 510

Met Val Tyr Ala Leu Asp His Asp Pro Val Glu Asn Lys Ile Tyr Phe
        515                 520                 525

-continued

```
Ala His Thr Ala Leu Lys Trp Ile Glu Arg Ala Asn Met Asp Gly Ser
    530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
                580                 585                 590

Thr Lys Glu Asn Ile Ser Gln Pro Arg Gly Ile Ala Val His Pro Met
            595                 600                 605

Ala Lys Arg Leu Phe Trp Thr Asp Thr Gly Ile Asn Pro Arg Ile Glu
        610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
                660                 665                 670

Gly Ser Lys Arg Arg Arg Leu Thr Gln Asn Asp Val Gly His Pro Phe
            675                 680                 685

Ala Val Ala Val Phe Glu Asp Tyr Val Trp Phe Ser Asp Trp Ala Met
        690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val Val His Pro
                725                 730                 735

Leu Ala Lys Pro Gly Ala Asp Pro Cys Leu Tyr Gln Asn Gly Gly Cys
                740                 745                 750

Glu His Ile Cys Lys Lys Arg Leu Gly Thr Ala Trp Cys Ser Cys Arg
            755                 760                 765

Glu Gly Phe Met Lys Ala Ser Asp Gly Lys Thr Cys Leu Ala Leu Asp
        770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
                820                 825                 830

Asp Asp Cys Ala Pro Val Gly Cys Ser Met Tyr Ala Arg Cys Ile Ser
            835                 840                 845

Glu Gly Glu Asp Ala Thr Cys Gln Cys Leu Lys Gly Phe Ala Gly Asp
850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
                900                 905                 910

Ser Thr Pro Pro Pro His Leu Arg Glu Asp Asp His His Tyr Ser Val
            915                 920                 925

Arg Asn Ser Asp Ser Glu Cys Pro Leu Ser His Asp Gly Tyr Cys Leu
        930                 935                 940

His Asp Gly Val Cys Met Tyr Ile Glu Ala Leu Asp Lys Tyr Ala Cys
```

```
                  945               950               955               960
Asn Cys Val Val Gly Tyr Ile Gly Glu Arg Cys Gln Tyr Arg Asp Leu
                      965               970               975

Lys Trp Trp Glu Leu Arg His Ala Gly His Gly Gln Gln Gln Lys Val
                      980               985               990

Ile Val Val Ala Val Cys Val Val Leu Val Met Leu Leu Leu Leu
                      995              1000              1005

Ser Leu Trp Gly Ala His Tyr Tyr Arg Thr Gln Lys Leu Leu Ser
                     1010              1015              1020

Lys Asn Pro Lys Asn Pro Tyr Glu Glu Ser Ser Arg Asp Val Arg
                     1025              1030              1035

Ser Arg Arg Pro Ala Asp Thr Glu Asp Gly Met Ser Ser Cys Pro
                     1040              1045              1050

Gln Pro Trp Phe Val Val Ile Lys Glu His Gln Asp Leu Lys Asn
                     1055              1060              1065

Gly Gly Gln Pro Val Ala Gly Glu Asp Gly Gln Ala Ala Asp Gly
                     1070              1075              1080

Ser Met Gln Pro Thr Ser Trp Arg Gln Glu Pro Gln Leu Cys Gly
                     1085              1090              1095

Met Gly Thr Glu Gln Gly Cys Trp Ile Pro Val Ser Ser Asp Lys
                     1100              1105              1110

Gly Ser Cys Pro Gln Val Met Glu Arg Ser Phe His Met Pro Ser
                     1115              1120              1125

Tyr Gly Thr Gln Thr Leu Glu Gly Gly Val Glu Lys Pro His Ser
                     1130              1135              1140

Leu Leu Ser Ala Asn Pro Leu Trp Gln Gln Arg Ala Leu Asp Pro
                     1145              1150              1155

Pro His Gln Met Glu Leu Thr Gln
                     1160              1165

<210> SEQ ID NO 61
<211> LENGTH: 53
<212> TYPE: PRT
<213> ORGANISM: Homo sapiens

<400> SEQUENCE: 61

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
                20                  25                  30

Cys Val Val Gly Tyr Ile Gly Glu Arg Cys Gln Tyr Arg Asp Leu Lys
            35                  40                  45

Trp Trp Glu Leu Arg
    50

<210> SEQ ID NO 62
<211> LENGTH: 208
<212> TYPE: PRT
<213> ORGANISM: Homo sapiens

<400> SEQUENCE: 62

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
                20                  25                  30

Leu Ala Ala Gly Thr Ser Asn Pro Asp Pro Pro Thr Val Ser Thr Asp
```

```
                35                  40                  45
Gln Leu Leu Pro Leu Gly Gly Gly Arg Asp Arg Lys Val Arg Asp Leu
         50                  55                  60
Gln Glu Ala Asp Leu Asp Leu Leu Arg Val Thr Leu Ser Ser Lys Pro
 65                  70                  75                  80
Gln Ala Leu Ala Thr Pro Asn Lys Glu Glu His Gly Lys Arg Lys Lys
                 85                  90                  95
Lys Gly Lys Gly Leu Gly Lys Lys Arg Asp Pro Cys Leu Arg Lys Tyr
            100                 105                 110
Lys Asp Phe Cys Ile His Gly Glu Cys Lys Tyr Val Lys Glu Leu Arg
        115                 120                 125
Ala Pro Ser Cys Ile Cys His Pro Gly Tyr His Gly Glu Arg Cys His
    130                 135                 140
Gly Leu Ser Leu Pro Val Glu Asn Arg Leu Tyr Thr Tyr Asp His Thr
145                 150                 155                 160
Thr Ile Leu Ala Val Val Ala Val Val Leu Ser Ser Val Cys Leu Leu
                165                 170                 175
Val Ile Val Gly Leu Leu Met Phe Arg Tyr His Arg Arg Gly Gly Tyr
            180                 185                 190
Asp Val Glu Asn Glu Glu Lys Val Lys Leu Gly Met Thr Asn Ser His
        195                 200                 205

<210> SEQ ID NO 63
<211> LENGTH: 86
<212> TYPE: PRT
<213> ORGANISM: Homo sapiens

<400> SEQUENCE: 63

Asp Leu Gln Glu Ala Asp Leu Asp Leu Leu Arg Val Thr Leu Ser Ser
  1               5                  10                  15
Lys Pro Gln Ala Leu Ala Thr Pro Asn Lys Glu Glu His Gly Lys Arg
             20                  25                  30
Lys Lys Lys Gly Lys Gly Leu Gly Lys Lys Arg Asp Pro Cys Leu Arg
         35                  40                  45
Lys Tyr Lys Asp Phe Cys Ile His Gly Glu Cys Lys Tyr Val Lys Glu
     50                  55                  60
Leu Arg Ala Pro Ser Cys Ile Cys His Pro Gly Tyr His Gly Glu Arg
 65                  70                  75                  80
Cys His Gly Leu Ser Leu
                 85

<210> SEQ ID NO 64
<211> LENGTH: 160
<212> TYPE: PRT
<213> ORGANISM: Homo sapiens

<400> SEQUENCE: 64

Met Val Pro Ser Ala Gly Gln Leu Ala Leu Phe Ala Leu Gly Ile Val
  1               5                  10                  15
Leu Ala Ala Cys Gln Ala Leu Glu Asn Ser Thr Ser Pro Leu Ser Ala
             20                  25                  30
Asp Pro Pro Val Ala Ala Ala Val Ser His Phe Asn Asp Cys Pro
         35                  40                  45
Asp Ser His Thr Gln Phe Cys Phe His Gly Thr Cys Arg Phe Leu Val
     50                  55                  60
Gln Glu Asp Lys Pro Ala Cys Val Cys His Ser Gly Tyr Val Gly Ala
```

```
                65                  70                  75                  80
Arg Cys Glu His Ala Asp Leu Leu Ala Val Val Ala Ala Ser Gln Lys
                    85                  90                  95
Lys Gln Ala Ile Thr Ala Leu Val Val Val Ser Ile Val Ala Leu Ala
                100                 105                 110
Val Leu Ile Ile Thr Cys Val Leu Ile His Cys Cys Gln Val Arg Lys
                115                 120                 125
His Cys Glu Trp Cys Arg Ala Leu Ile Cys Arg His Glu Lys Pro Ser
            130                 135                 140
Ala Leu Leu Lys Gly Arg Thr Ala Cys Cys His Ser Glu Thr Val Val
145                 150                 155                 160

<210> SEQ ID NO 65
<211> LENGTH: 159
<212> TYPE: PRT
<213> ORGANISM: Homo sapiens

<400> SEQUENCE: 65

Met Val Pro Ser Ala Gly Gln Leu Ala Leu Phe Ala Leu Gly Ile Val
1               5                   10                  15
Leu Ala Ala Cys Gln Ala Leu Glu Asn Ser Thr Ser Pro Leu Ser Asp
                20                  25                  30
Pro Pro Val Ala Ala Ala Val Val Ser His Phe Asn Asp Cys Pro Asp
            35                  40                  45
Ser His Thr Gln Phe Cys Phe His Gly Thr Cys Arg Phe Leu Val Gln
        50                  55                  60
Glu Asp Lys Pro Ala Cys Val Cys His Ser Gly Tyr Val Gly Ala Arg
65                  70                  75                  80
Cys Glu His Ala Asp Leu Leu Ala Val Val Ala Ala Ser Gln Lys Lys
                85                  90                  95
Gln Ala Ile Thr Ala Leu Val Val Val Ser Ile Val Ala Leu Ala Val
                100                 105                 110
Leu Ile Ile Thr Cys Val Leu Ile His Cys Cys Gln Val Arg Lys His
            115                 120                 125
Cys Glu Trp Cys Arg Ala Leu Ile Cys Arg His Glu Lys Pro Ser Ala
        130                 135                 140
Leu Leu Lys Gly Arg Thr Ala Cys Cys His Ser Glu Thr Val Val
145                 150                 155

<210> SEQ ID NO 66
<211> LENGTH: 161
<212> TYPE: PRT
<213> ORGANISM: Homo sapiens

<400> SEQUENCE: 66

Met Val Pro Ser Ala Gly Gln Leu Ala Leu Phe Ala Leu Gly Ile Val
1               5                   10                  15
Leu Ala Ala Cys Gln Ala Leu Glu Asn Ser Thr Ser Pro Leu Ser Asp
                20                  25                  30
Pro Pro Val Ala Ala Ala Val Val Ser His Phe Asn Asp Cys Pro Asp
            35                  40                  45
Ser His Thr Gln Phe Cys Phe His Gly Thr Cys Arg Phe Leu Val Gln
        50                  55                  60
Glu Asp Lys Pro Ala Cys Val Cys His Ser Gly Tyr Val Gly Ala Arg
65                  70                  75                  80
Cys Glu His Ala Asp Leu Leu Ala Val Val Ala Ala Ser Gln Lys Lys
```

```
                    85                  90                  95

Gln Ala Ile Thr Ala Leu Val Val Ser Ile Val Ala Leu Ala Val
                100                 105                 110

Leu Ile Ile Thr Cys Val Leu Ile His Cys Cys Gln Val Arg Lys His
            115                 120                 125

Cys Glu Trp Cys Arg Ala Leu Ile Cys Arg His Glu Lys Pro Ser Ala
        130                 135                 140

Leu Leu Lys Gly Arg Thr Ala Cys Cys His Ser Glu Thr Ala Thr Leu
145                 150                 155                 160

Gly

<210> SEQ ID NO 67
<211> LENGTH: 163
<212> TYPE: PRT
<213> ORGANISM: Homo sapiens

<400> SEQUENCE: 67

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
                20                  25                  30

Asp Pro Pro Val Ala Ala Val Val Ser His Phe Asn Asp Cys Pro
            35                  40                  45

Asp Ser His Thr Gln Phe Cys Phe His Gly Thr Cys Arg Phe Leu Val
        50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Val Ala Ala Ser Gln Lys
                85                  90                  95

Lys Gln Ala Ile Thr Ala Leu Val Val Ser Ile Val Ala Leu Ala
                100                 105                 110

Val Leu Ile Ile Thr Cys Val Leu Ile His Cys Cys Gln Val Arg Lys
            115                 120                 125

His Cys Glu Trp Cys Arg Ala Leu Ile Cys Arg His Glu Lys Pro Ser
        130                 135                 140

Ala Leu Leu Lys Gly Arg Thr Ala Cys Cys His Ser Glu Thr Gly Cys
145                 150                 155                 160

Arg Leu Tyr

<210> SEQ ID NO 68
<211> LENGTH: 163
<212> TYPE: PRT
<213> ORGANISM: Homo sapiens

<400> SEQUENCE: 68

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
                20                  25                  30

Asp Pro Pro Val Ala Ala Val Val Ser His Phe Asn Asp Cys Pro
            35                  40                  45

Asp Ser His Thr Gln Phe Cys Phe His Gly Thr Cys Arg Phe Leu Val
        50                  55                  60

Gln Glu Asp Lys Pro Ala Cys Val Cys His Ser Gly Tyr Val Gly Ala
65                  70                  75                  80
```

Arg Cys Glu His Ala Asp Leu Leu Ala Val Ala Ala Ser Gln Lys
                85                  90                  95

Lys Gln Ala Ile Thr Ala Leu Val Val Ser Ile Val Ala Leu Ala
            100                 105                 110

Val Leu Ile Ile Thr Cys Val Leu Ile His Cys Cys Gln Val Arg Lys
            115                 120                 125

His Cys Glu Trp Cys Arg Ala Leu Ile Cys Arg His Glu Lys Pro Ser
    130                 135                 140

Ala Leu Leu Lys Gly Arg Thr Ala Cys Cys His Ser Glu Thr Gly Cys
145                 150                 155                 160

Arg Leu Tyr

<210> SEQ ID NO 69
<211> LENGTH: 50
<212> TYPE: PRT
<213> ORGANISM: Homo sapiens

<400> SEQUENCE: 69

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

<210> SEQ ID NO 70
<211> LENGTH: 252
<212> TYPE: PRT
<213> ORGANISM: Homo sapiens

<400> SEQUENCE: 70

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60

Pro Val Ser Glu Met Pro Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
    130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile

```
                180             185             190
Asp Ser Ser Leu Ser Lys Ile Ala Leu Ala Ala Ile Ala Ala Phe Met
            195                 200                 205

Ser Ala Val Ile Leu Thr Ala Val Ala Val Ile Thr Val Gln Leu Arg
            210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250

<210> SEQ ID NO 71
<211> LENGTH: 87
<212> TYPE: PRT
<213> ORGANISM: Homo sapiens

<400> SEQUENCE: 71

Ser Val Arg Val Glu Gln Val Val Lys Pro Pro Gln Asn Lys Thr Glu
1               5                   10                  15

Ser Glu Asn Thr Ser Asp Lys Pro Lys Arg Lys Lys Lys Gly Gly Lys
            20                  25                  30

Asn Gly Lys Asn Arg Arg Asn Arg Lys Lys Lys Asn Pro Cys Asn Ala
        35                  40                  45

Glu Phe Gln Asn Phe Cys Ile His Gly Glu Cys Lys Tyr Ile Glu His
    50                  55                  60

Leu Glu Ala Val Thr Cys Lys Cys Gln Gln Glu Tyr Phe Gly Glu Arg
65                  70                  75                  80

Cys Gly Glu Lys Ser Met Lys
                85

<210> SEQ ID NO 72
<211> LENGTH: 169
<212> TYPE: PRT
<213> ORGANISM: Homo sapiens

<400> SEQUENCE: 72

Met Thr Ala Gly Arg Arg Met Glu Met Leu Cys Ala Gly Arg Val Pro
1               5                   10                  15

Ala Leu Leu Leu Cys Leu Gly Phe His Leu Leu Gln Ala Val Leu Ser
            20                  25                  30

Thr Thr Val Ile Pro Ser Cys Ile Pro Gly Glu Ser Ser Asp Asn Cys
        35                  40                  45

Thr Ala Leu Val Gln Thr Glu Asp Asn Pro Arg Val Ala Gln Val Ser
    50                  55                  60

Ile Thr Lys Cys Ser Ser Asp Met Asn Gly Tyr Cys Leu His Gly Gln
65                  70                  75                  80

Cys Ile Tyr Leu Val Asp Met Ser Gln Asn Tyr Cys Arg Cys Glu Val
                85                  90                  95

Gly Tyr Thr Gly Val Arg Cys Glu His Phe Phe Leu Thr Val His Gln
            100                 105                 110

Pro Leu Ser Lys Glu Tyr Val Ala Leu Thr Val Ile Leu Ile Ile Leu
        115                 120                 125

Phe Leu Ile Thr Val Val Gly Ser Thr Tyr Tyr Phe Cys Arg Trp Tyr
    130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val
```

-continued

165

<210> SEQ ID NO 73
<211> LENGTH: 49
<212> TYPE: PRT
<213> ORGANISM: Homo sapiens

<400> SEQUENCE: 73

Val Ala Gln Val Ser Ile Thr Lys Cys Ser Ser Asp Met Asn Gly Tyr
1               5                   10                  15

Cys Leu His Gly Gln Cys Ile Tyr Leu Val Asp Met Ser Gln Asn Tyr
                20                  25                  30

Cys Arg Cys Glu Val Gly Tyr Thr Gly Val Arg Cys Glu His Phe Phe
            35                  40                  45

Leu

<210> SEQ ID NO 74
<211> LENGTH: 154
<212> TYPE: PRT
<213> ORGANISM: Homo sapiens

<400> SEQUENCE: 74

Met Ala Leu Gly Val Pro Ile Ser Val Tyr Leu Leu Phe Asn Ala Met
1               5                   10                  15

Thr Ala Leu Thr Glu Glu Ala Ala Val Thr Val Thr Pro Pro Ile Thr
                20                  25                  30

Ala Gln Gln Gly Asn Trp Thr Val Asn Lys Thr Glu Ala Asp Asn Ile
            35                  40                  45

Glu Gly Pro Ile Ala Leu Lys Phe Ser His Leu Cys Leu Glu Asp His
50                  55                  60

Asn Ser Tyr Cys Ile Asn Gly Ala Cys Ala Phe His His Glu Leu Glu
65                  70                  75                  80

Lys Ala Ile Cys Arg Cys Phe Thr Gly Tyr Thr Gly Glu Arg Cys Glu
                85                  90                  95

His Leu Thr Leu Thr Ser Tyr Ala Val Asp Ser Tyr Glu Lys Tyr Ile
                100                 105                 110

Ala Ile Gly Ile Gly Val Gly Leu Leu Leu Ser Gly Phe Leu Val Ile
            115                 120                 125

Phe Tyr Cys Tyr Ile Arg Lys Arg Cys Leu Lys Leu Lys Ser Pro Tyr
        130                 135                 140

Asn Val Cys Ser Gly Glu Arg Arg Pro Leu
145                 150

<210> SEQ ID NO 75
<211> LENGTH: 133
<212> TYPE: PRT
<213> ORGANISM: Homo sapiens

<400> SEQUENCE: 75

Met Ala Leu Gly Val Pro Ile Ser Val Tyr Leu Leu Phe Asn Ala Met
1               5                   10                  15

Thr Ala Leu Thr Glu Glu Ala Ala Val Thr Val Thr Pro Pro Ile Thr
                20                  25                  30

Ala Gln Gln Ala Asp Asn Ile Glu Gly Pro Ile Ala Leu Lys Phe Ser
            35                  40                  45

His Leu Cys Leu Glu Asp His Asn Ser Tyr Cys Ile Asn Gly Ala Cys
50                  55                  60

```
Ala Phe His His Glu Leu Glu Lys Ala Ile Cys Arg Cys Phe Thr Gly
 65                  70                  75                  80

Tyr Thr Gly Glu Arg Cys Glu His Leu Thr Leu Thr Ser Tyr Ala Val
                 85                  90                  95

Asp Ser Tyr Glu Lys Tyr Ile Ala Ile Gly Ile Gly Val Gly Leu Leu
            100                 105                 110

Leu Ser Gly Phe Leu Val Ile Phe Tyr Cys Tyr Ile Arg Lys Arg Tyr
        115                 120                 125

Glu Lys Asp Lys Ile
        130

<210> SEQ ID NO 76
<211> LENGTH: 112
<212> TYPE: PRT
<213> ORGANISM: Homo sapiens

<400> SEQUENCE: 76

Met Ala Leu Gly Val Pro Ile Ser Val Tyr Leu Leu Phe Asn Ala Met
  1               5                  10                  15

Thr Ala Leu Thr Glu Glu Ala Ala Val Thr Val Thr Pro Pro Ile Thr
                 20                  25                  30

Ala Gln Gln Gly Asn Trp Thr Val Asn Lys Thr Glu Ala Asp Asn Ile
             35                  40                  45

Glu Gly Pro Ile Ala Leu Lys Phe Ser His Leu Cys Leu Glu Asp His
         50                  55                  60

Asn Ser Tyr Cys Ile Asn Gly Ala Cys Ala Phe His His Glu Leu Glu
 65                  70                  75                  80

Lys Ala Ile Cys Arg Cys Phe Thr Gly Tyr Thr Gly Glu Arg Cys Leu
                 85                  90                  95

Lys Leu Lys Ser Pro Tyr Asn Val Cys Ser Gly Glu Arg Arg Pro Leu
            100                 105                 110

<210> SEQ ID NO 77
<211> LENGTH: 103
<212> TYPE: PRT
<213> ORGANISM: Homo sapiens

<400> SEQUENCE: 77

Met Ala Leu Gly Val Pro Ile Ser Val Tyr Leu Leu Phe Asn Ala Met
  1               5                  10                  15

Thr Ala Leu Thr Glu Glu Ala Ala Val Thr Val Thr Pro Pro Ile Thr
                 20                  25                  30

Ala Gln Gln Gly Asn Trp Thr Val Asn Lys Thr Glu Ala Asp Asn Ile
             35                  40                  45

Glu Gly Pro Ile Ala Leu Lys Phe Ser His Leu Cys Leu Glu Asp His
         50                  55                  60

Asn Ser Tyr Cys Ile Asn Gly Ala Cys Ala Phe His His Glu Leu Glu
 65                  70                  75                  80

Lys Ala Ile Cys Arg Cys Leu Lys Leu Lys Ser Pro Tyr Asn Val Cys
                 85                  90                  95

Ser Gly Glu Arg Arg Pro Leu
            100

<210> SEQ ID NO 78
<211> LENGTH: 103
<212> TYPE: PRT
<213> ORGANISM: Homo sapiens
```

<400> SEQUENCE: 78

Met Ala Leu Gly Val Pro Ile Ser Val Tyr Leu Leu Phe Asn Ala Met
1               5                   10                  15

Thr Ala Leu Thr Glu Glu Ala Ala Val Thr Val Thr Pro Pro Ile Thr
            20                  25                  30

Ala Gln Gln Ala Asp Asn Ile Glu Gly Pro Ile Ala Leu Lys Phe Ser
        35                  40                  45

His Leu Cys Leu Glu Asp His Asn Ser Tyr Cys Ile Asn Gly Ala Cys
    50                  55                  60

Ala Phe His His Glu Leu Glu Lys Ala Ile Cys Arg Cys Phe Thr Gly
65                  70                  75                  80

Tyr Thr Gly Glu Arg Cys Leu Lys Leu Lys Ser Pro Tyr Asn Val Cys
                85                  90                  95

Ser Gly Glu Arg Arg Pro Leu
            100

<210> SEQ ID NO 79
<211> LENGTH: 94
<212> TYPE: PRT
<213> ORGANISM: Homo sapiens

<400> SEQUENCE: 79

Met Ala Leu Gly Val Pro Ile Ser Val Tyr Leu Leu Phe Asn Ala Met
1               5                   10                  15

Thr Ala Leu Thr Glu Glu Ala Ala Val Thr Val Thr Pro Pro Ile Thr
            20                  25                  30

Ala Gln Gln Ala Asp Asn Ile Glu Gly Pro Ile Ala Leu Lys Phe Ser
        35                  40                  45

His Leu Cys Leu Glu Asp His Asn Ser Tyr Cys Ile Asn Gly Ala Cys
    50                  55                  60

Ala Phe His His Glu Leu Glu Lys Ala Ile Cys Arg Cys Leu Lys Leu
65                  70                  75                  80

Lys Ser Pro Tyr Asn Val Cys Ser Gly Glu Arg Arg Pro Leu
                85                  90

<210> SEQ ID NO 80
<211> LENGTH: 73
<212> TYPE: PRT
<213> ORGANISM: Homo sapiens

<400> SEQUENCE: 80

Met Ala Leu Gly Val Pro Ile Ser Val Tyr Leu Leu Phe Asn Ala Asp
1               5                   10                  15

Asn Ile Glu Gly Pro Ile Ala Leu Lys Phe Ser His Leu Cys Leu Glu
            20                  25                  30

Asp His Asn Ser Tyr Cys Ile Asn Gly Ala Cys Ala Phe His His Glu
        35                  40                  45

Leu Glu Lys Ala Ile Cys Arg Cys Leu Lys Leu Lys Ser Pro Tyr Asn
    50                  55                  60

Val Cys Ser Gly Glu Arg Arg Pro Leu
65                  70

<210> SEQ ID NO 81
<211> LENGTH: 132
<212> TYPE: PRT
<213> ORGANISM: Homo sapiens

<400> SEQUENCE: 81

-continued

Ala Ala Val Thr Val Thr Pro Pro Ile Thr Ala Gln Gln Gly Asn Trp
1               5                   10                  15

Thr Val Asn Lys Thr Glu Ala Asp Asn Ile Glu Gly Pro Ile Ala Leu
                20                  25                  30

Lys Phe Ser His Leu Cys Leu Glu Asp His Asn Ser Tyr Cys Ile Asn
            35                  40                  45

Gly Ala Cys Ala Phe His His Glu Leu Glu Lys Ala Ile Cys Arg Cys
        50                  55                  60

Phe Thr Gly Tyr Thr Gly Glu Arg Cys Glu His Leu Thr Leu Thr Ser
65                  70                  75                  80

Tyr Ala Val Asp Ser Tyr Glu Lys Tyr Ile Ala Ile Gly Ile Gly Val
                85                  90                  95

Gly Leu Leu Leu Ser Gly Phe Leu Val Ile Phe Tyr Cys Tyr Ile Arg
            100                 105                 110

Lys Arg Cys Leu Lys Leu Lys Ser Pro Tyr Asn Val Cys Ser Gly Glu
            115                 120                 125

Arg Arg Pro Leu
        130

<210> SEQ ID NO 82
<211> LENGTH: 178
<212> TYPE: PRT
<213> ORGANISM: Homo sapiens

<400> SEQUENCE: 82

Met Asp Arg Ala Ala Arg Cys Ser Gly Ala Ser Ser Leu Pro Leu Leu
1               5                   10                  15

Leu Ala Leu Ala Leu Gly Leu Val Ile Leu His Cys Val Val Ala Asp
                20                  25                  30

Gly Asn Ser Thr Arg Ser Pro Glu Thr Asn Gly Leu Leu Cys Gly Asp
            35                  40                  45

Pro Glu Glu Asn Cys Ala Ala Thr Thr Thr Gln Ser Lys Arg Lys Gly
        50                  55                  60

His Phe Ser Arg Cys Pro Lys Gln Tyr Lys His Tyr Cys Ile Lys Gly
65                  70                  75                  80

Arg Cys Arg Phe Val Val Ala Glu Gln Thr Pro Ser Cys Val Cys Asp
                85                  90                  95

Glu Gly Tyr Ile Gly Ala Arg Cys Glu Arg Val Asp Leu Phe Tyr Leu
            100                 105                 110

Arg Gly Asp Arg Gly Gln Ile Leu Val Ile Cys Leu Ile Ala Val Met
        115                 120                 125

Val Val Phe Ile Ile Leu Val Ile Gly Val Cys Thr Cys Cys His Pro
130                 135                 140

Leu Arg Lys Arg Arg Lys Arg Lys Lys Glu Glu Glu Met Glu Thr
145                 150                 155                 160

Leu Gly Lys Asp Ile Thr Pro Ile Asn Glu Asp Ile Glu Glu Thr Asn
                165                 170                 175

Ile Ala

<210> SEQ ID NO 83
<211> LENGTH: 80
<212> TYPE: PRT
<213> ORGANISM: Homo sapiens

<400> SEQUENCE: 83

-continued

```
Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Thr Gln Ser Lys Arg Lys
            20              25              30

Gly His Phe Ser Arg Cys Pro Lys Gln Tyr Lys His Tyr Cys Ile Lys
        35              40              45

Gly Arg Cys Arg Phe Val Val Ala Glu Gln Thr Pro Ser Cys Val Cys
    50              55              60

Asp Glu Gly Tyr Ile Gly Ala Arg Cys Glu Arg Val Asp Leu Phe Tyr
65              70              75              80
```